(12) United States Patent
Nawana et al.

(10) Patent No.: US 12,178,979 B2
(45) Date of Patent: Dec. 31, 2024

(54) DERMAL PATCH FOR DELIVERING A PHARMACEUTICAL

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 18/090,107

(22) Filed: Dec. 28, 2022

(65) Prior Publication Data

US 2023/0233824 A1 Jul. 27, 2023

Related U.S. Application Data

(63) Continuation-in-part of application No. 17/994,454, filed on Nov. 28, 2022, now Pat. No. 11,877,848, and a continuation-in-part of application No. 17/991,284, filed on Nov. 21, 2022, now Pat. No. 12,048,543, and a continuation-in-part of application No. 17/971,142, filed on Oct. 21, 2022, now Pat. No. 12,053,284, and a continuation-in-part of application No. 17/903,802, filed on Sep. 6, 2022, and a continuation-in-part of
(Continued)

(51) Int. Cl.
*A61M 37/00* (2006.01)
*A61M 5/142* (2006.01)

(52) U.S. Cl.
CPC .... *A61M 37/0015* (2013.01); *A61M 5/14212* (2013.01); *A61M 2037/0023* (2013.01); *A61M 2037/0061* (2013.01); *A61M 2202/30* (2013.01); *A61M 2205/6063* (2013.01)

(58) Field of Classification Search
CPC .......... A61M 37/0015; A61M 5/14212; A61M 2037/0023; A61M 2037/0061; A61M 2202/30
USPC ........................................................ 604/506
See application file for complete search history.

(56) References Cited

U.S. PATENT DOCUMENTS

| 5,015,228 A | 5/1991 | Columbus et al. |
| 5,338,308 A | 8/1994 | Wilk |

(Continued)

FOREIGN PATENT DOCUMENTS

| AU | 2006283345 A1 | 3/2007 |
| AU | 2016266112 A1 | 12/2016 |

(Continued)

OTHER PUBLICATIONS

International Search Report and Written Opinion for PCT/US2022/046384 mailed Jan. 5, 2023.
(Continued)

*Primary Examiner* — Phillip A Gray
(74) *Attorney, Agent, or Firm* — Potomac Law Group, PLLC; Reza Mollaaghababa

(57) ABSTRACT

A dermal patch system for administering a pharmaceutical includes a vial that stores a pharmaceutical and a cartridge coupled to the vial. The cartridge includes a pull mechanism, a pump, a plurality of microneedles in communication with the vial. The microneedles are configured to move between an undeployed position to a deployed position. When pulled, the pull mechanism is configured to cause the microneedles to move from the undeployed position to the deployed position and cause the pump to pump the pharmaceutical from the vial and to the microneedles.

16 Claims, 81 Drawing Sheets

Related U.S. Application Data application No. 17/500,873, filed on Oct. 13, 2021, now Pat. No. 11,964,121.

(56) References Cited

U.S. PATENT DOCUMENTS

| | | |
|---|---|---|
| 5,441,490 A | 8/1995 | Svedman |
| 5,527,288 A | 6/1996 | Gross et al. |
| 5,602,037 A | 2/1997 | Ostgaard et al. |
| 5,636,640 A | 6/1997 | Staehlin |
| 5,680,872 A | 10/1997 | Sesekura et al. |
| 5,848,991 A | 12/1998 | Gross et al. |
| 5,997,501 A | 12/1999 | Gross et al. |
| 6,234,980 B1 | 5/2001 | Bell |
| 6,315,985 B1 | 11/2001 | Wu et al. |
| 6,454,140 B1 | 9/2002 | Jinks |
| 6,500,150 B1 | 12/2002 | Gross et al. |
| 6,506,168 B1 | 1/2003 | Fathallah et al. |
| 6,524,284 B1 | 2/2003 | Marshall |
| 6,610,273 B2 | 8/2003 | Wu et al. |
| 6,623,457 B1 | 9/2003 | Rosenberg |
| 6,644,517 B2 | 11/2003 | Thiel et al. |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,796,429 B2 | 9/2004 | Cameron et al. |
| 6,808,506 B2 | 10/2004 | Lastovich et al. |
| 6,893,655 B2 | 5/2005 | Flanigan et al. |
| 6,932,082 B2 | 8/2005 | Stein |
| 6,960,193 B2 | 11/2005 | Rosenberg |
| 6,994,691 B2 | 2/2006 | Ejlersen |
| 7,004,928 B2 | 2/2006 | Aceti et al. |
| 7,083,592 B2 | 8/2006 | Lastovich et al. |
| 7,101,534 B1 | 9/2006 | Schultz et al. |
| 7,156,838 B2 | 1/2007 | Gabel et al. |
| 7,175,642 B2 | 2/2007 | Briggs et al. |
| 7,182,955 B2 | 2/2007 | Hart et al. |
| 7,250,037 B2 | 7/2007 | Shermer et al. |
| 7,252,651 B2 | 8/2007 | Haider et al. |
| 7,282,058 B2 | 10/2007 | Levin et al. |
| 7,308,893 B2 | 12/2007 | Boot |
| 7,435,415 B2 | 10/2008 | Gelber |
| 7,637,891 B2 | 12/2009 | Wall |
| 7,651,475 B2 | 1/2010 | Angel et al. |
| 7,678,079 B2 | 3/2010 | Shermer et al. |
| 7,846,488 B2 | 12/2010 | Johnson et al. |
| 7,905,866 B2 | 3/2011 | Haider et al. |
| 8,048,019 B2 | 11/2011 | Nisato et al. |
| 8,057,842 B2 | 11/2011 | Choi et al. |
| 8,066,680 B2 | 11/2011 | Alchas et al. |
| 8,079,960 B2 | 12/2011 | Briggs et al. |
| 8,104,469 B2 | 1/2012 | Dams |
| 8,108,023 B2 | 1/2012 | Mir et al. |
| 8,157,768 B2 | 4/2012 | Haider et al. |
| 8,206,336 B2 | 6/2012 | Shantha |
| 8,246,582 B2 | 8/2012 | Angel et al. |
| 8,246,893 B2 | 8/2012 | Ferguson et al. |
| 8,252,268 B2 | 8/2012 | Slowey et al. |
| 8,267,889 B2 | 9/2012 | Cantor et al. |
| 8,303,518 B2 | 11/2012 | Aceti et al. |
| D681,195 S | 4/2013 | Skulley et al. |
| 8,409,140 B2 | 4/2013 | Ejlersen et al. |
| 8,414,503 B2 | 4/2013 | Briggs et al. |
| 8,414,959 B2 | 4/2013 | Hye-Ok et al. |
| 8,430,097 B2 | 4/2013 | Jinks et al. |
| 8,459,253 B2 | 6/2013 | Howgill |
| 8,491,500 B2 | 7/2013 | Briggs et al. |
| 8,496,601 B2 | 7/2013 | Briggs et al. |
| D687,550 S | 8/2013 | Moeckly et al. |
| D687,551 S | 8/2013 | Moeckly et al. |
| D687,945 S | 8/2013 | Brewer et al. |
| D687,946 S | 8/2013 | Brewer et al. |
| D687,947 S | 8/2013 | Brewer et al. |
| 8,512,244 B2 | 8/2013 | Jennewine |
| 8,517,019 B2 | 8/2013 | Brewer et al. |
| 8,554,317 B2 | 10/2013 | Duan |
| 8,556,861 B2 | 10/2013 | Tsals |
| 8,561,795 B2 | 10/2013 | Schott |
| D693,921 S | 11/2013 | Burton et al. |
| 8,602,271 B2 | 12/2013 | Winker et al. |
| 8,603,040 B2 | 12/2013 | Haider et al. |
| 8,608,889 B2 | 12/2013 | Sever et al. |
| 8,622,963 B2 | 1/2014 | Iwase et al. |
| 8,696,619 B2 | 4/2014 | Schnall |
| 8,696,637 B2 | 4/2014 | Ross |
| D705,422 S | 5/2014 | Burton et al. |
| 8,715,232 B2 | 5/2014 | Yodfat et al. |
| 8,740,014 B2 | 6/2014 | Purkins et al. |
| 8,741,377 B2 | 6/2014 | Choi et al. |
| 8,784,363 B2 | 7/2014 | Frederickson et al. |
| 8,808,202 B2 | 8/2014 | Brancazio |
| 8,808,786 B2 | 8/2014 | Jinks et al. |
| 8,814,009 B2 | 8/2014 | Hodson et al. |
| 8,814,035 B2 | 8/2014 | Stuart |
| 8,821,412 B2 | 9/2014 | Gonzalez-Zugasti et al. |
| 8,821,446 B2 | 9/2014 | Trautman et al. |
| 8,821,779 B2 | 9/2014 | Ferguson et al. |
| 8,827,971 B2 | 9/2014 | Gonzalez-Zugasti et al. |
| 8,870,821 B2 | 10/2014 | Laufer |
| 8,900,180 B2 | 12/2014 | Wolter et al. |
| 8,900,194 B2 | 12/2014 | Clarke et al. |
| 8,945,071 B2 | 2/2015 | Christensen |
| 8,961,431 B2 | 2/2015 | Roe et al. |
| 9,022,973 B2 | 5/2015 | Sexton et al. |
| 9,033,898 B2 | 5/2015 | Chickering, III et al. |
| 9,041,541 B2 | 5/2015 | Levinson et al. |
| D733,290 S | 6/2015 | Burton et al. |
| 9,067,031 B2 | 6/2015 | Jinks et al. |
| 9,072,664 B2 | 7/2015 | Stein et al. |
| 9,089,661 B2 | 7/2015 | Stuart et al. |
| 9,089,677 B2 | 7/2015 | Soo et al. |
| 9,113,836 B2 | 8/2015 | Bernstein et al. |
| 9,119,578 B2 | 9/2015 | Haghgooie et al. |
| 9,119,945 B2 | 9/2015 | Simons et al. |
| 9,133,024 B2 | 9/2015 | Phan et al. |
| 9,144,651 B2 | 9/2015 | Stuart |
| 9,144,671 B2 | 9/2015 | Cantor et al. |
| 9,173,994 B2 | 11/2015 | Ziaie et al. |
| 9,174,035 B2 | 11/2015 | Ringsred et al. |
| 9,186,097 B2 | 11/2015 | Frey et al. |
| 9,227,021 B2 | 1/2016 | Buss |
| 9,289,763 B2 | 3/2016 | Berthier et al. |
| 9,289,925 B2 | 3/2016 | Ferguson et al. |
| 9,289,968 B2 | 3/2016 | Sever et al. |
| 9,295,417 B2 | 3/2016 | Haghgooie et al. |
| 9,295,987 B2 | 3/2016 | Kelly et al. |
| 9,339,956 B2 | 5/2016 | Rendon |
| 9,380,972 B2 | 7/2016 | Fletcher et al. |
| 9,380,973 B2 | 7/2016 | Fletcher et al. |
| 9,468,404 B2 | 10/2016 | Hayden |
| 9,480,428 B2 | 11/2016 | Colin et al. |
| 9,504,813 B2 | 11/2016 | Buss |
| 9,522,225 B2 | 12/2016 | Chong et al. |
| 9,549,700 B2 | 1/2017 | Fletcher et al. |
| 9,555,187 B2 | 1/2017 | Sonderegger et al. |
| 9,566,393 B2 | 2/2017 | Iwase et al. |
| 9,579,461 B2 | 2/2017 | Sonderegger et al. |
| 9,623,087 B2 | 4/2017 | Zhang et al. |
| 9,642,895 B2 | 5/2017 | Dai et al. |
| 9,643,229 B2 | 5/2017 | Wilson et al. |
| 9,675,675 B2 | 6/2017 | Zhang et al. |
| 9,675,752 B2 | 6/2017 | Christensen |
| 9,682,222 B2 | 6/2017 | Burton et al. |
| 9,693,950 B2 | 7/2017 | Determan et al. |
| 9,694,149 B2 | 7/2017 | Jinks et al. |
| 9,717,850 B2 | 8/2017 | Sonderegger |
| 9,724,462 B2 | 8/2017 | Rotem |
| 9,730,624 B2 | 8/2017 | Gonzalez-Zugasti et al. |
| 9,770,578 B2 | 9/2017 | Chowdhury |
| 9,775,551 B2 | 10/2017 | Bernstein et al. |
| 9,782,574 B2 | 10/2017 | Simmers |
| 9,789,249 B2 | 10/2017 | Frederickson et al. |
| 9,789,299 B2 | 10/2017 | Simmers |
| 9,844,631 B2 | 12/2017 | Bureau |
| 9,849,270 B2 | 12/2017 | Stockholm |

(56) References Cited

U.S. PATENT DOCUMENTS

| | | |
|---|---|---|
| D808,515 S | 1/2018 | Atkin et al. |
| 9,861,580 B2 | 1/2018 | Mueting et al. |
| 9,861,801 B2 | 1/2018 | Baker et al. |
| 9,872,975 B2 | 1/2018 | Burton et al. |
| 9,884,151 B2 | 2/2018 | Sullivan et al. |
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |
| 10,010,706 B2 | 7/2018 | Gonzalez et al. |
| 10,010,707 B2 | 7/2018 | Colburn et al. |
| 10,016,315 B2 | 7/2018 | Letourneau et al. |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 | 4/2019 | Holmes et al. |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1 | 3/2020 | Peeters et al. |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 | 8/2020 | Hooven et al. |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 | 2/2021 | Lanigan et al. |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,452,474 B1 | 9/2022 | Nawana et al. |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1 | 6/2002 | Lin et al. |
| 2002/0193740 A1 | 12/2002 | Alchas et al. |
| 2004/0002121 A1 | 1/2004 | Regan et al. |
| 2004/0010207 A1 | 1/2004 | Flaherty et al. |
| 2004/0059256 A1 | 3/2004 | Perez |
| 2004/0059366 A1 | 3/2004 | Sato et al. |
| 2004/0106904 A1 | 6/2004 | Gonnelli et al. |
| 2004/0162467 A1 | 8/2004 | Cook |
| 2005/0106713 A1 | 5/2005 | Phan et al. |
| 2005/0118388 A1 | 6/2005 | Kingsford |
| 2005/0203461 A1 | 9/2005 | Flaherty et al. |
| 2006/0047243 A1 | 3/2006 | Rosenberg |
| 2006/0068490 A1 | 3/2006 | Tang et al. |
| 2006/0142651 A1 | 6/2006 | Brister et al. |
| 2006/0271084 A1 | 11/2006 | Schraga |
| 2007/0004989 A1 | 1/2007 | Dhillon |
| 2007/0191696 A1 | 8/2007 | Mischler et al. |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0099427 A1 | 4/2009 | Jina et al. |
| 2009/0105614 A1 | 4/2009 | Momose et al. |
| 2009/0112125 A1 | 4/2009 | Tamir |
| 2009/0198215 A1* | 8/2009 | Chong ............... A61M 5/1413 604/506 |
| 2009/0259176 A1 | 10/2009 | Yairi |
| 2010/0121271 A1 | 5/2010 | Perriere |
| 2010/0198107 A1 | 8/2010 | Groll et al. |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1 | 6/2011 | Pesach et al. |
| 2011/0172508 A1 | 7/2011 | Chickering, III et al. |
| 2011/0172510 A1 | 7/2011 | Chickering, III et al. |
| 2011/0198221 A1 | 8/2011 | Angelescu |
| 2011/0213335 A1 | 9/2011 | Burton et al. |
| 2011/0245635 A1 | 10/2011 | Fujiwara et al. |

(56) References Cited

U.S. PATENT DOCUMENTS

| | | |
|---|---|---|
| 2011/0257497 A1 | 10/2011 | Tamada et al. |
| 2011/0288389 A9 | 11/2011 | Levinson et al. |
| 2012/0016308 A1 | 1/2012 | Schott |
| 2012/0041338 A1 | 2/2012 | Chickering et al. |
| 2012/0046203 A1 | 2/2012 | Walsh et al. |
| 2012/0078224 A1 | 3/2012 | Lerner et al. |
| 2012/0109066 A1 | 5/2012 | Chase et al. |
| 2012/0123297 A1 | 5/2012 | Brancazio |
| 2012/0259599 A1 | 10/2012 | Deck et al. |
| 2012/0271123 A1 | 10/2012 | Castle et al. |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2013/0018279 A1 | 1/2013 | Plante et al. |
| 2013/0158468 A1 | 6/2013 | Bernstein et al. |
| 2013/0158482 A1 | 6/2013 | Davis et al. |
| 2013/0211289 A1 | 8/2013 | Moga et al. |
| 2013/0253446 A1 | 9/2013 | Duan et al. |
| 2013/0269423 A1 | 10/2013 | Angelescu |
| 2014/0066843 A1 | 3/2014 | Zhang et al. |
| 2014/0109900 A1 | 4/2014 | Jinks |
| 2014/0194854 A1 | 7/2014 | Tsals |
| 2014/0305823 A1 | 10/2014 | Gelfand et al. |
| 2014/0309555 A1 | 10/2014 | Gelfand et al. |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1 | 7/2016 | Matsunami et al. |
| 2016/0256095 A1 | 9/2016 | Krasnow et al. |
| 2016/0262676 A1 | 9/2016 | Haghgooie et al. |
| 2016/0315123 A1 | 10/2016 | Kim et al. |
| 2016/0324506 A1 | 11/2016 | Tariyal et al. |
| 2016/0354589 A1 | 12/2016 | Kobayashi et al. |
| 2016/0361006 A1 | 12/2016 | Bullington et al. |
| 2017/0001192 A1 | 1/2017 | Kelly et al. |
| 2017/0014822 A1 | 1/2017 | Ker |
| 2017/0021067 A1 | 1/2017 | Todd et al. |
| 2017/0021117 A1 | 1/2017 | Howgill |
| 2017/0035337 A1 | 2/2017 | Wilkinson et al. |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1 | 5/2017 | Holmes et al. |
| 2017/0127991 A1 | 5/2017 | Bernstein et al. |
| 2017/0173288 A1 | 6/2017 | Stam et al. |
| 2017/0197029 A1 | 7/2017 | Cindrich et al. |
| 2017/0224912 A1 | 8/2017 | Yodfat et al. |
| 2017/0231543 A1 | 8/2017 | Cunningham et al. |
| 2017/0290977 A1 | 10/2017 | Schauderna et al. |
| 2018/0001029 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury et al. |
| 2018/0021559 A1 | 1/2018 | Xu |
| 2018/0078241 A1 | 3/2018 | Moga et al. |
| 2018/0103884 A1 | 4/2018 | Delamarche et al. |
| 2018/0126058 A1 | 5/2018 | Nakka David et al. |
| 2018/0132515 A1 | 5/2018 | Lawrence et al. |
| 2018/0132774 A1 | 5/2018 | Gonzalez-Zugasti et al. |
| 2018/0242890 A1 | 8/2018 | Chickering, III et al. |
| 2018/0243543 A1 | 8/2018 | Baek et al. |
| 2018/0296148 A1 | 10/2018 | Gelfand et al. |
| 2018/0304063 A1 | 10/2018 | Gonzalez et al. |
| 2018/0344631 A1 | 12/2018 | Zhang et al. |
| 2018/0369512 A1 | 12/2018 | Blatchford et al. |
| 2019/0000365 A1 | 1/2019 | Beyerlein et al. |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1 | 5/2019 | Diebold et al. |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1 | 3/2020 | Berthier et al. |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1 | 8/2020 | Ivosevic et al. |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1 | 12/2021 | Weidemaier et al. |
| 2022/0031211 A1 | 2/2022 | Yakhnich et al. |
| 2022/0058895 A1 | 2/2022 | Han |
| 2022/0062607 A1 | 3/2022 | Davis et al. |
| 2022/0071534 A9 | 3/2022 | Gonzalez-Zugasti et al. |
| 2022/0133192 A1 | 5/2022 | Brancazio |
| 2022/0134072 A1 | 5/2022 | Kosel et al. |
| 2022/0215921 A1 | 7/2022 | Levinson et al. |
| 2022/0218251 A1 | 7/2022 | Jackson et al. |
| 2022/0233117 A1 | 7/2022 | Lee et al. |
| 2022/0249818 A1 | 8/2022 | Chickering, III et al. |
| 2022/0257158 A1 | 8/2022 | Haghgooie et al. |
| 2022/0287642 A1 | 9/2022 | Chickering, III et al. |
| 2022/0313128 A1 | 10/2022 | Bernstein et al. |
| 2022/0330860 A1 | 10/2022 | Nawana |
| 2022/0330861 A1 | 10/2022 | Nawana |
| 2022/0347451 A1 | 11/2022 | Jung et al. |
| 2022/0361784 A1 | 11/2022 | Jordan et al. |
| 2022/0369957 A1 | 11/2022 | Nawana |
| 2023/0109881 A1 | 4/2023 | Nawana et al. |

FOREIGN PATENT DOCUMENTS

| | | |
|---|---|---|
| CN | 101296752 A | 10/2008 |
| EP | 0931507 A1 | 7/1999 |
| EP | 1769735 A1 | 4/2007 |

(56) References Cited

FOREIGN PATENT DOCUMENTS

| | | |
|---|---|---|
| EP | 2493537 A2 | 9/2012 |
| EP | 3513833 A1 | 7/2019 |
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| GB | 2428197 A | 1/2007 |
| JP | 2004024164 A | 1/2004 |
| JP | 2018538535 A | 12/2018 |
| KR | 100873642 B1 | 12/2008 |
| KR | 101857300 B1 | 5/2018 |
| NO | 2010101625 A2 | 9/2010 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2010117602 A3 | 3/2011 |
| WO | 2011016615 A3 | 4/2011 |
| WO | 2011053787 A2 | 5/2011 |
| WO | 2011053788 A2 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012028675 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149143 A1 | 11/2012 |
| WO | 2012154362 | 12/2012 |
| WO | 2012173971 A1 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |
| WO | 2013055641 A1 | 4/2013 |
| WO | 2013059409 A1 | 4/2013 |
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |

(56) References Cited

FOREIGN PATENT DOCUMENTS

| | | |
|---|---|---|
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014172246 A1 | 10/2014 |
| WO | 2014172247 A1 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |
| WO | 2016009986 A1 | 1/2016 |
| WO | 2016099986 A1 | 1/2016 |
| WO | 2016018892 A1 | 2/2016 |
| WO | 2016081843 A1 | 5/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017024115 A1 | 2/2017 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Search Report and Written Opinion for PCT/US2022/048913 mailed Feb. 21, 2023.
International Search Report and Written Opinion for PCT/US22/029829 mailed Nov. 23, 2022.
International Preliminary Report of Patentability, PCT/US2022/029829, dated Nov. 21, 2023.
International Preliminary Report on Patentability, PCT/US2022/024607 dated Oct. 12, 2023.
Written Opinion for International Application, No. PCT/US2022/024607, dated Oct. 12, 2023.
International Search Report and Written Opinion, PCT/US2022/024607, dated Aug. 4, 2022.
Taiwan Office Action, TW111142334, dated Dec. 12, 2023.
Taiwan Office Action, TW111142334, dated May 18, 2023.
International Preliminary Report of Patentability for PCT/US2022/046384 issued Apr. 16, 2024.
International Preliminary Report of Patentability for PCT/US2022/048913 dated May 2, 2024.
International Search Report and Written Opinion for International Application No. PCT/US2023/080656 dated Feb. 19, 2024.
International Search Report and Written Opinion for International Application No. PCT/US2023/086234 dated Mar. 7, 2024.
International Search Report and Written Opinion for PCT/US2023/086151 dated May 13, 2024.
International Search Report for International Application No. PCT/2023/086214 dated Apr. 8, 2024.

* cited by examiner

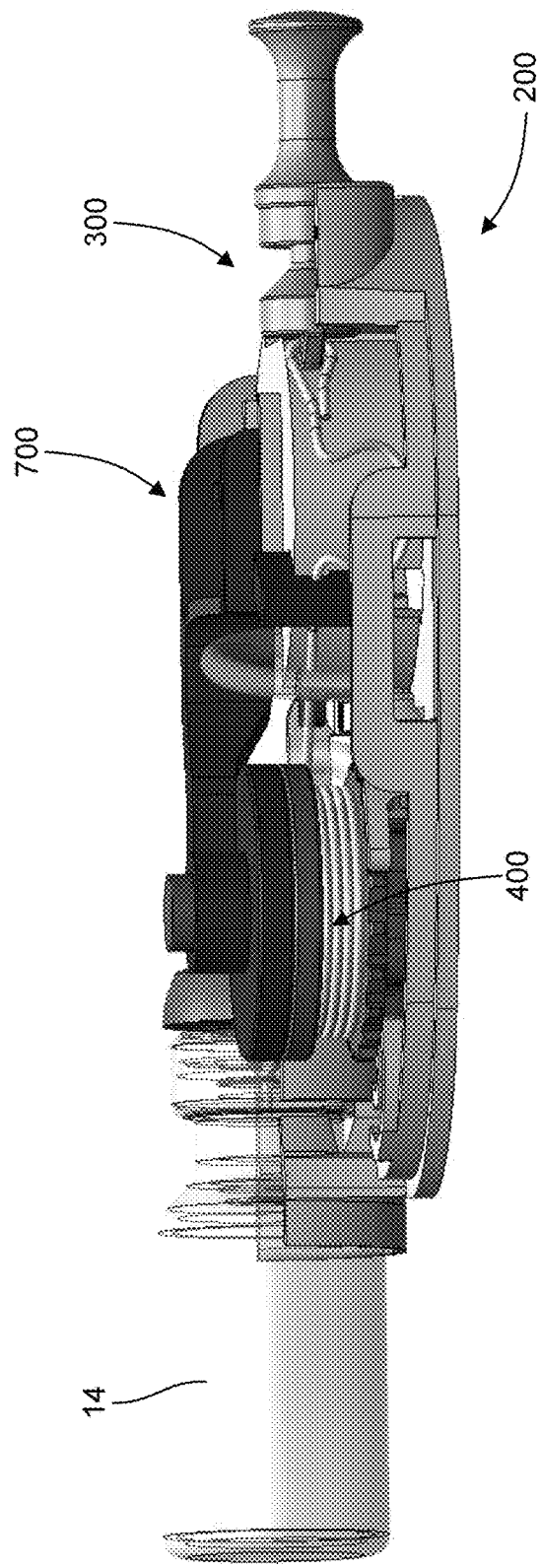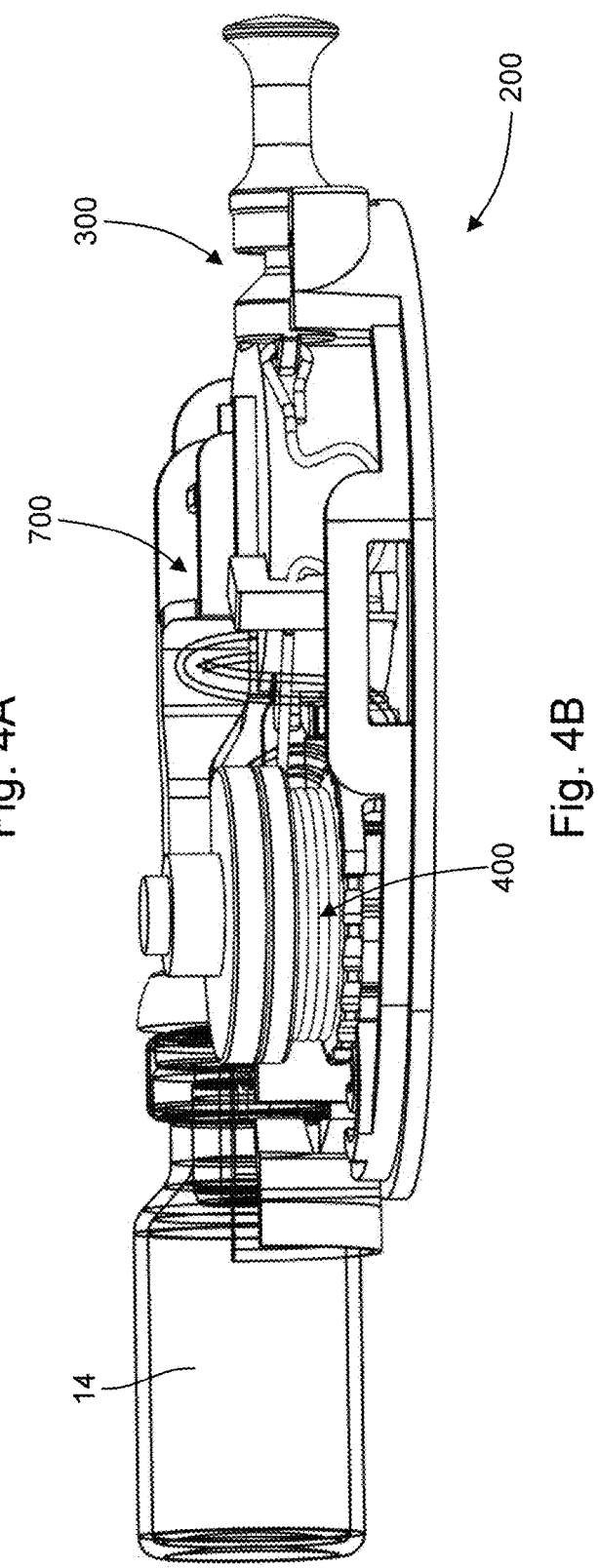
Fig. 4A
Fig. 4B

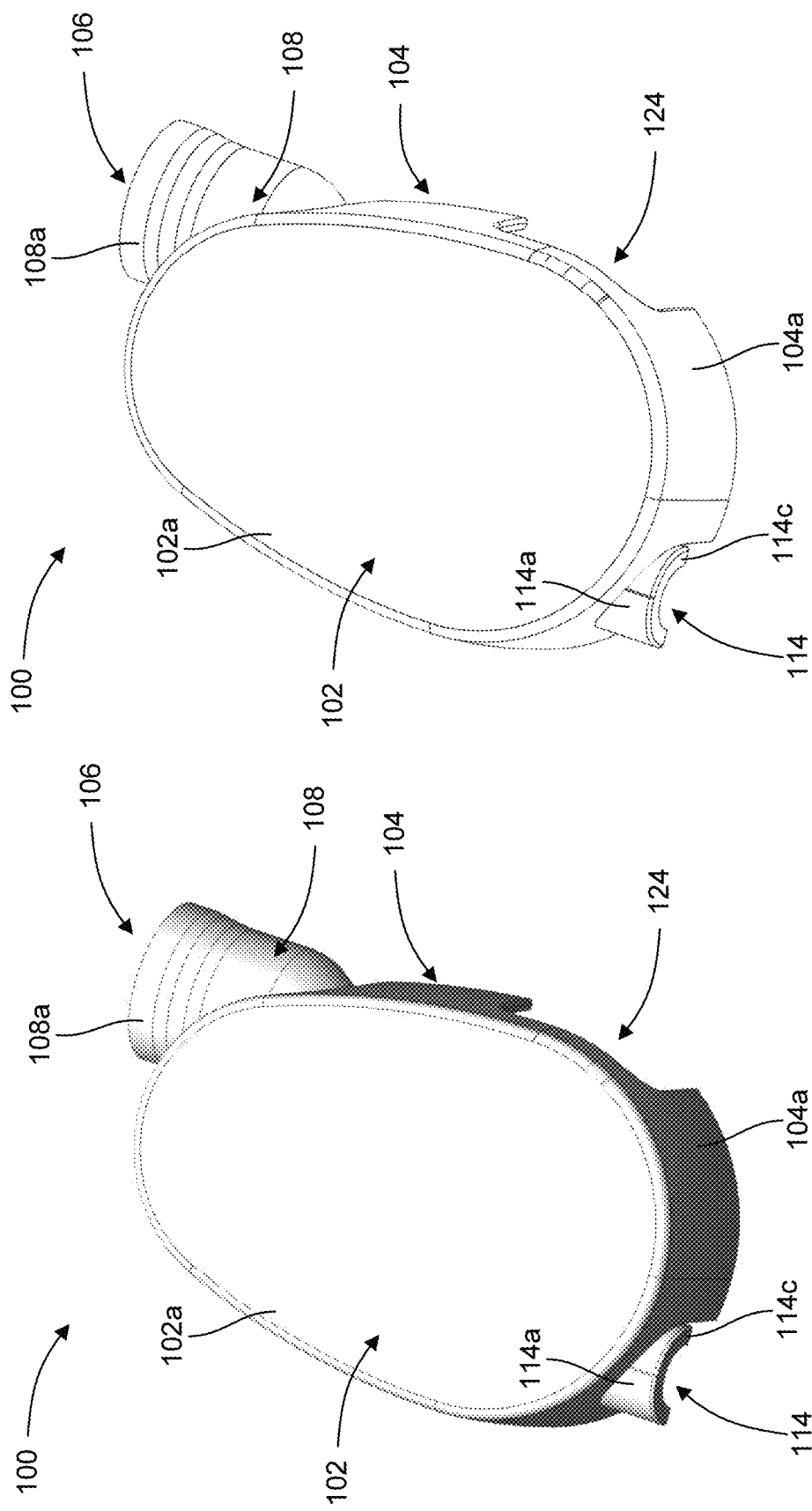

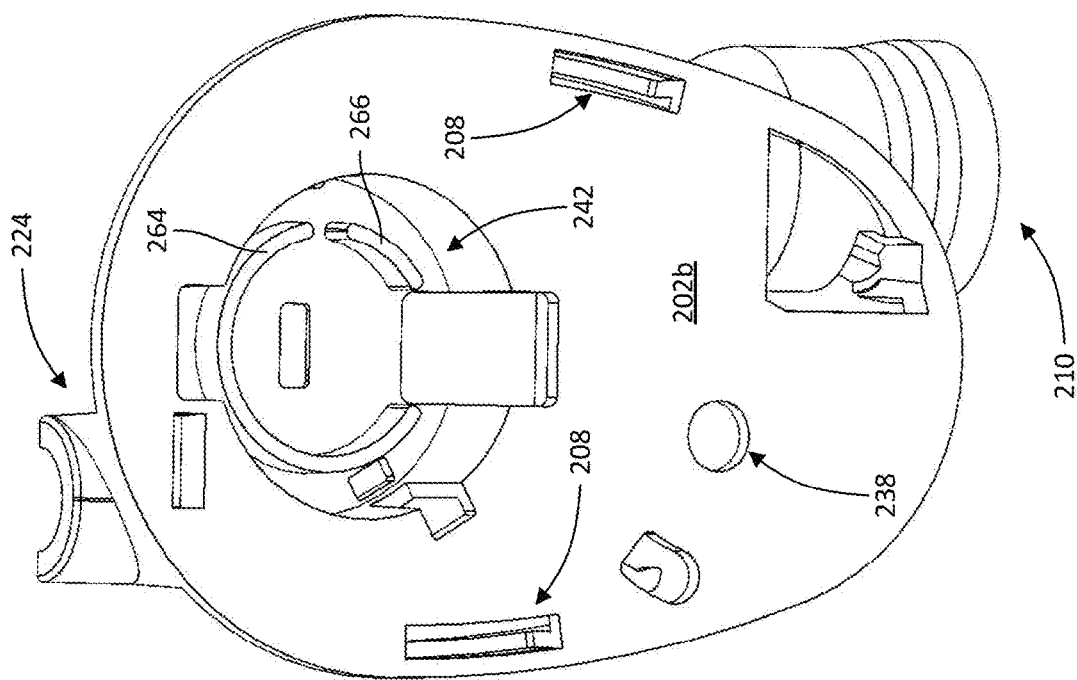
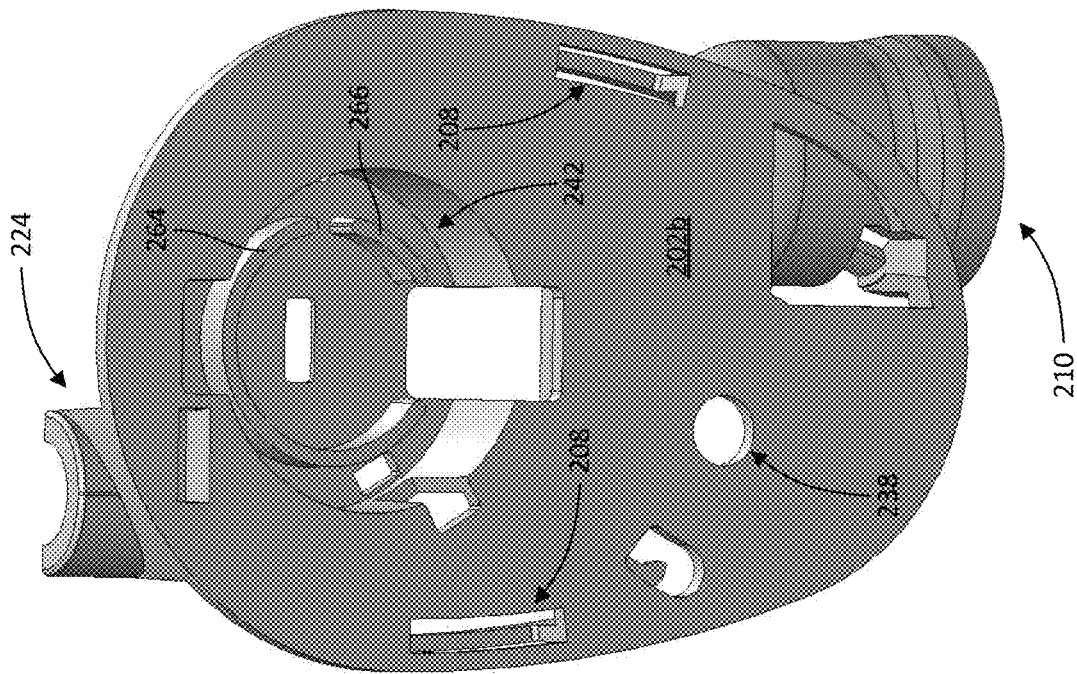

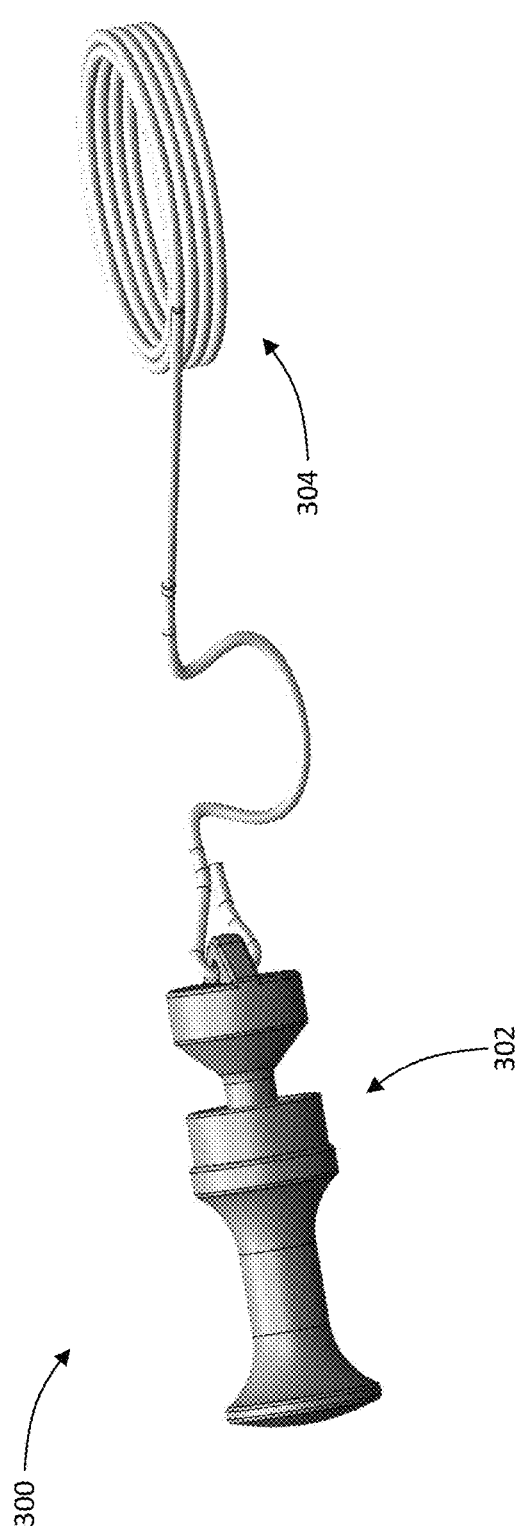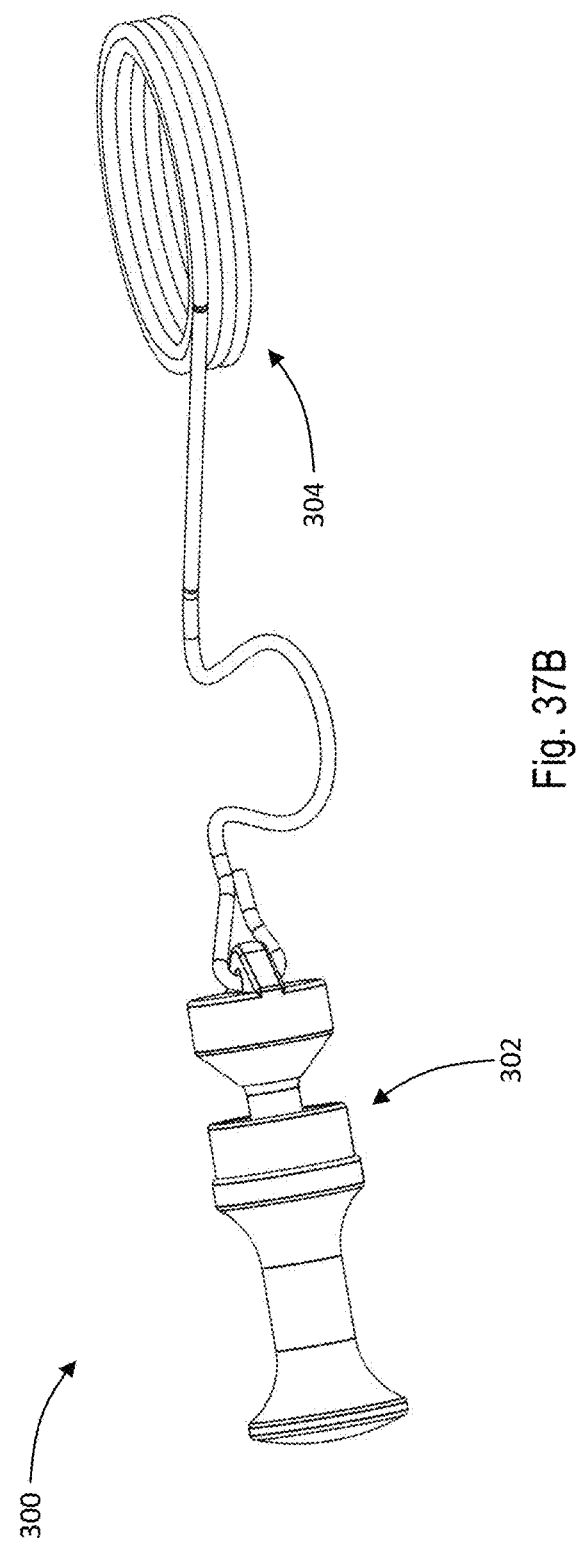
Fig. 37A
Fig. 37B

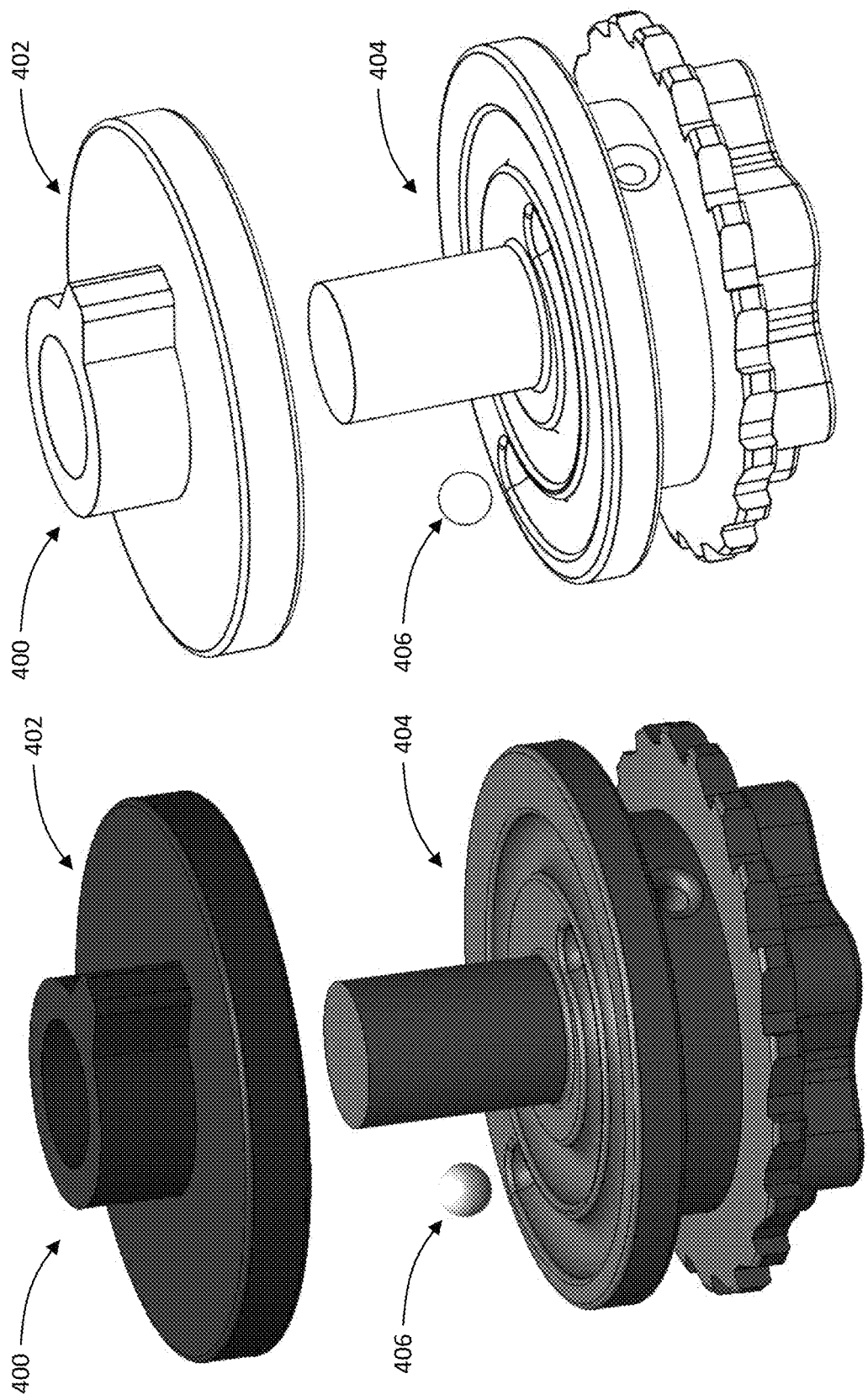

DERMAL PATCH FOR DELIVERING A PHARMACEUTICAL

RELATED APPLICATIONS

The present application is a continuation-in-part of U.S. patent application Ser. No. 17/903,802 (entitled Dual Lever Dermal Patch System and filed on Sep. 6, 2022), Ser. No. 17/500,873 (entitled Mono Dose Dermal Patch for Pharmaceutical Delivery and filed on Oct. 13, 2021), Ser. No. 17/994,454 (entitled Dermal Patch for Collecting a Physiological Sample and filed on Nov. 28, 2022), Ser. No. 17/971,142 (entitled Dermal Patch for Collecting a Physiological Sample and filed on Oct. 21, 2022), and Ser. No. 17/991,284 (entitled Dermal Patch for Collecting a Physiological Sample with Removable Vial and filed on Nov. 21, 2022). Each of these applications is herein incorporated by reference in its entirety.

TECHNICAL FIELD

The present teachings are generally directed to dermal patch systems (herein also referred to as dermal patches) that can be employed to deliver a pharmaceutical to a subject.

BACKGROUND

Typically, administration of pharmaceuticals (e.g., vaccines) is carried out via a standard vial and a syringe. In large majority, the delivery is intramuscular. This mode of administration requires the expertise of a medical professional, which can limit the availability of life-saving pharmaceuticals to certain patient populations. For example, in many developing areas of the world where access to medical professionals may be limited, such conventional modes of parenteral administration may deprive large segments of the population from access to needed pharmaceuticals.

SUMMARY

Aspects of the present disclosure address the above-referenced problems and/or others.

In one aspect, a dermal patch system for administering a pharmaceutical includes a vial that stores a pharmaceutical, and a cartridge coupled to the vial. The dermal patch includes a pull mechanism, a pump, and a plurality of microneedles in communication with the vial. In some embodiments, after a user properly positions the dermal patch system on the skin of a subject, a user can pull the pull mechanism which causes the dermal patch system to prime the microneedles with the pharmaceutical stored in the vial and move the microneedles from an undeployed position to a deployed position and causes the pump to pump the pharmaceutical from the vial. That is, the microneedles are configured to move between an undeployed position to a deployed position, and when pulled, the pull mechanism is configured to cause the pump to pump the pharmaceutical from the vial and to the microneedles and to cause the microneedles to move to the deployed position. In some embodiments, the pump is configured to prime the microneedles with an amount of pharmaceutical before the microneedles are moved to the deployed position for puncturing the subject's skin. In certain embodiments, the cartridge further includes a tube configured to carry the pharmaceutical from the vial to the plurality of microneedles.

In some embodiments, the pump can be a positive rotatable positive displacement pump and pulling the pull mechanism can cause the pump to rotate which causes the pump to force the pharmaceutical through the tube via positive displacement. In certain embodiments, the tube is a first tube, and the cartridge includes a second tube connected to the vial, and wherein rotation of the pump further causes the pump to force air into the vial through the second tube via positive displacement. In some embodiments, the cartridge also includes a latch that allows the pump to rotate in a first direction and prevents the pump from rotating in an opposite second direction. In certain embodiments, the pull mechanism is configured to move when then the cartridge has a first orientation and is prevented from moving when the cartridge has a different second orientation. In some embodiments the cartridge further includes a trigger that is configured to move from a first position to a second position when the pull mechanism is pulled. In the first position the trigger retains the microneedles in the undeployed position and in the second position, the trigger is configured to release the microneedles to a deployed position.

In certain embodiments, the pump is configured to move the trigger from the first position to the second position when the pull mechanism is pulled. In some embodiments the cartridge further includes an injection spring that is in a compressed state when the trigger is in the first position and is in an extended state when the trigger is in the second position. The injection spring is configured to move the microneedles to the deployed position when in the extended position. In certain embodiments, the cartridge further includes a retraction button configured to move the microneedles from the deployed position to the undeployed position. In some embodiments, the cartridge further includes a latch that prevents a user from removing the vial from the cartridge. In some embodiments, the pharmaceutical is a vaccine (e.g., Monkeypox vaccine, Flu vaccine, COVID-19 vaccine, Yellow Fever vaccine, Malaria vaccine, Dengue vaccine, etc.). In certain embodiments, the vial includes a fractional dose of the vaccine. In certain embodiments, the cartridge includes a quick response code that is associated with an electronic medical record.

In a related aspect a method for administering a pharmaceutical to a subject includes inserting a vial containing a pharmaceutical into a cartridge and attaching the cartridge to the subject's skin. The cartridge includes a pump and a plurality of microneedles. The method further includes pulling the pull mechanism to cause the microneedles to move from an undeployed position to a deployed position such that the microneedles puncture the skin of the subject when in the deployed position. Furthermore, pulling the pull mechanism causes the pump to pump the pharmaceutical to the microneedles thereby delivering the pharmaceutical to the subject. In some embodiments, the pharmaceutical is a vaccine. In certain embodiments, a fractional dose of the vaccine is delivered to the subject. In some embodiments, the method includes priming the microneedles by delivering a portion of the pharmaceutical to the microneedles before moving the microneedles to a deployed position. In certain embodiments, the cartridge further includes a tube that carries the pharmaceutical from the vial to the microneedles. In some embodiments, the pump pumps the pharmaceutical from the vial to the microneedles via positive displacement.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which:

FIGS. 3A, 3B, 4A, and 4B depict the dermal patch system without a cover in accordance with an exemplary embodiment;

FIGS. 7A and 7B-13A and 13B depict a cover of the dermal patch system in accordance with an exemplary embodiment;

FIGS. 14A and 14B-23 depict a base of the dermal patch system in accordance with an exemplary embodiment;

FIGS. 24A and 24B-26 depict a vial guide of the base of the dermal patch system in accordance with an exemplary embodiment;

FIGS. 27A and 27B-29A and 29B depict a handle retention feature of the base of the dermal patch system in accordance with an exemplary embodiment;

FIGS. 30A and 30B-33A and 33B depict a microneedle array housing of the dermal patch system in accordance with an exemplary embodiment;

FIGS. 34A and 34B-36 depict the cartridge of the dermal patch system without the cover and without the pump assembly in accordance with an exemplary embodiment;

FIGS. 37A and 37B depict a pull mechanism of the cartridge of the dermal patch system in accordance with an exemplary embodiment;

FIGS. 40A, 40B, 41A, and 41B depict a pump assembly of the cartridge of the dermal patch system in accordance with an exemplary embodiment;

FIGS. 42A and 42B-45A and 45B depict a trigger portion of the pump assembly of the cartridge of the dermal patch system in accordance with an exemplary embodiment;

FIGS. 46A and 46B-50A and 50B depict a pump portion of the pump assembly of the cartridge of the dermal patch system in accordance with an exemplary embodiment;

FIGS. 53A and 53B-56A and 56B depict a microneedle array holder of the microneedle array assembly in accordance with an exemplary embodiment;

FIGS. 58A and 58B-61A and 61B depict a microneedle array of the microneedle array assembly in accordance with an exemplary embodiment;

FIGS. 63A and 63B-67A and 67B depict a retraction button of the cartridge of the dermal patch system in accordance with an exemplary embodiment;

FIGS. 68A and 68B-70A and 70B depict a trigger of the cartridge of the dermal patch system in accordance with an exemplary embodiment;

DETAILED DESCRIPTION

Figure 1A:
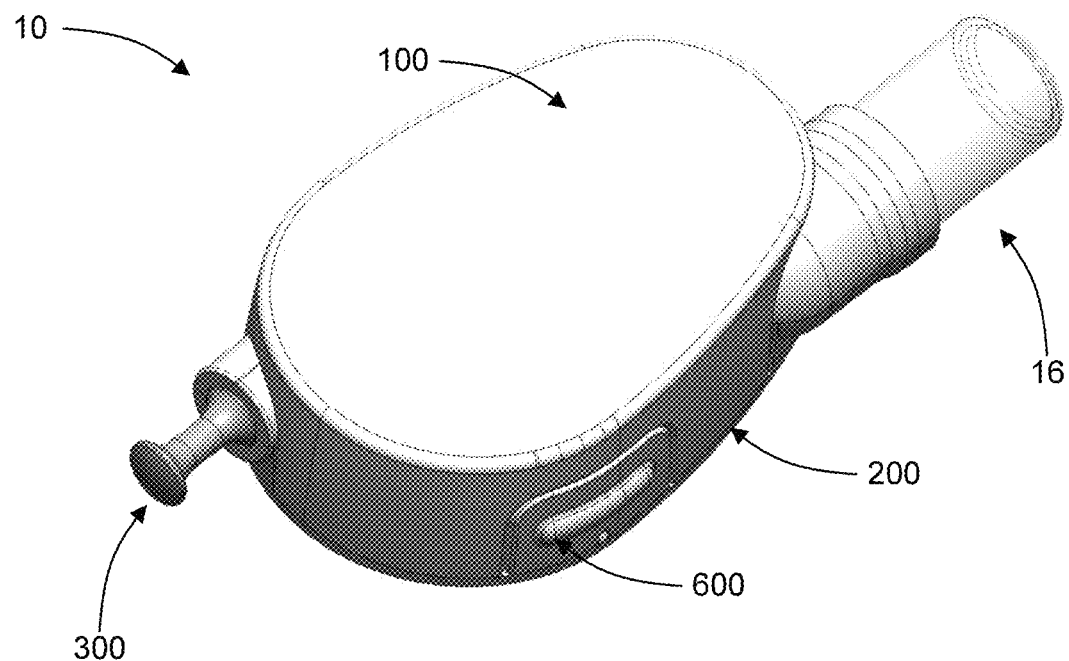
FIGS. 1A, 1B, 2A, and 2B depict a dermal patch system in accordance with an exemplary embodiment.
Figure 1B:
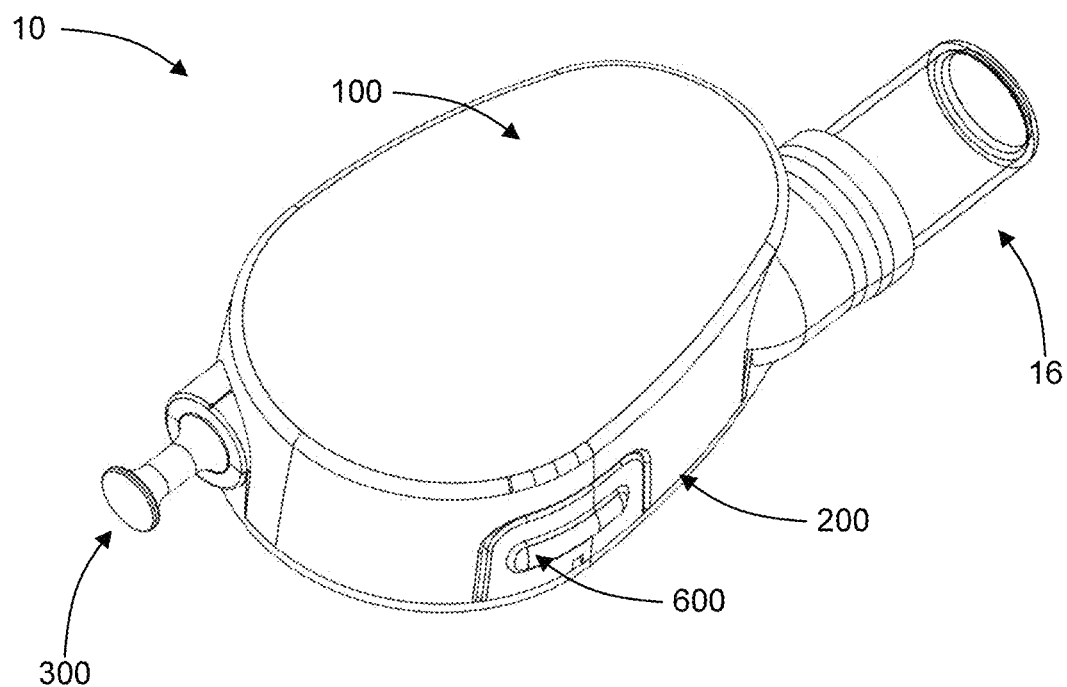
Figure 2A:
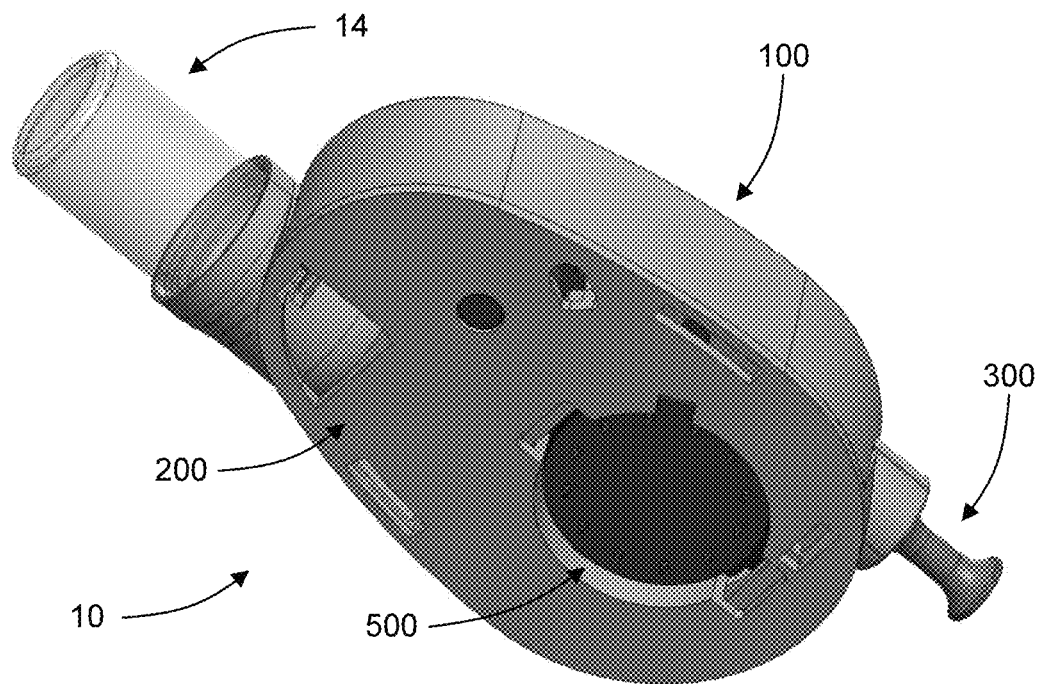
Figure 2B:
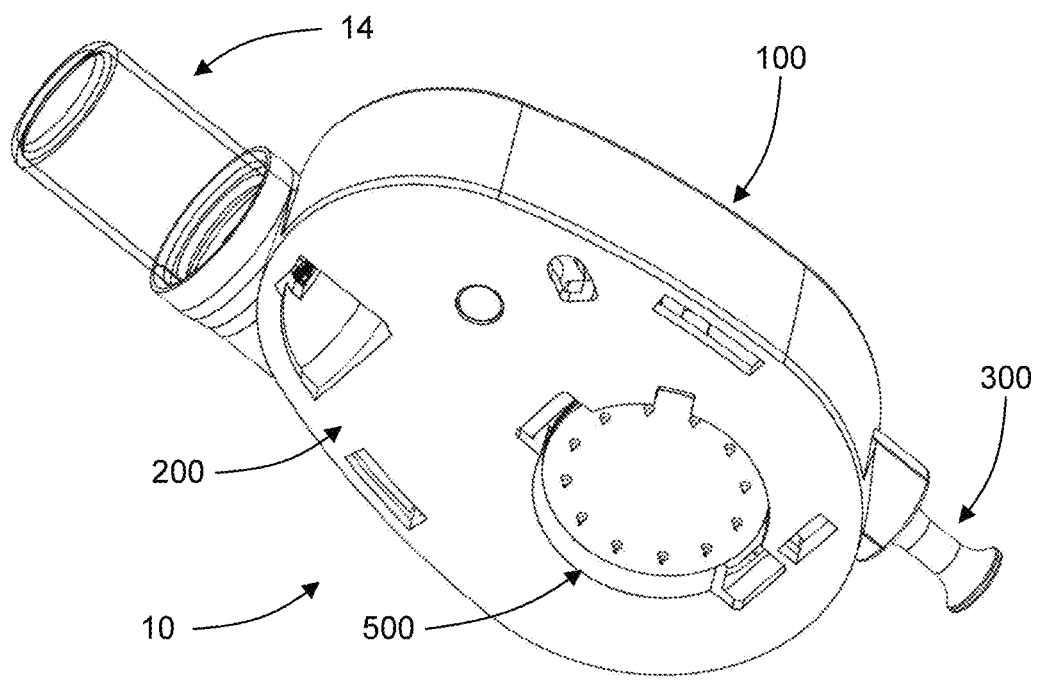

The present disclosure generally relates to a dermal patch that may be utilized to deliver a pharmaceutical to a subject.

In some embodiments, a dermal patch may be used to deliver a pharmaceutical via a vial that can be attached to the dermal patch. Dermal patches disclosed herein may allow for the delivery of a pharmaceutical in a variety of environments (e.g., in the home, in the field, in a medical facility, etc.).

The term "about," as used herein, denotes a deviation of at most 10% relative to a numerical value. For example, about 100 μm means in the range of 90 μm-110 μm.

The term "substantially," as used herein, refers to a deviation, if any, of at most 10% from a complete state and/or condition.

The term "subject" as used herein refers to a human subject or an animal subject (i.e., chicken, pig, cattle, dog, cat, etc.).

The term "pharmaceutical" as used herein refers to a substance that is used in diagnosis, treatment, or prevention of a disease or a substance that restores, corrects, or modifies a biological function.

The term "fractional dose" as used herein refers to a dose of a pharmaceutical, particularly a vaccine, that is a fraction of a standard dose of that pharmaceutical (e.g., one-fifth, two-thirds, three-fourths, etc.) administered by a same or an alternative route (e.g., intradermally rather than subcutaneously or intramuscular, etc.). For example, if a standard dose of a vaccine includes a 100 µg dose, a fractional dose of that vaccine may include a 20 µg dose, a 25 µg dose, a 50 µg dose, a 75 µg dose, etc. With respect to a fractional dose of a vaccine, fractional dose vaccination may reduce a number of infections within a population while administering only a fraction of the dose of the vaccine to a number of subjects which in turn may allow more individuals to become vaccinated.

The term "transparent," as used herein, indicates that light can substantially pass through an object (e.g., a window) to allow visualization of a material disposed behind the object. For example, in some embodiments, a transparent object allows the passage of at least 70%, or at least 80%, or at least 90% of visible light therethrough.

The term "needle" as used herein, refers to a component with a pointed tip that is configured to pierce an outer surface of an element (e.g., skin of a subject) to provide a passageway through the skin. A needle can be hollow to allow a fluid (e.g., a pharmaceutical) to pass therethrough.

The term "microneedle" as used herein, refers to micron scaled needles used to administer a pharmaceutical. A microneedle can have length between about 1 mm and about 3 mm. Furthermore, the microneedles can administer a pharmaceutical to a subject at a rate of about 250 µl/min per microneedle. A microneedle can have a diameter between about 50 and about 350 microns wide or can have a gauge between 28 and 36 and can have a tip thickness between about 1 and about 25 microns.

The term "tube" as used herein, refers to hollow cylinder that provides a fluidic channel for transporting liquids or gases.

The present disclosure generally relates to a device, which is herein also referred to as a dermal patch or a dermal patch system, for delivering a pharmaceutical to a subject. In some embodiments discussed below, such a dermal patch system can include a cartridge that can be affixed to a subject's skin (e.g., via an adhesive layer), a separate vial containing a pharmaceutical can be attached to the cartridge and an at least one microneedles and more typically an array of microneedles disposed within the cartridge can be deployed to puncture the subject's skin and deliver the pharmaceutical to the subject. In some embodiments, the microneedles deliver the pharmaceutical intradermally. In some such embodiments, the dermal patch system is configured to deliver a single fractional dose of the pharmaceutical stored within the vial. As discussed in more detail below, the cartridge includes a pull mechanism that deploys the microneedle array and causes the cartridge to pump a dose of the pharmaceutical into the subject via the deployed microneedles. The cartridge can also include a push button mechanism. After a user administers the pharmaceutical, the user can push the push button mechanism into the cartridge which causes the microneedle array to retract into the cartridge which in turn allows the user to remove the cartridge from the subject. In this manner, the dermal patch system remains safe before it is engaged and after delivery of the pharmaceutical as in both cases the microneedle array is retained within the cartridge.

In some embodiments, the pull mechanism cannot be pulled unless the dermal patch system has a proper orientation on a subject's skin (e.g., a substantially vertical position). As such, the dermal patch system may administer the pharmaceutical only when the dermal patch has a given orientation. Providing a dermal patch system that administers a pharmaceutical when in a specific orientation may ensure that the subject receives all or substantially all of the pharmaceutical from a vial as the dermal patch may be aided by gravity when administering the pharmaceutical.

Referring now to FIGS. 1A, 1B-4A and 4B, a dermal patch system 10 is shown in accordance with an exemplary embodiment. In this embodiment, the dermal patch system 10 includes a cartridge 12 that can be affixed to a subject's skin via an adhesive layer. The dermal patch system 10 also includes a vial 14 that contains a pharmaceutical. The vial 14 can be inserted into the cartridge 12 for delivery of the pharmaceutical stored therein. In some embodiments, the vial 14 includes a single fractional dose of a pharmaceutical. More particularly, in some embodiments, the vial 14 includes a single fractional dose of a vaccine.

The cartridge 12 includes a cover 100 and a base 200 that can couple to the cover 100. For example, the cover 100 and the base 200 can be formed as two separate components that are removably coupled to one another (e.g., via a snap fitting). In other embodiments, the cover 100 and the base 200 form an integral unitary cartridge 12. In some of these embodiments, the cover 100 can be coupled to the base 200 via an adhesive, laser welding, etc.

The cartridge 12 may be formed using a variety of suitable materials including, but not limited to, polymeric materials (e.g., polyolefins, polyethylene terephthalate (PET), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, photocross linkable polymers, etc.). In some embodiments, some of the cover 100 may be formed of poly(dimethylsiloxane) (PDMS) to allow visibility of components disposed within the cartridge 12.

The cartridge 12 also includes a pull mechanism 300, a pump assembly 400 coupled to the pull mechanism 300, a microneedle array assembly 500, a retraction button 600, and a trigger 700. As will be discussed in further detail herein, when pulled, the pull mechanism 300 causes the trigger 700 to release the microneedle array assembly 500 thereby allowing microneedle array assembly 500 to move to a deployed position to puncture the skin of a subject. Furthermore, when pulled and after causing the microneedle array assembly 500 to deploy, the pull mechanism 300 causes the pump assembly 400 to pump the pharmaceutical from the vial 14 (when the vial 14 is coupled to the cartridge 12) through the microneedle array assembly 500 into the subject. After the pharmaceutical has been administered to the subject, a user can push the retraction button 600, which causes the microneedle array assembly 500 to retract into the cartridge 12 which allows the dermal patch system 10 to be removed from the subject. Providing dermal patch system 10 which places the microneedle array assembly 500 in a stored position before and after use keeps the dermal patch system 10 in a safe state. In other words, the microneedle array assembly 500 is securely retained within the cartridge 12 when the cartridge is not in use.

With particular reference to FIGS. 7A and 7B-13A and 13B, the cover 100 is shown in accordance with an exemplary embodiment.

In this embodiment, the cover 100 includes a top wall 102 and a side wall 104. The side wall 104 extends vertically from and perpendicular to the top wall 102. The top wall 102 extends longitudinally from and perpendicular to the side wall 104. The top wall 102 includes an outer surface 102a and an opposed inner surface 102b. The side wall 104 includes an outer surface 104a and an opposed inner surface 104b.

The cover 100 includes a first vial guide 106 which includes an outer wall 108 and an inner end wall 110. The outer wall 108 includes an outer surface 108a and an opposed inner surface 108b. The end wall 110 includes an outer surface 110a and opposed inner surface 110b. The outer wall 108 extends longitudinally from and perpendicular to the outer surface 104a of the side wall 104 and the outer surface 110a of the end wall 110. At least a portion of the inner surface 108b of outer wall 108 of the vial guide 106 has a similar shape and dimension as the outer surface of the vial 14 such that a portion of the outer surface of the vial 14 contacts the inner surface 108b. The end wall 110 defines a U-shaped opening 112.

The cover 100 further includes a first handle retention element 114 which includes an outer surface 114a and an inner surface 114b. The outer surface 114a of the first handle retention element 114 extends from and perpendicular to the outer surface 104a of the side wall 104. The inner surface 114b of the first handle retention element 114 includes a first groove 116, a second groove 118, and a third groove 120. Furthermore, the first handle retention element 114 extends vertically from and perpendicular to the inner surface 102b of the top wall 102. The first handle retention element 114 also includes protrusions 122. As will be discussed in further detail herein, the protrusions 122 aid in coupling the cover 100 to the base 200.

The cover 100 also includes a retraction button opening 124 and retraction button guides 126. The retraction button opening 124 extends through the side wall 104. That is, the retraction button opening 124 extends between the outer surface 104a and the inner surface 104b of the side wall 104. The retraction button guides 126 extend longitudinally from and perpendicular to the inner surface 104b of the side wall 104 and extend vertically from and perpendicular to the inner surface 102b of the top wall 102. The retraction button guides 126 are aligned with the retraction button opening 124 within the cover 100.

The cover 100 further includes a plurality of locking members 128 that extend longitudinally from and perpendicular to the inner surface 104b of the side wall 104. As will be discussed in further detail herein, the locking members 128 couple the cover 100 to the base 200. The cover 100 also includes a circular retention member 130 and a latch guide 132. The circular retention member 130 and the latch guide 132 extend vertically from and perpendicular to the inner surface 102b of the top wall 102.

Referring now to FIGS. 14A and 14B-23, the base 200 is shown in accordance with an exemplary embodiment.

The base 200 includes a bottom wall 202 with a top surface 202a and an opposed bottom surface 202b. The bottom wall 202 and the side wall 104 have the same perimeter shape such that when the cover 100 is coupled to the base 200, the cover 100 is flush with the base 200. Furthermore, when the cover 100 is coupled to the base 200 the side wall 104 of the cover 100 contacts the top surface 202a of the bottom wall 202. The base 200 further includes a plurality of extensions 206 that extend vertically from and perpendicular to the top surface 202a of the bottom wall 202. The extensions 206 and the bottom wall 202 define gaps 208. These gaps, and therefore the extensions 206, are shaped and dimensioned to accept a locking member 128 of the cover 100 such that an extension 206 couples to a locking member 128 via a snap fitting. The gaps 208 extend through the bottom wall 202 which provides access to an inner volume of the cartridge 12.

The base 200 further includes a second vial guide 210. The second vial guide 210 includes an outer wall 212 and an inner end wall 214. The outer wall 212 includes an outer surface 212a and an opposed inner surface 212b. The end wall 214 includes an outer surface 214a and an opposed inner surface 214b. At least a portion of the inner surface 212b of the outer wall 212 has a similar shape and dimension to the outer surface of the vial 14 such that a portion of the outer surface of the vial 14 contacts the inner surface 212b of the outer wall 212. The end wall 214 defines a U-shaped opening 216.

The second vial guide 210 also includes a latch 218, a gap 220, and a protrusion 222. The latch 218 extends longitudinally from the outer wall 212 towards a center of the second vial guide 210. The gap 220 is defined by the outer wall 212. The latch 218 extends at least partially across the gap 220. The protrusion 222 extends vertically from the inner surface 212b of the outer wall 212 and extends longitudinally from the outer surface 214a of the end wall 214.

The first vial guide 106 and the second vial guide 210 have a similar shape and dimension and align with one another when the cover 100 is coupled to the base 200. Together, the first vial guide 106 and the second vial guide 210 are referred to as a vial receptacle. Similarly, the end walls 110 and 214 have a similar shape and dimension such that when the cover 100 is coupled to the base 200 the end walls 110 and 214 align and the openings 112 and 216 together define an aperture that provides access to the inner volume of the cartridge 12. Furthermore, the outer surface 108a of the wall 108 of the first vial guide 106 and the outer surface 212a of the outer wall 212 of the second vial guide 210 have a similar shape and dimension such that when the cover 100 is coupled to the base 200, the outer walls 108 and 212 form a uniform cylinder that extends outwardly from the cartridge 12. The inner surface 108b of the outer wall 108 and the inner surface 212b of the outer wall 212 also have a similar shape and dimension such that the inner surfaces 108b and 212b align when the cover 100 is coupled to the base 200. Together, the inner surfaces 108b and 212b with the outer surfaces 110a and 214a define an inner chamber of the vial receptacle.

With particular reference to FIGS. 34A and 34B-36, the cartridge 12 includes a stop 16 that is generally cylindrical in shape. The stop 16 may be formed of a polymeric or an elastomeric material. When the cover 100 is coupled to the base 200, the stop 16 is disposed within the inner volume of the vial receptacle and is held in place by the protrusion 222. A portion of the inner surface 108b of the outer wall 108 and a portion of the inner surface 212b of the outer wall 212 has a similar shape and dimension as the outer surface of the stop 16 such that the inner surfaces 108b and 212b retain the stop 16 within the vial receptacle. That is, when the stop 16 is disposed within the inner volume of the vial receptacle, the stop 16 contacts portions of the inner surfaces 108b and 212b and contacts the outer surfaces 110a and 214a of the end walls 110 and 214 respectively. Furthermore, when the cover 100 is coupled to the base 200, a portion of the stop 16 extends through the aperture defined by the end walls 110 and 214.

In some embodiments, the cartridge 12 includes a first hollow needle 18 and a second hollow needle 20 that extend through the stop 16. When the vial 14 is inserted into the vial receptacle defined by the walls 108 and 212, the needles 18 and 20 pierce a cap of the vial 14 to provide access to a pharmaceutical stored therein. Furthermore, while the vial 14 is being inserted into the vial receptacle, the latch 218 is compressed into the gap 220m which allows the vial 14 to extend into the vial receptacle until the end of the vial 14 contacts the stop 16. When the vial 14 is completely inserted, the latch 218 returns to its original position. In this position, when the vial 14 is pulled, the cap of the vial 14 contacts the latch 218 which prevents the vial 14 from being removed from the cartridge 12.

With continued reference to FIGS. 27A and 27B-29A and 29B, the base 200 further includes a second handle retention element 224. second handle retention element 224 includes an outer surface 224a and an opposed inner surface 224b. The inner surface 224b of the second handle retention element 224 includes a first groove 226, a second groove 228, and a third groove 230. Furthermore, the second handle retention element 224 extends vertically from and perpendicular to the top surface 202a of the bottom wall 202. The second handle retention element 224 includes cavities 232. When the cover 100 is coupled to the base 200, the protrusions 122 extend into the cavities 232 to couple the cover 100 to the base 200.

The first handle retention element 114 and the second handle retention element 224 have a similar shape and dimension and align with one another when the cover 100 is coupled to the base 200. Together, the first handle retention element 114 and the second handle retention element 224 are referred to as a handle receptacle. Furthermore, when the cover 100 is coupled to the base 200, the first handle retention element 114 and the second handle retention element 224 align such that the handle receptacle has an outer opening and inner opening which allows at least a portion of the pull mechanism to extend through the handle receptacle. The outer surface 114a of the first handle retention element 114 and the outer surface 224a of the second handle retention element 224 have a similar shape and dimension such that when the cover 100 is coupled to the base 200, the outer surfaces 114a and 224a form a uniform cylinder that extends outwardly from the cartridge 12. The inner surface 114b and the inner surface 224b also have a similar shape and dimension such that the inner surfaces 114b and 224b align when the cover 100 is coupled to the base 200. Together, the inner surfaces 114b and 224b define an inner chamber of the handle receptacle.

Furthermore, the first grooves 116 and 226 have a similar shape and dimension, the second grooves 118 and 228 have a similar shape and dimension, and the third grooves 120 and 230 have a similar shape and dimension. When the cover 100 is coupled to the base 200, the first grooves 116 and 226 align, the second grooves 118 and 228 align and the third grooves 120 and 230 align. Together, the first grooves 116 and 226 are referred to as a first handle retention groove, the second grooves 118 and 228 are referred to as a ball retention groove, and the third grooves 120 and 230 are referred to as a second handle retention groove.

Figure 3A:
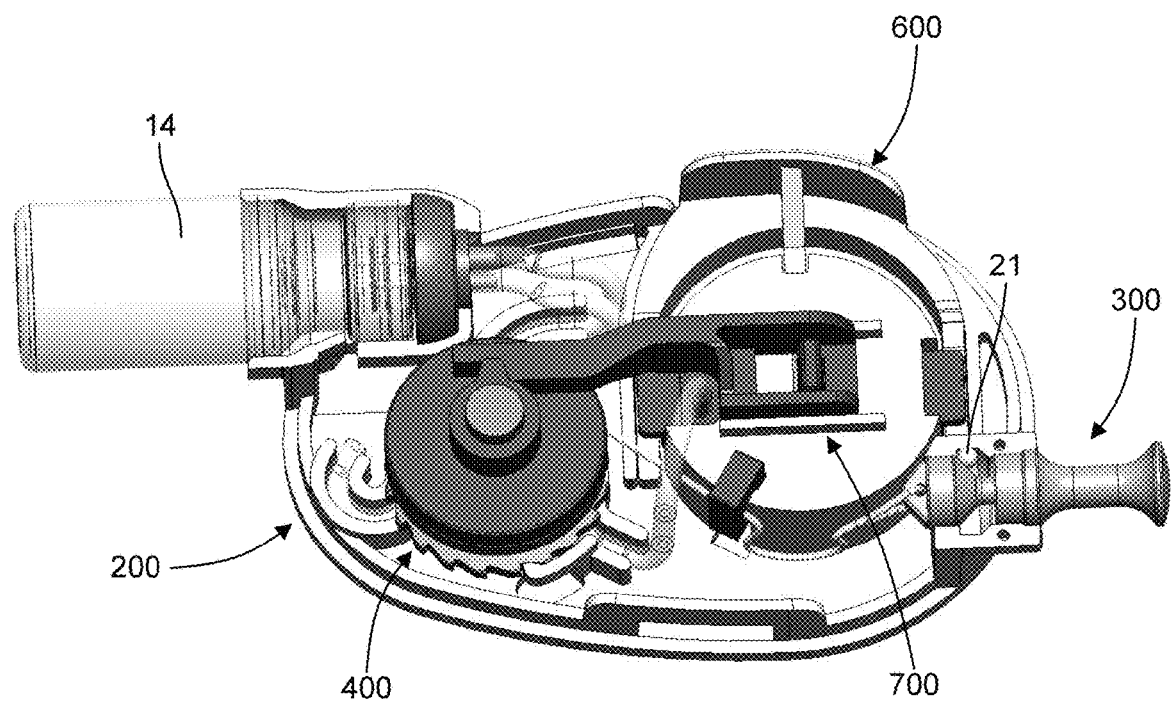
Figure 3B:
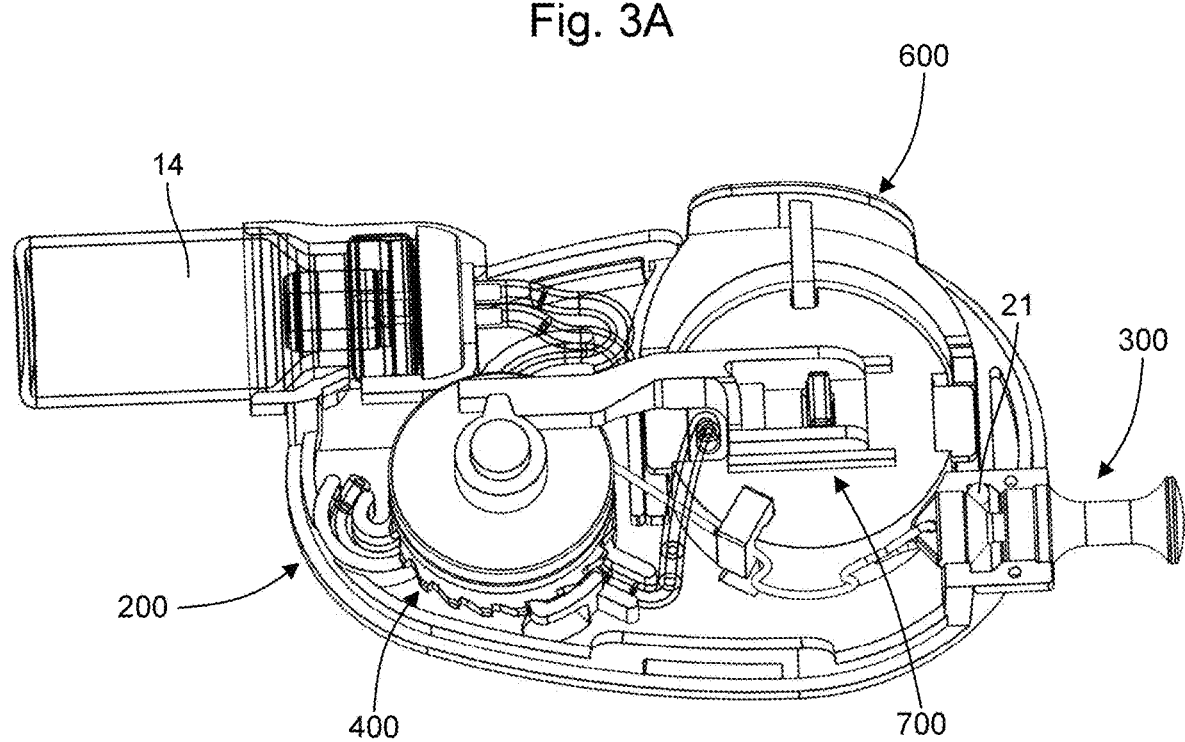
Figure 5A:
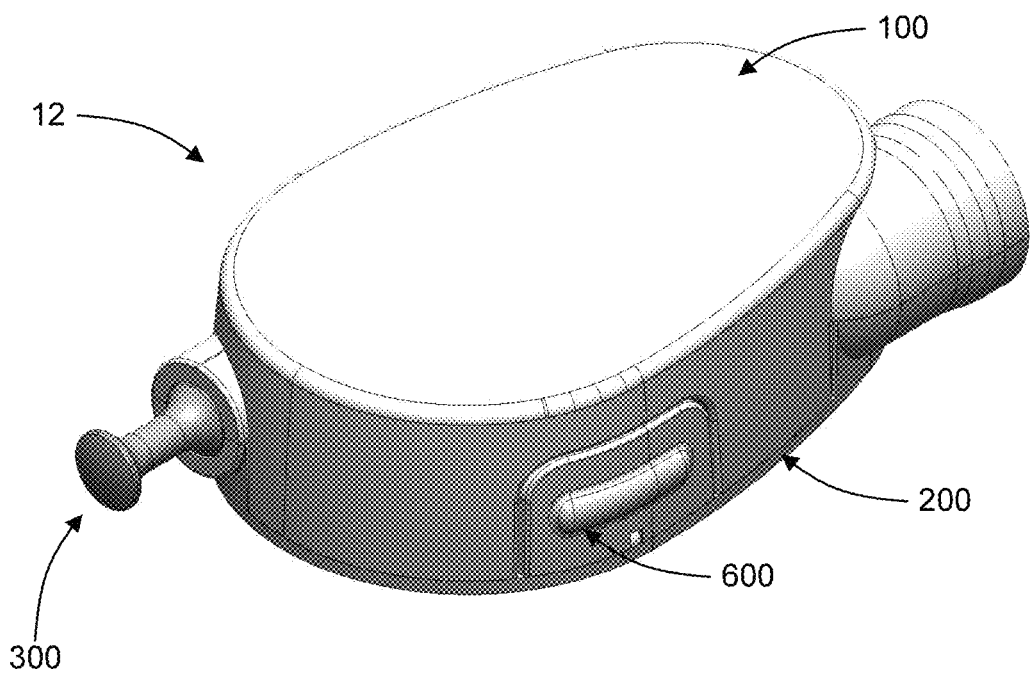
FIGS. 5A, 5B, 6A, and 6B depict a cartridge of the dermal patch system in accordance with an exemplary embodiment.
Figure 5B:
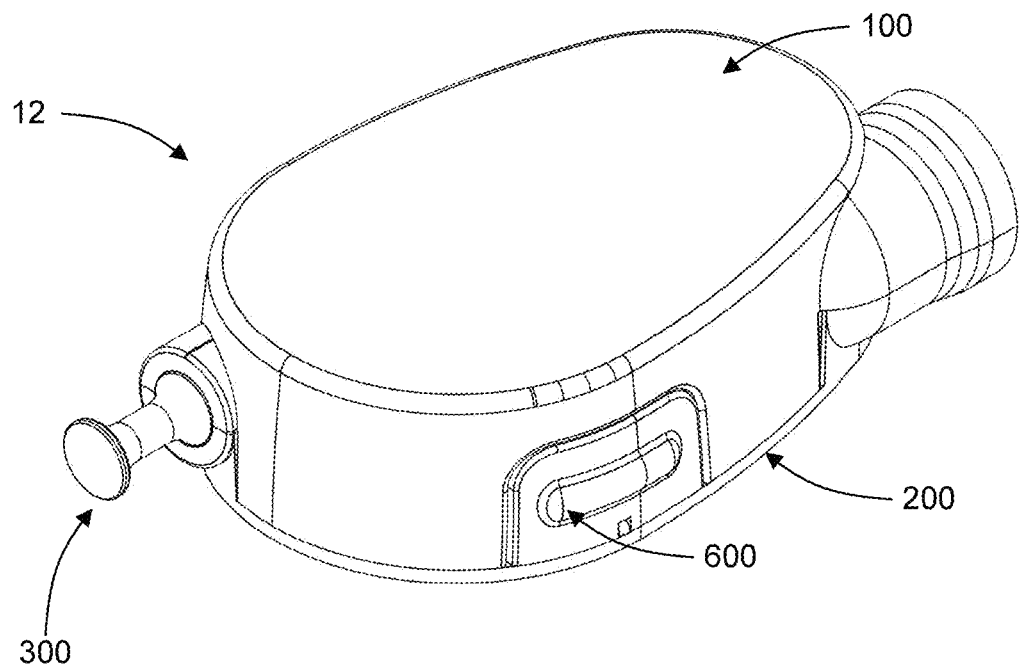
Figure 6A:
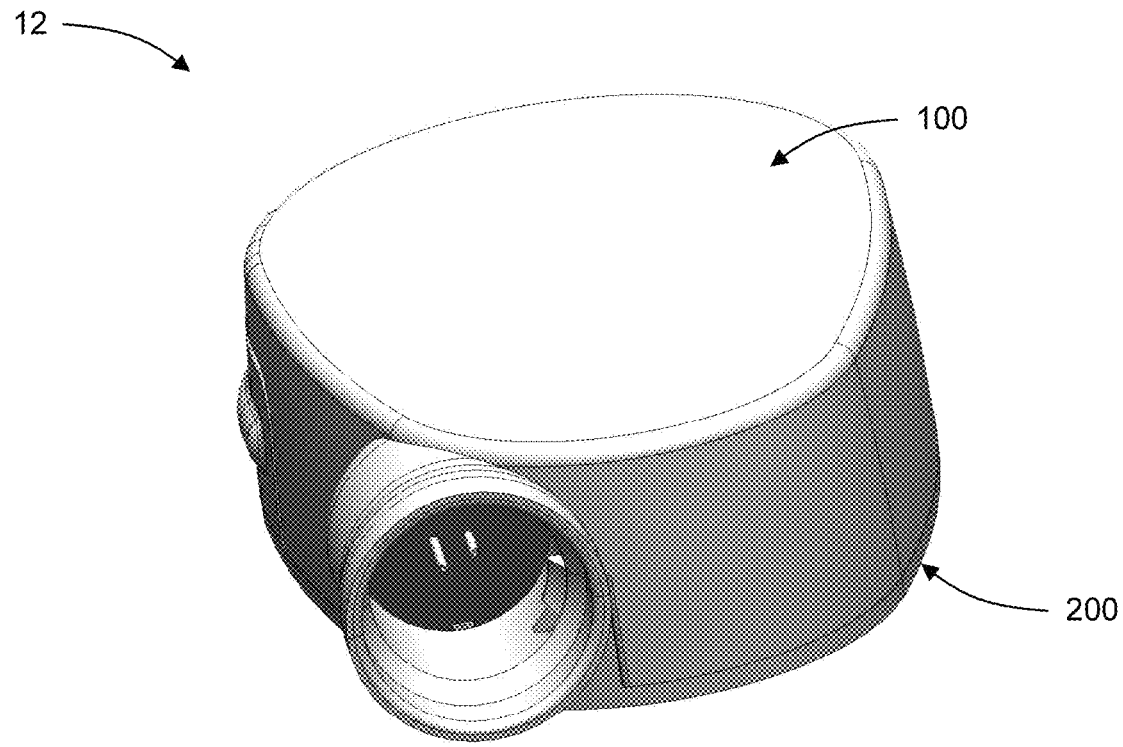
Figure 6B:
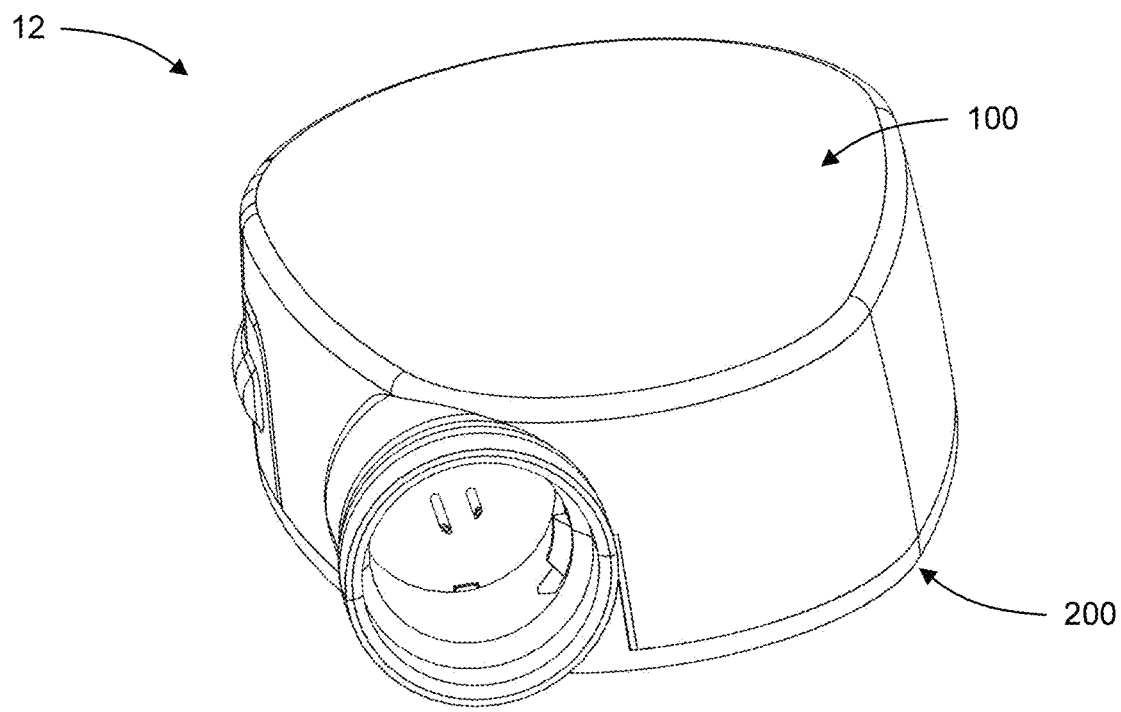
Figure 8A:
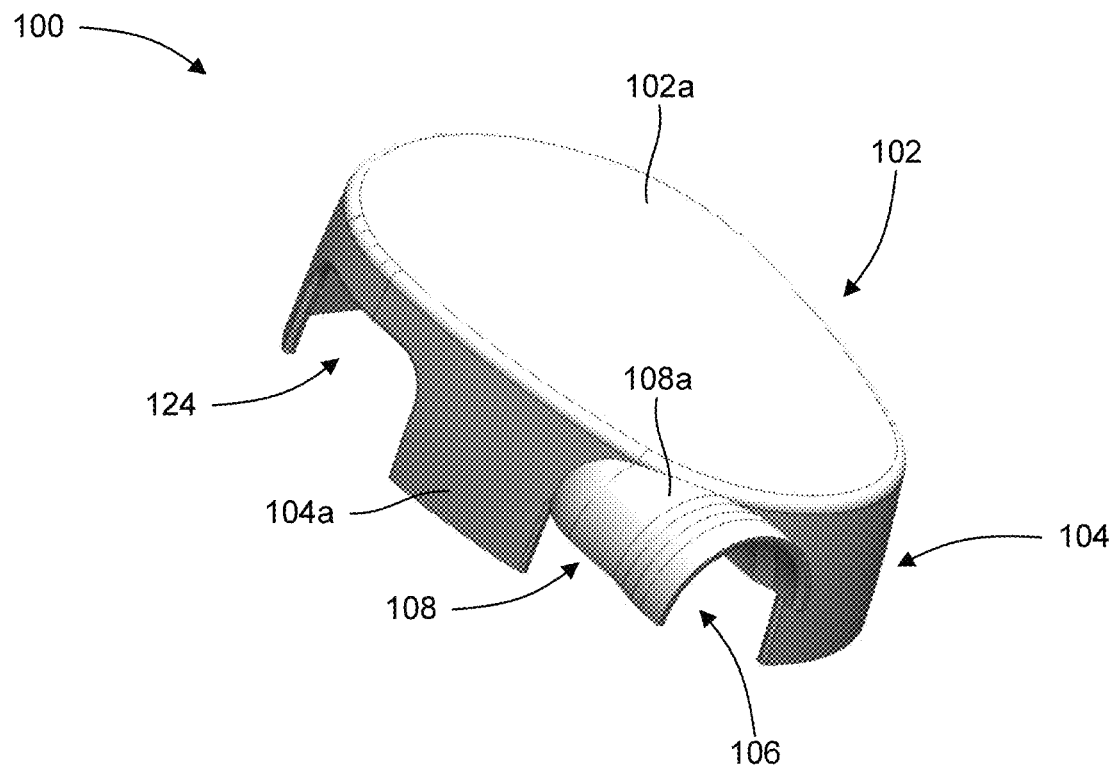
Figure 8B:
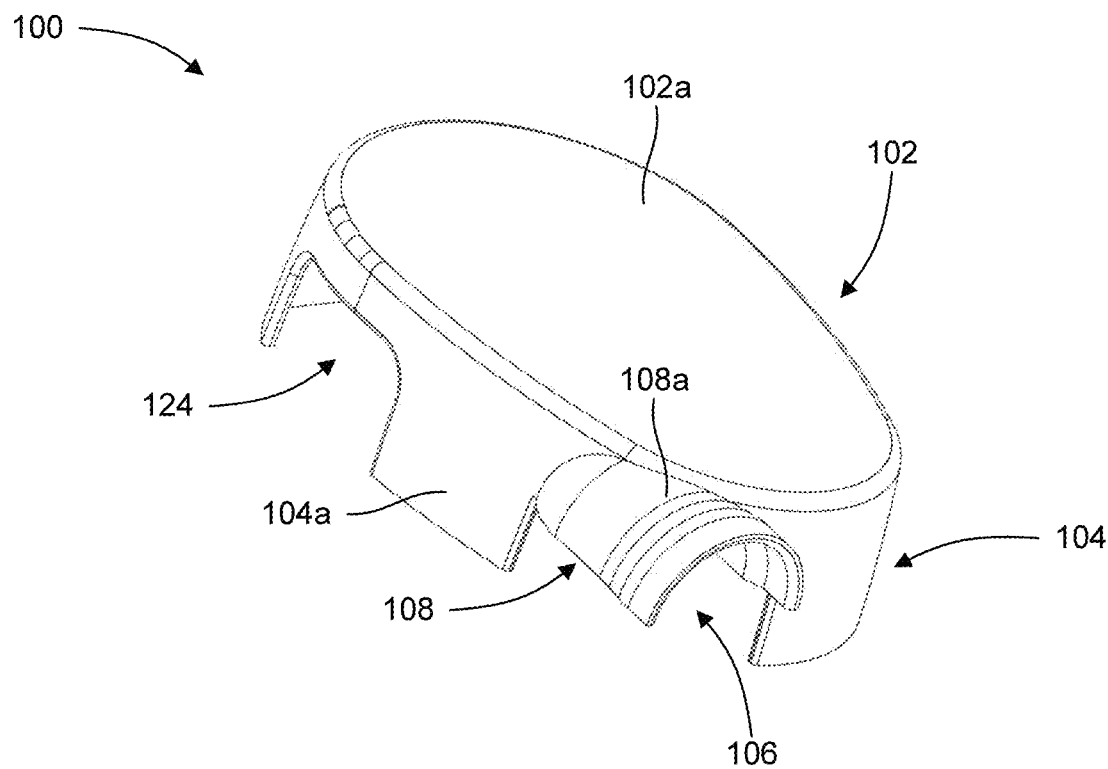
Figure 9A:
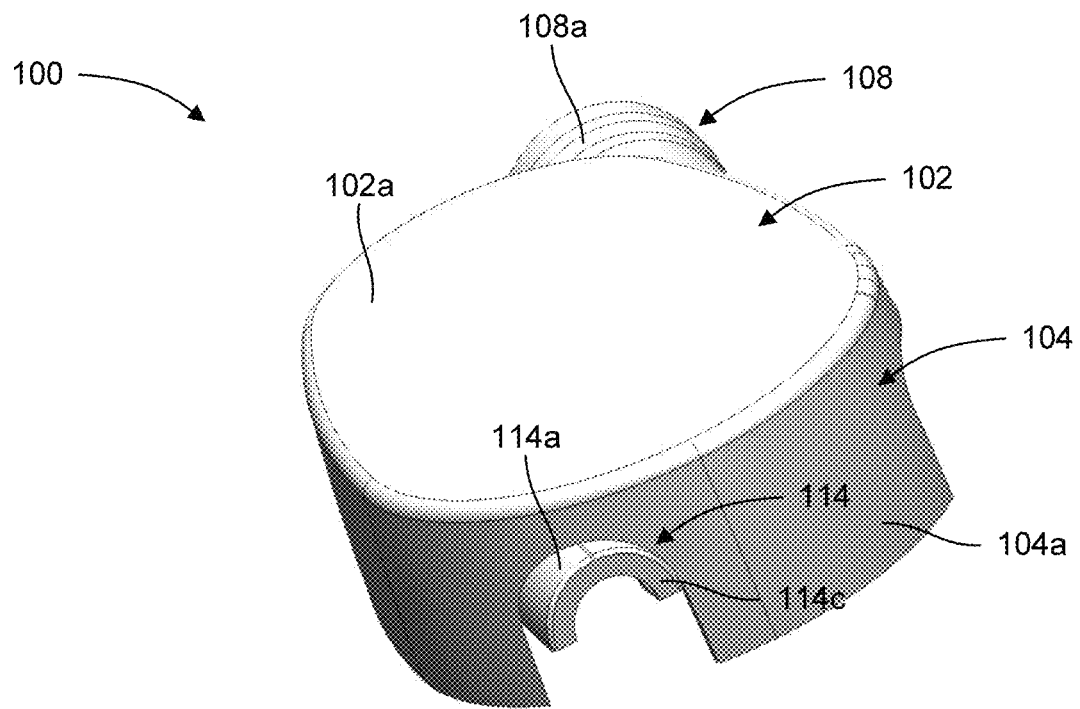
Figure 9B:
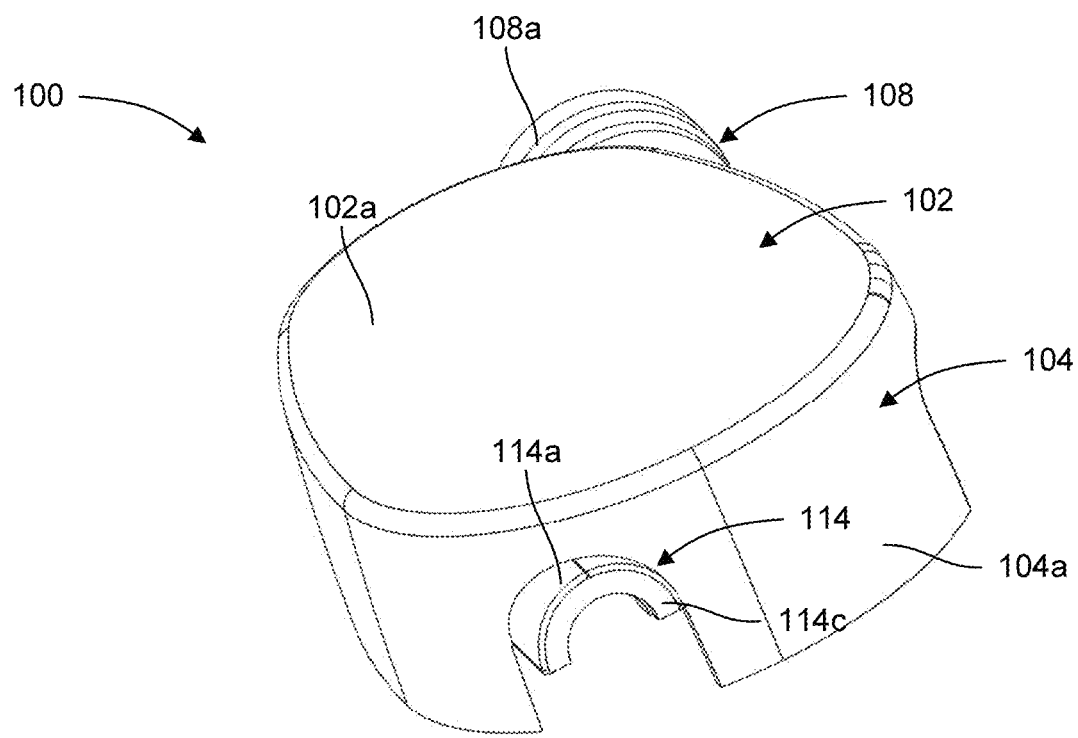
Figure 10A:
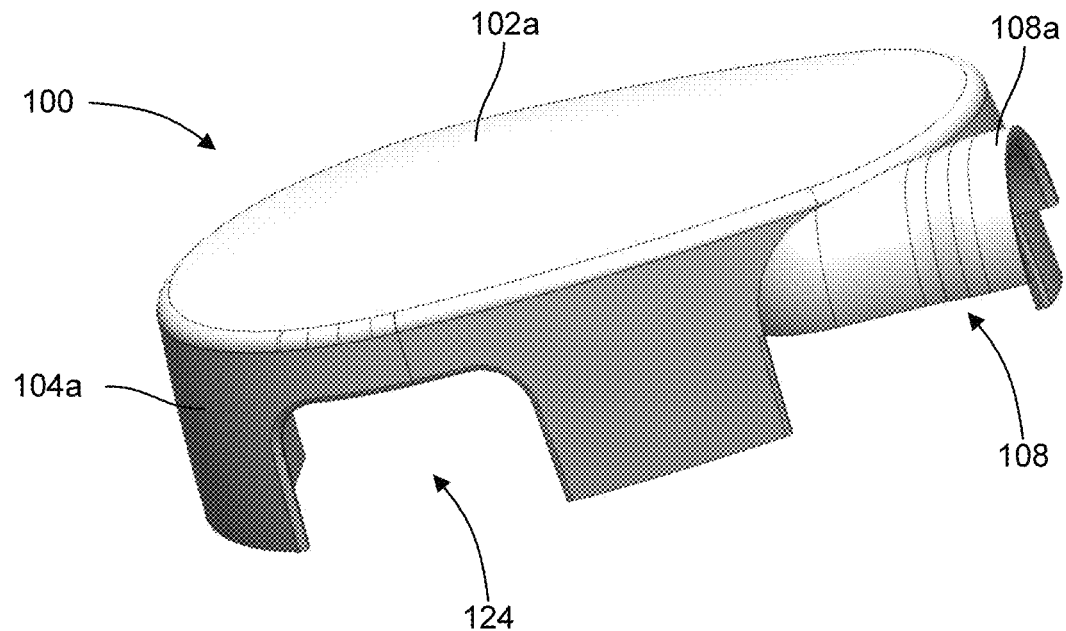
Figure 10B:
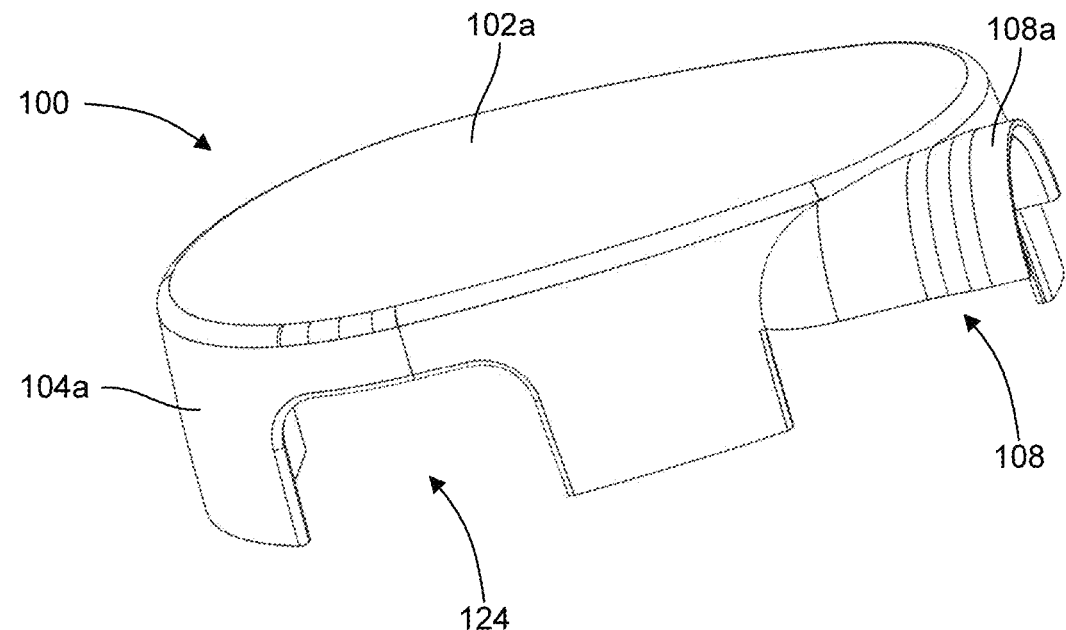
Figure 11A:
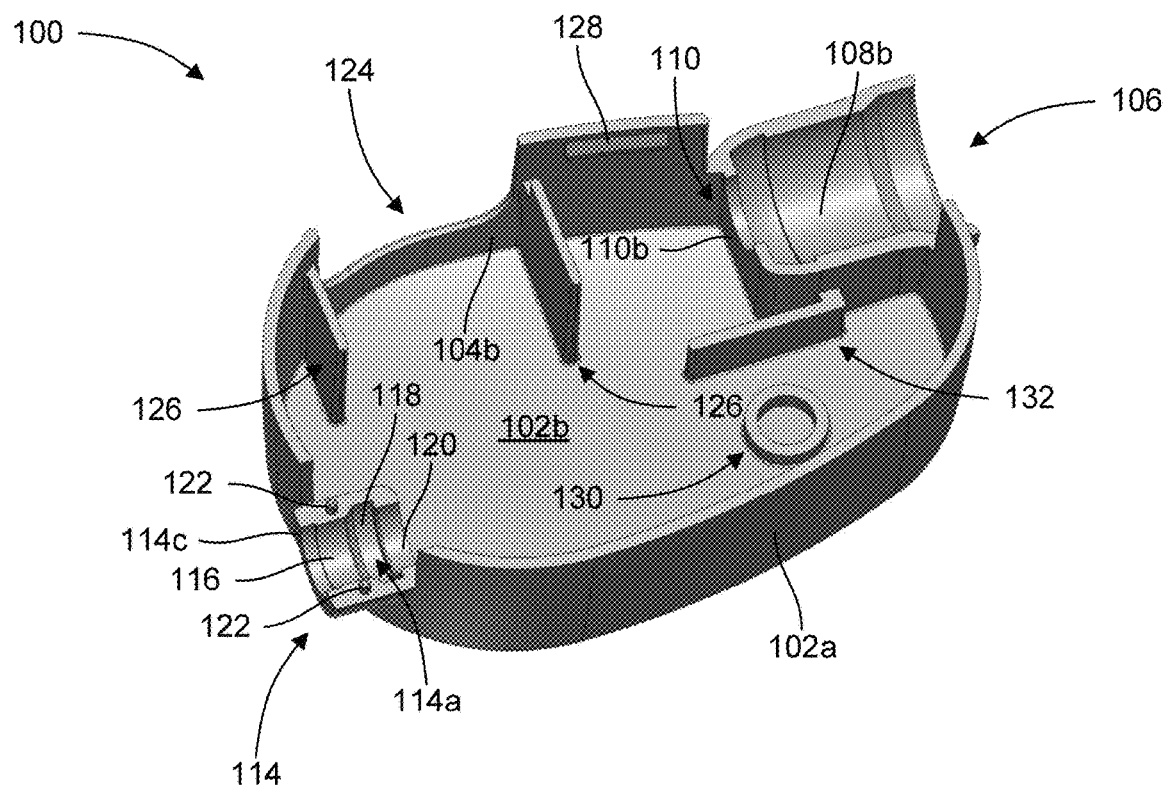
Figure 11B:
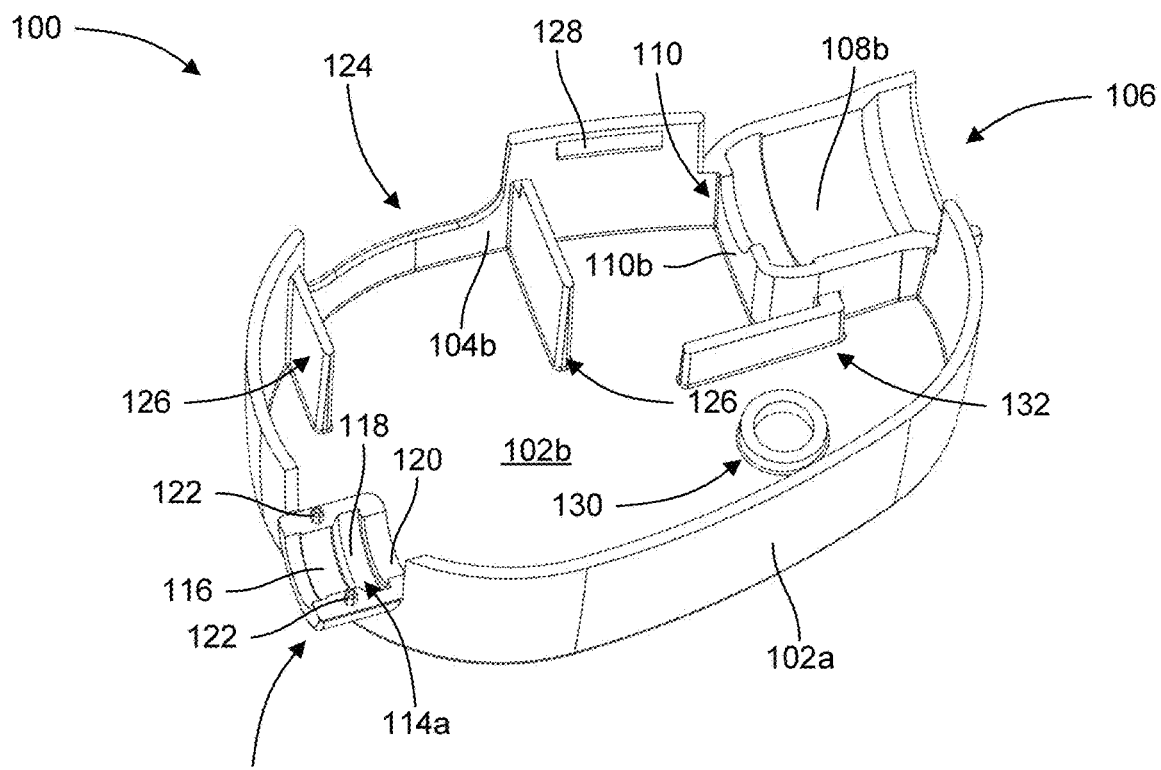
Figure 12A:
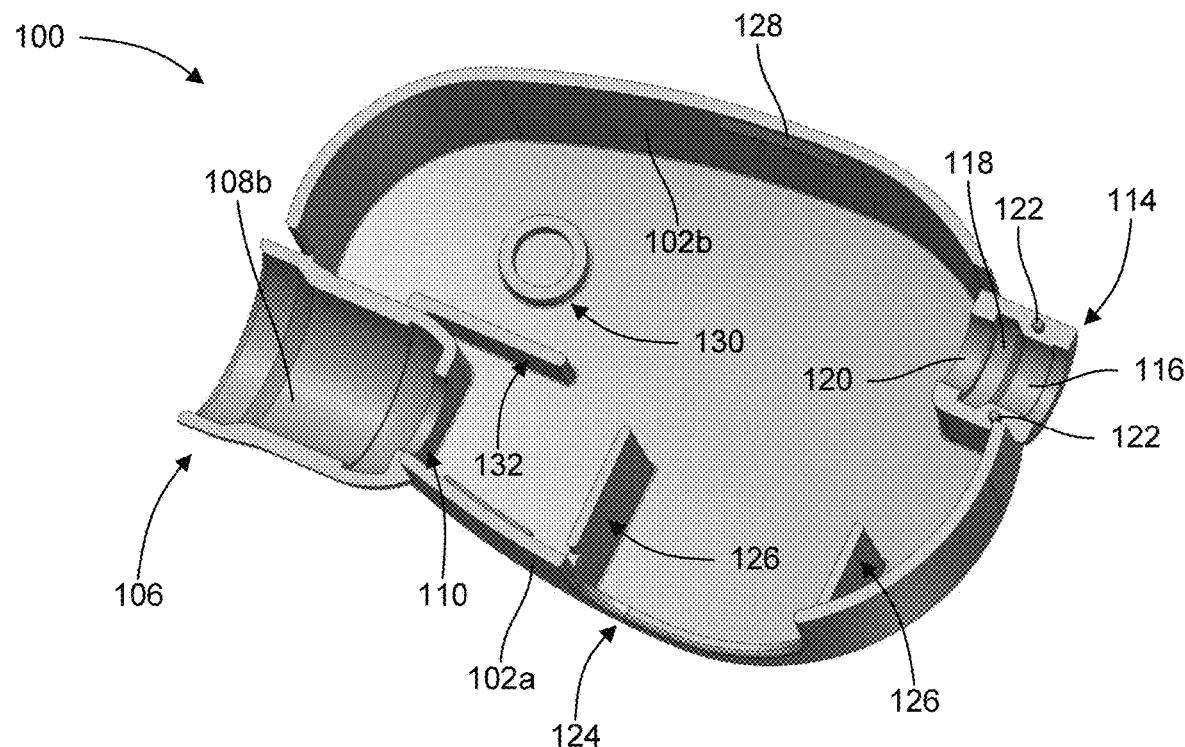
Figure 12B:
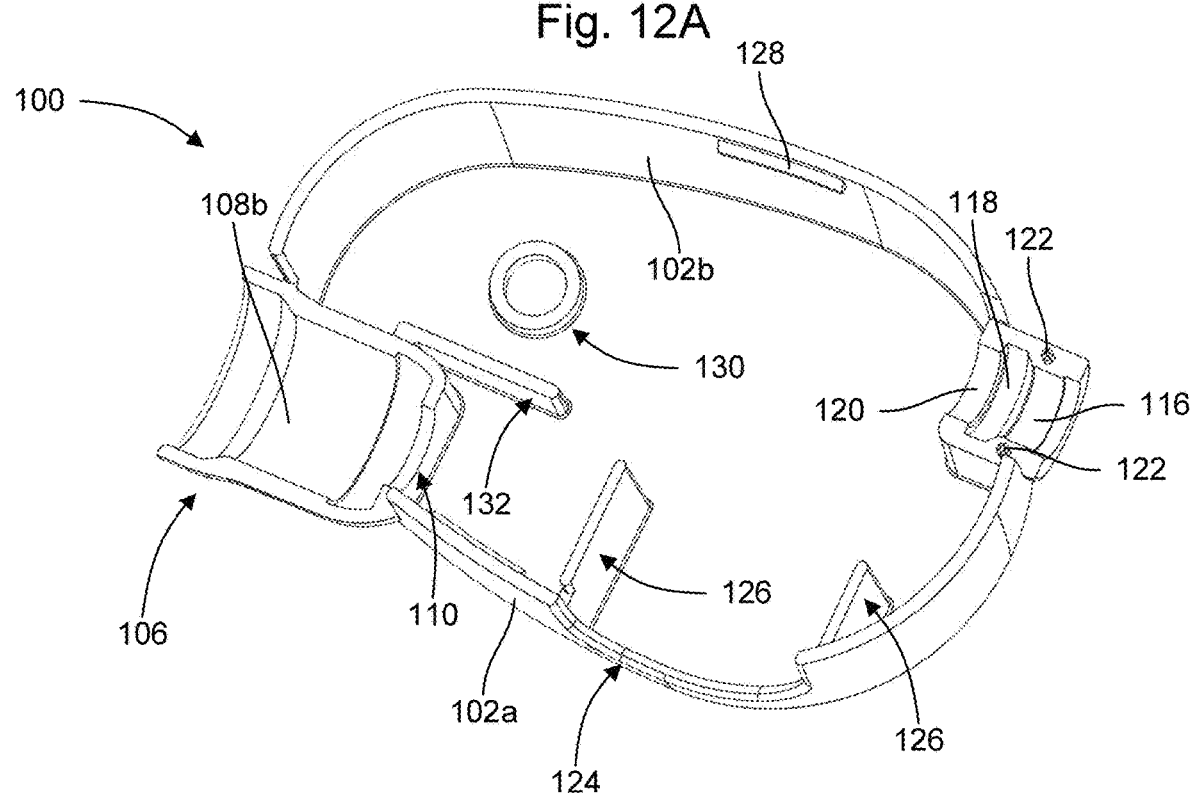
Figure 13A:
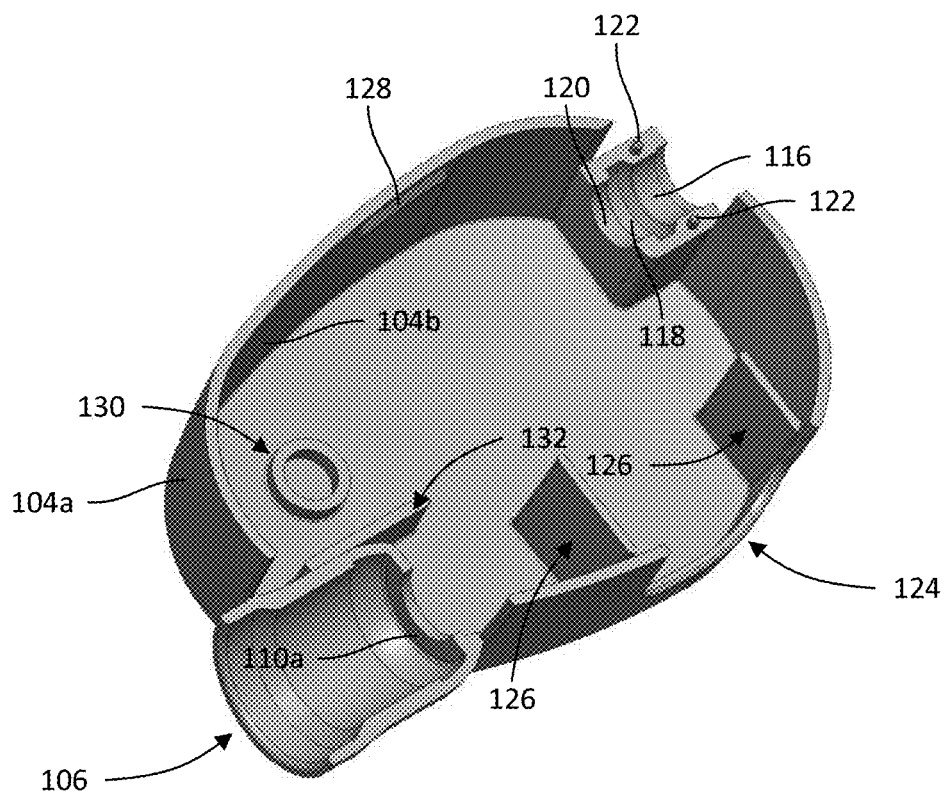
Figure 13B:
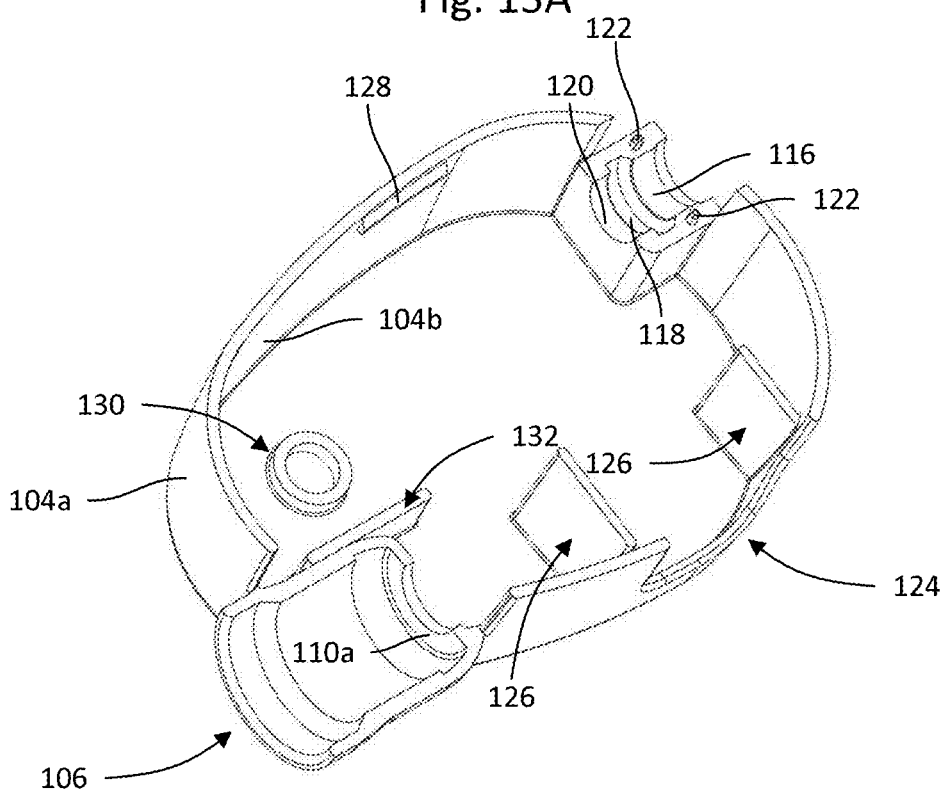
Figure 14A:
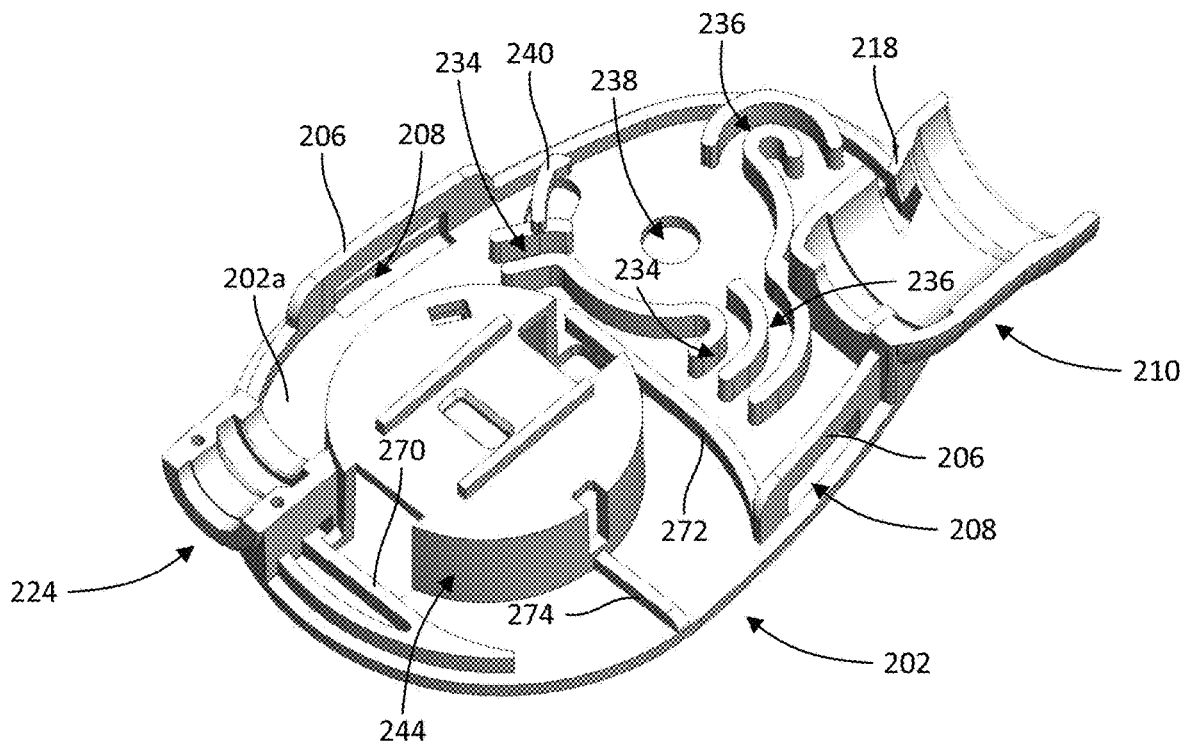
Figure 14B:
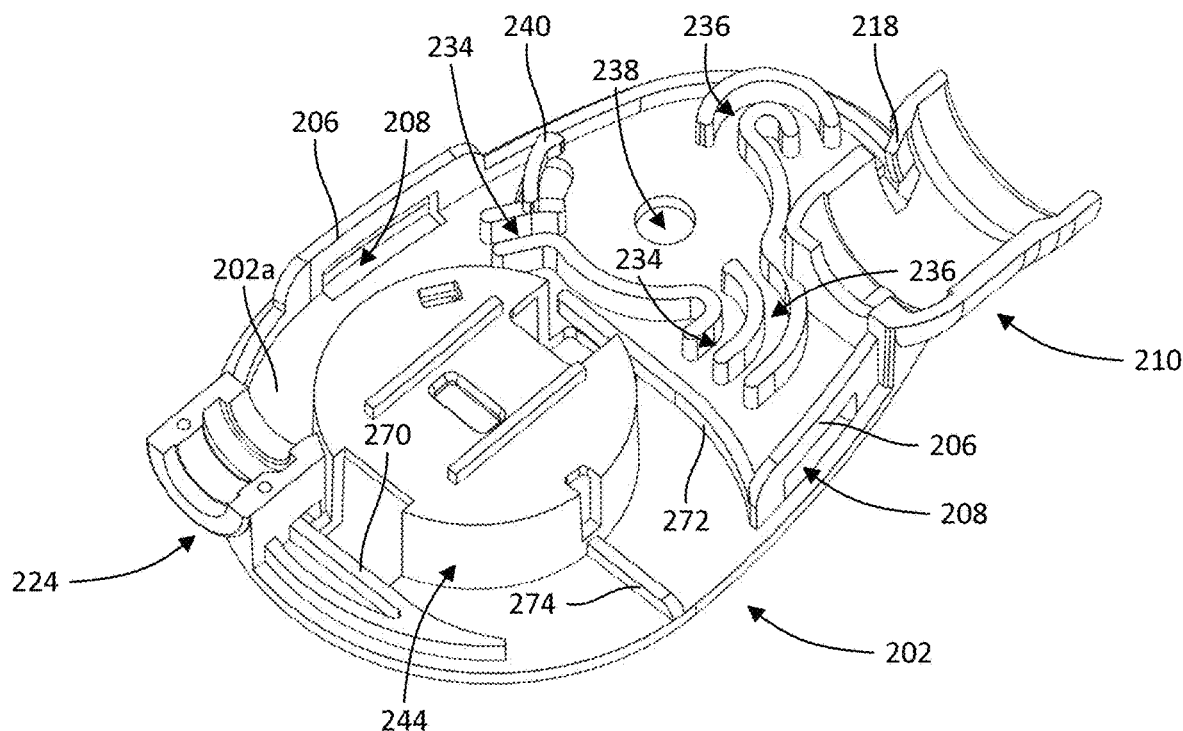
Figure 15A:
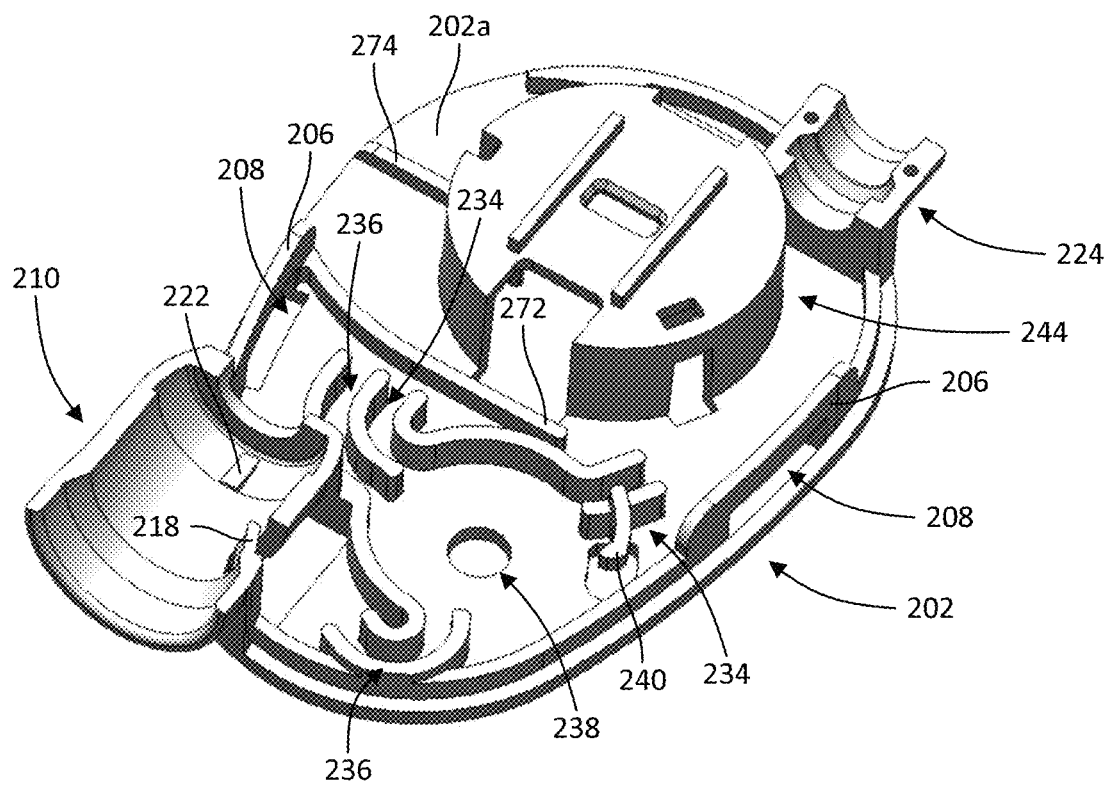
Figure 15B:
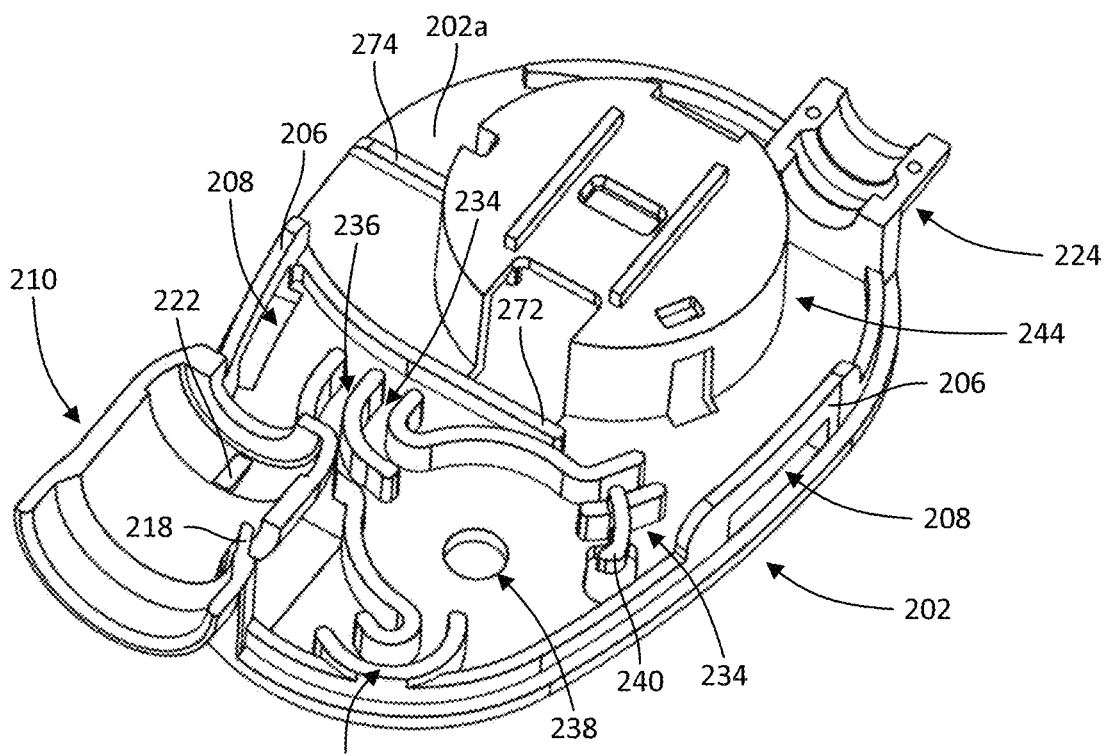
Figure 16A:
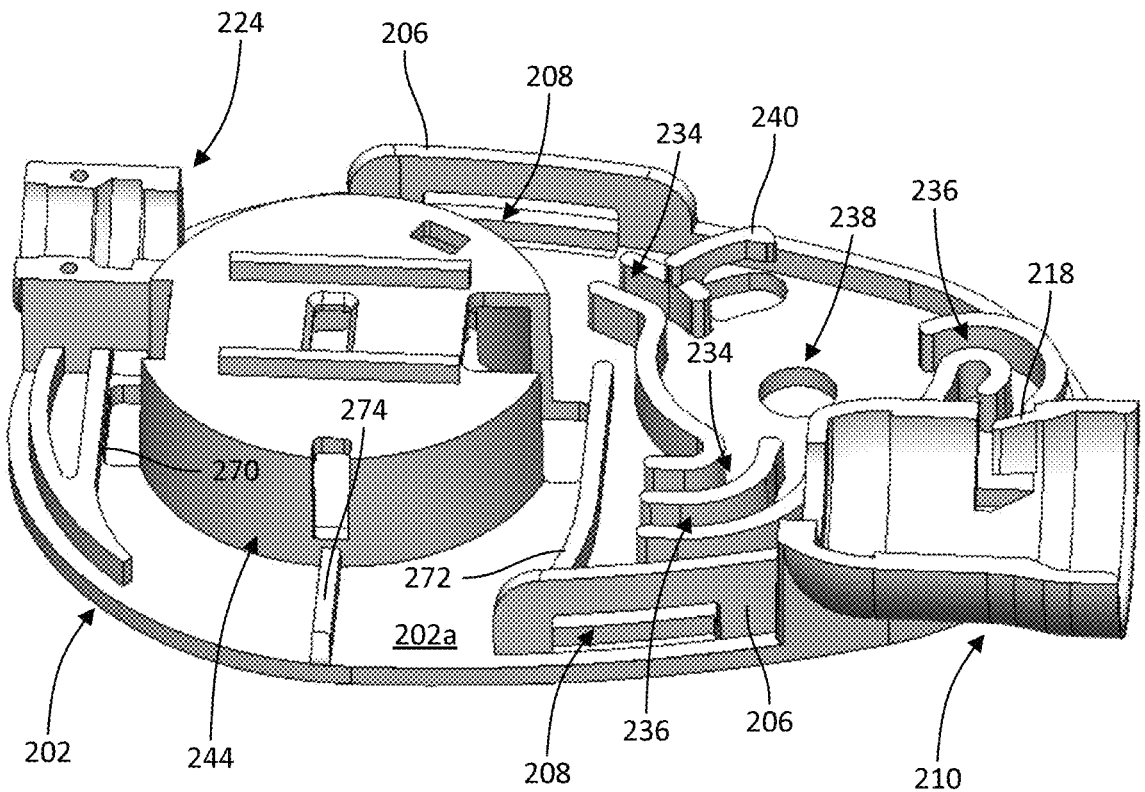
Figure 16B:
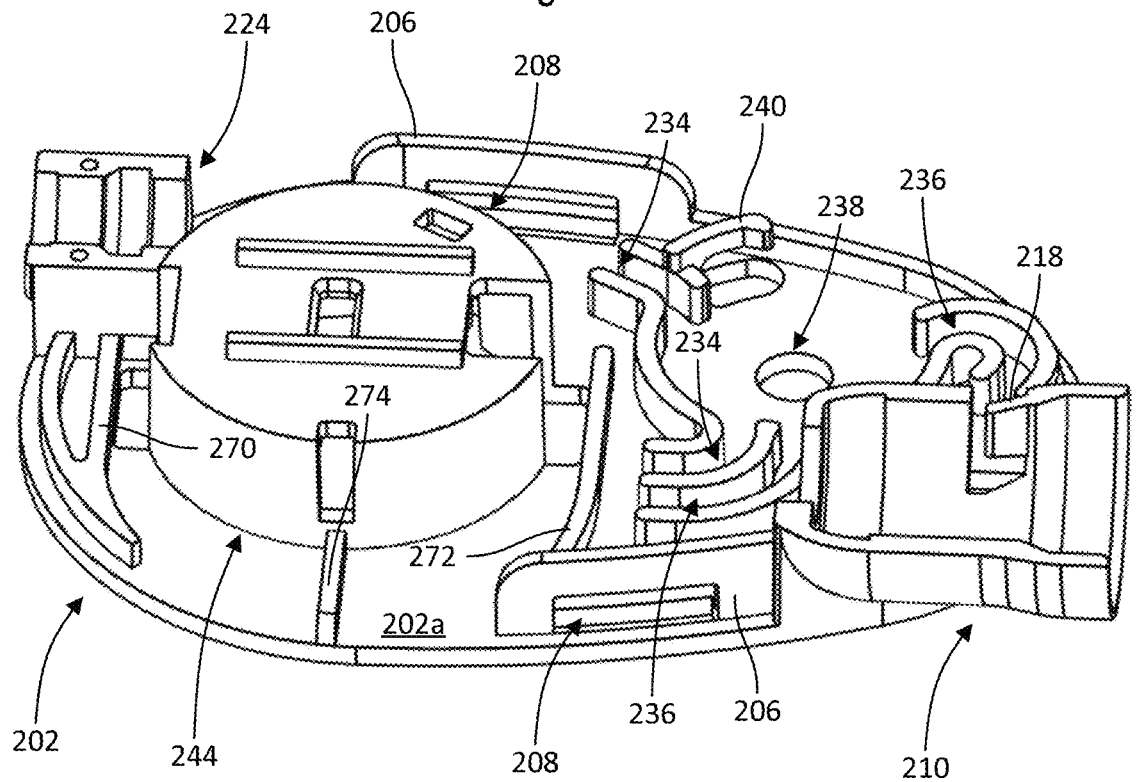
Figure 17A:
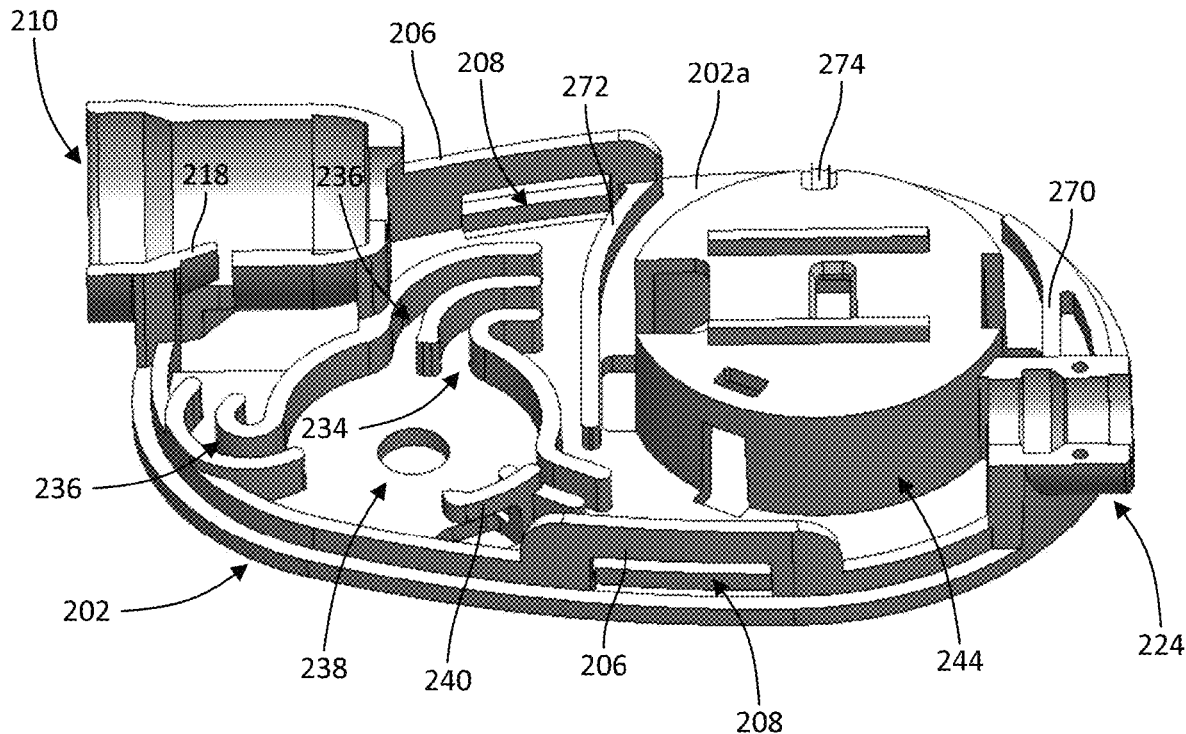
Figure 17B:
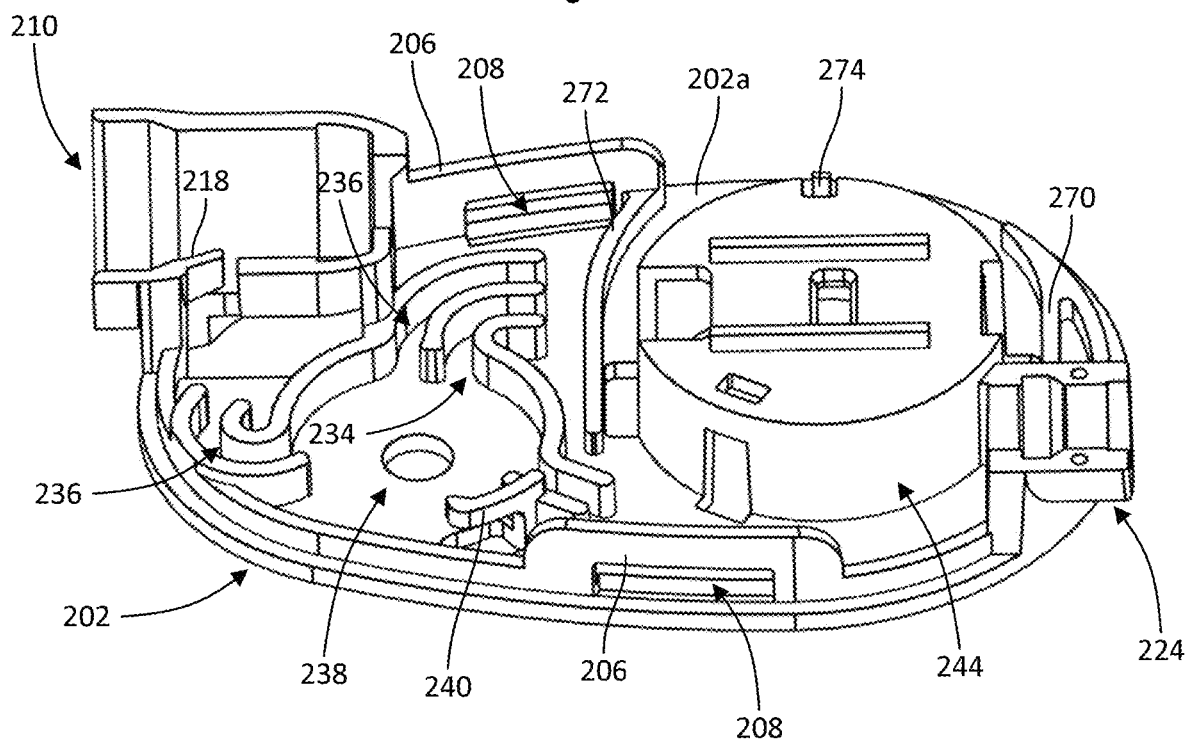
Figure 18:
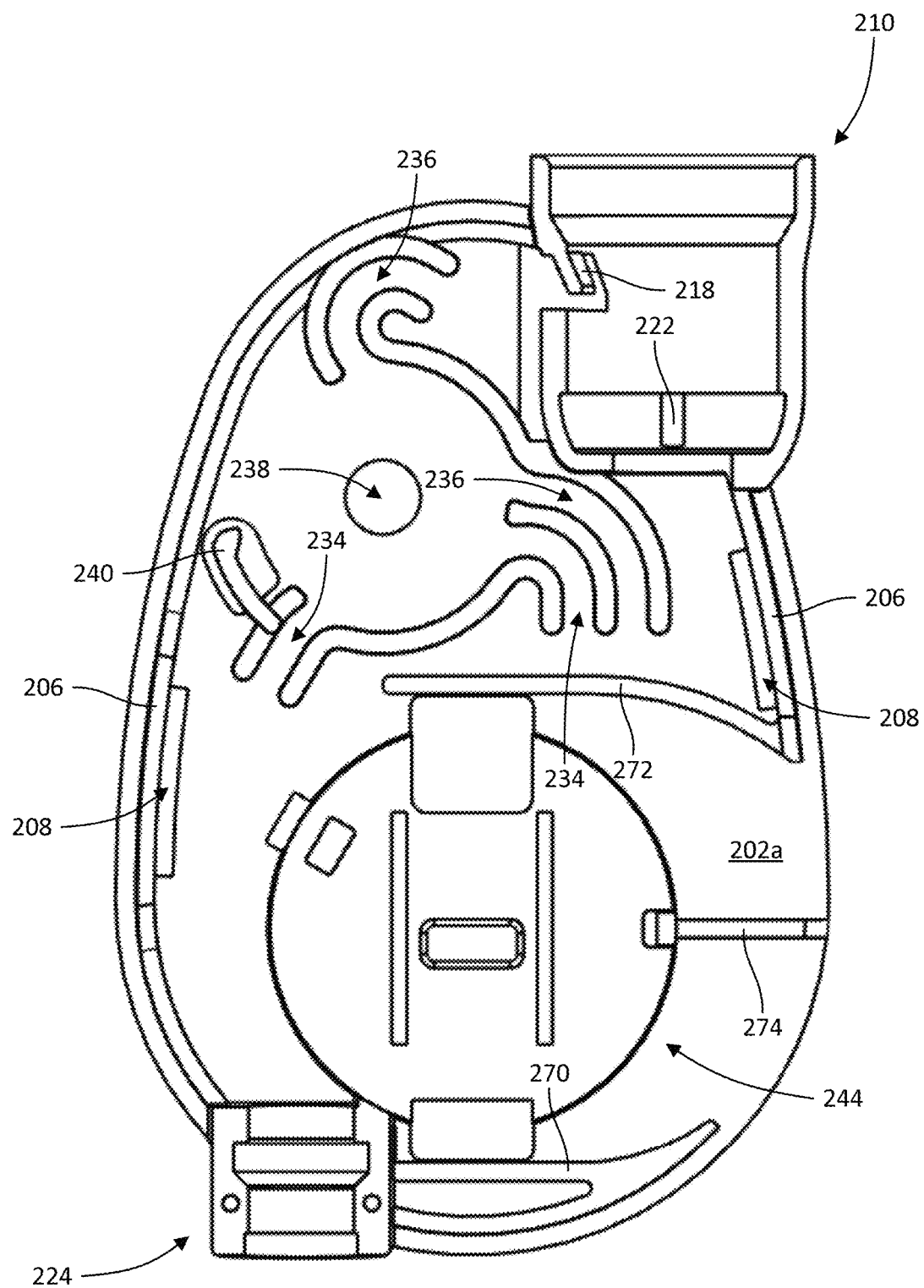
Figure 19A:
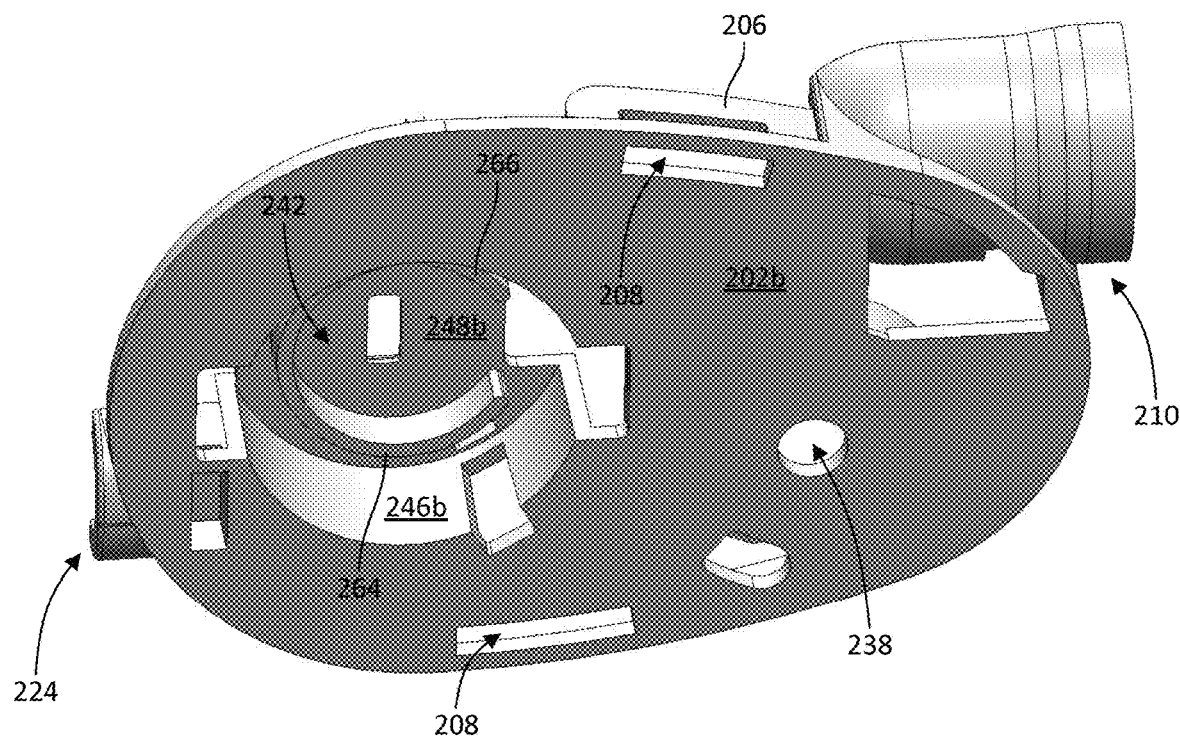
Figure 19B:
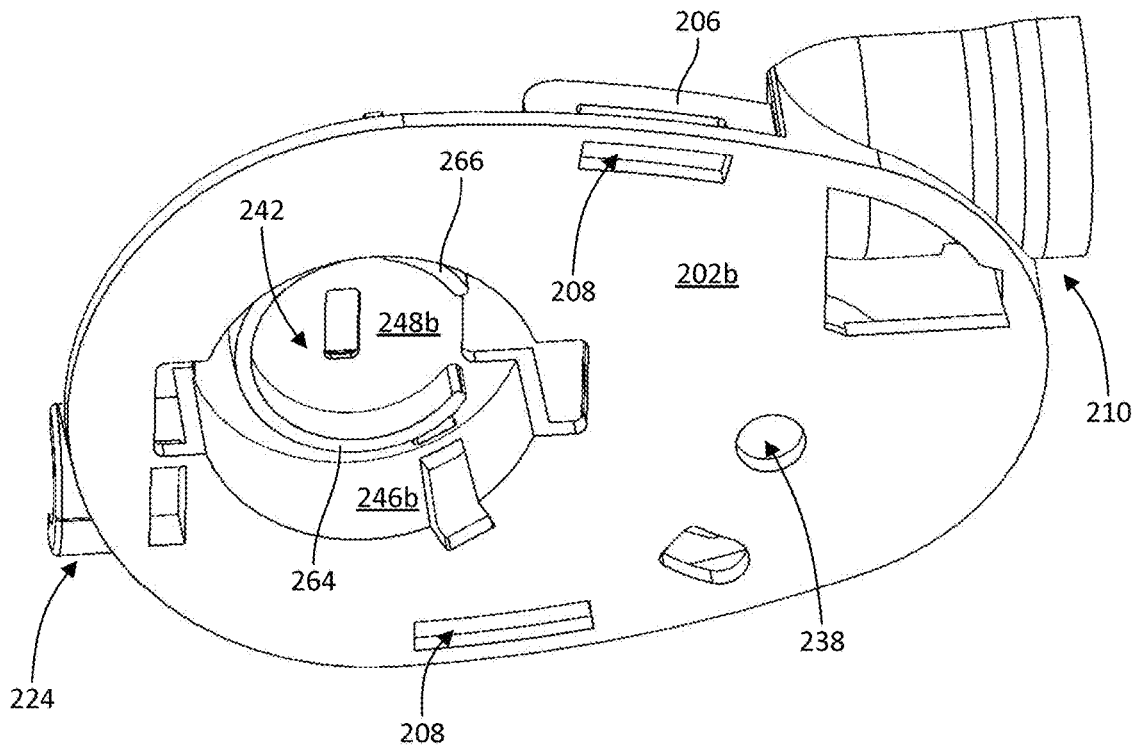
Figure 20A:
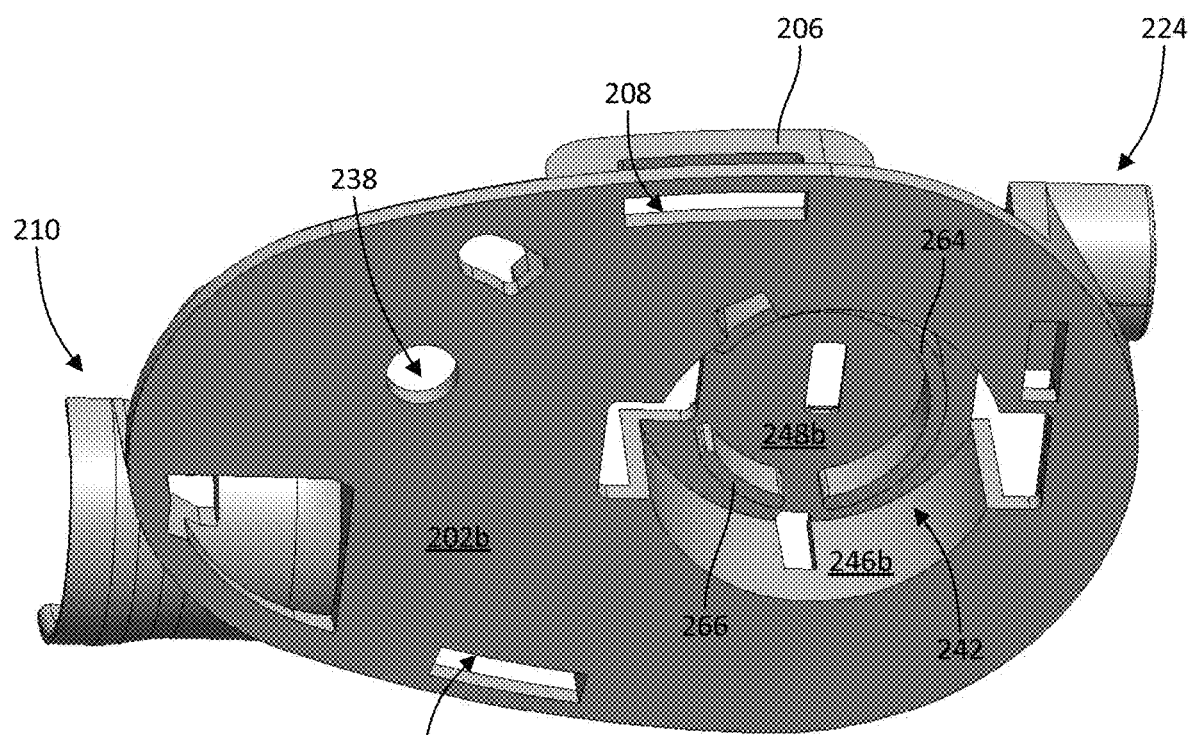
Figure 20B:
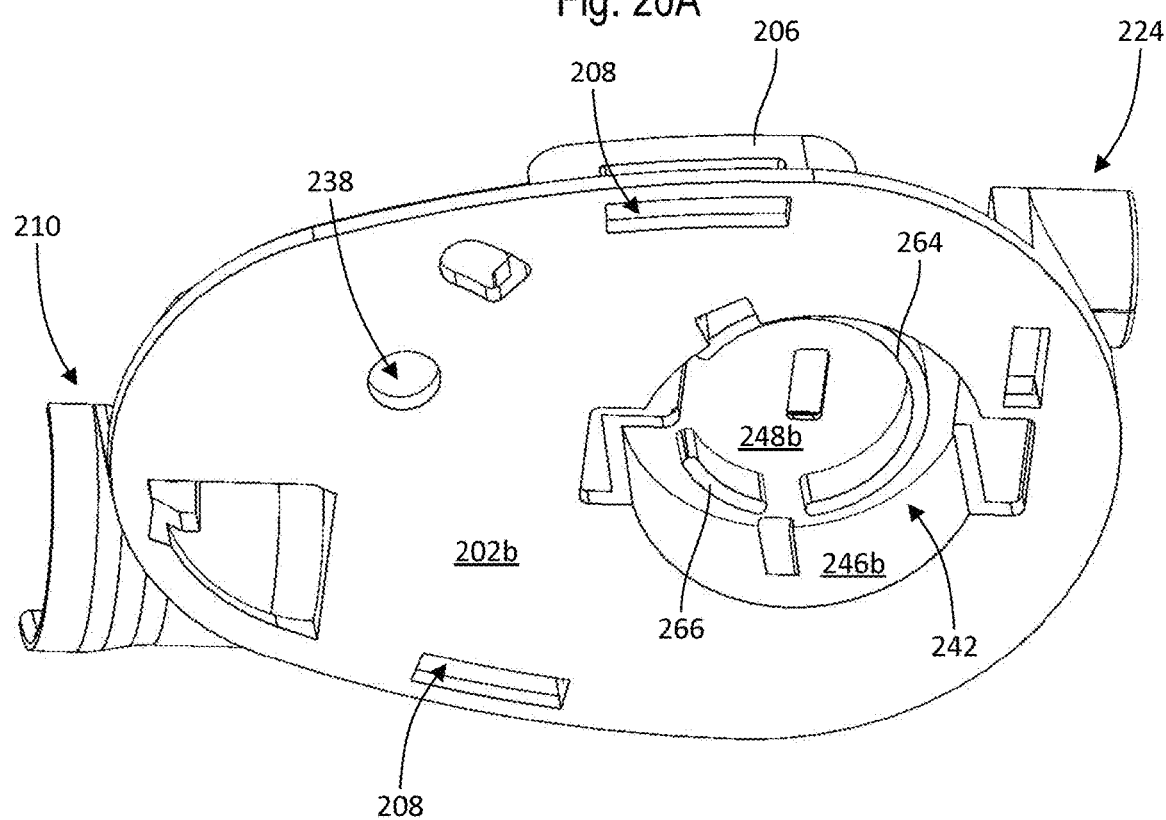
Figure 22B:
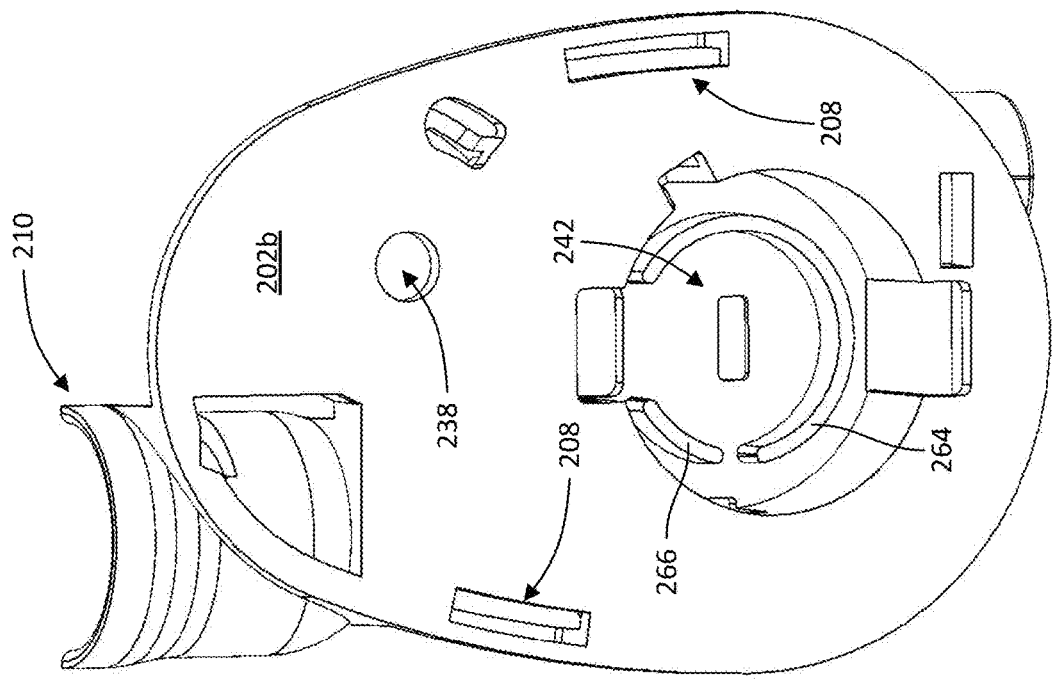
Figure 22A:
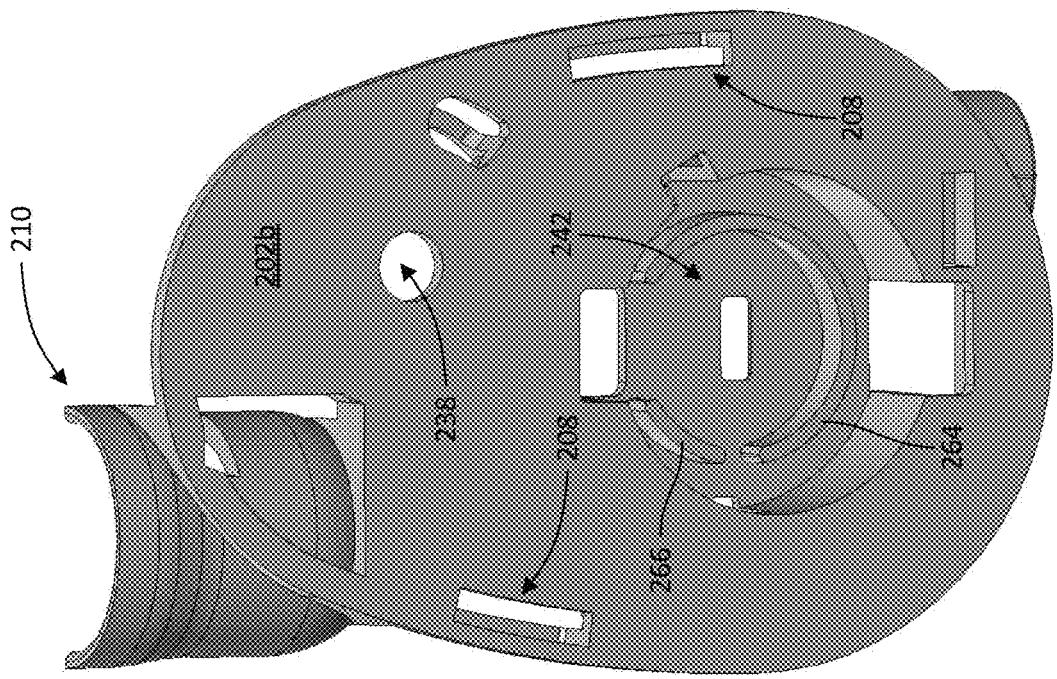
Figure 23:
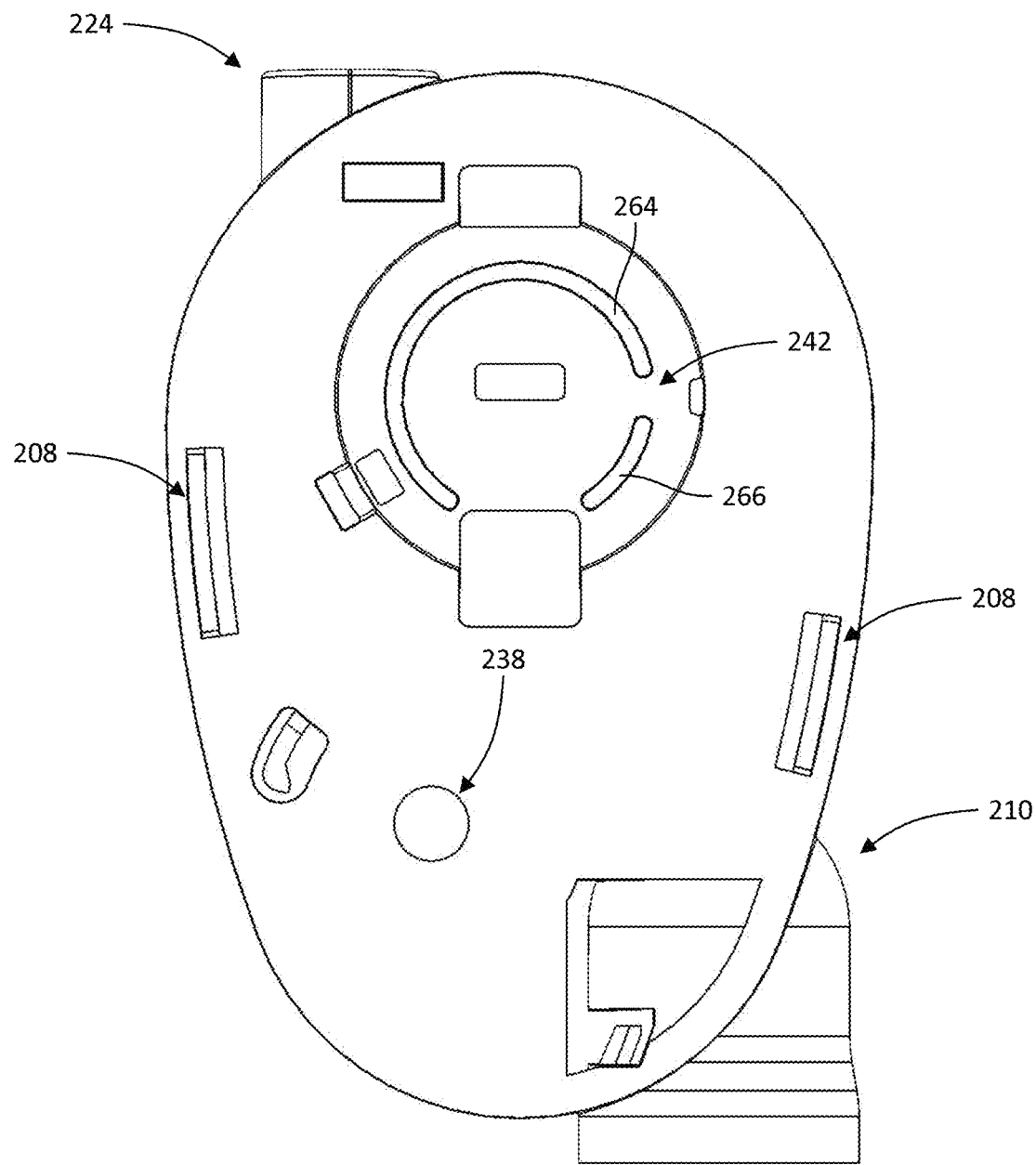
Figure 24A:
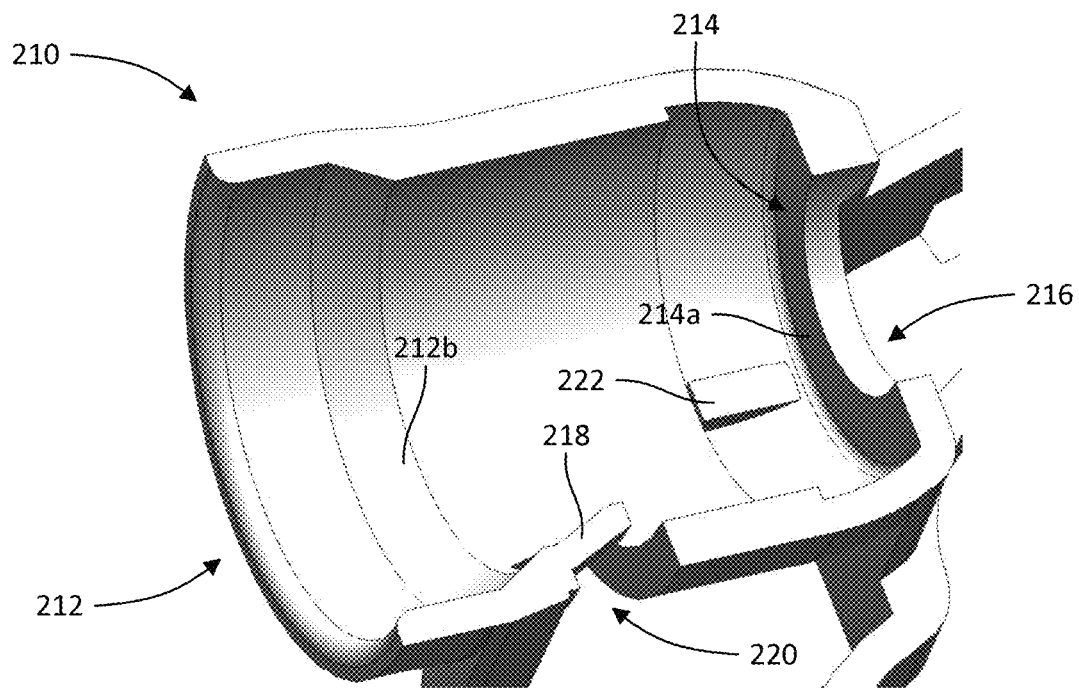
Figure 24B:
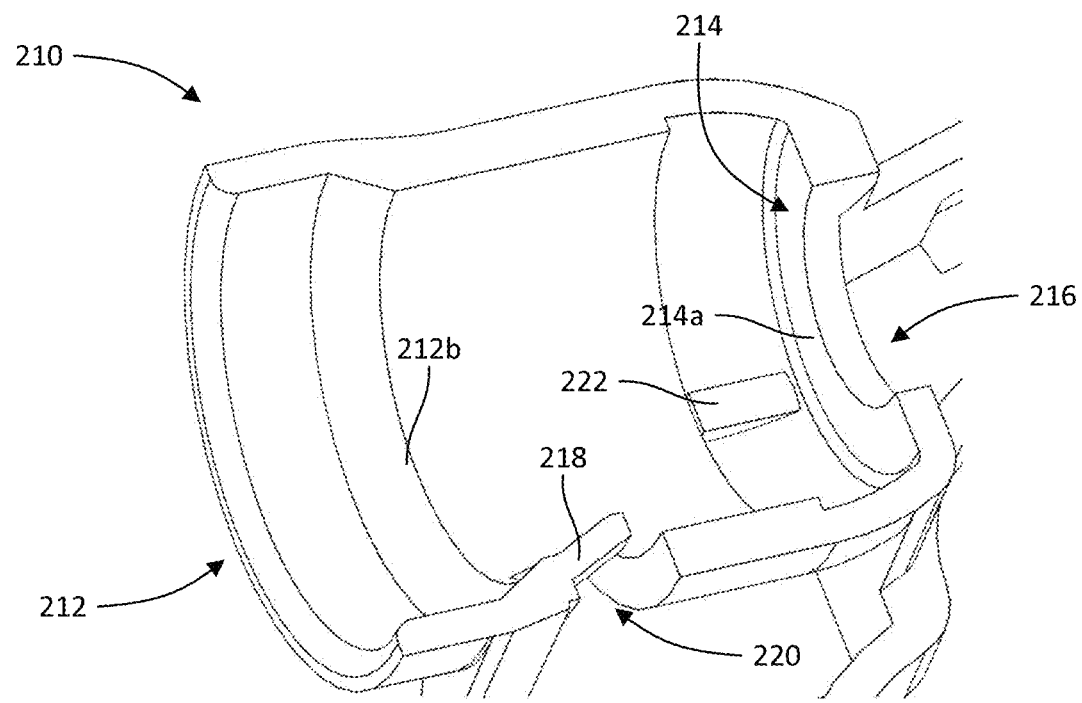
Figure 25A:
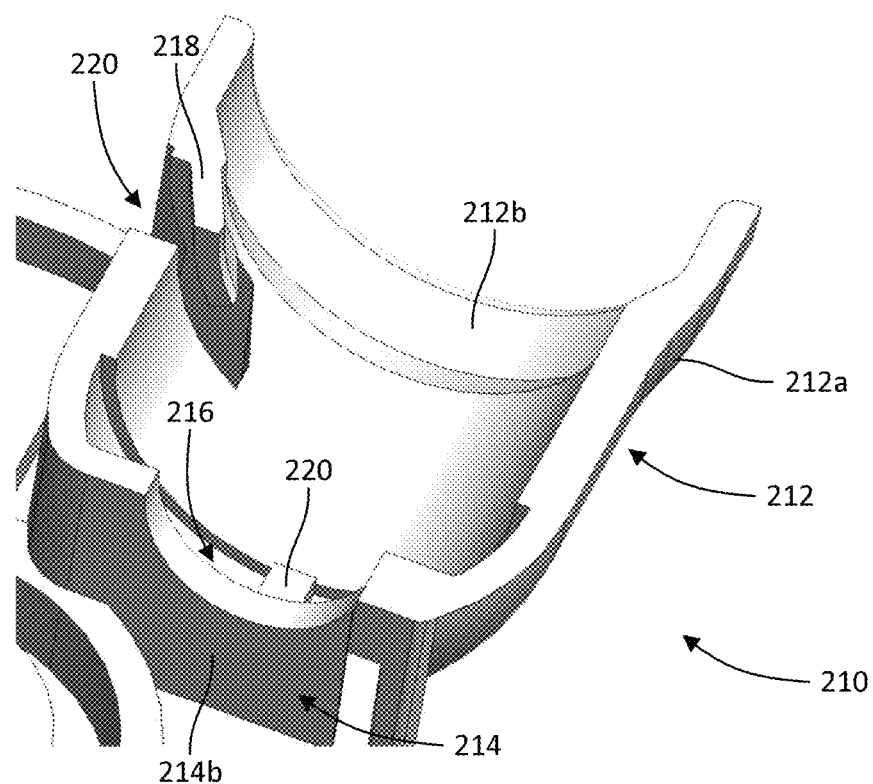
Figure 25B:
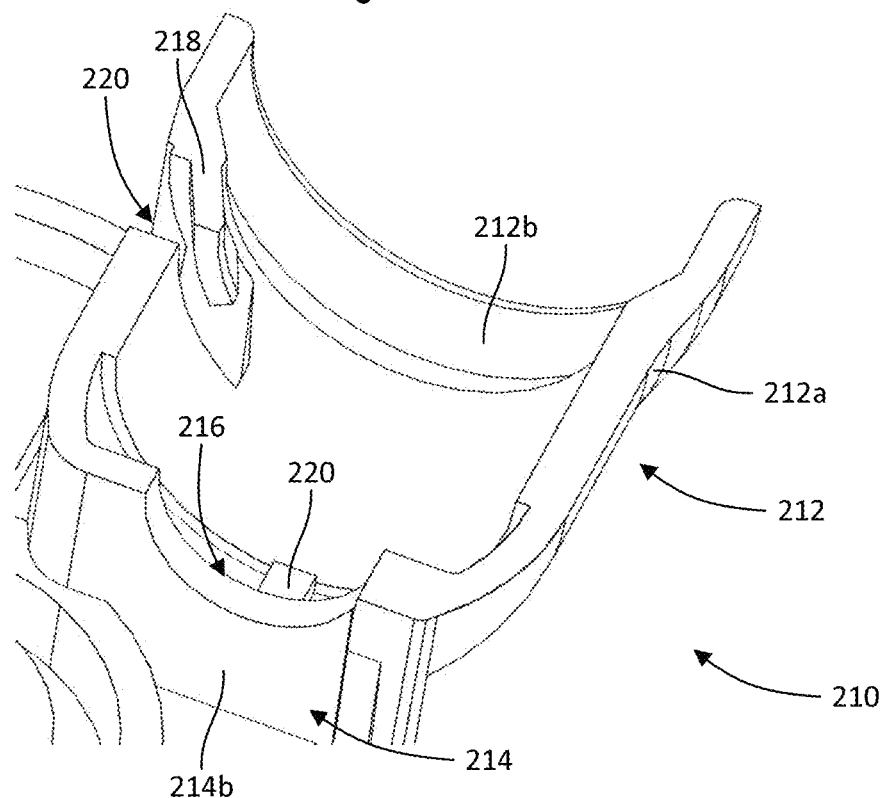
Figure 26:
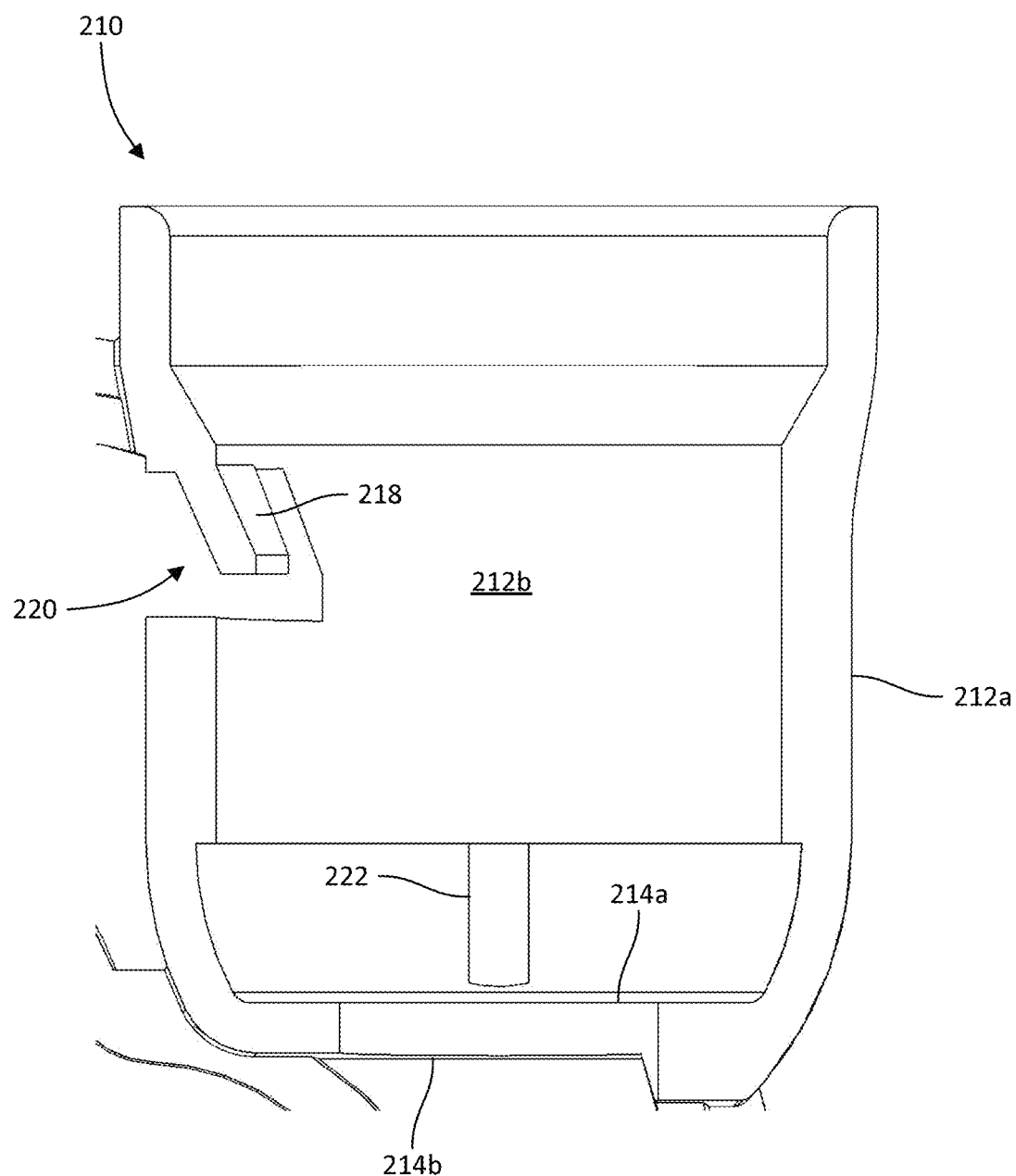
Figure 27A:
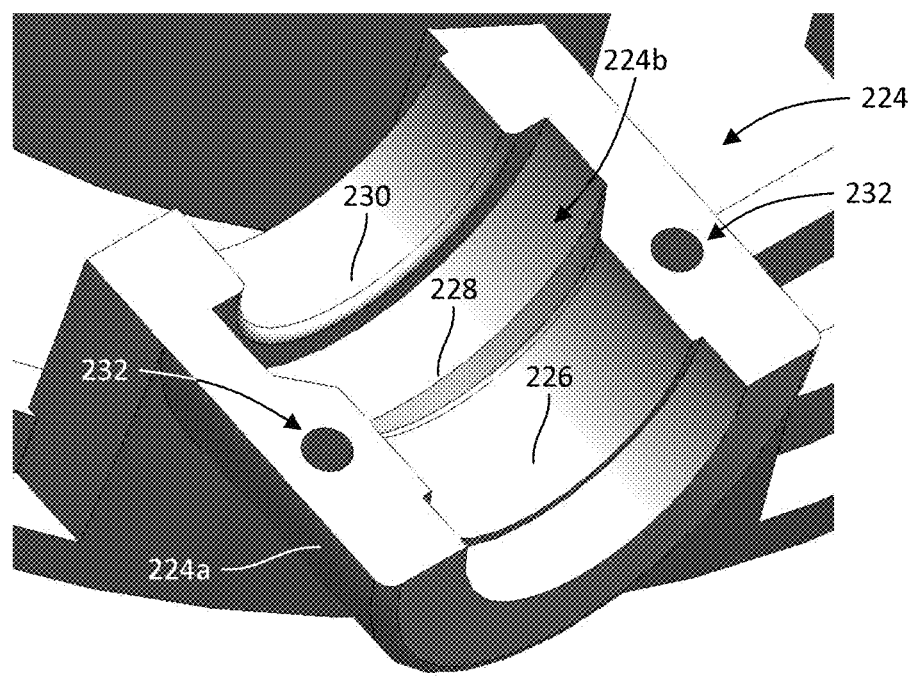
Figure 27B:
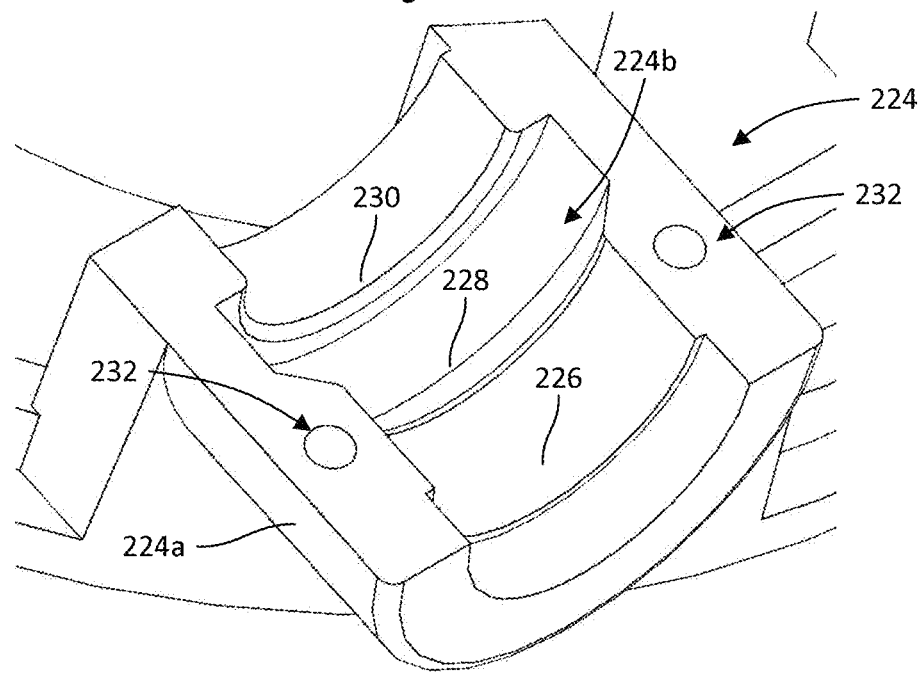
Figure 28A:
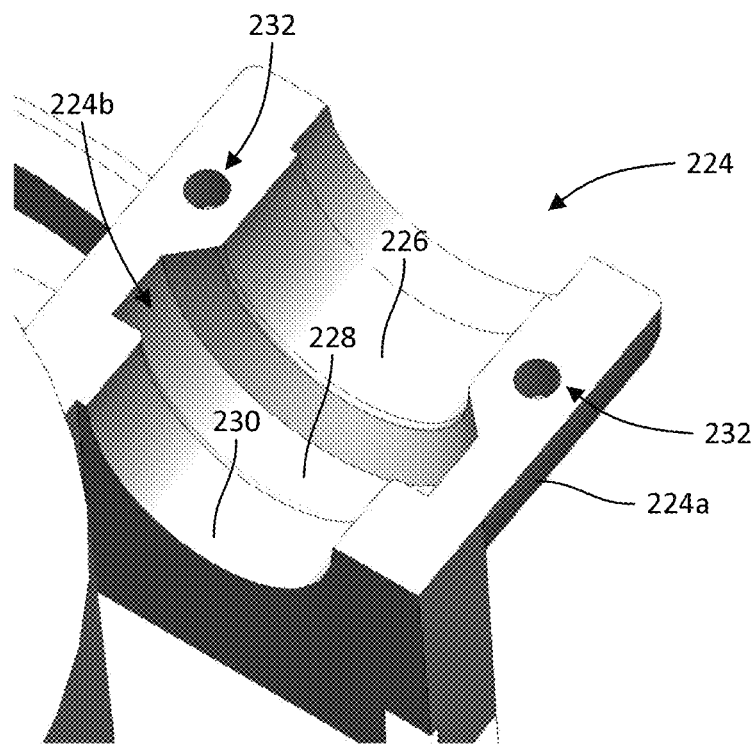
Figure 28B:
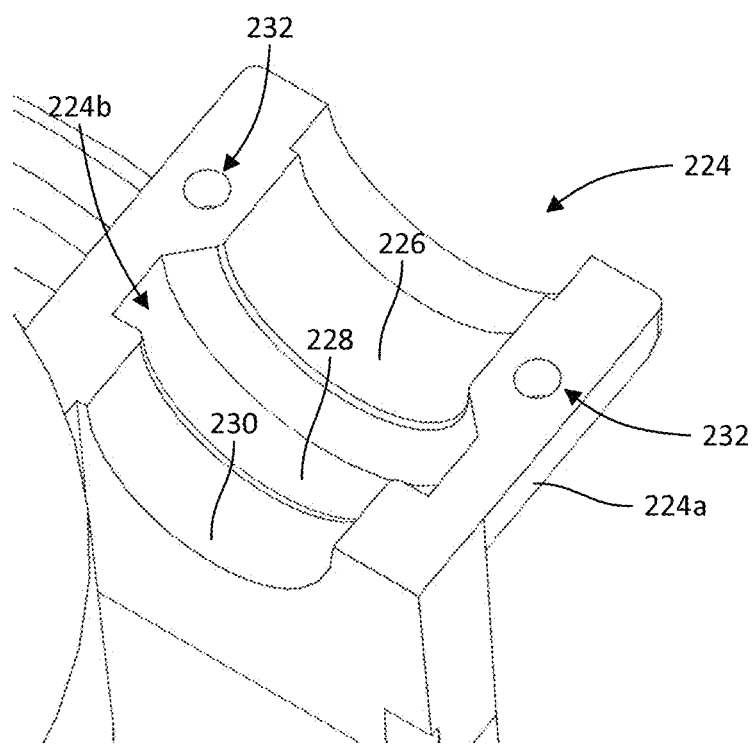
Figure 29A:
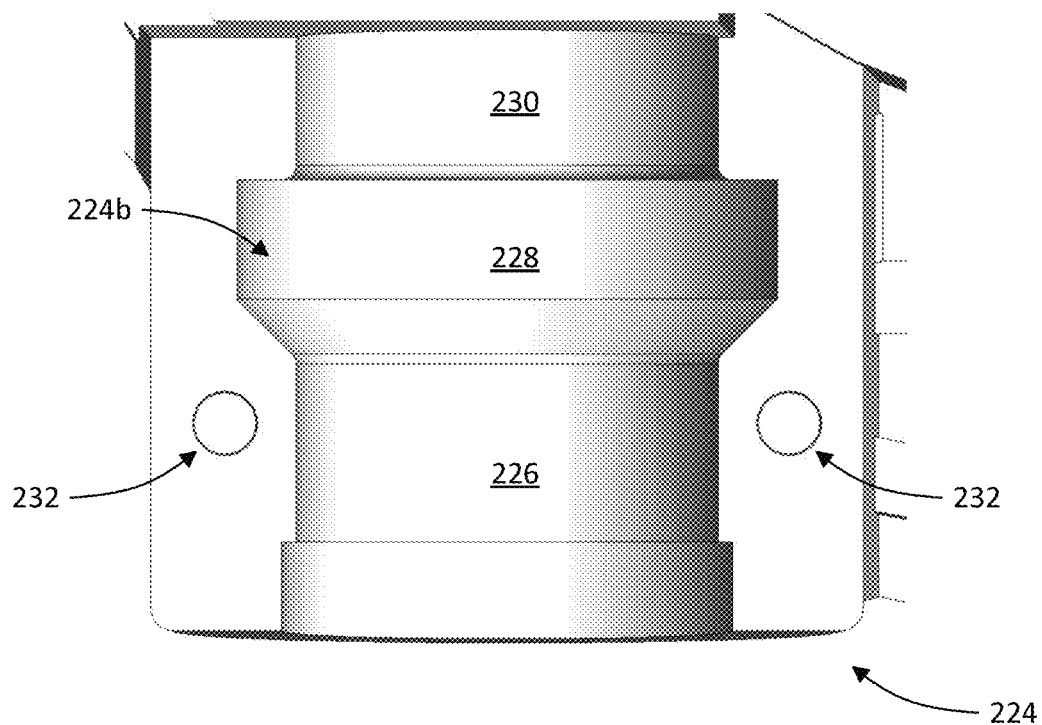
Figure 29B:
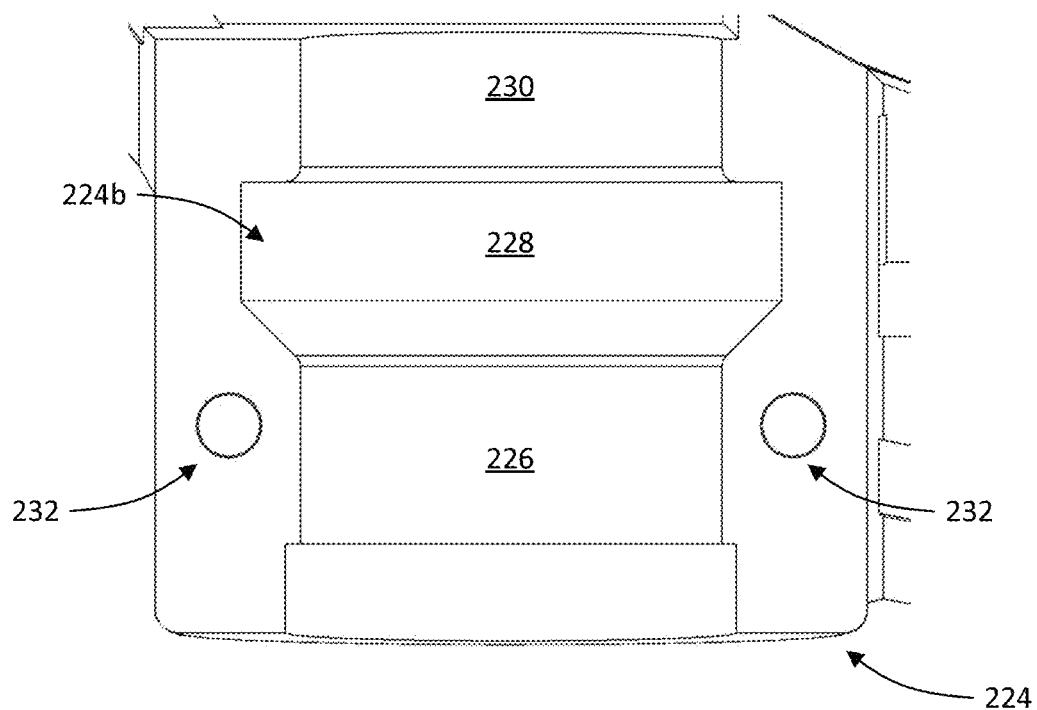
Figure 30A:
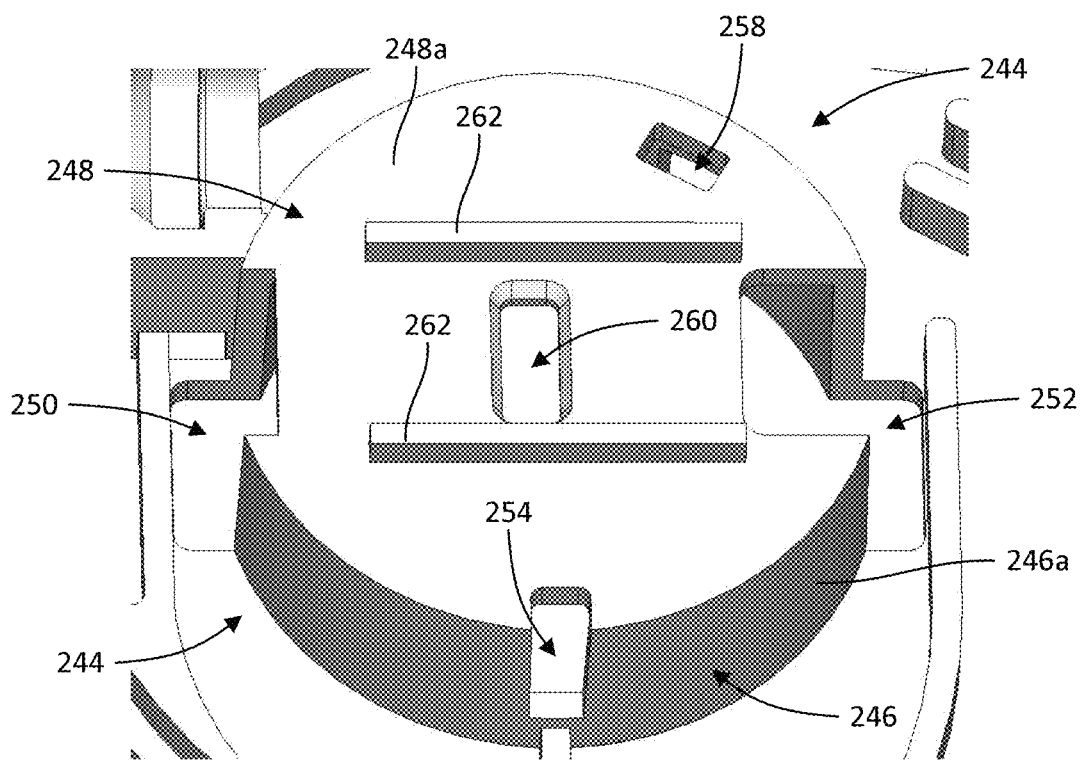
Figure 30B:
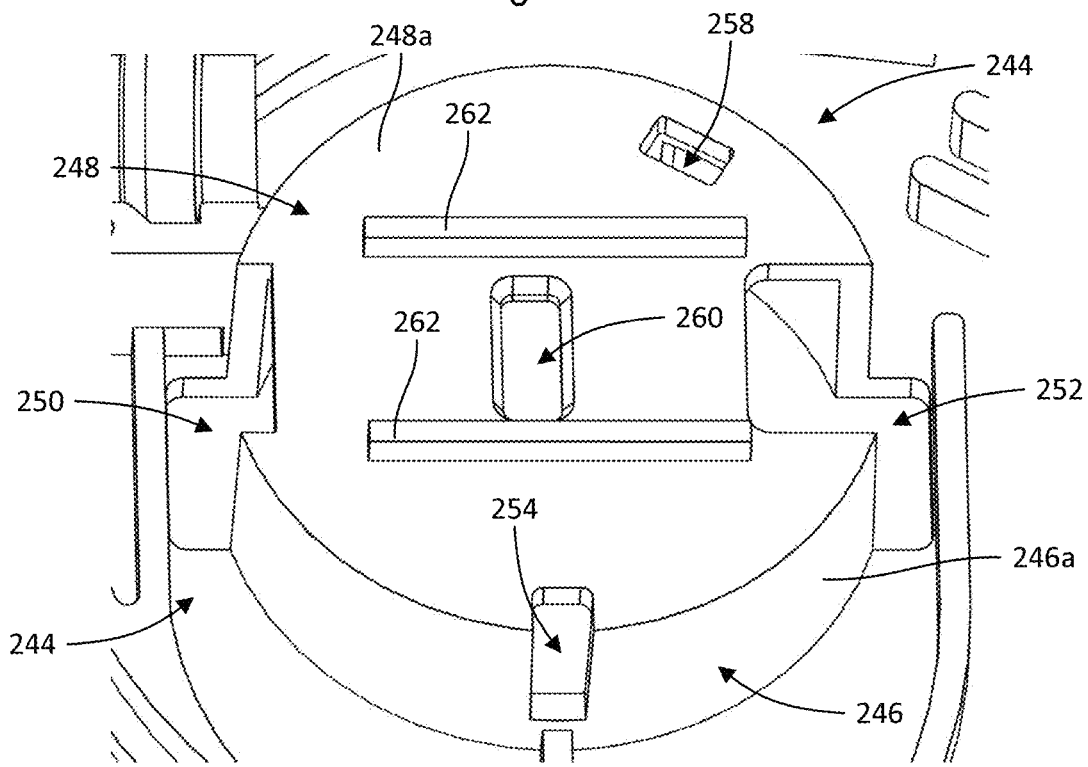
Figure 31A:
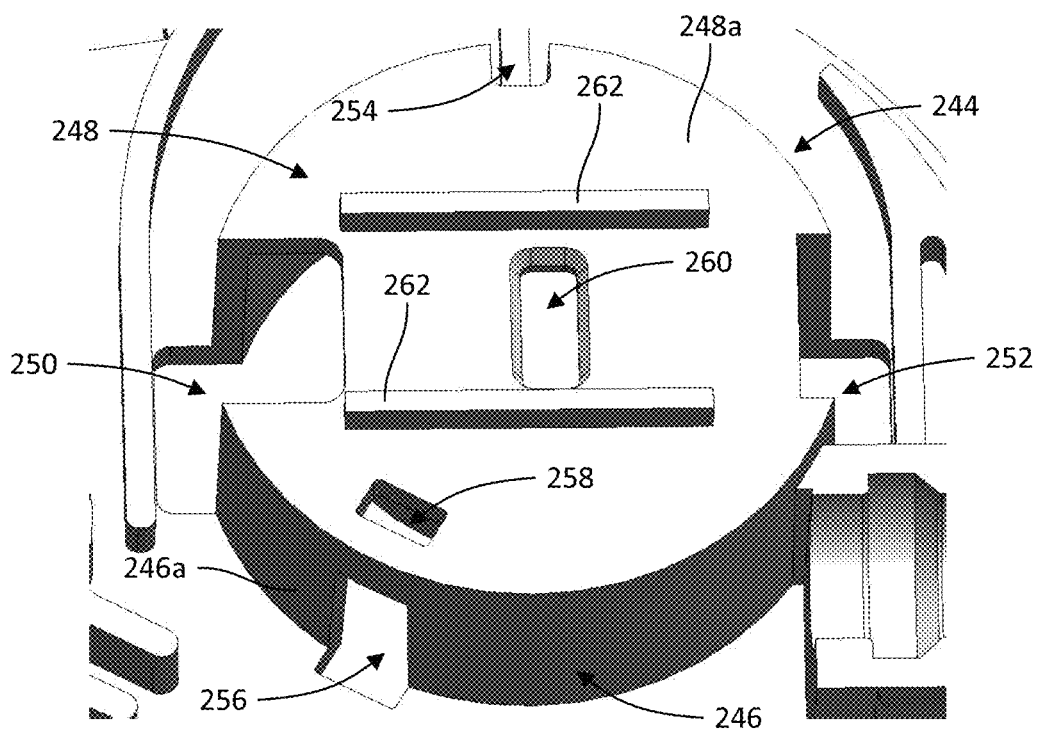
Figure 31B:
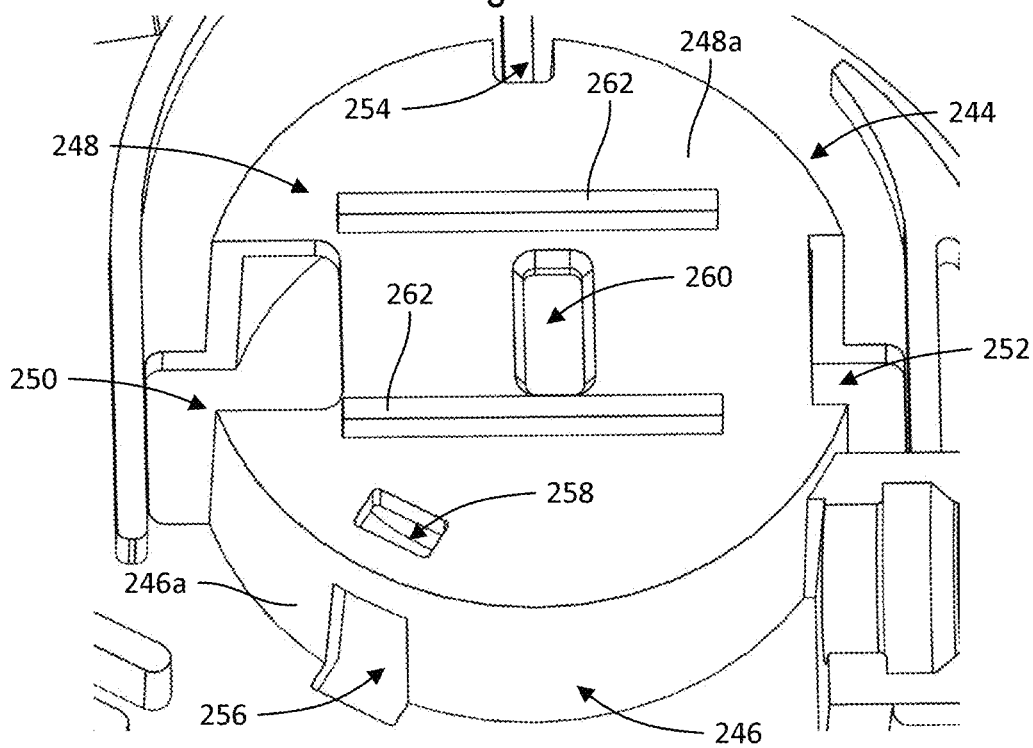
Figure 32A:
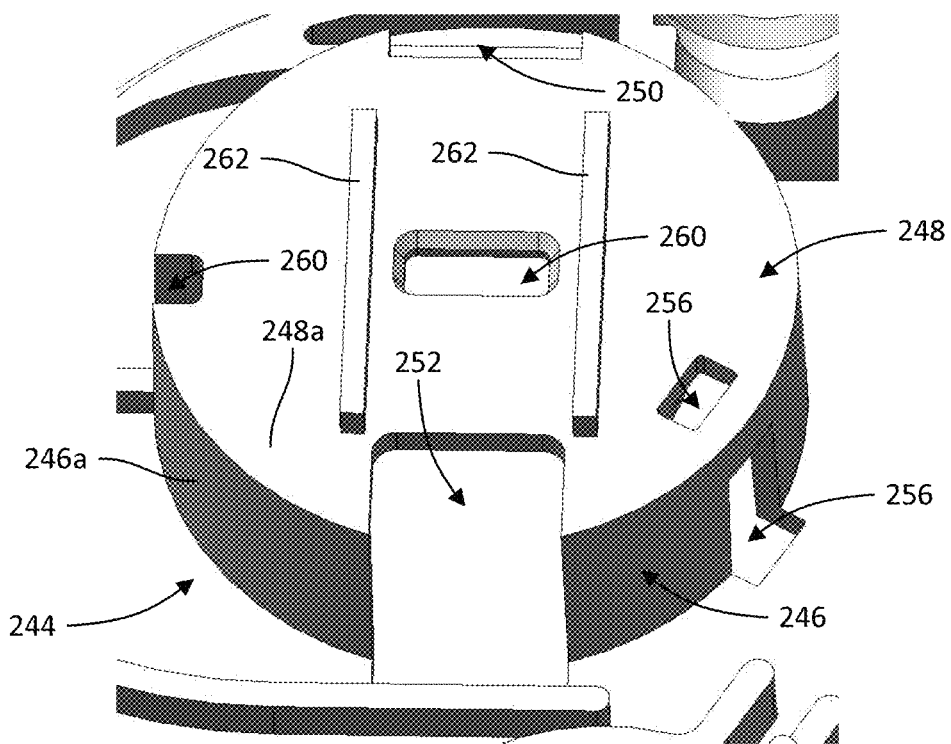
Figure 32B:
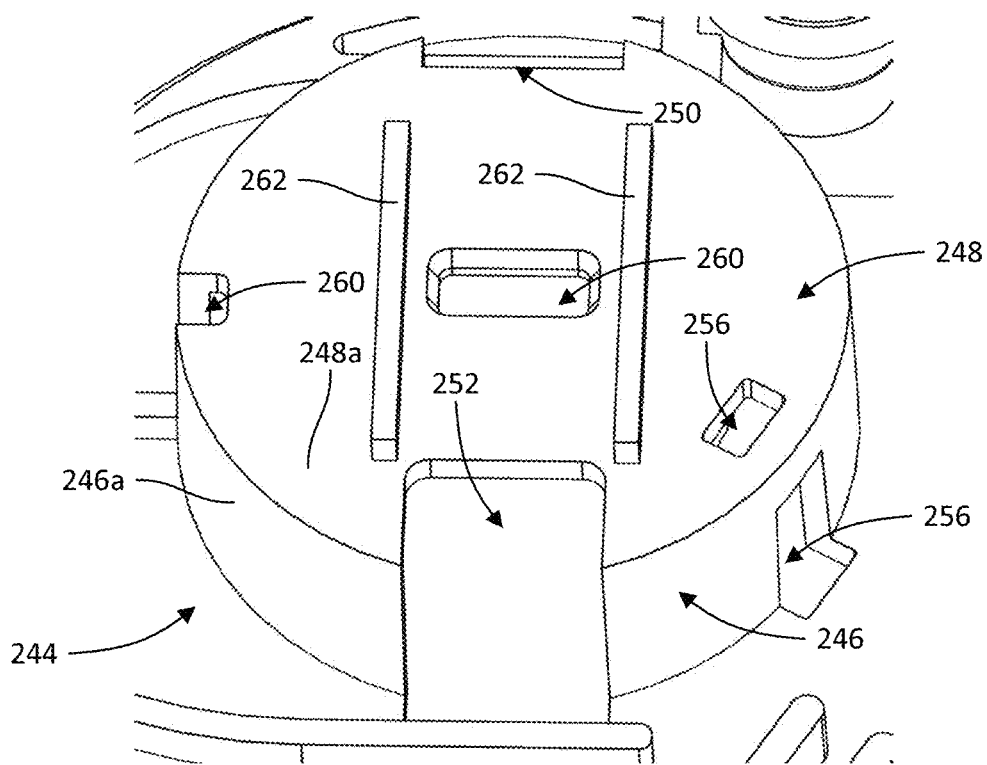
Figure 33A:
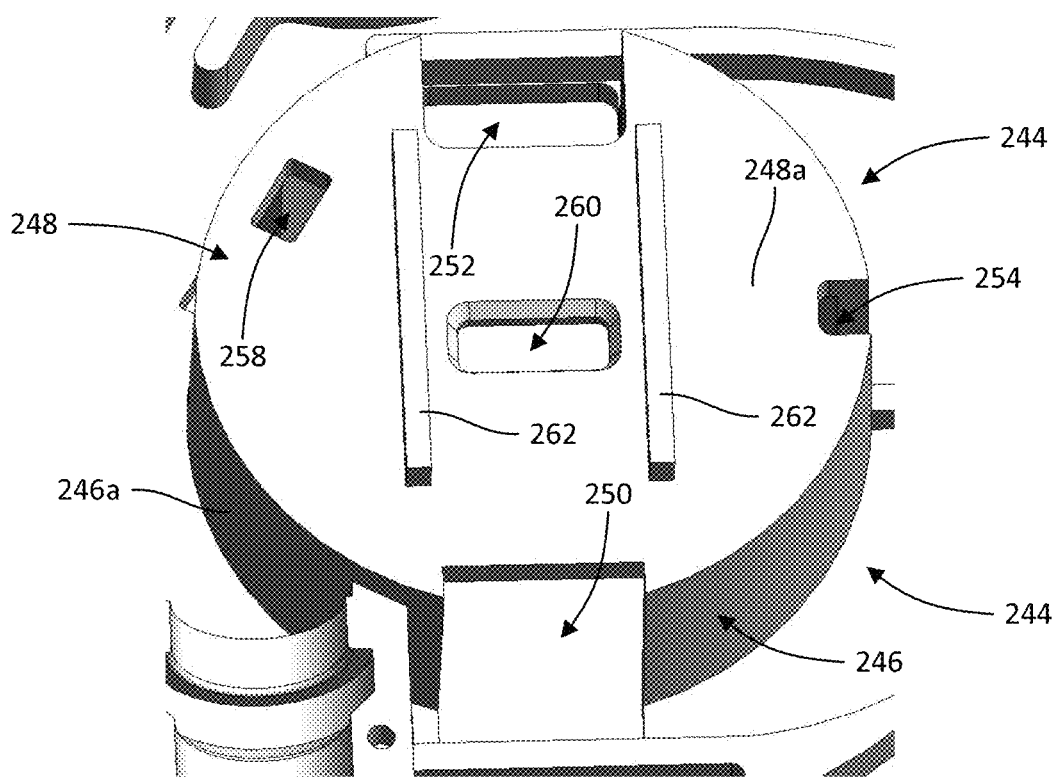
Figure 33B:
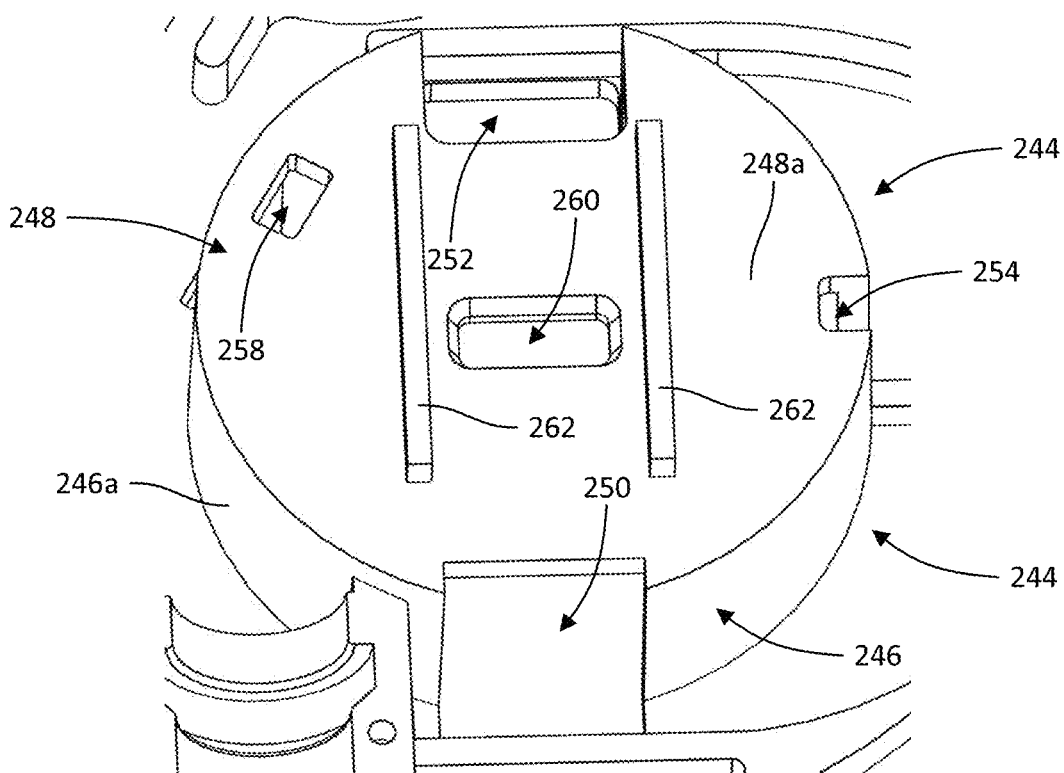
Figure 34A:
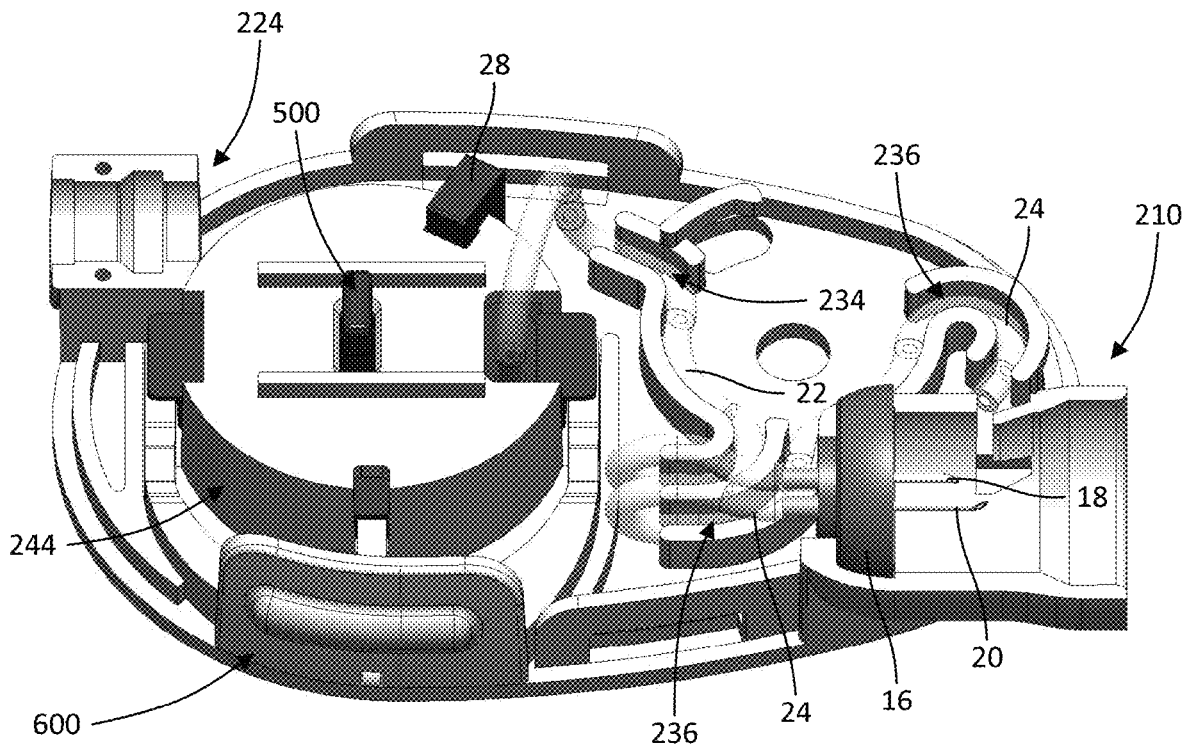
Figure 34B:
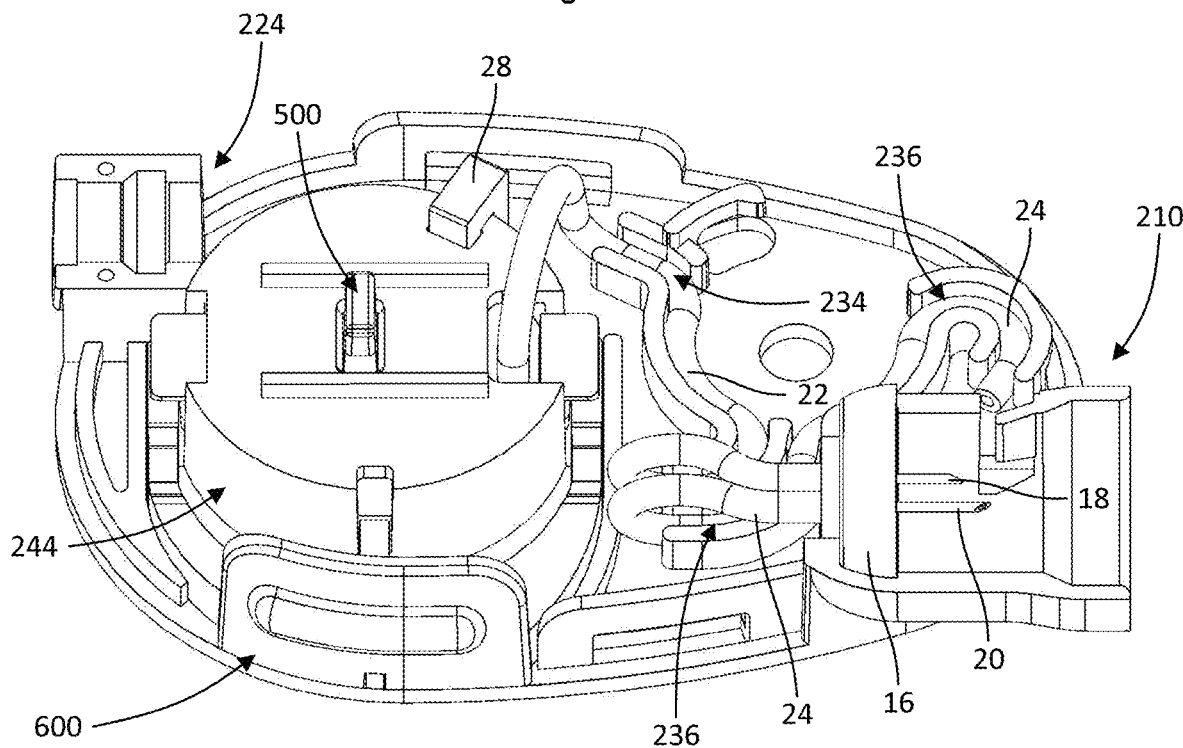
Figure 35A:
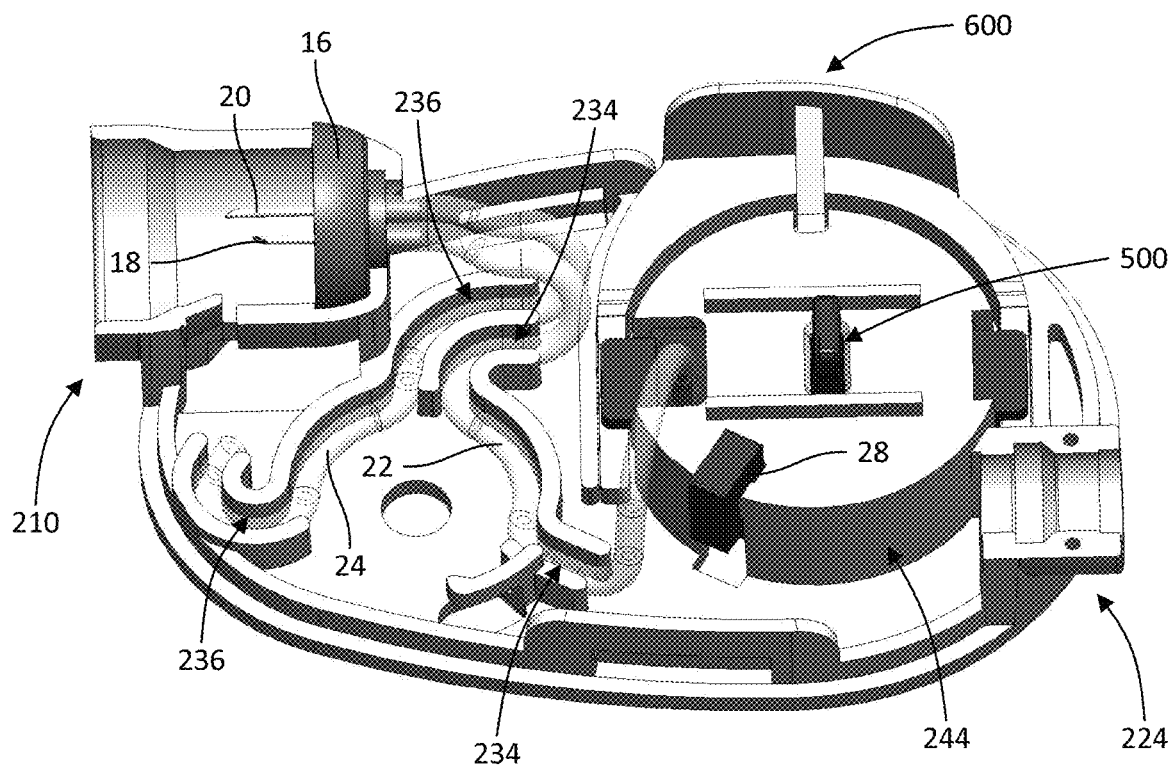
Figure 35B:
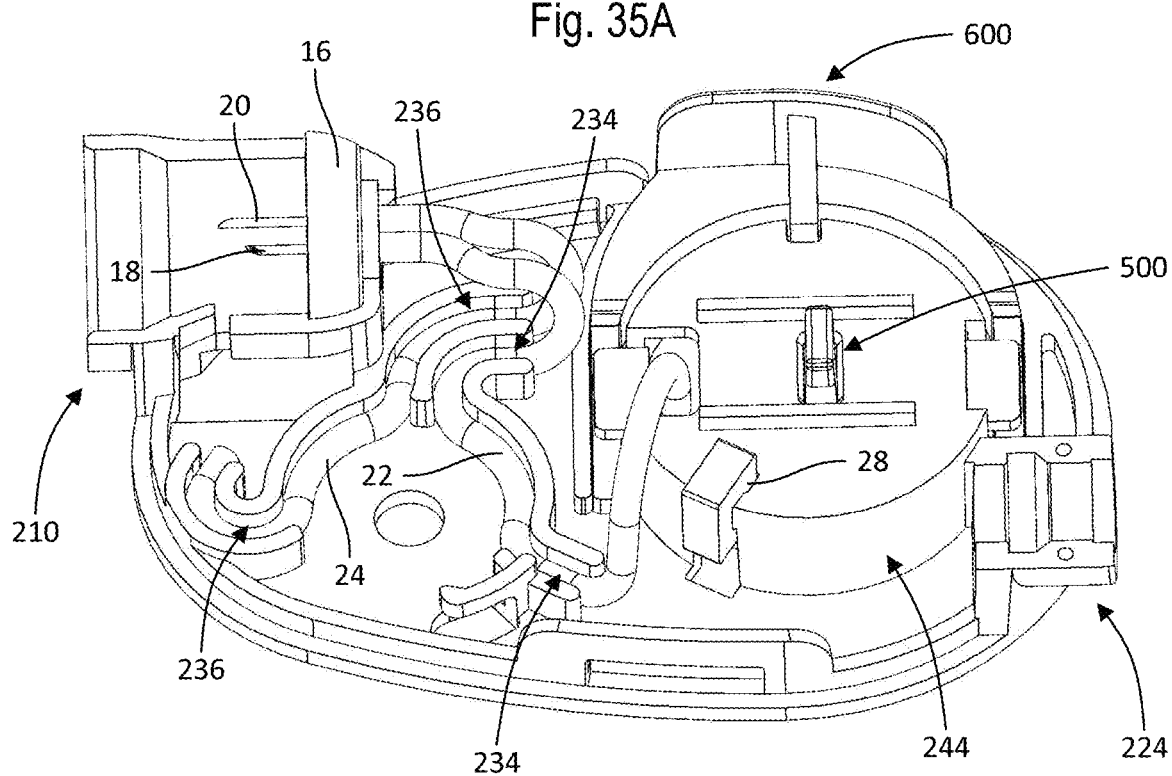
Figure 36:
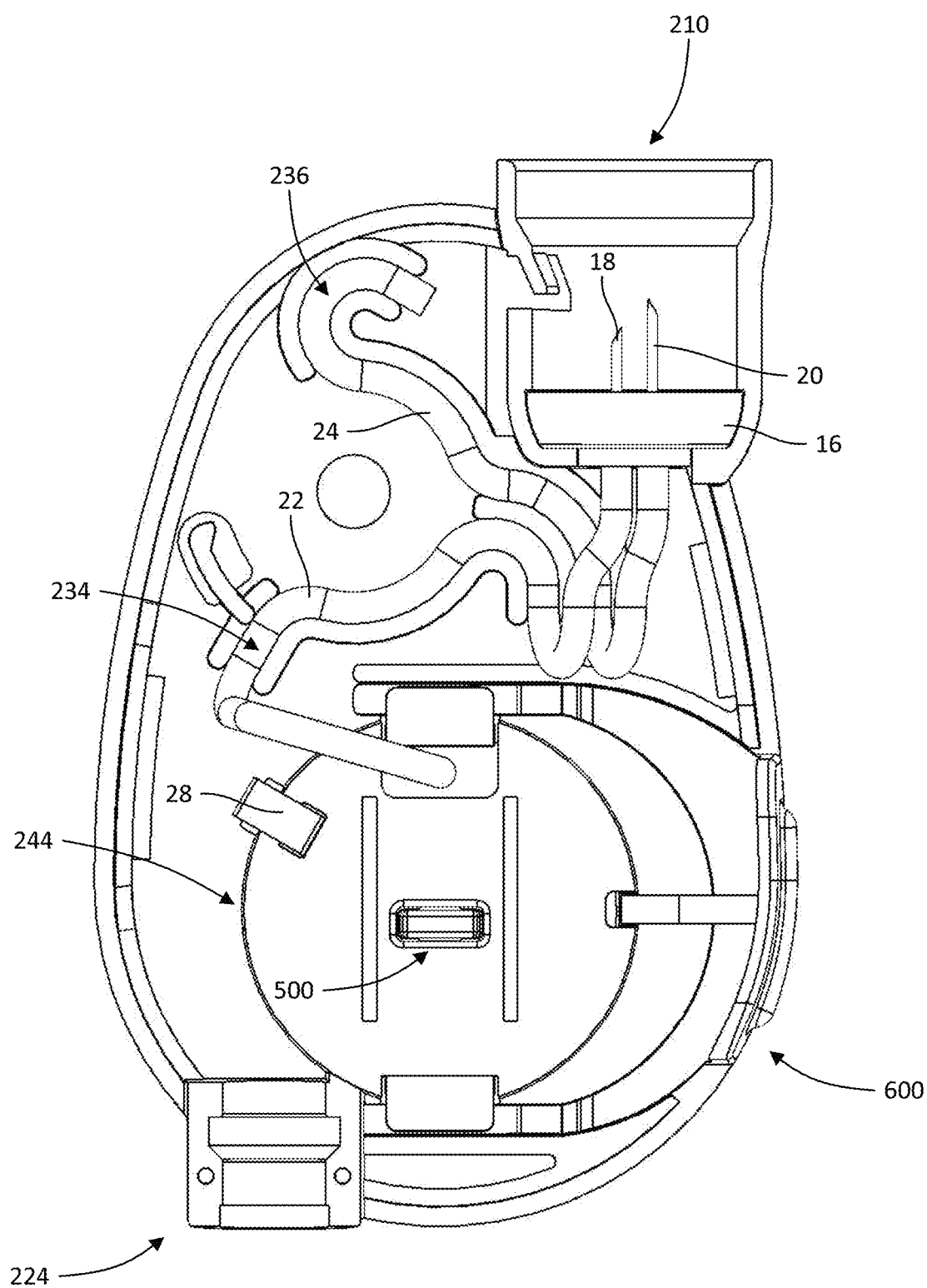
Figure 38A:
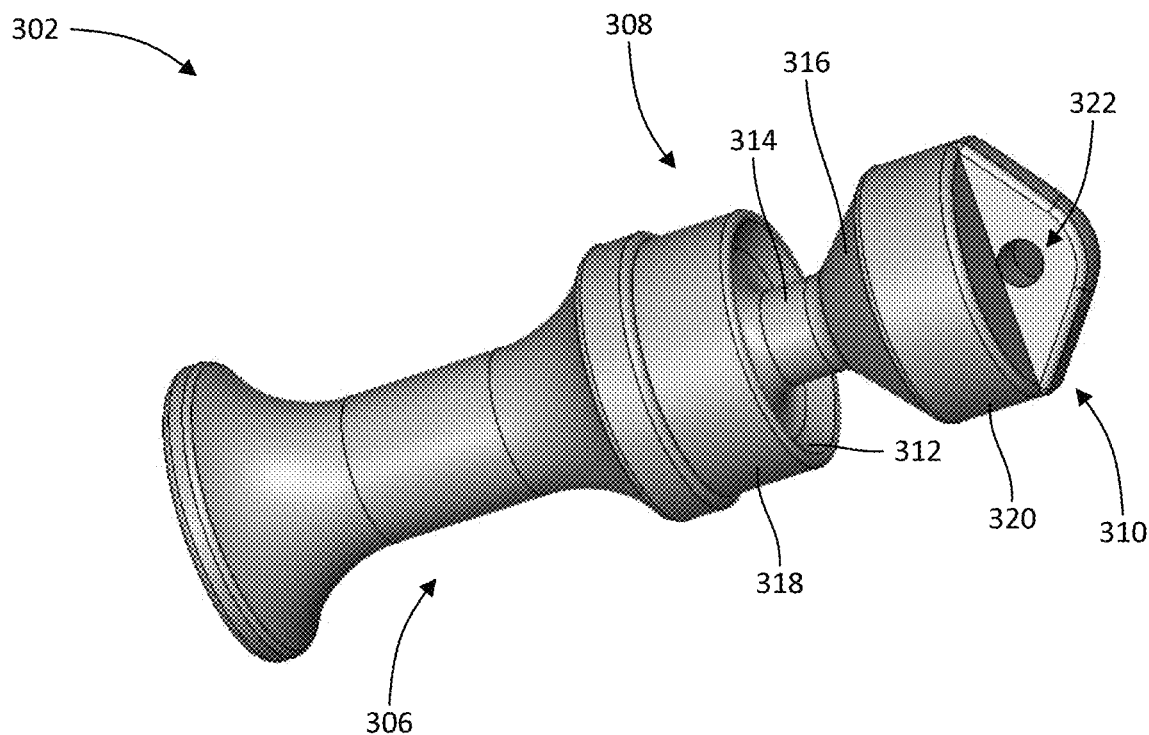
FIGS. 38A, 38B, 39A, and 39B depict a handle of the pull mechanism in accordance with an exemplary embodiment.
Figure 38B:
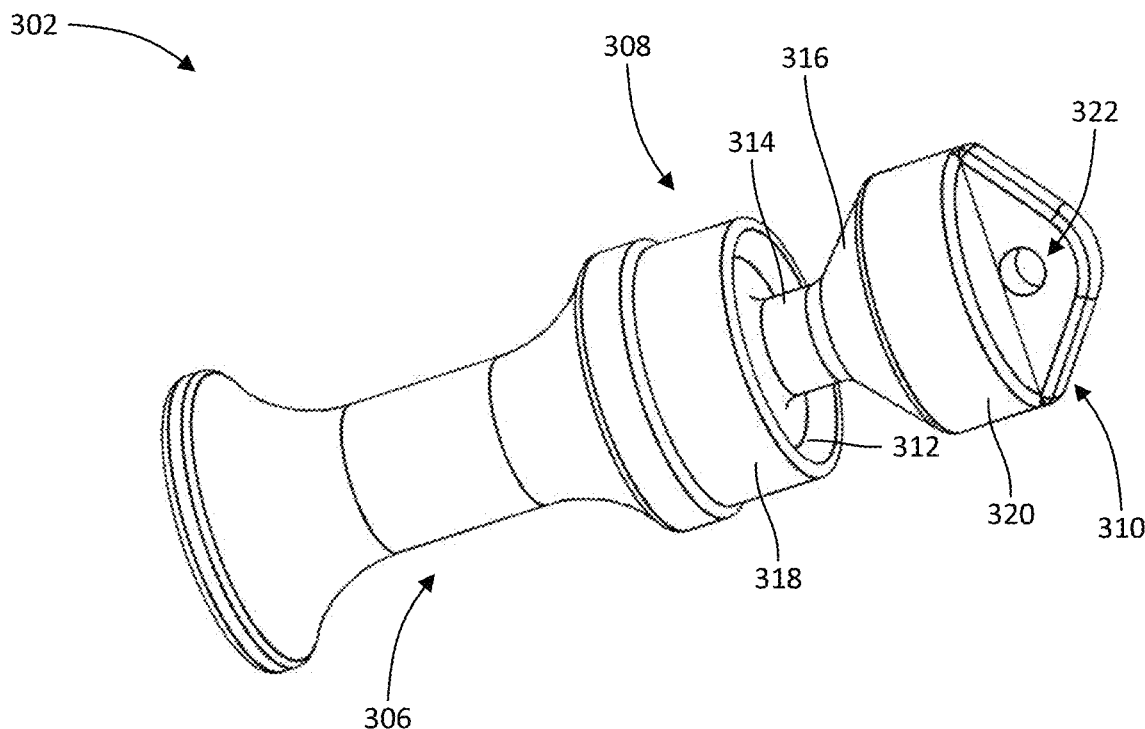
Figure 39A:
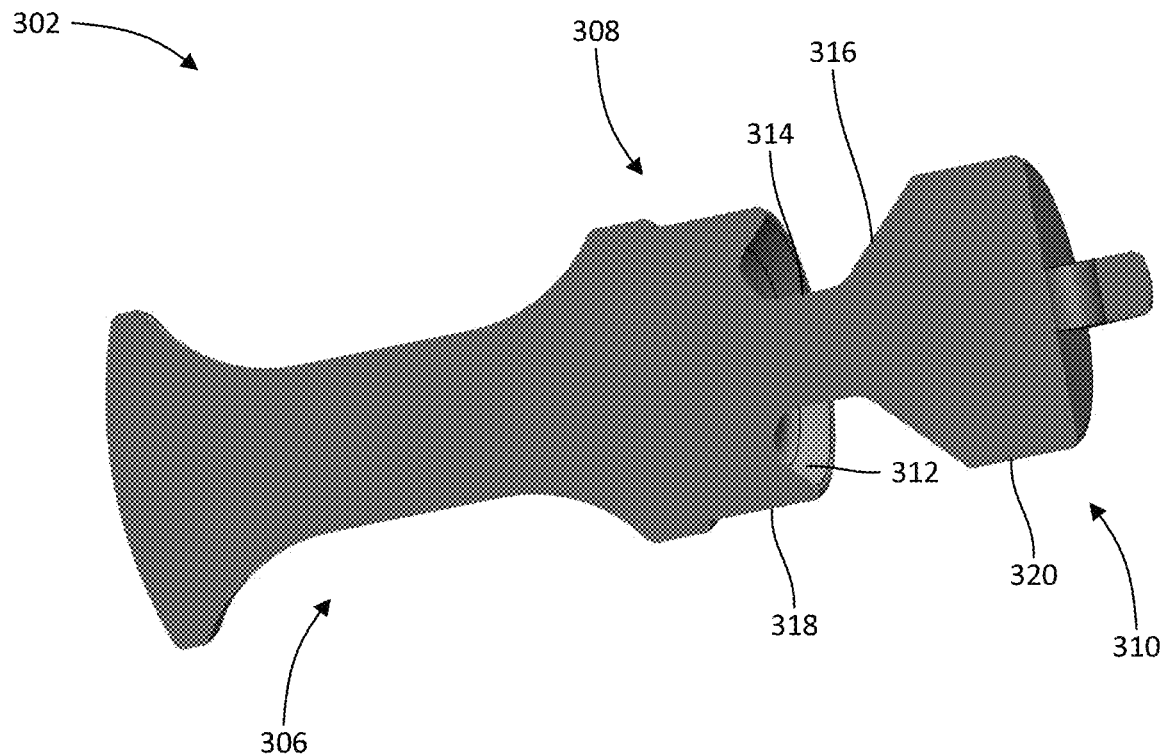
Figure 39B:
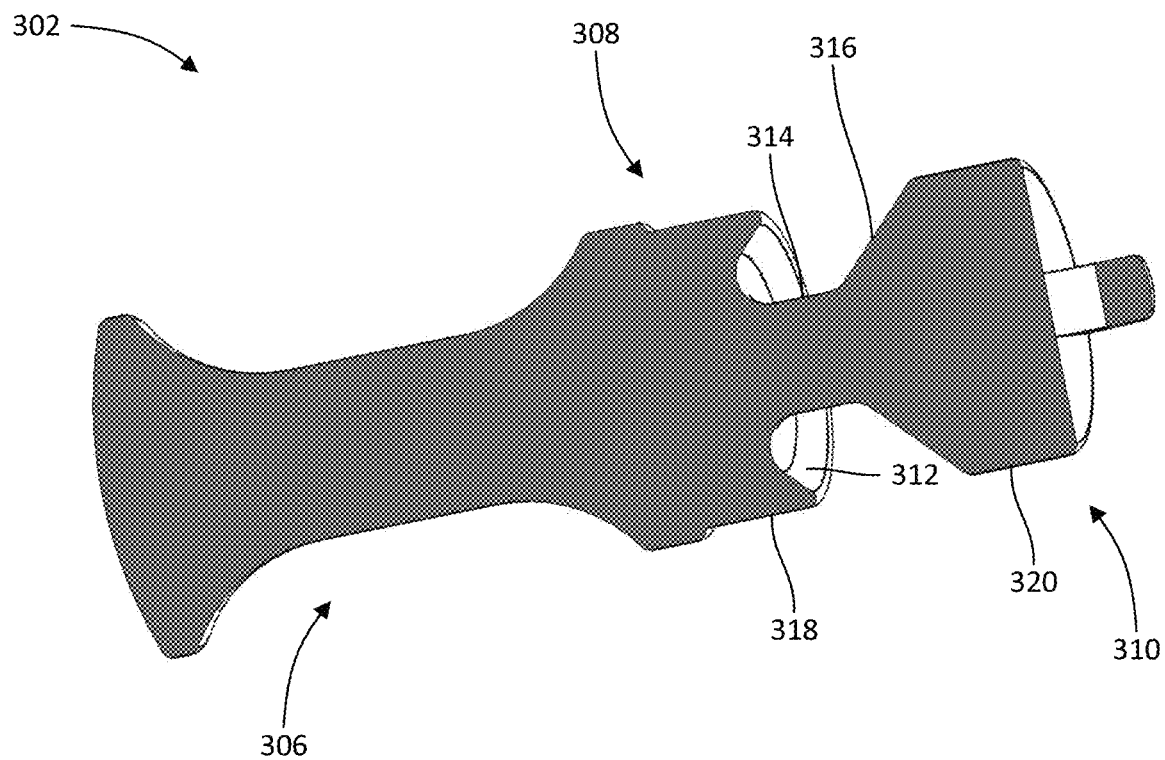
Figure 40B:
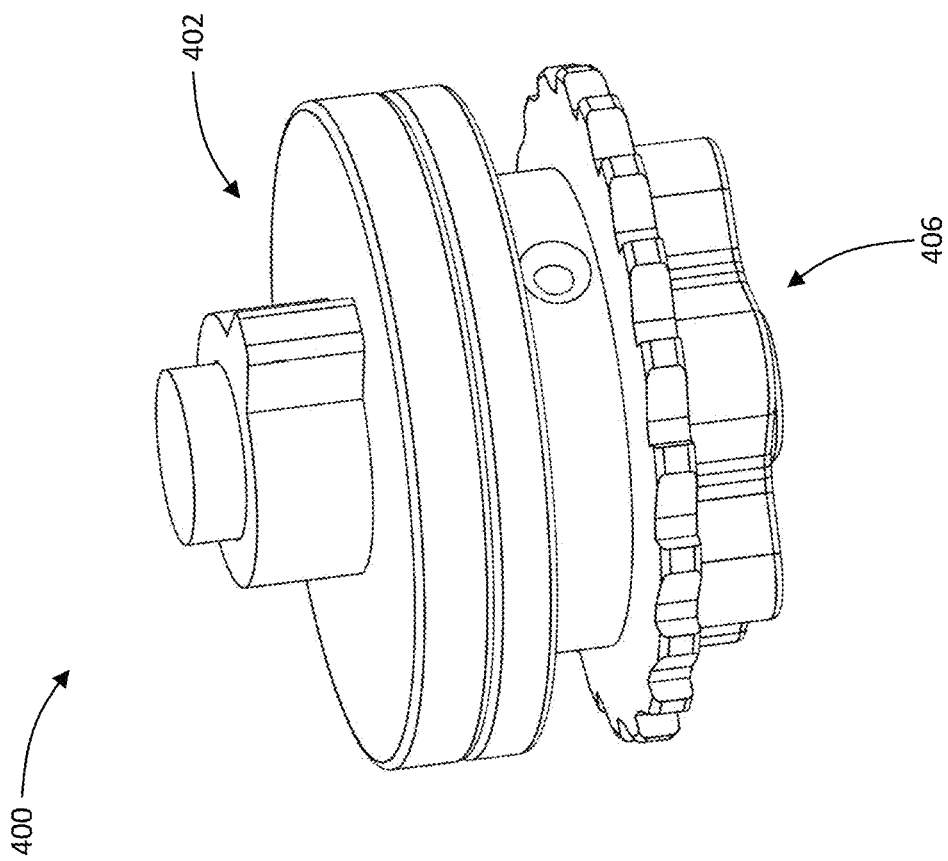
Figure 40A:
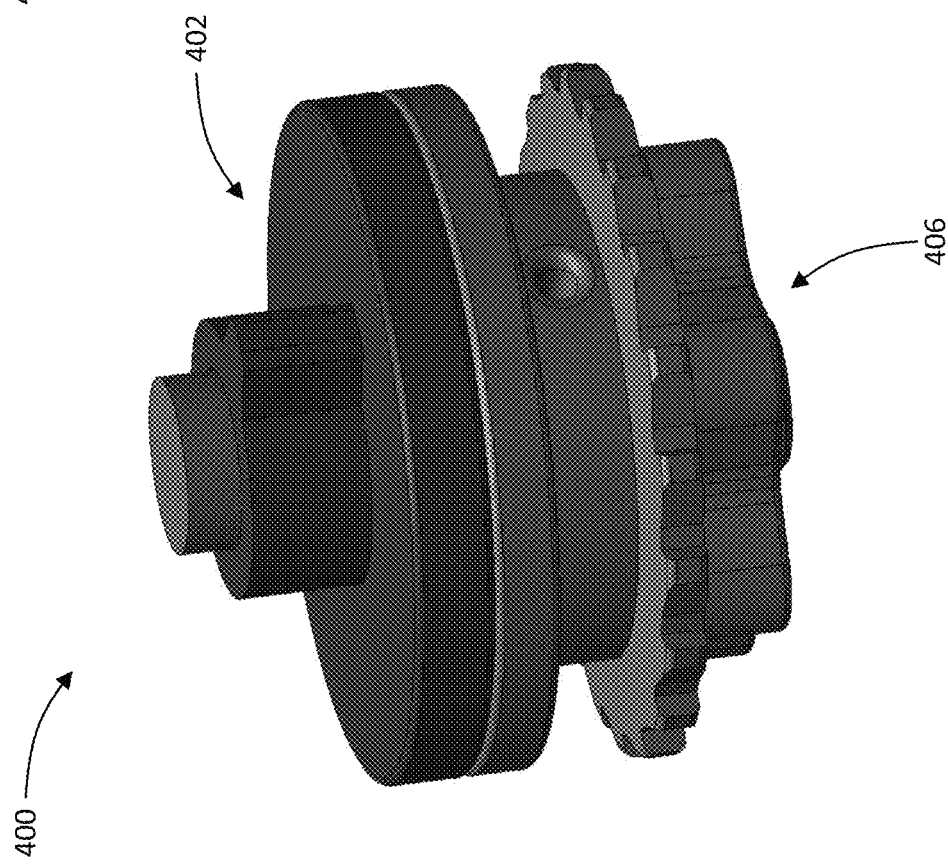
Figure 42A:
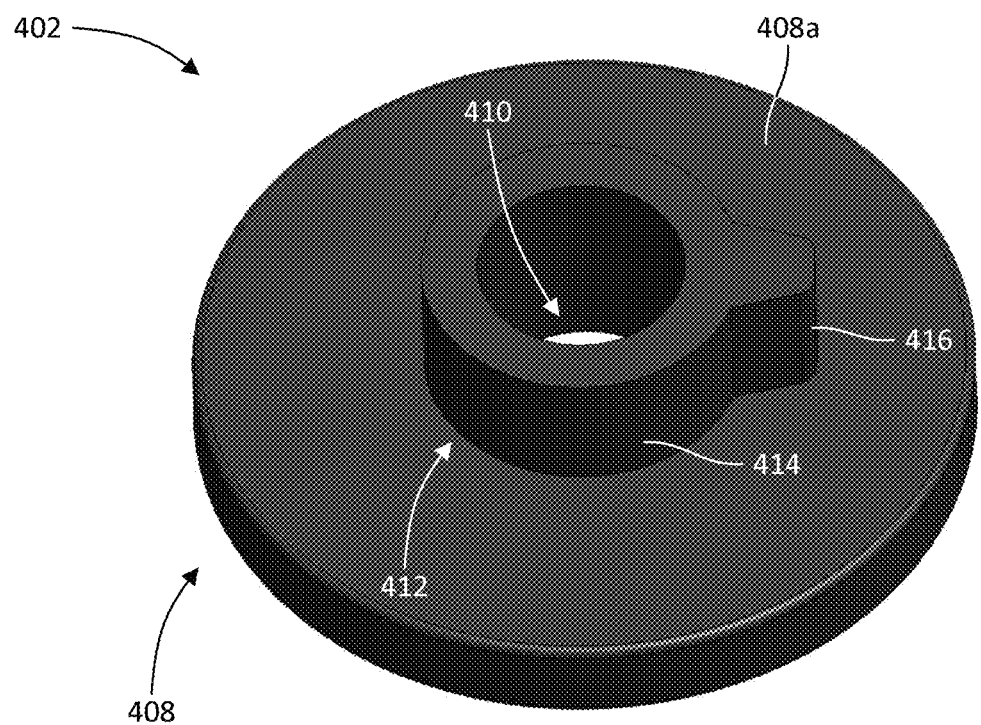
Figure 42B:
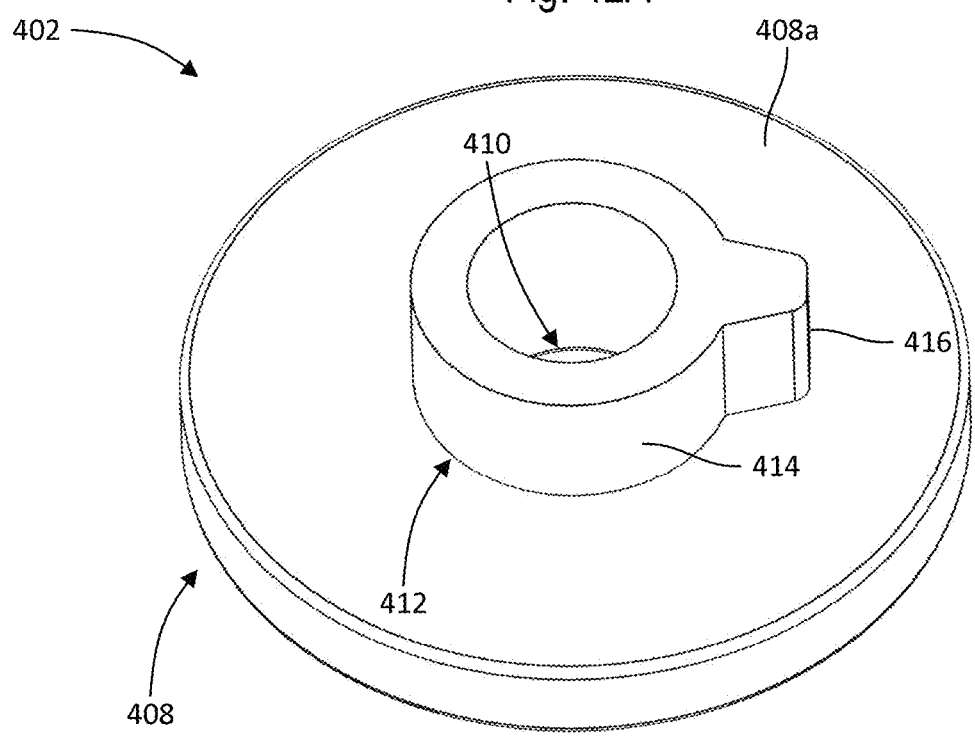
Figure 43A:
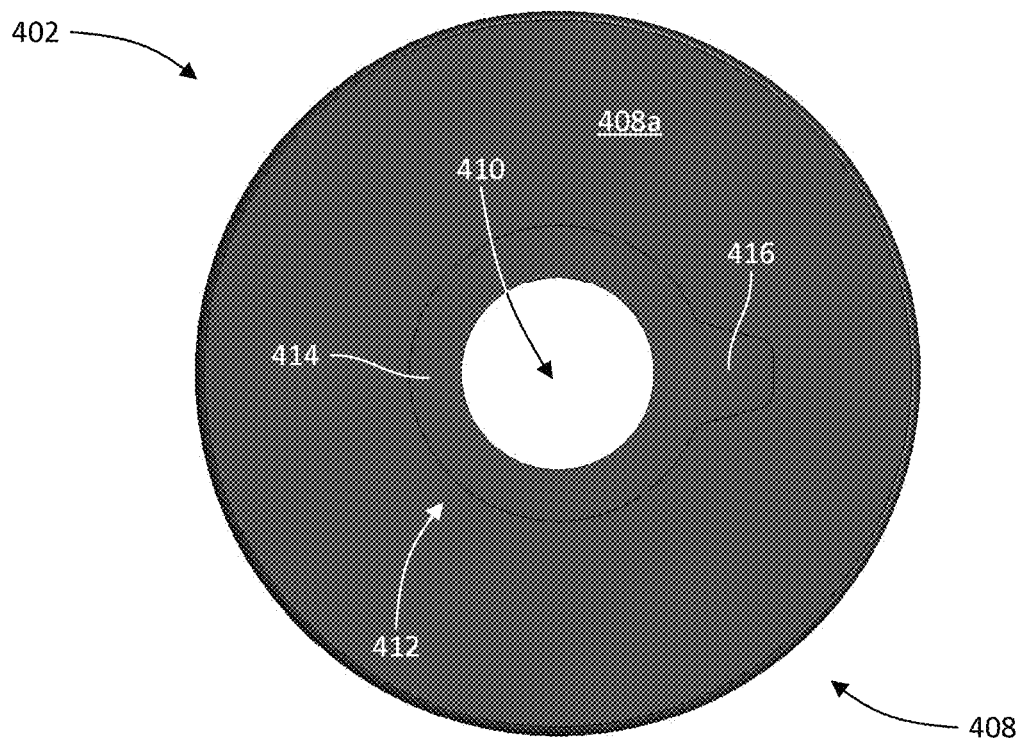
Figure 43B:
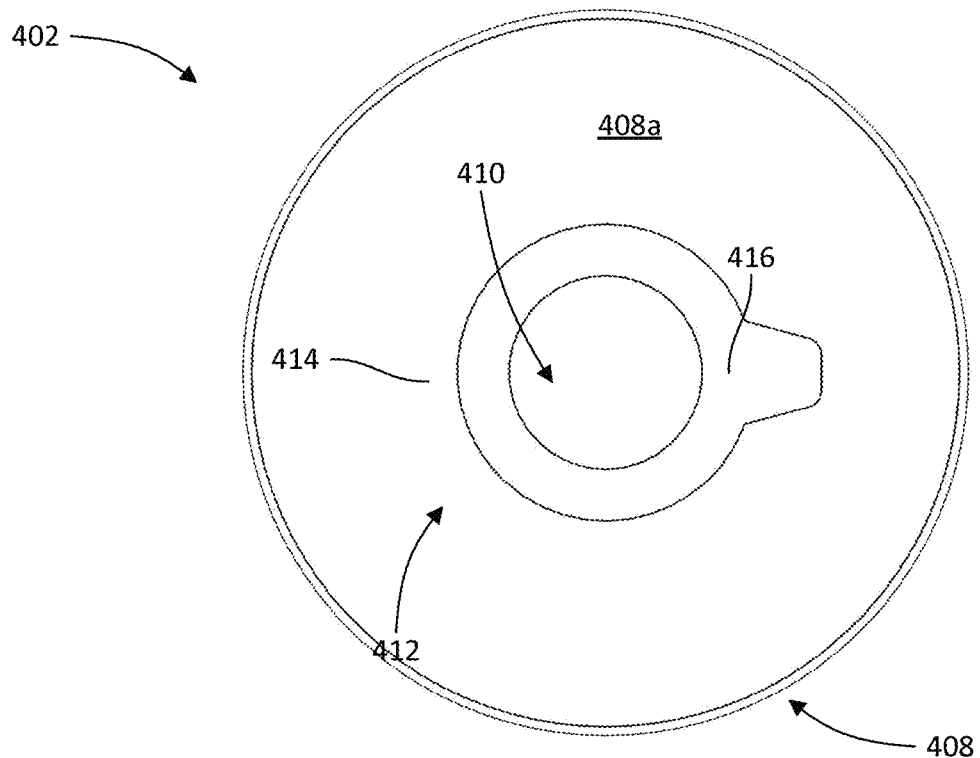
Figure 44A:
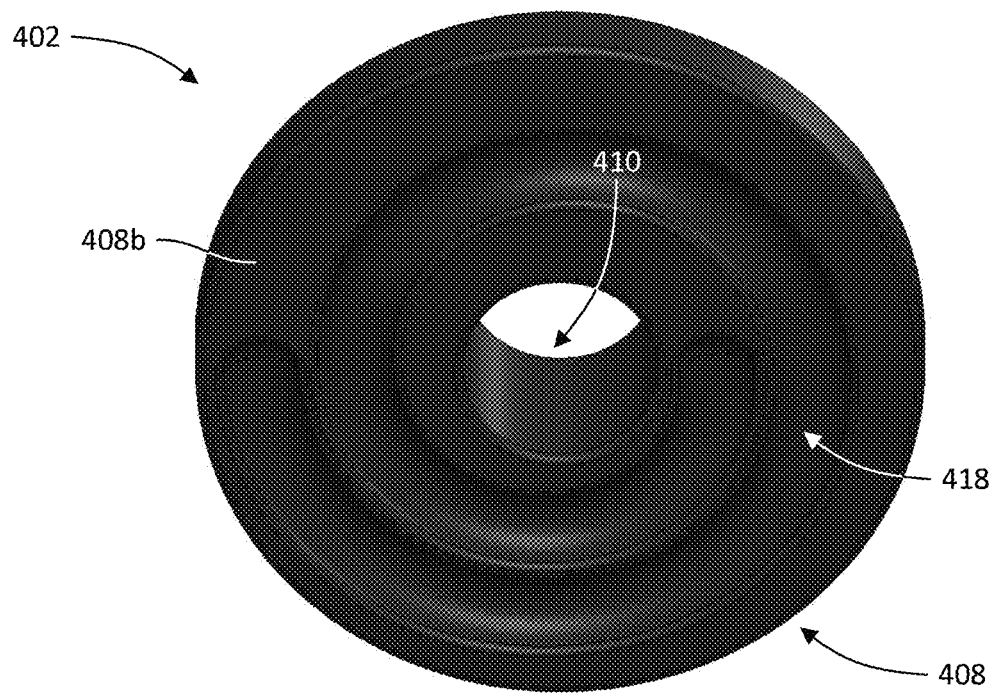
Figure 44B:
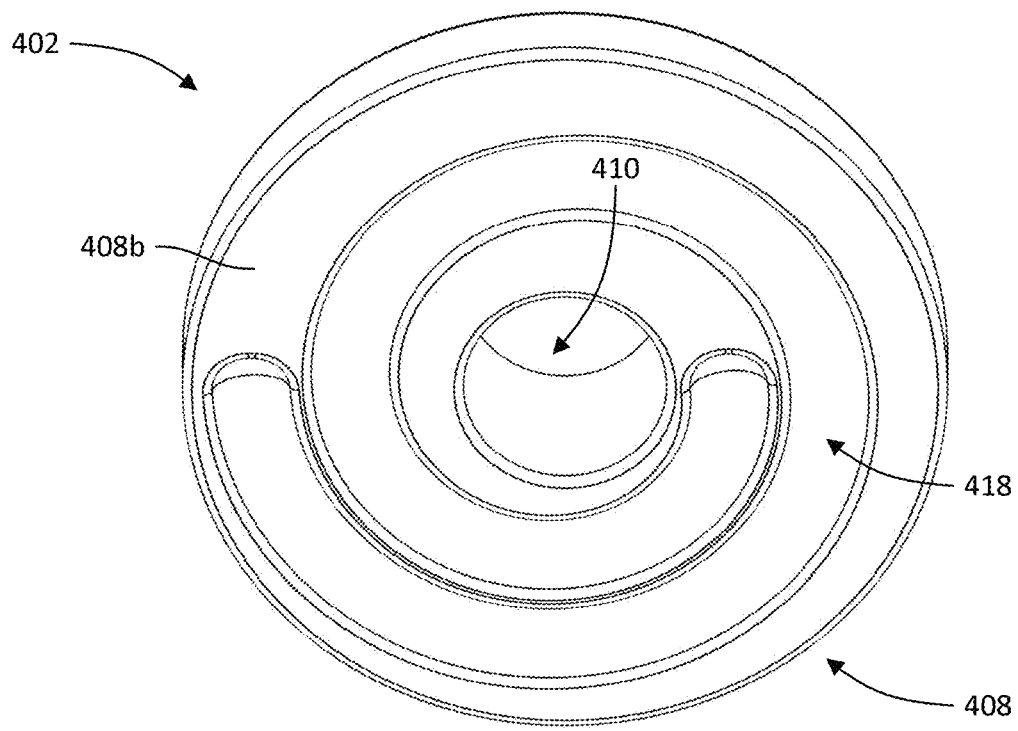
Figure 45A:
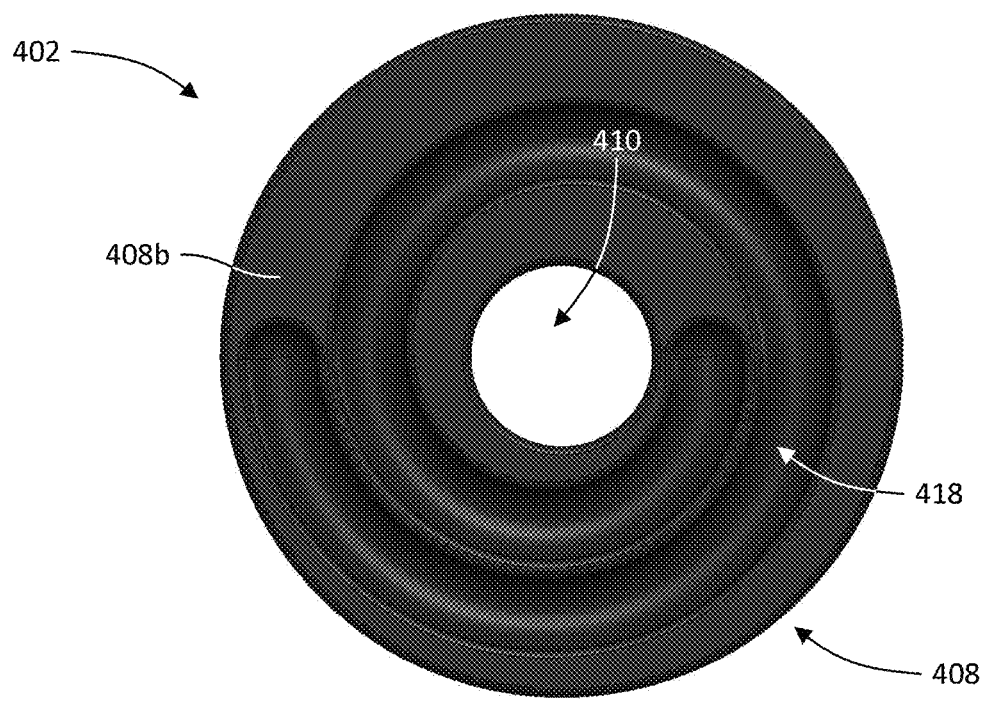
Figure 45B:
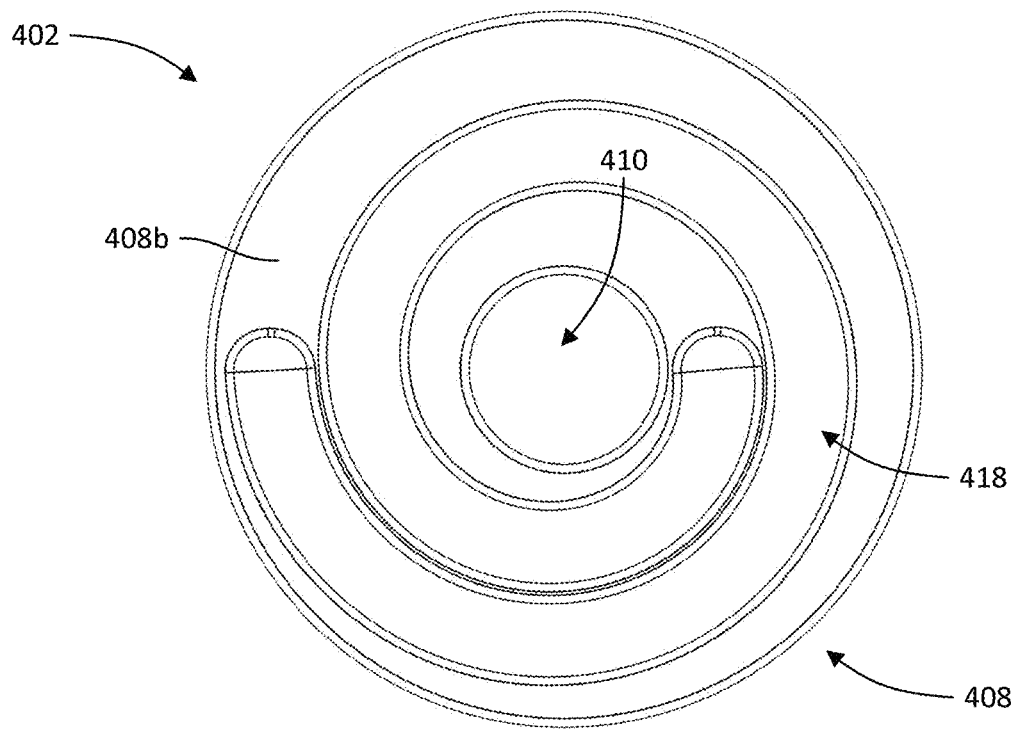
Figure 46A:
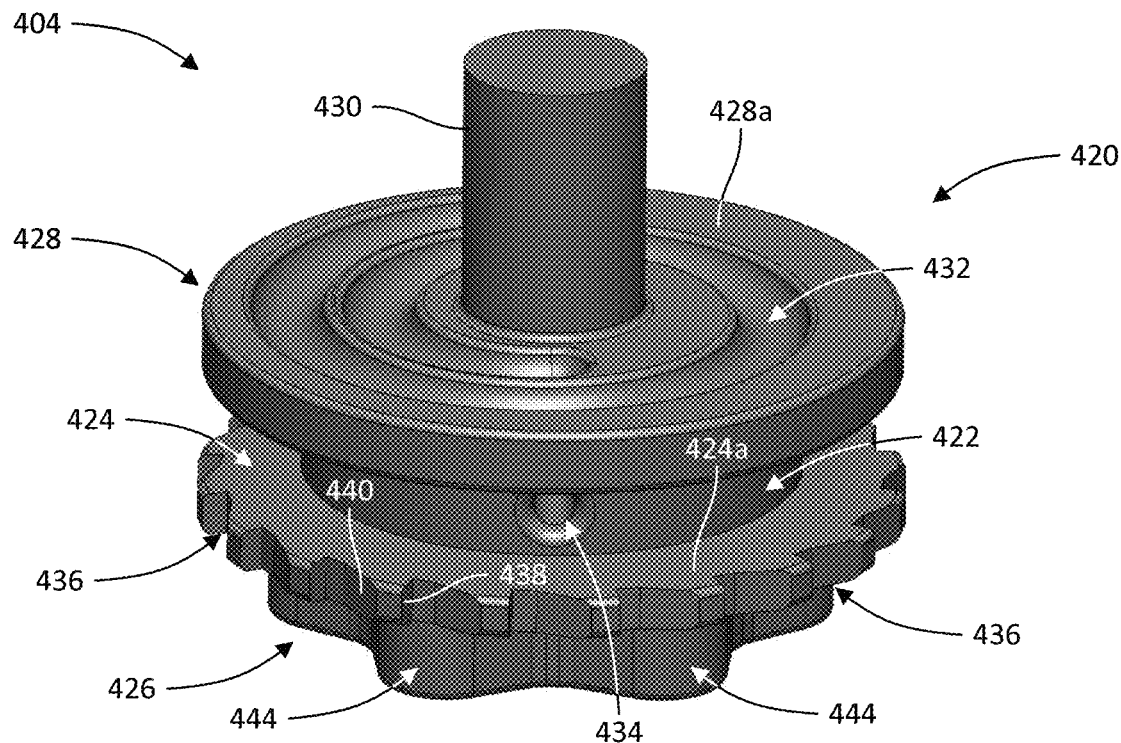
Figure 46B:
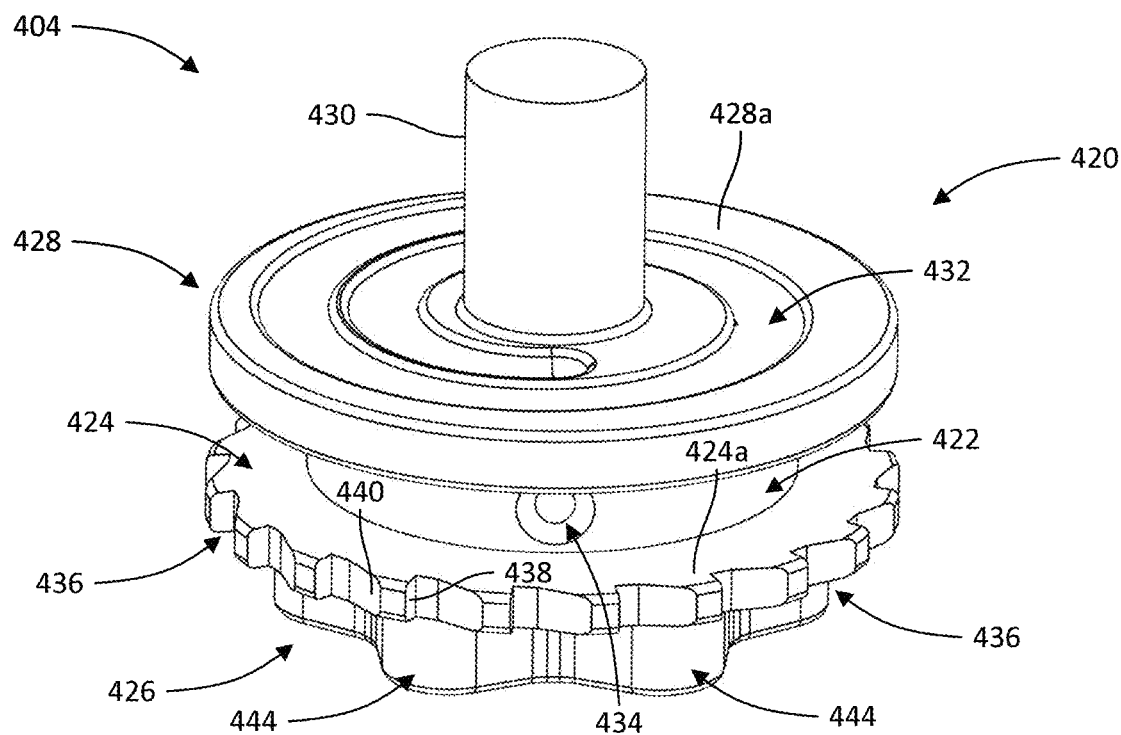
Figure 47A:
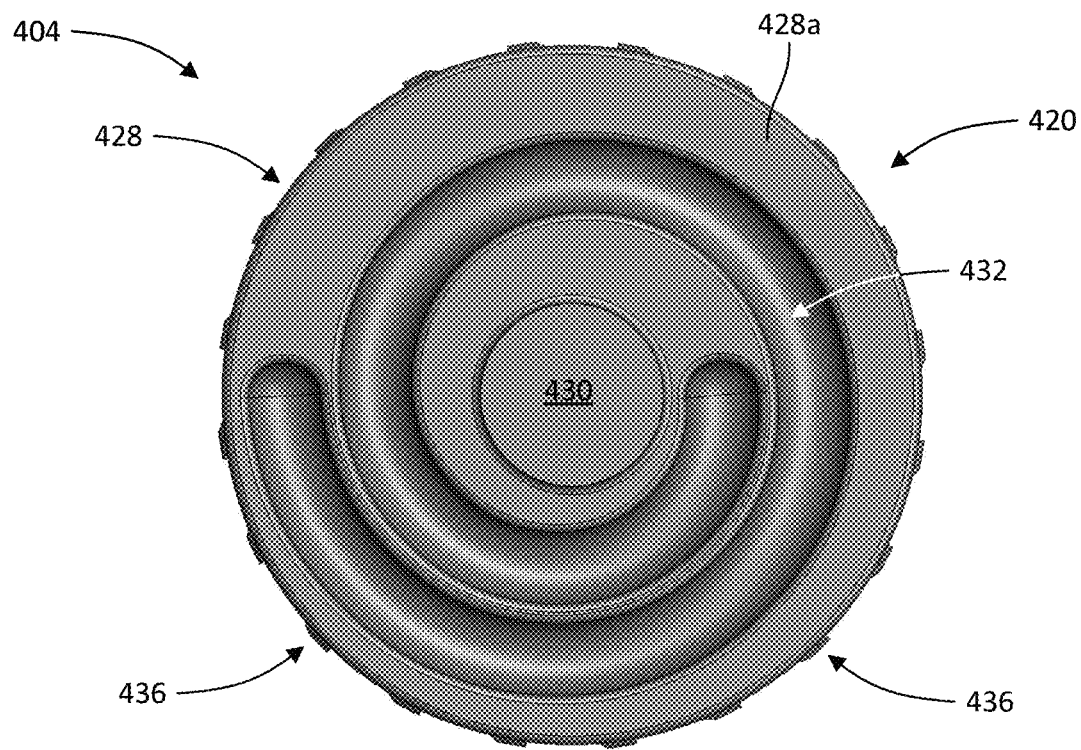
Figure 47B:
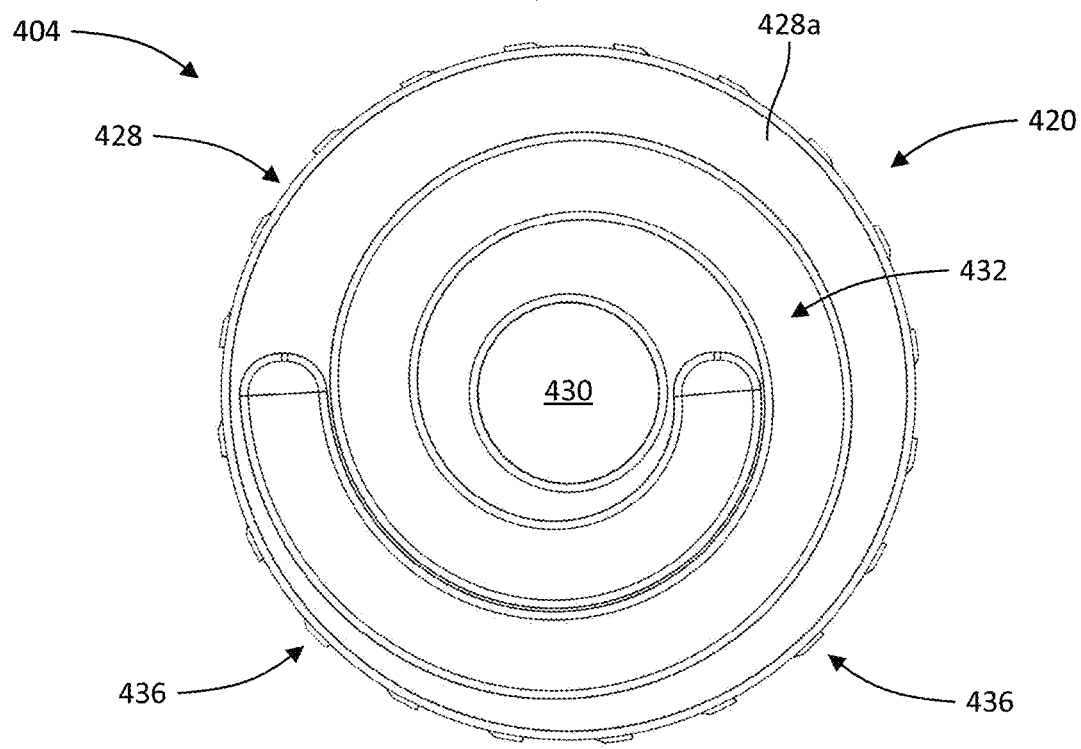
Figure 48A:
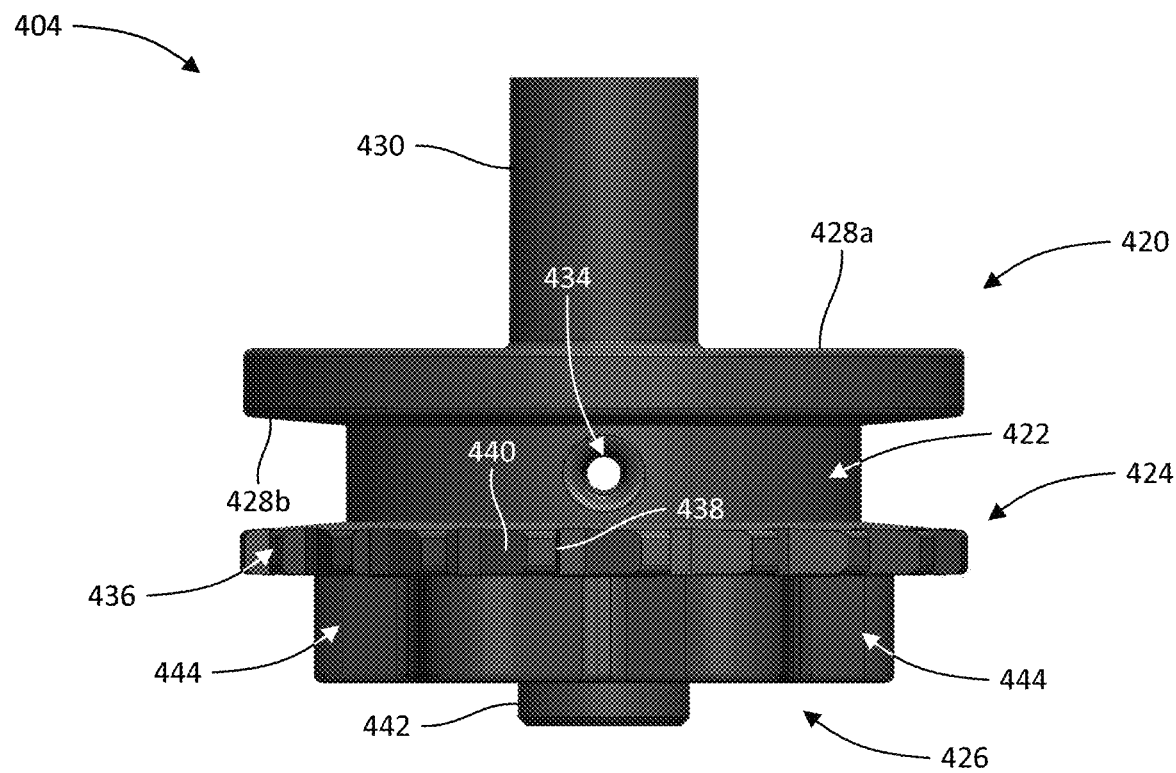
Figure 48B:
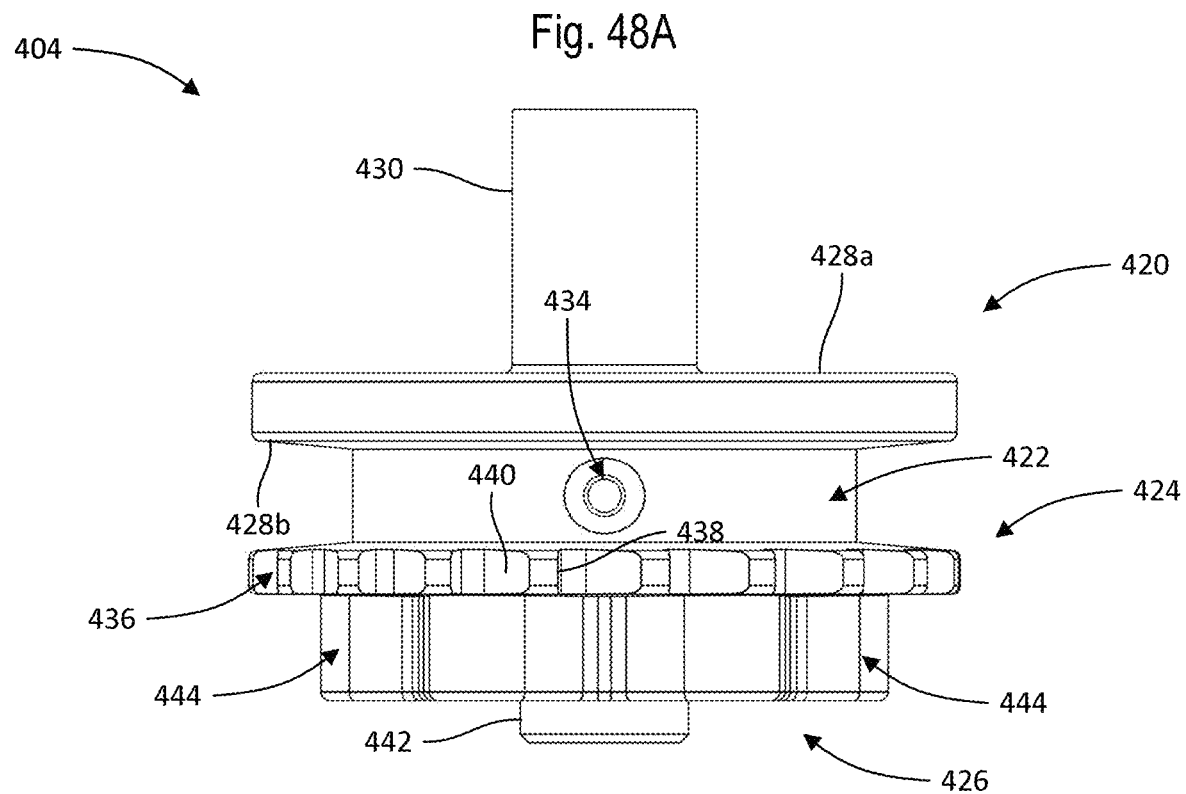
Figure 49A:
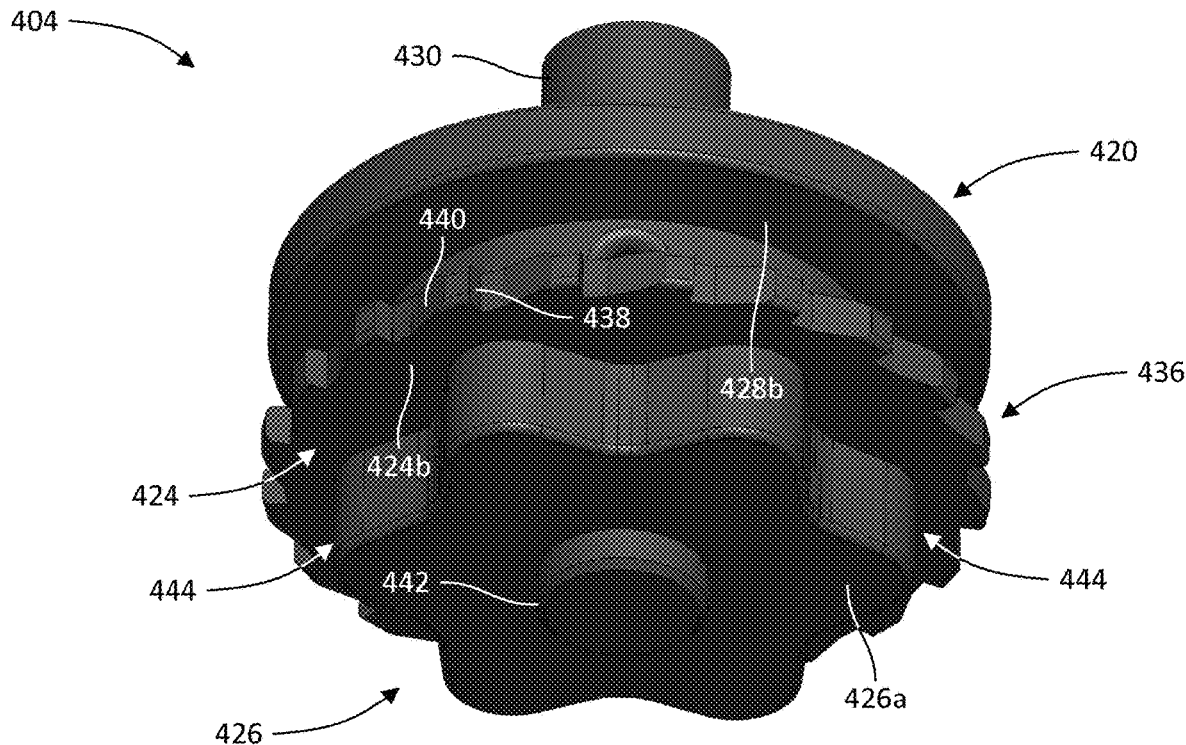
Figure 49B:
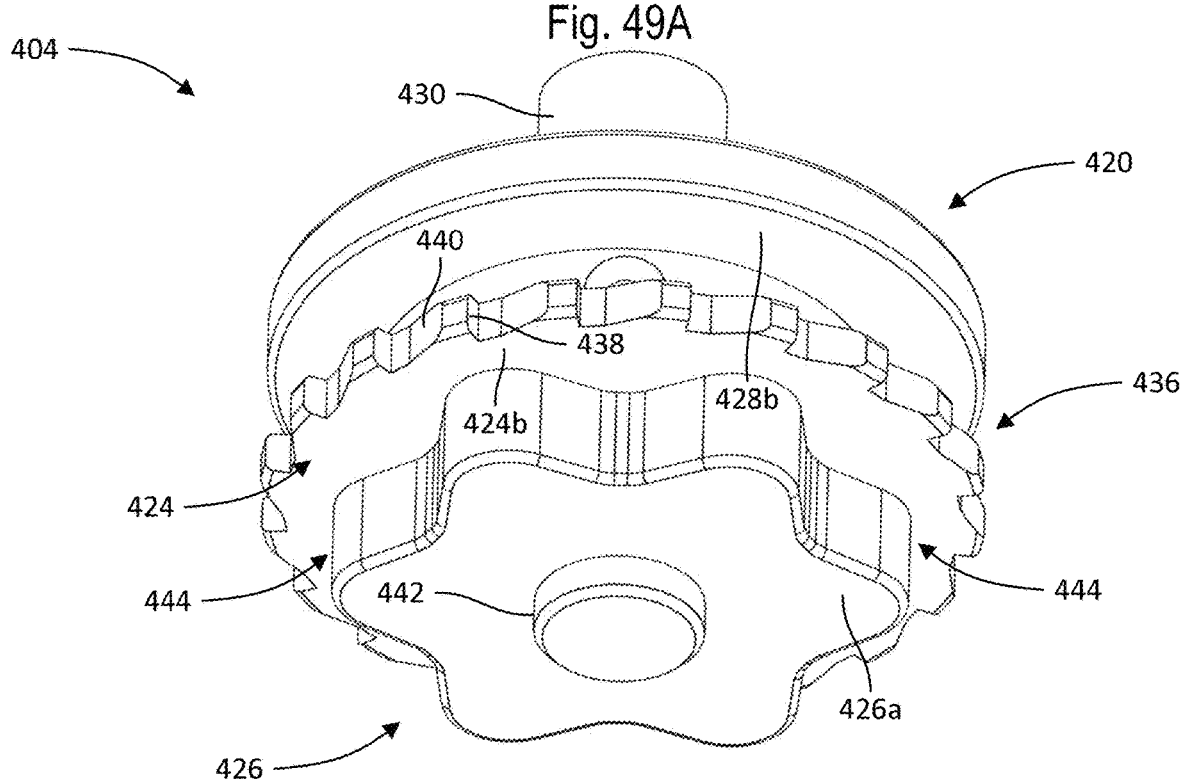
Figure 50A:
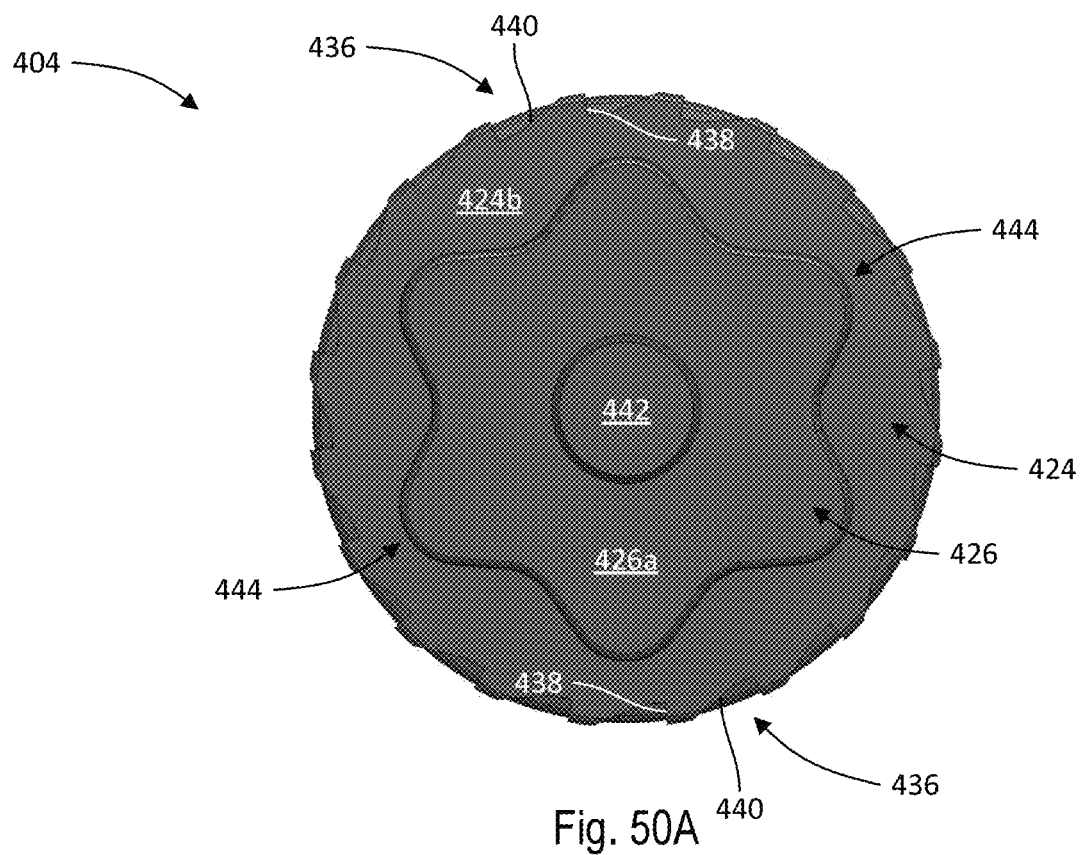
Figure 50B:
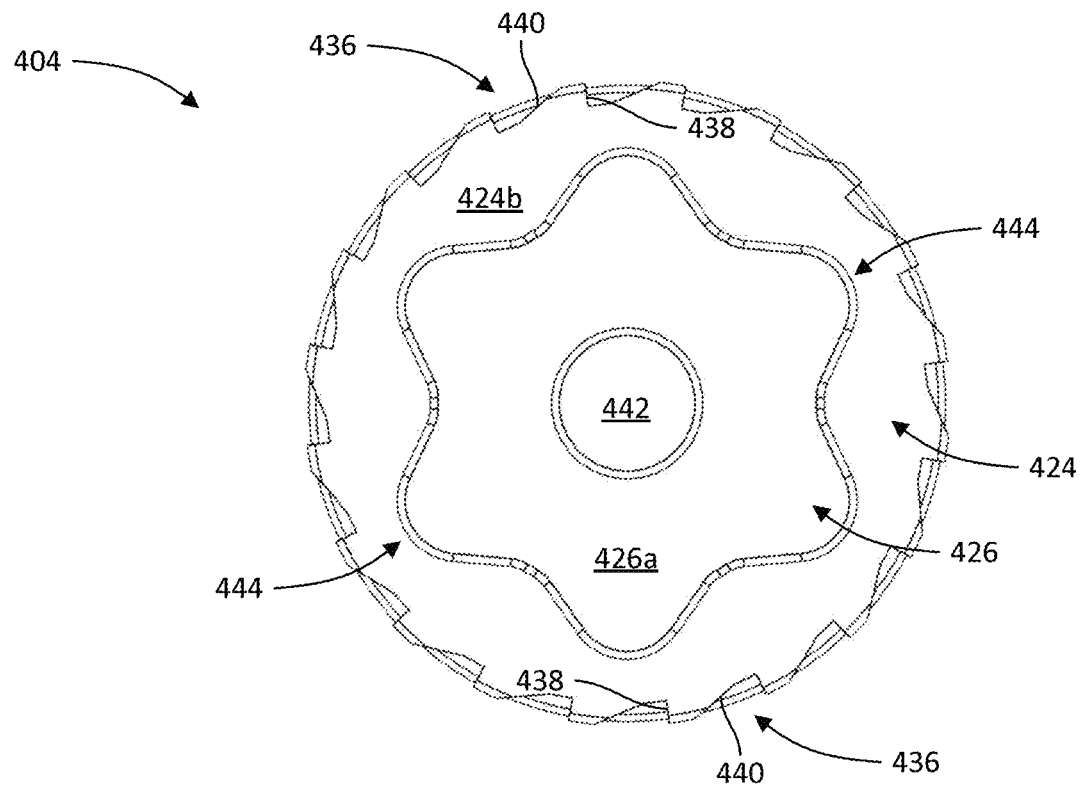
Figure 51A:
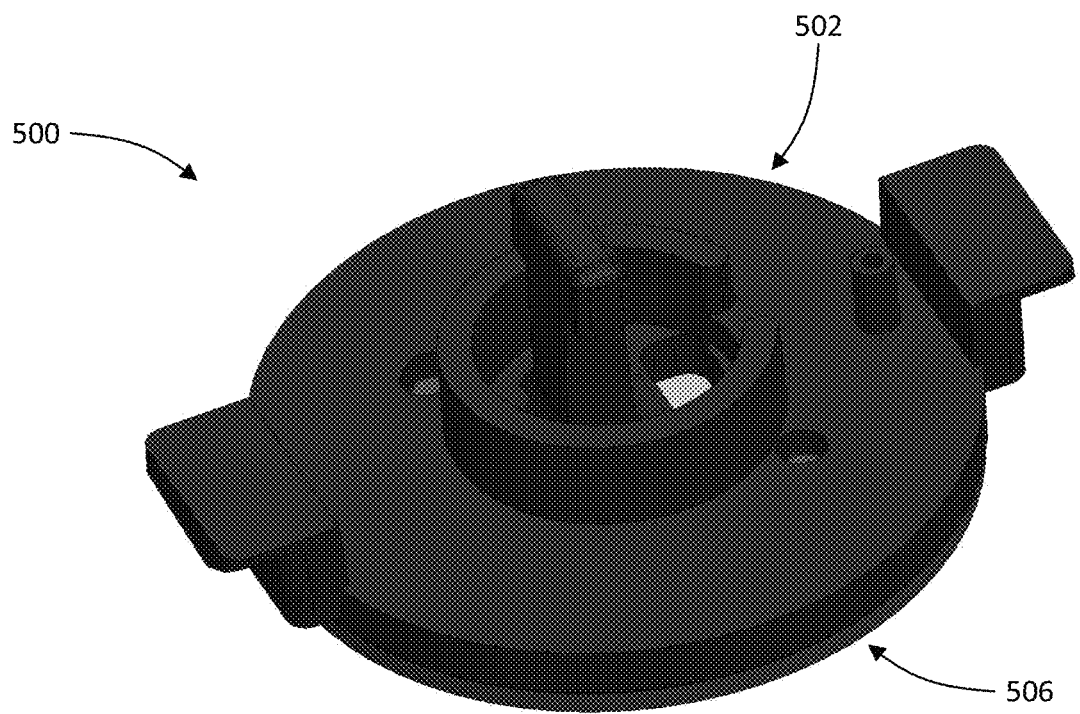
FIGS. 51A, 51B, 52A, and 52B depict a microneedle array assembly of the cartridge of the dermal patch system in accordance with an exemplary embodiment.
Figure 51B:
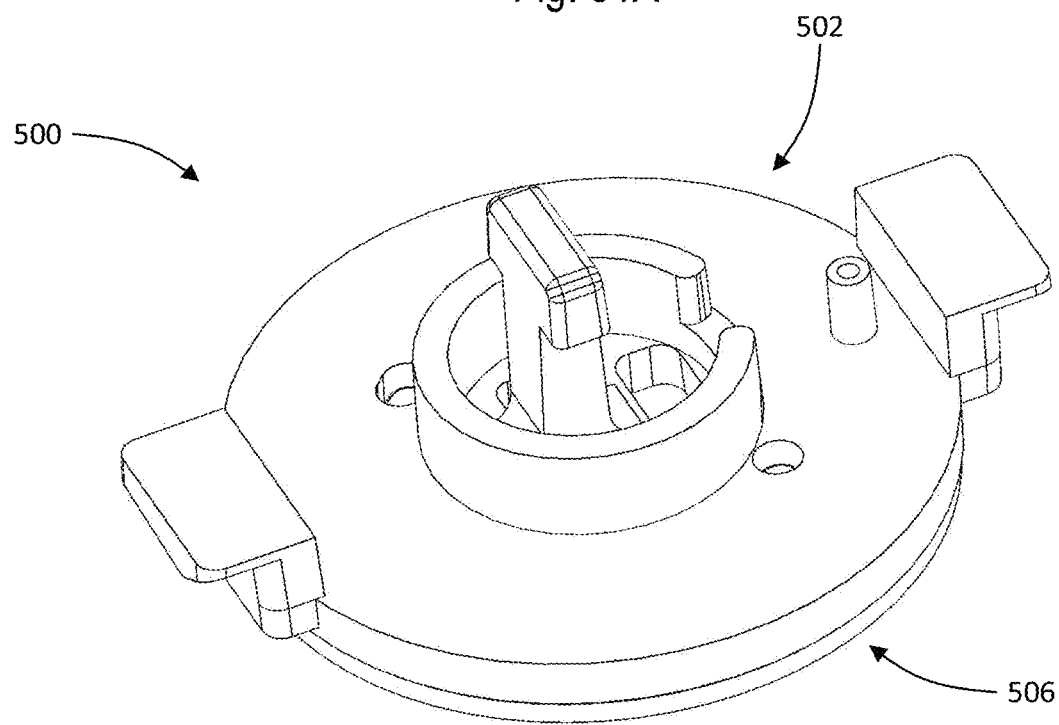
Figure 52A:
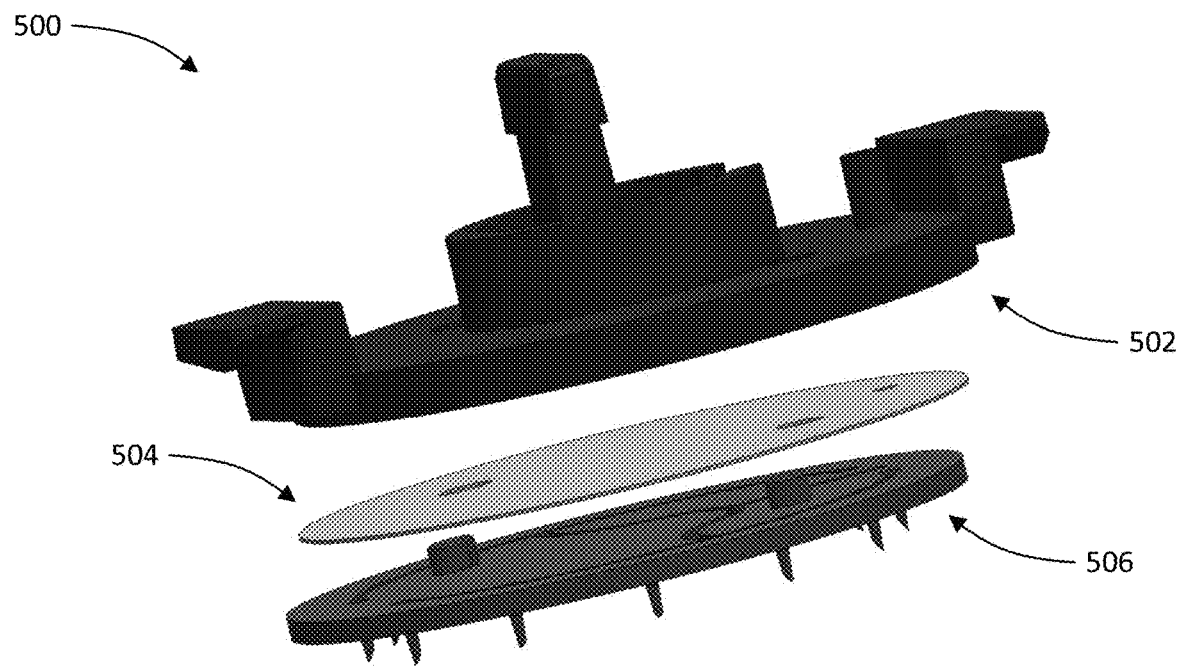
Figure 52B:
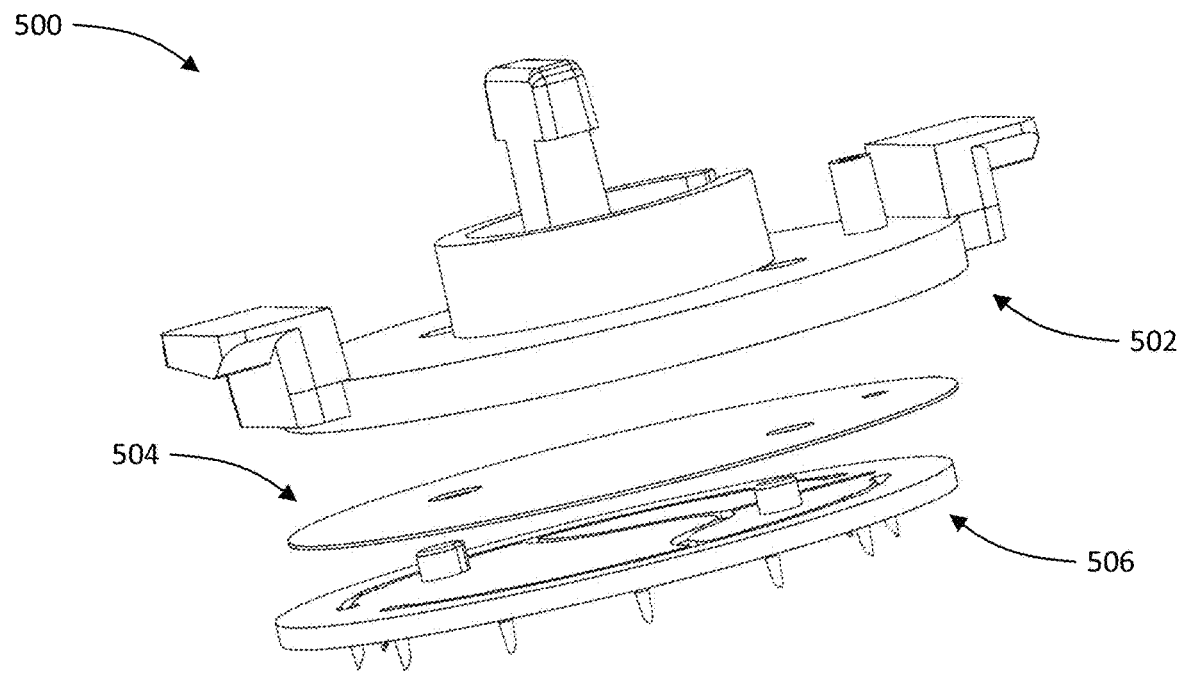
Figure 53A:
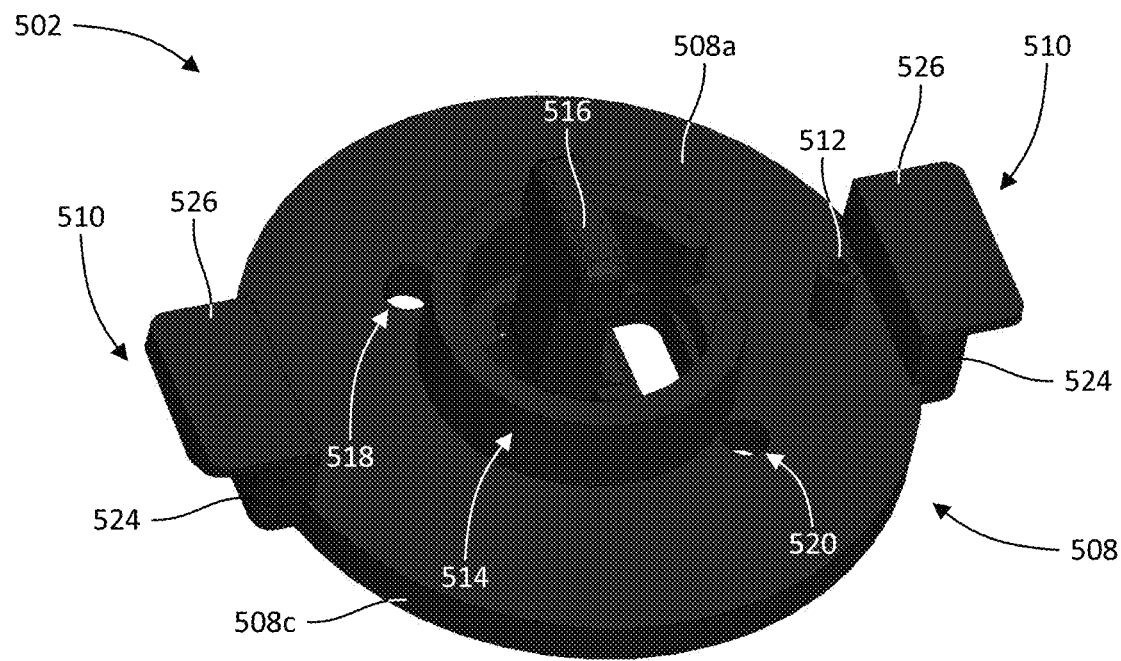
Figure 53B:
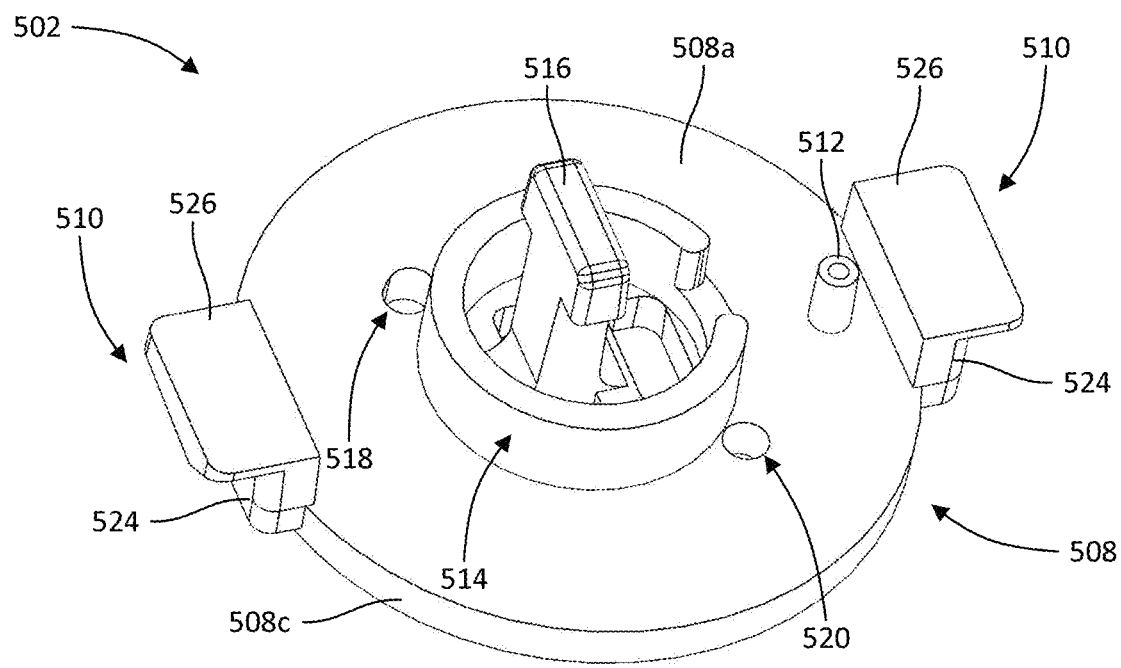
Figure 54B:
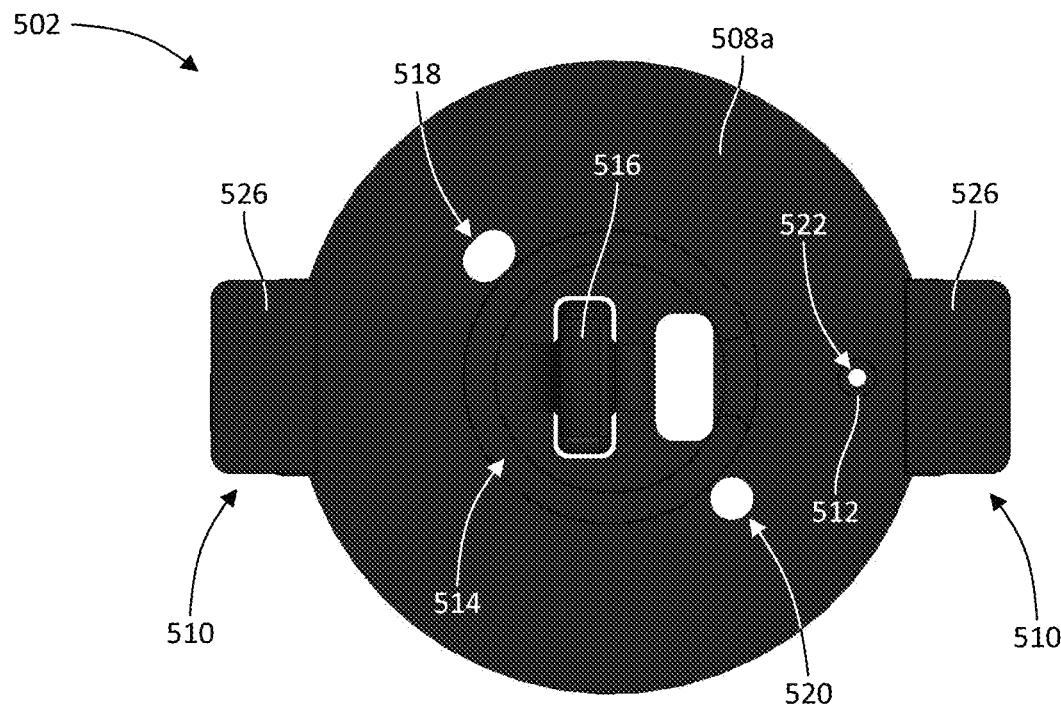
Figure 54A:
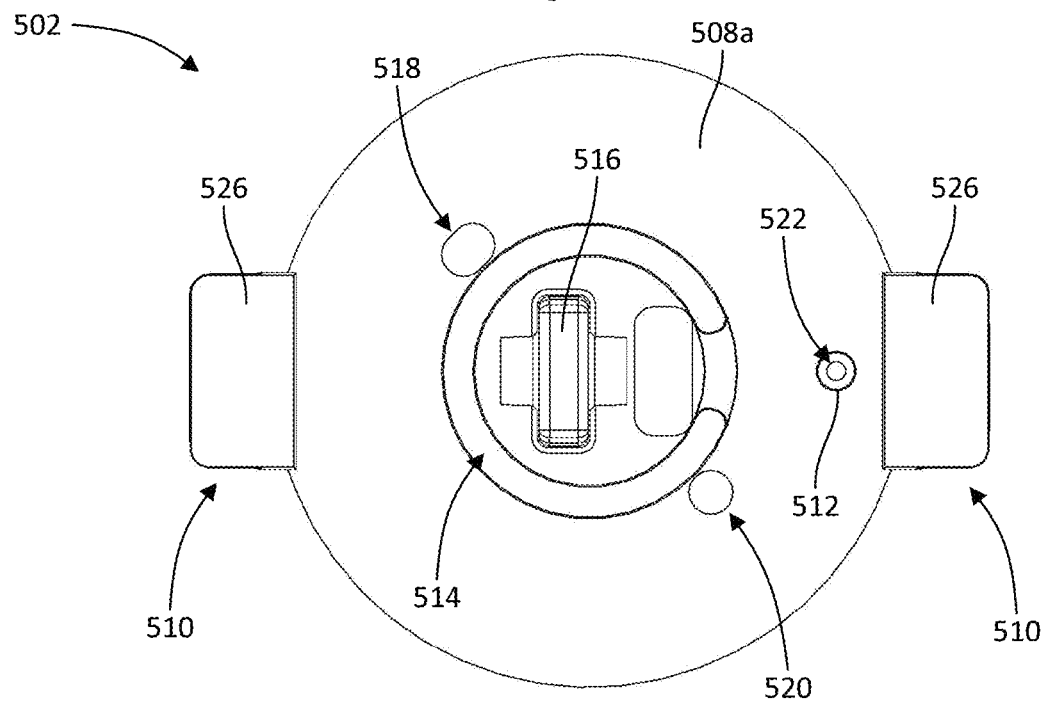
Figure 55A:
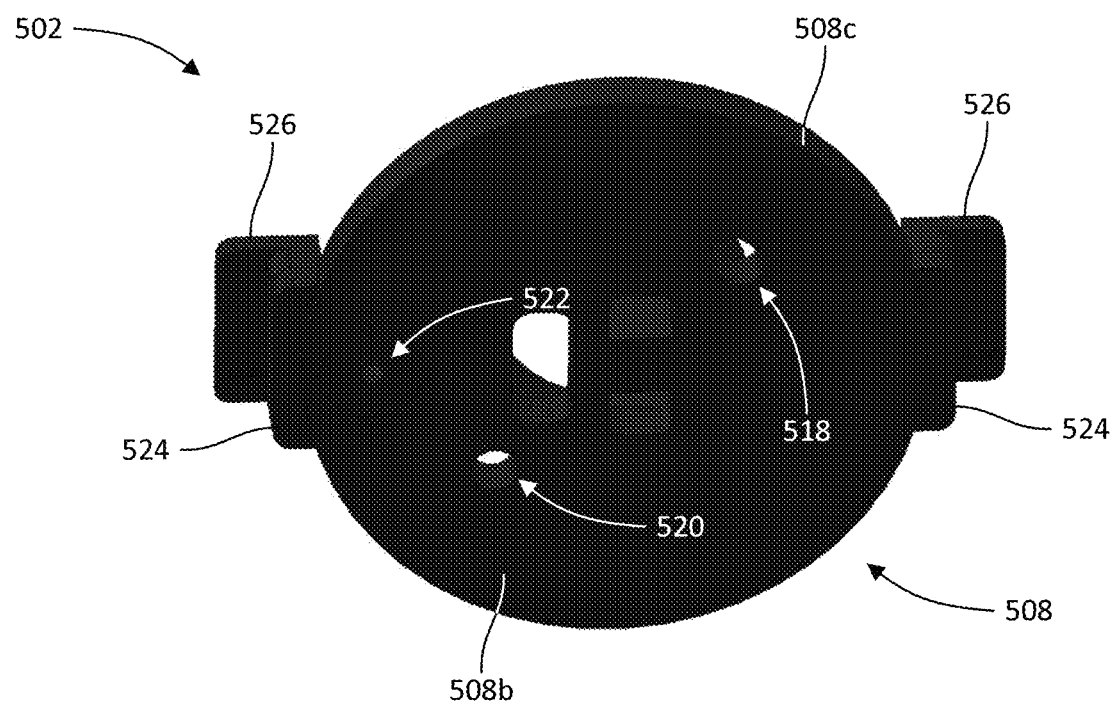
Figure 55B:
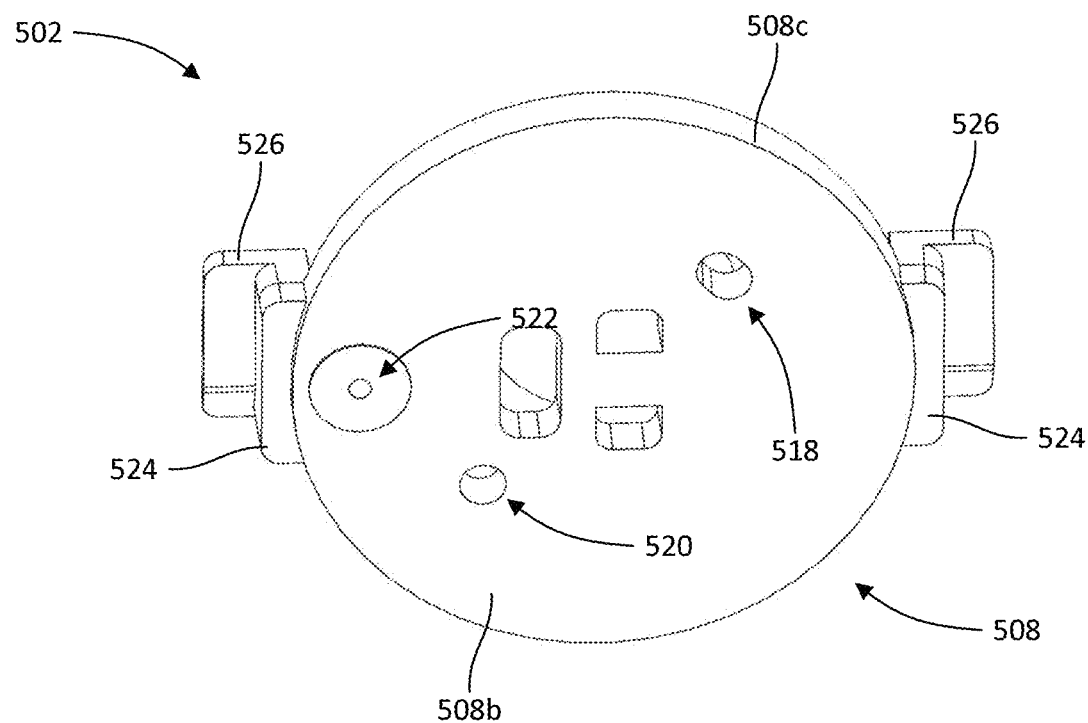
Figure 56A:
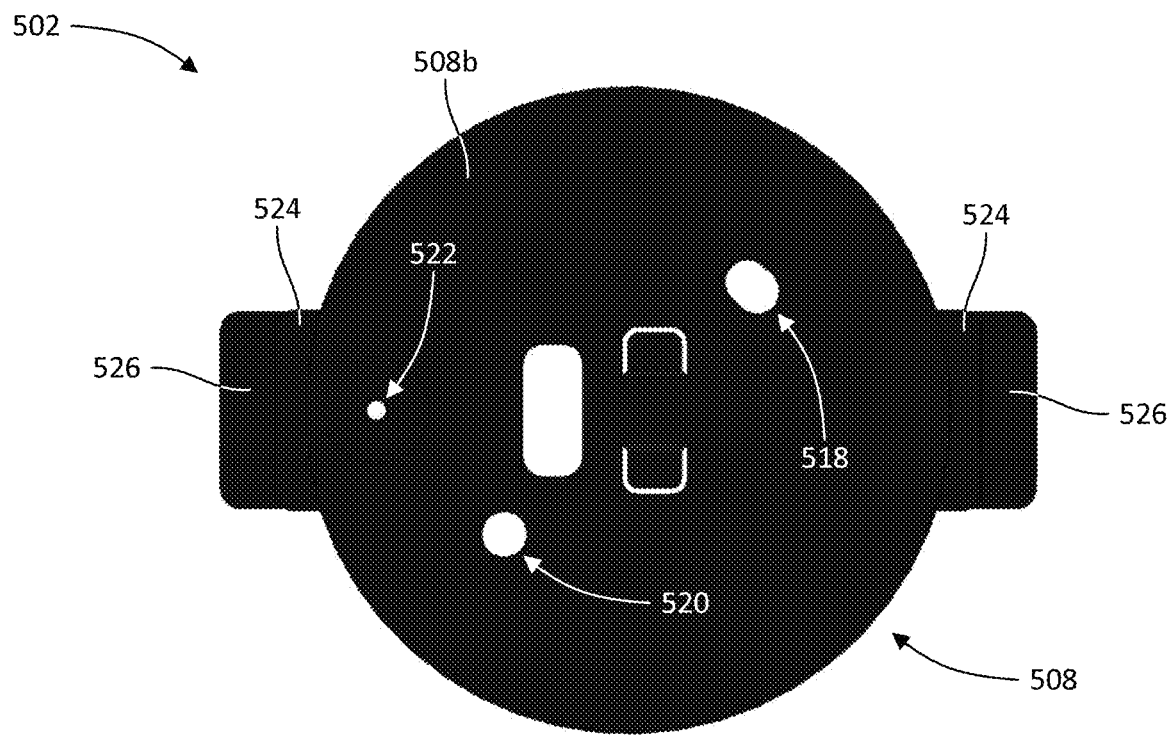
Figure 56B:
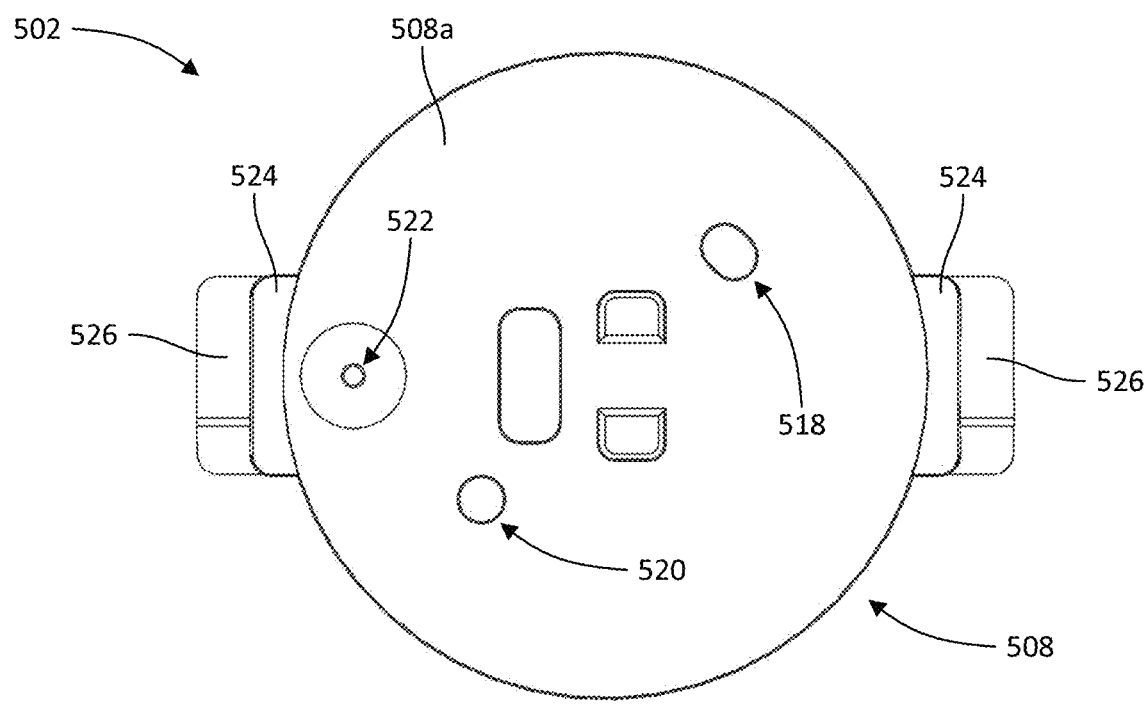

The base 200 further includes a first tube guide 234 and a second tube guide 236 that extend vertically from and the top surface 202a of the bottom wall 202. In some embodiments, as depicted in FIGS. 34A and 34B-36, the cartridge 12 includes a first tube 22 and a second tube 24. In these embodiments, the first tube guide 234 retains the first tube 22 and the second tube guide 236 retains the second tube 24 within the cartridge 10. The tube guides 234 and 236 direct the tubes 22 and 24 around a portion of the pump assembly 400 (FIGS. 3A and 3B). Furthermore, the first tube guide 234 directs the first tube 22 towards the microneedle array assembly 500. The first tube 22 and the second tube 24 fit around the first needle 18 and the second needle 20 respectively. As such, the tubes 22 and 24 are in open communication with the vial 14 via the needles 18 and 20. In other embodiments, the second tube 24 may be omitted. In these embodiments, air may enter the vial 14 via the second needle 20.

With continued reference to FIGS. 14A and 14B-23, the base 200 further includes retention aperture 238 that extends through the bottom wall 202. Stated another way, the retention aperture 238 extends between the top surface 202a and the bottom surface 202b of the bottom wall 202. When the cover 100 is coupled to the base 200, the retention aperture 238 is disposed vertically below the circular retention member 130. As will be discussed in further detail herein, the circular retention member 130 and the retention aperture 238 aid in coupling the pump assembly to the cover 100 and the base 200.

The base 200 also includes a latch 240 that extends vertically from and perpendicular to a portion of the first tube guide 234. As will be discussed in further detail herein, the latch 240 allows the pump to pump the pharmaceutical from the vial and to the microneedle assembly 400. The latch 240 allows the pump assembly 400 to rotate in a clockwise direction and prevents the pump assembly 400 from rotating in a counterclockwise direction. Rotating in the counterclockwise direction would result in the pump assembly 400 failing to pump the pharmaceutical.

The base 200 further includes a microneedle array aperture 242 and a microneedle array housing 244. The microneedle array aperture 242 extends through the bottom wall 202. That is, the microneedle array aperture 242 extends between the top surface 202a and the bottom surface 202b of the bottom wall 202. The microneedle array aperture 242 is shaped and dimensioned to allow a portion of the microneedle array assembly 500 to extend through the bottom wall 202.

The microneedle array housing 244 is generally cylindrical in shape and is shaped and dimensioned to house the microneedle array assembly 500. While the microneedle array housing 244 and the microneedle array assembly 500 are depicted as being cylindrical, it is understood that the microneedle array housing 244 and the microneedle array assembly 500 may have a different shape. The microneedle array housing 244 extends vertically from and perpendicular to the top surface 202a of the bottom wall 202. The microneedle array housing 244 includes a side wall 246 and a top wall 248. The side wall 246 extends vertically between and perpendicular to the top surface 202a of the bottom wall 202 and the top wall 248. The top wall 248 extends longitudinally between the side wall 246. The side wall 246 includes an outer surface 246a and an opposed inner surface 246b. The top wall 248 includes an outer surface 248a and an opposed inner surface 248b.

The microneedle array housing 244 and the bottom wall 202 include a first extension opening 250 and a second extension opening 252 that are positioned on opposite sides of the microneedle array housing 244. The extension openings 250 and 252 extend through the walls 246 and 248. That is, the extension openings 250 and 252 extend between the outer surface 246a and the inner surface 246b of the side wall 246, extend between the surfaces 248a and 248b of the top wall 248, and extend between the top surface 202a and the bottom surface 202b of the bottom wall 202. The microneedle array housing 244 further includes an opening 254 that is positioned between the extension openings 250 and 252. The opening 254 extends through the side wall 246 and the top wall 248. That is, the opening 254 extends between the surfaces 246a and 246b of the side wall 246 and extends between the surfaces 248a and 248b of the top wall 248.

The microneedle array housing 244 also includes a first tensioner opening 256 and a second tensioner opening 258 that are aligned with one another. A portion of the first tensioner opening 256 extends through the side wall 246 and another portion of the first tensioner opening 256 extends through the bottom wall 202. That is, the first tensioner opening 256 extends between the outer surface 246a and the inner surface 246b of the side wall 246 and extends between the top surface 202a and the bottom surface 202b of the bottom wall 202. The second tensioner opening 258 extends through the top wall 248 of the microneedle array housing 244. That is, the second tensioner opening 258 extends between the outer surface 248a and the inner surface 248b of the top wall 248.

The top wall 248 of the microneedle array housing 244 also includes a microneedle array assembly aperture 260 that extends through the top wall 248 of the microneedle array housing 244. That is, the microneedle array assembly aperture 260 extends between the outer surface 246a and the inner surface 246b of the wall 246. The top wall 248 of the microneedle array housing 244 also includes a first and second trigger guide 262. The trigger guides 262 extend vertically from and perpendicular to the outer surface 248a of the top wall 248. The trigger guides 262 are positioned on opposite sides of the microneedle array assembly aperture 260.

The microneedle array housing 244 further includes a first partially circular projection 264 and a second partially circular projection 266 that extend vertically from and perpendicular to the inner surface 248b of the top wall 248.

Referring again to FIGS. 14A and 14B-23, the base 200 includes a first button guide 270 and a second button guide 272 that extend vertically from and perpendicular to the top surface 202a of the bottom wall 202. The first and second button guides 270 and 272 extend along opposite sides of the microneedle array housing 244. Furthermore, the first button guide 270 extends along the first extension opening 250 and the second button guide 272 extends along the second extension opening 252. As will be discussed in further detail herein, the first and second button guides 270 and 272 direct a portion of the retraction button 600 towards the first extension opening 250 and second extension opening 252. The base 200 further includes a third button guide 274. The third button guide 274 extends vertically from and perpendicular to the top surface 202a of the bottom wall 202. The third button guide 274 is disposed between the first and second button guides 270 and 272 and is aligned with the opening 254 of the microneedle array housing 244. As will be discussed in further detail herein, the third button guide 274 directs a portion of the retraction button 600 towards the opening 254.

Referring now to FIGS. 37A and 37B-39A and 39B, the pull mechanism 300 is shown in accordance with an exemplary embodiment. The pull mechanism 300 includes a handle 302 and a cord 304 that is connected to the handle 302.

The handle 302 includes a grip 306, a ball retention feature 308, and an anchor portion 310. The grip 306 defines a distal end of the handle 302 and the ball retention feature 308 defines a proximal end of the handle 302.

The ball retention feature 308 includes a rounded inner surface 312, a cylinder 314 and an angled surface 316. As will be discussed in further detail herein, the rounded inner surface 312, the cylinder 314, and the angled surface 316 are shaped and dimensioned to retain a ball 21 of the cartridge 12 when the cartridge 12 is in a given orientation and is shaped and dimensioned to release the ball 21 when the cartridge 12 is in any other orientation. The ball retention feature 308 includes a first outer surface 318 and a second outer surface 320. The outer surfaces 318 and 320 have a similar shape and dimensioned as the first handle retention grove and the second handle retention grove which allows the handle retention features 114 and 224 to retain the handle 302 of the pull mechanism 300.

The anchor portion 310 includes an aperture 322 that extends through the anchor portion 310. The cord 304 extends through the aperture 322 which allows securing the cord 304 to the anchor portion 310.

Referring now to FIGS. 40A and 40B-50A and 50B, the pump assembly 400 is shown in accordance with an exemplary embodiment. In this embodiment, the pump assembly 400 includes a trigger portion 402 and a pump portion 404 that are coupled to one another. The pump assembly 400 also includes a ball 406 that is disposed between the trigger portion 402 and the pump portion 404.

The trigger portion 402 includes a base 408 with a top surface 408a and an opposed bottom surface 408b. The base 408 includes an aperture 410 that extends through the base 408. That is, the aperture 410 extends between the top surface 408a and the bottom surface 408b. The trigger portion 402 further includes a latch 412 which extends vertically from and perpendicular to the top surface 408a of the base 408. The latch 412 includes a circular portion 414 and an extension 416. The circular portion extends circumferentially around the aperture 410 and the extension 416 extends longitudinally from and perpendicular to the circular portion 414. The bottom surface 408b of the base 408 defines a spiral groove 418. The spial groove 418 is shaped and dimensioned to retain the ball 406 therein.

With reference to FIGS. 46A and 46B-50A and 50B, the pump portion 404 includes a top portion 420, a middle support portion 422, a ratchet 424, and a cog 426.

The top portion 420 includes a base 428 with a top surface 428a and an opposed bottom surface 428b. The top portion 420 further includes a top cylinder 430 that extends vertically from and perpendicular to the top surface 428a of the base 428. When the trigger portion 402 is coupled to the pump portion 404, the top cylinder 430 extends through the aperture 410 and beyond the circular portion 414 of the latch 412. Furthermore, when the pump assembly 400 is disposed within the cartridge 12, the top cylinder 430 extends into the circular retention member 130 of the cover 100 which aids in coupling the pump assembly 400 to the cover 100. As will be discussed in further detail herein, the circular retention member 130 maintains the pump assembly 400 in a given position while allowing the pump assembly 400 to rotate.

The top surface 428a of the base 428 defines a spiral groove 432 that is shaped and dimensioned to retain the ball 406 therein. The base 408 of the trigger portion 402 has a similar shape and dimension as the base 428. Furthermore, the spiral groove 418 of the base 408 and the spiral groove 432 of the base 428 have a similar shape and dimension and when the trigger portion 402 is coupled to the pump portion 404, the spiral grooves 418 and 432 align with one another and retain the ball 406 therebetween. Together, the spiral groove 418 and the spiral groove 432 are referred to as a spiral ball retention groove.

The middle support portion 422 includes an aperture 434 that extends longitudinally through the middle support portion 422. The aperture 434 is shaped and dimensioned to accept the cord 304 of the pull mechanism 300 which allows the cord 304 to detachably couple to the pump assembly 400. As depicted in FIGS. 4A and 4B, when coupled to the pump assembly 400 via the aperture 434, the cord 304 wraps around the middle support portion 422.

The ratchet 424 includes a top surface 424a and an opposed bottom surface 424b. Furthermore, the middle support portion 422 extends vertically between the bottom surface 428b of the base 428 and the top surface 424a of the ratchet 424. The ratchet 424 also includes a plurality of teeth 436 that extend circumferentially around the ratchet 424 and extends vertically between the top surface 424a and the bottom surface 424b. Each tooth 436 includes a vertical surface 438 and an angled surface 440. As depicted in FIGS. 3A and 3B, the latch 240 is disposed between two teeth 436. When the pump assembly 400 is rotated in the clockwise direction, the angled surfaces contact the latch 240 as the pump assembly is rotated. When the pump assembly 400 is rotated in the counterclockwise direction, a vertical surface 438 of a tooth 436 is pushed into the latch 240 which prevents the pump assembly 400 from rotating in the counterclockwise direction.

The cog 426 extends vertically from and perpendicular to the bottom surface 424b of the ratchet 424. The cog 426 includes a bottom surface 426a and the pump portion 404 includes a bottom cylinder 442 that extends vertically from and perpendicular to the surface 426a of the cog 426. When the pump assembly 400 is disposed within the cartridge 12, the bottom cylinder 442 extends into the retention aperture 238 of the base 200 which aids in coupling the pump assembly 400 to the base 200 and maintains the pump assembly 400 in a given position while allowing the pump assembly 400 to rotate. The cog 426 includes a plurality protrusions 444. As will be discussed in further detail herein, when the pump assembly 400 rotates, the cog 426 acts as a peristaltic pump as the protrusions force a pharmaceutical through the first tube 22 via positive displacement.

Referring now to FIGS. 51A, 51B and 52A and 52B, the microneedle array assembly 500 is shown in accordance with an exemplary embodiment. In this embodiment, the microneedle array assembly 500 includes a microneedle array holder 502, an adhesive film 504, and a microneedle array platform 506.

As depicted in FIGS. 53A and 53B-56A and 56B, the microneedle array holder 502 includes a circular base 508 extensions 510, a hollow cylinder 512, a circular projection 514, and a T-shaped column 516. The base 508 includes a top surface 508a, an opposed bottom surface 508b, and a side surface 508c that extends vertically between and perpendicular to the top surface 508a and the bottom surface 508b. The base 508 further includes a first circular opening 518 and a second circular opening 520 positioned on opposing sides of the circular projection 514. The base 508 also includes a circular aperture 522 that is positioned adjacent to an extension 510. The openings 518 and 520 and the circular aperture 522 extend through the base 508. That is the openings 518 and 520 and the circular aperture 522 extend between the top surface 508a and the bottom surface 508b of the base 508.

The extensions 510 include a vertical portion 524 and a horizontal portion 526. The vertical portion 524 extends longitudinally from and perpendicular to the side surface 508c of the base 508 and extends vertically from and perpendicular to the top surface 508a of the base 508. The horizontal portion 526 extends longitudinally from and perpendicular to the vertical portion 524.

The hollow cylinder 512 extends vertically from and perpendicular to the top surface 508a of the base 508. Furthermore, the hollow cylinder 512 extends circumferentially around the circular aperture 522 such that an opening extends through the hollow cylinder 512 and through the base 508.

Figure 71:
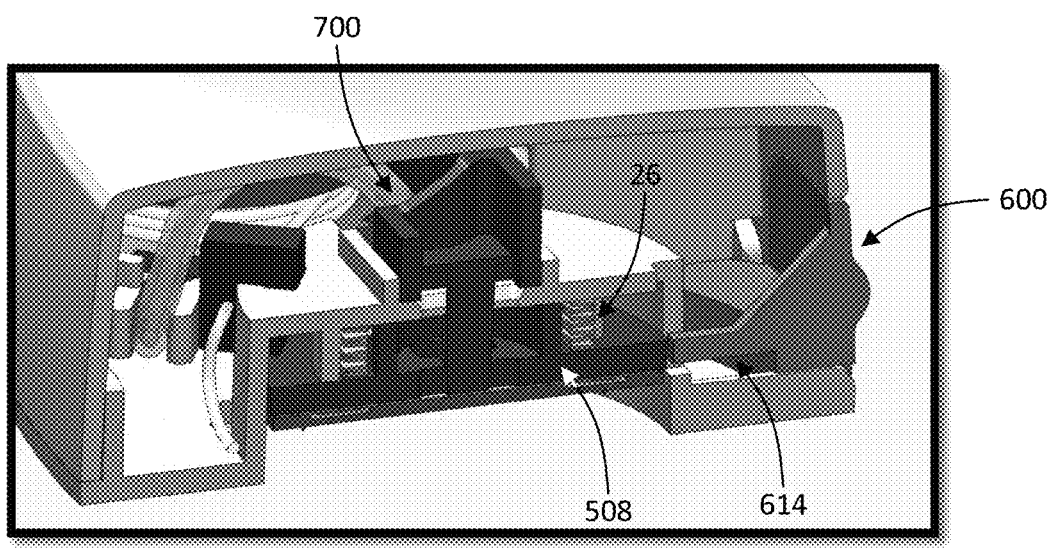
FIG. 71 depicts a retraction button of the cartridge contacting a microneedle array assembly of the cartridge in accordance with an exemplary embodiment.
Figure 72:
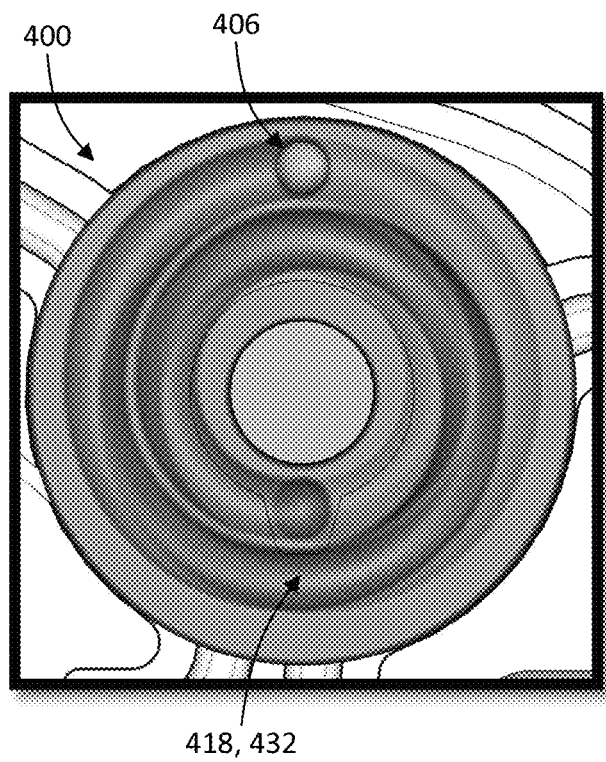
FIG. 72 depicts a ball of a pump assembly of the cartridge in a first position within the pump assembly in accordance with an exemplary embodiment.
Figure 73:
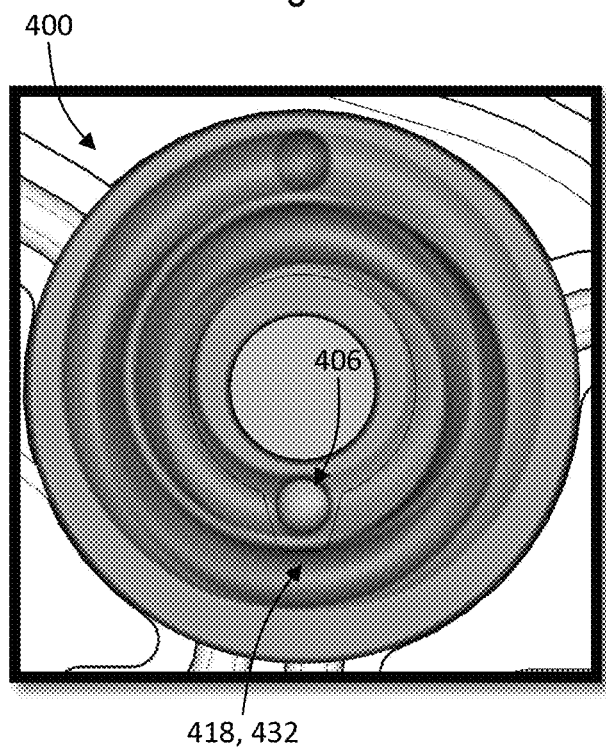
FIG. 73 depicts a ball of a pump assembly of the cartridge in a second position within the pump assembly in accordance with an exemplary embodiment.
Figure 76:
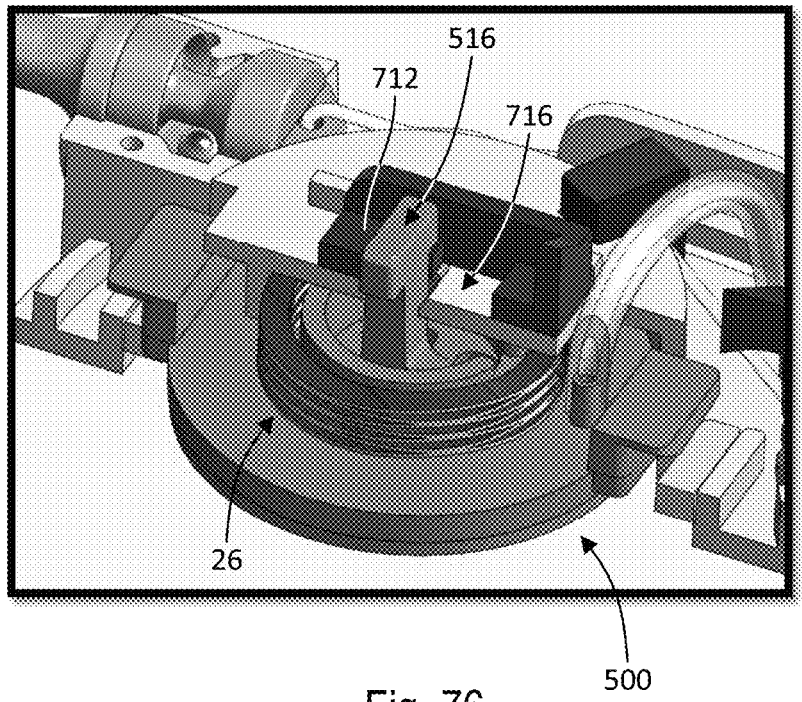
FIG. 76 depicts a microneedle array of the cartridge in an undeployed position in accordance with an exemplary embodiment.
Figure 77:
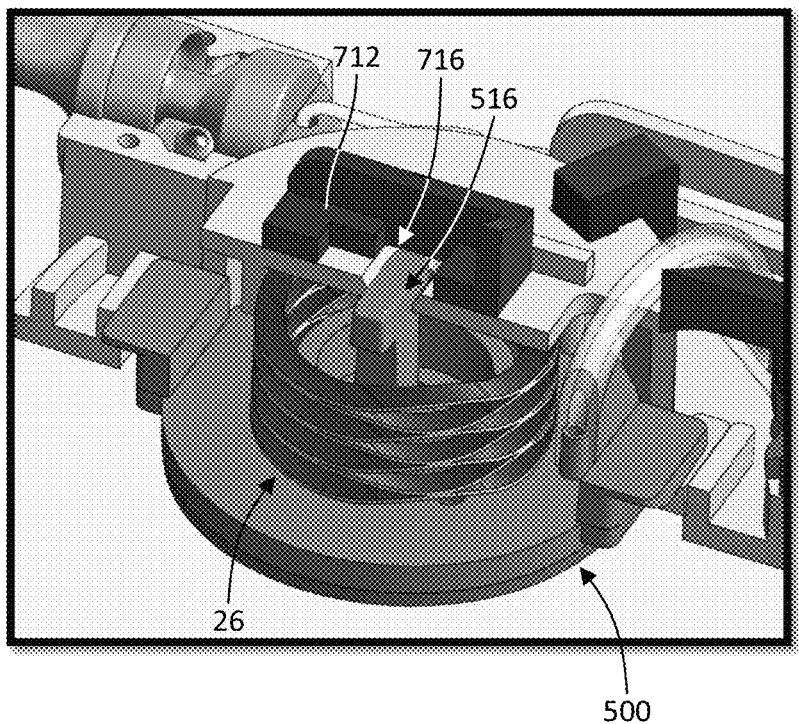
FIG. 77 depicts a microneedle array of the cartridge in a deployed position in accordance with an exemplary embodiment.

The circular projection 514 extends vertically from and perpendicular to the top surface 508a of the base 508 and surrounds the T-shaped column 516. As depicted in FIGS. 71, 76, and 77 the cartridge 12 includes an injection spring 26 that extends around the circular projection 514. As will be discussed in further detail herein, the injection spring 26 aids in moving the microneedle array assembly 500 from an undeployed position to a deployed position.

Figure 57:
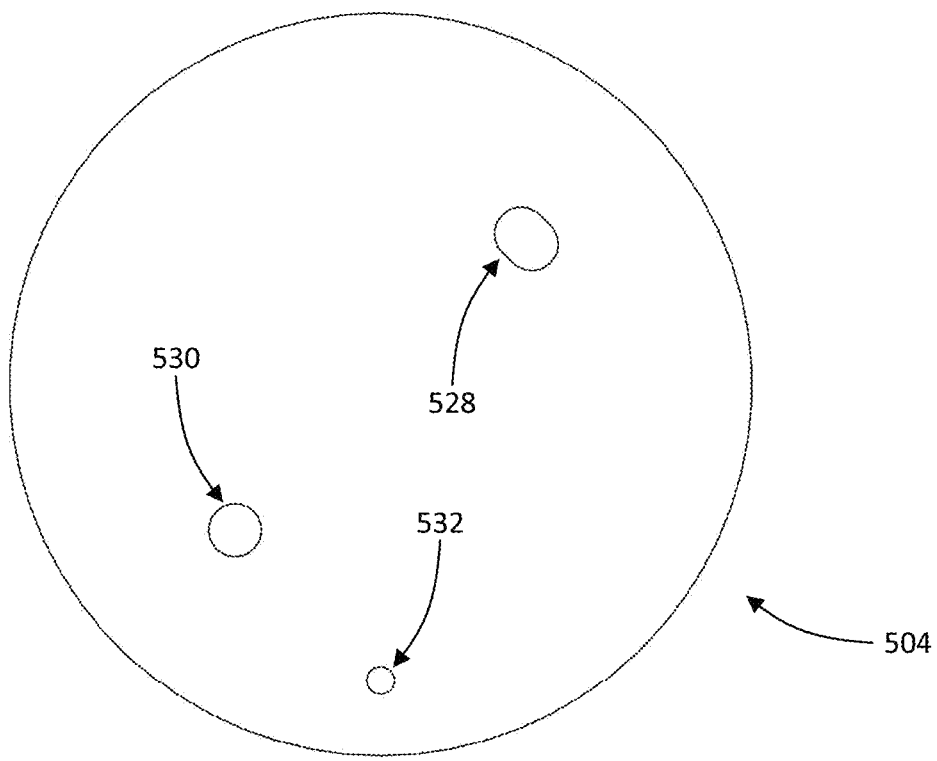
FIG. 57 depicts an adhesive film of the microneedle array holder in accordance with an exemplary embodiment.
Figure 58A:
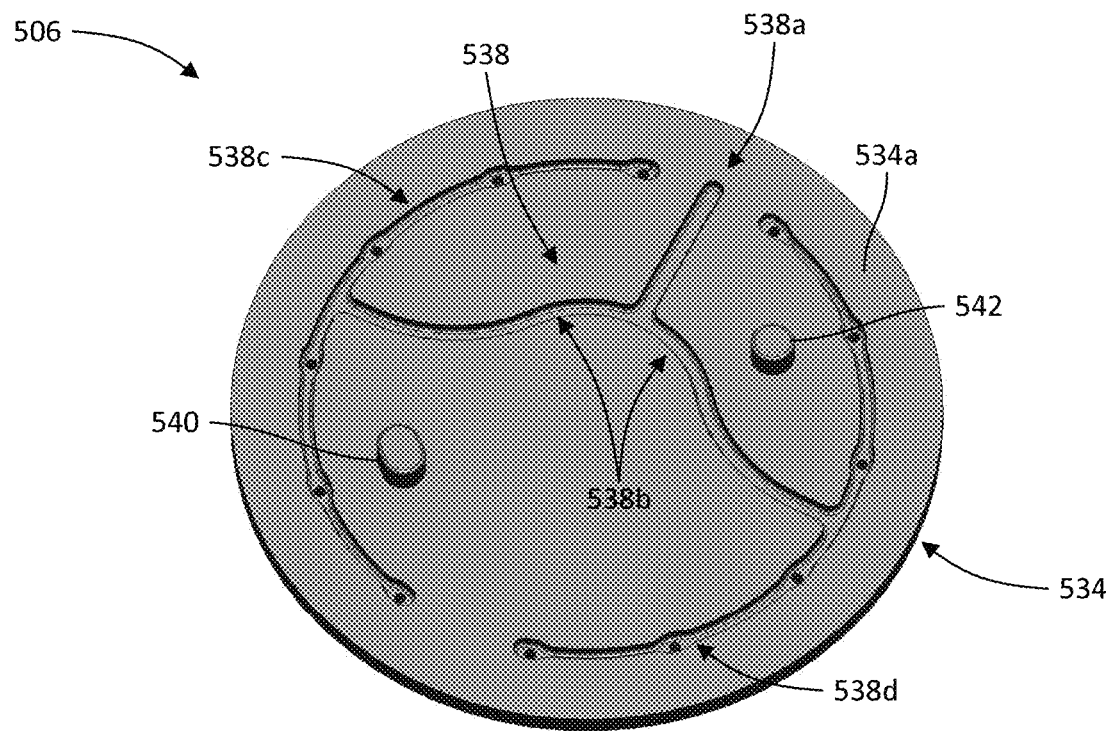
Figure 58B:
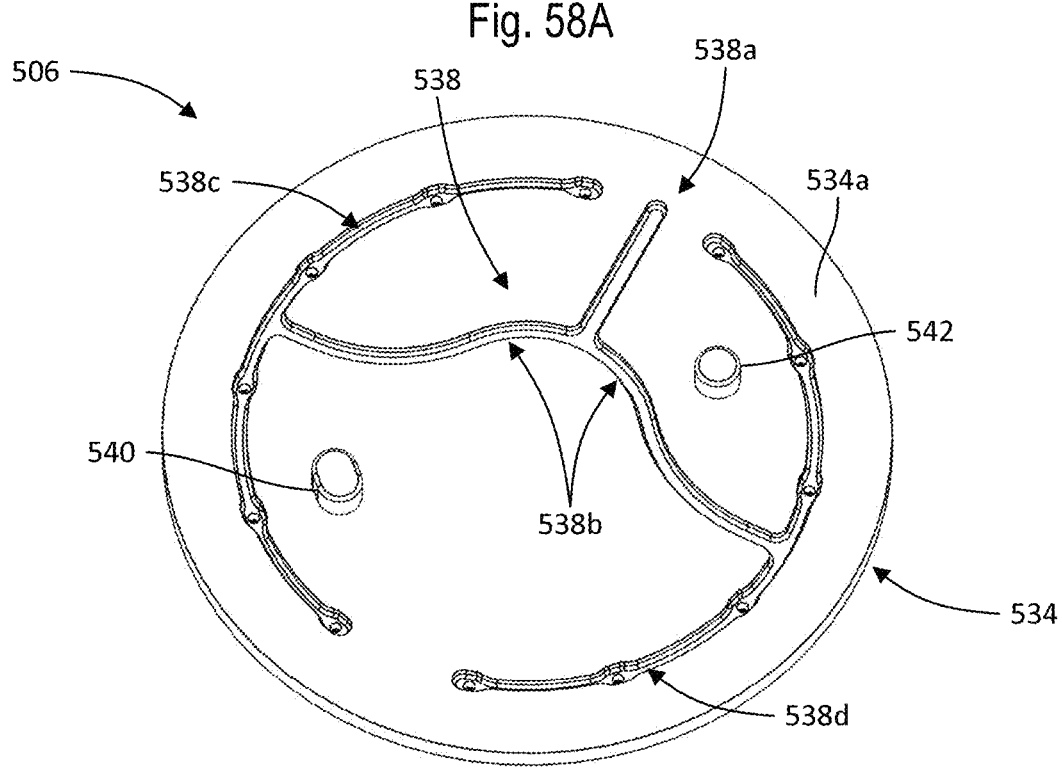

Referring now to FIG. 57, the adhesive film 504 is shown in accordance with an exemplary embodiment. The adhesive film 504 couples the microneedle array holder 502 to the microneedle array platform 506 and includes top surface and an opposed bottom surface. The top surface attaches to the microneedle array holder 502 and the bottom surface attaches to the microneedle array platform 506. The adhesive film 504 further includes a first opening 528, a second opening 530, and a third opening 532. When the adhesive film 504 is attached to the bottom surface of the base 508 of the microneedle array holder 502, the first opening 518 and the second opening 520 of the base 508 align with the first opening 528 and the second opening 530 of the film 504 respectively. Furthermore, when the adhesive film 504 is attached to the bottom surface of the base 508 of the microneedle array holder 502, the aperture 522 of the base 508 aligns with the third opening 532 of the film 504.

Referring now to FIGS. 58A and 58B-61A and 61B, the microneedle array platform 506 is shown in accordance with an exemplary embodiment. In this embodiment, the microneedle array platform 506 includes a base 534 that supports a plurality of hollow microneedles 536.

The base 534 of the microneedle array platform 506 includes a top surface 534a and an opposed bottom surface 534b. The plurality of microneedles 536 extend vertically from and perpendicular to the bottom surface 534b. The microneedles 536 are hollow such that the microneedles 536 include a lumen that extends through the base 534 such that an end of a microneedle 536 is in open communication with the top surface 534a of the base 534.

The top surface 534a of the base 534 defines an open fluidic channel 538 (e.g., a microfluidic channel) that includes a first portion 538a, a second portion 538b, a third portion 538c and a similar fourth portion 538d. The first portion 538a is generally linear, the second portion 538b extends in a T-junction from the first portion 538a and the third portion 538c and the fourth portion 538d extend from the second portion 538b. The third portion 538c and the fourth portion 538d extend around the circumference of the base 534. The openings of the lumens of the microneedles 536 extend to the third portion 538c and the fourth portion 538d of the open fluidic channel 538. As such, the lumens of the microneedles 536 are in open communication with the first portion 538a of the fluidic channel 538 via the second portion 538b, third portion 538c, and the fourth portion 538d.

The base 534 further includes a first extension 540 and a second extension 542 that extend vertically from and perpendicular to the top surface 534a of the base 534. When the top surface 534a of the base 534 is attached to the adhesive film 504, the first extension 540 extends through the first opening 528 and the second extension 542 extends through the second opening 530 of the adhesive film 504. Furthermore, when the microneedle array platform 506 is coupled to the microneedle array holder 502 via the adhesive film 504 the first extension 540 extends through the first circular opening 518 and the second circular opening 520 of the base 534 of the microneedle array platform 506 respectively. In another embodiment, the adhesive film 504 may be omitted and, in such an embodiment, the microneedle array holder 502 may be coupled to the microneedle array platform 506 via ultrasonic welding.

Figure 62A:
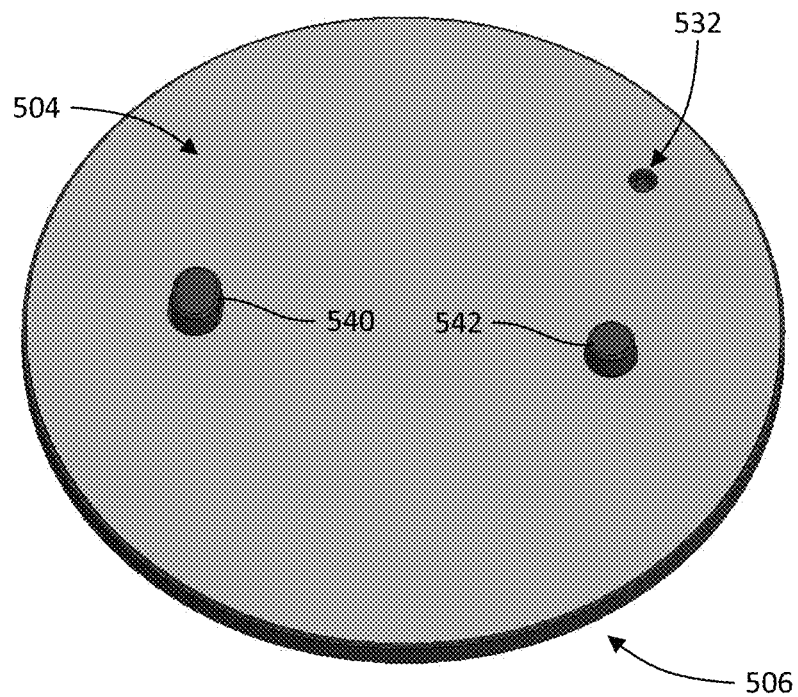
FIGS. 62A and 62B depict the microneedle array holder with the adhesive film in accordance with an exemplary embodiment.
Figure 62B:
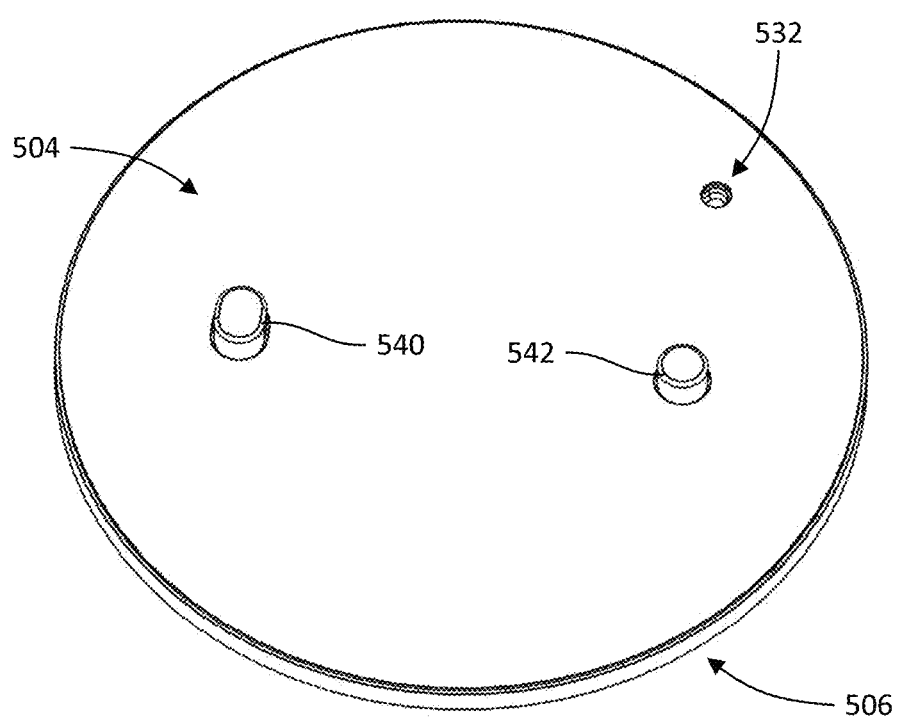
Figure 63A:
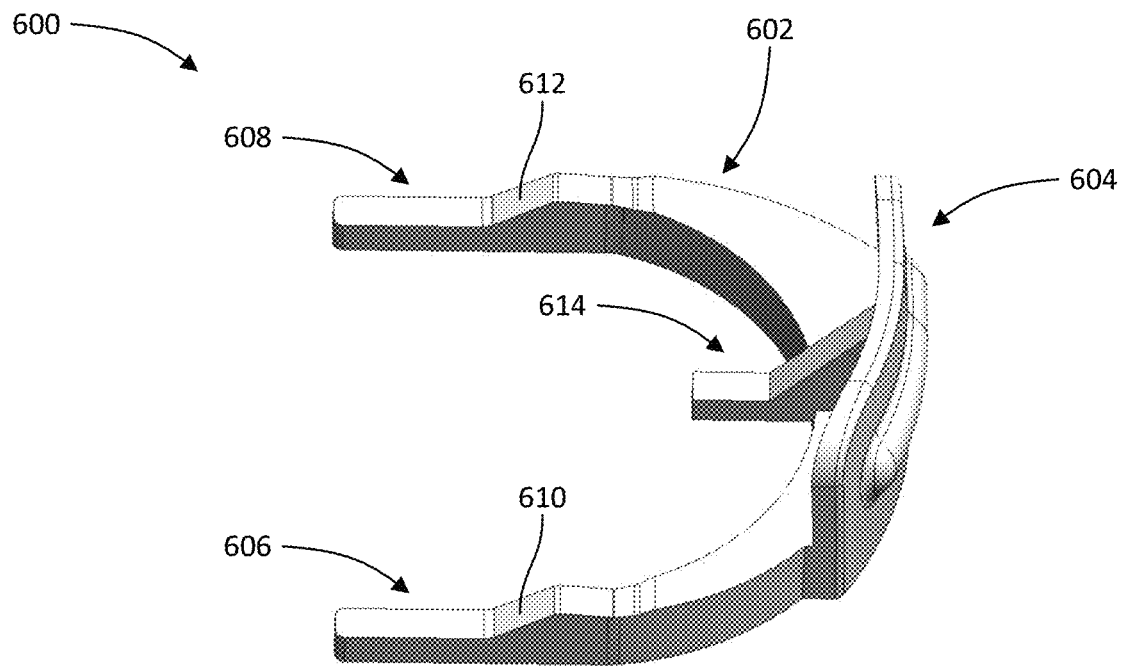
Figure 63B:
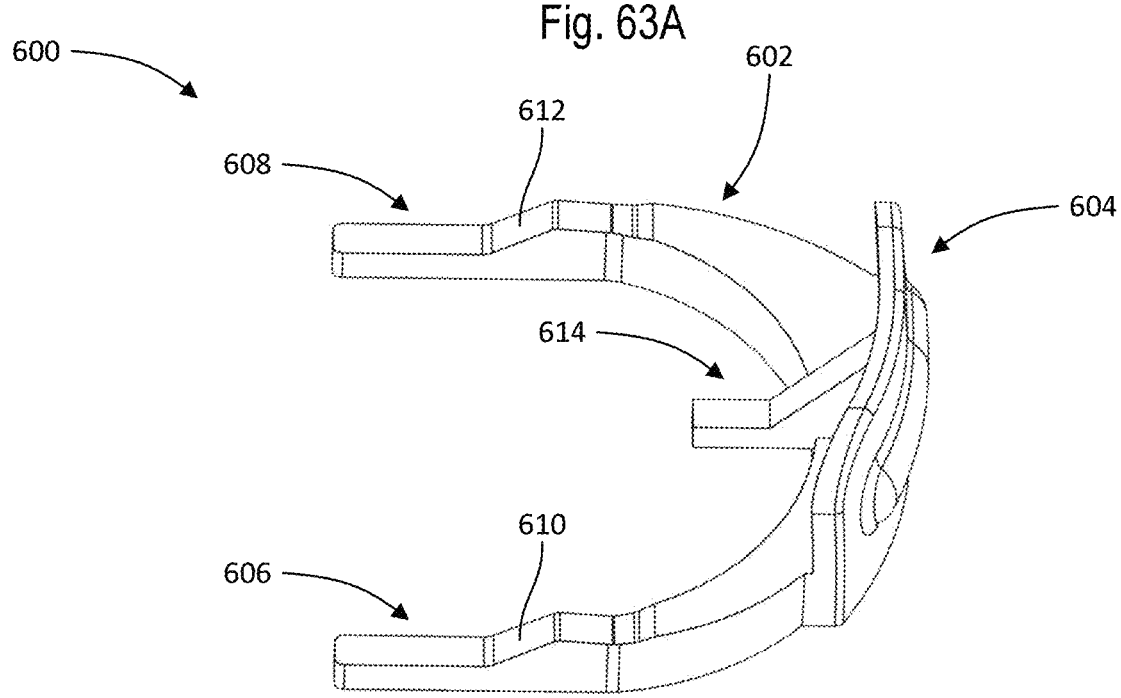
Figure 64A:
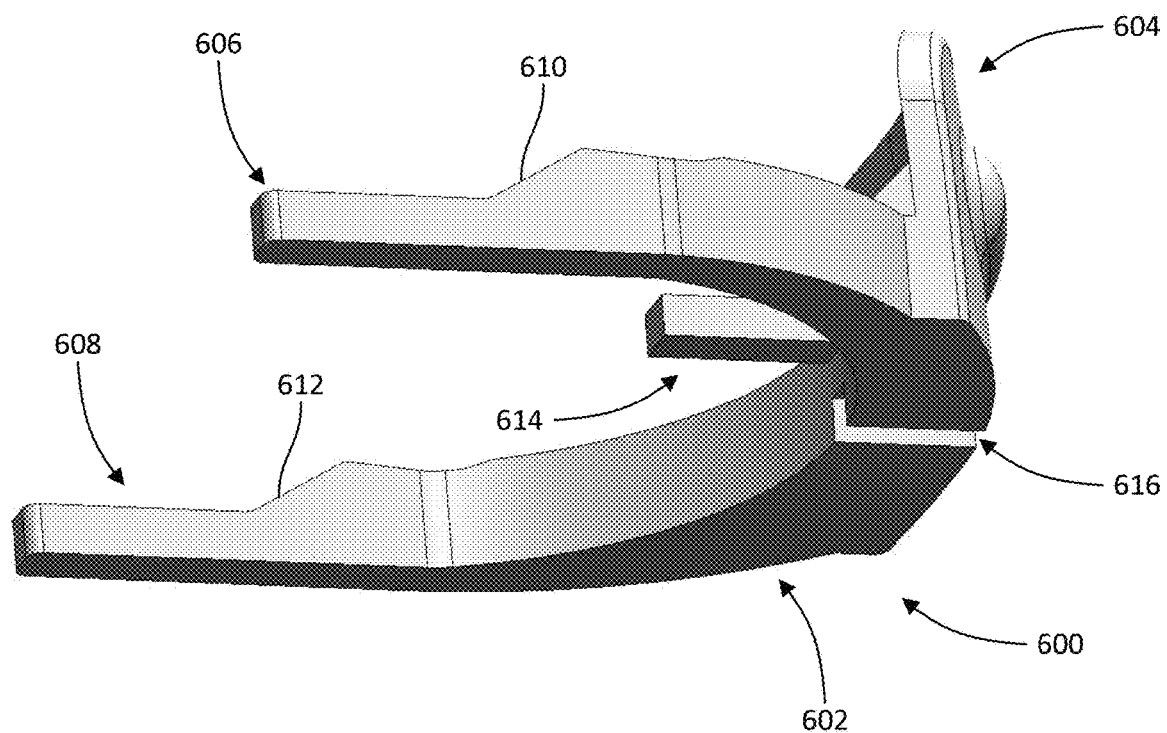
Figure 64B:
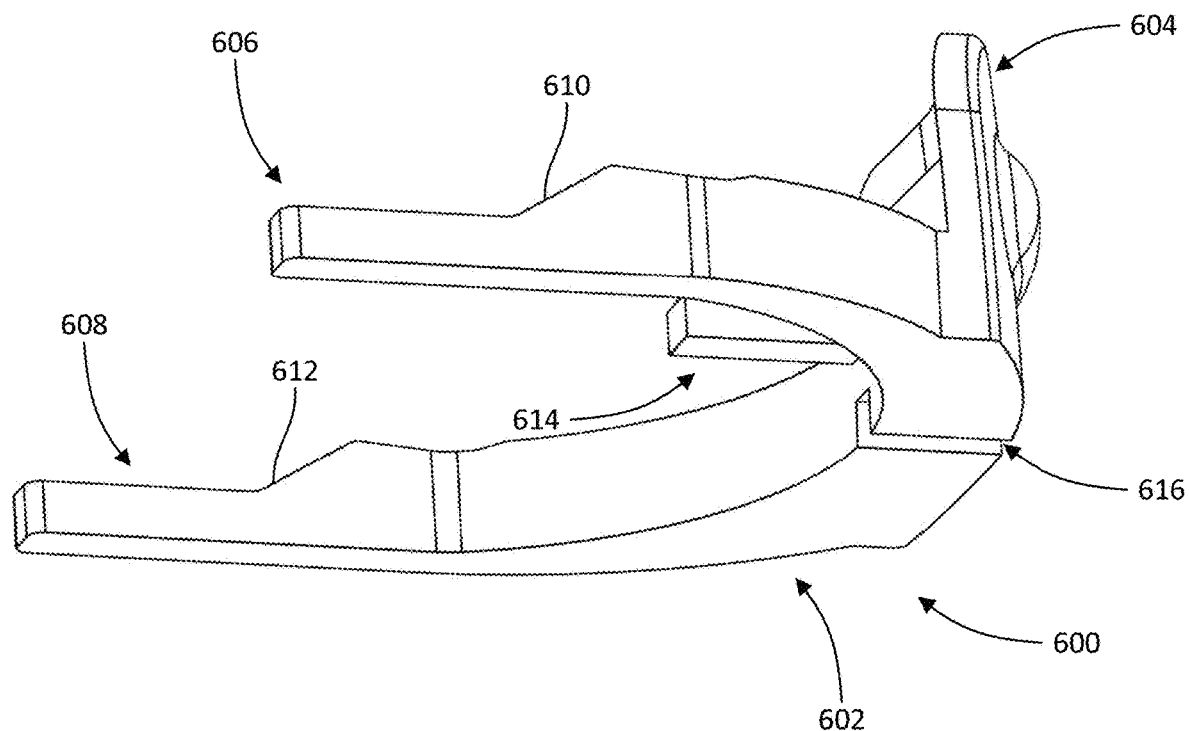
Figure 65A:
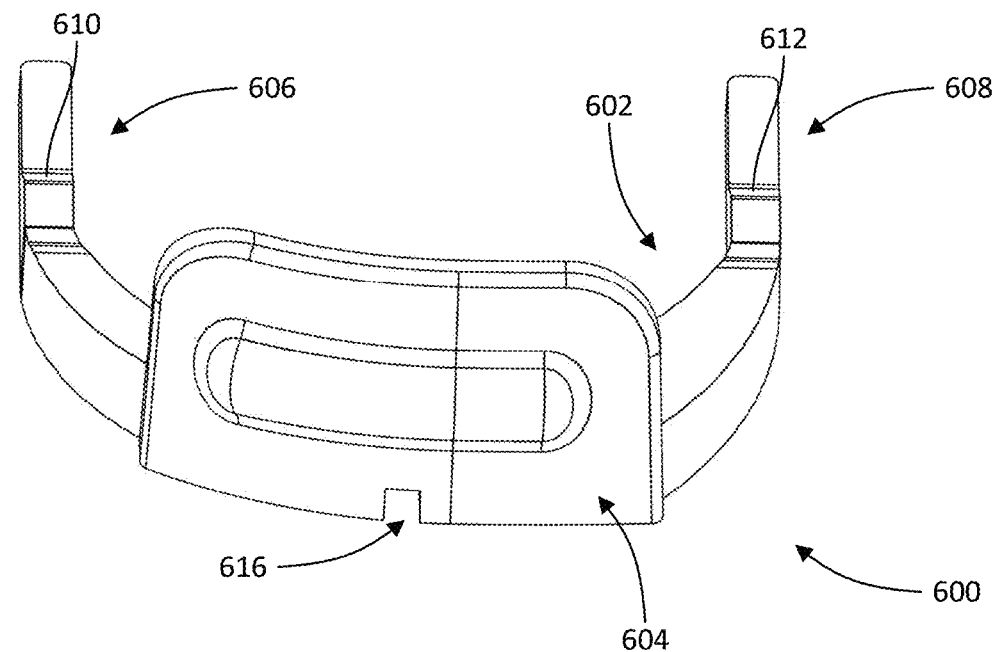
Figure 65B:
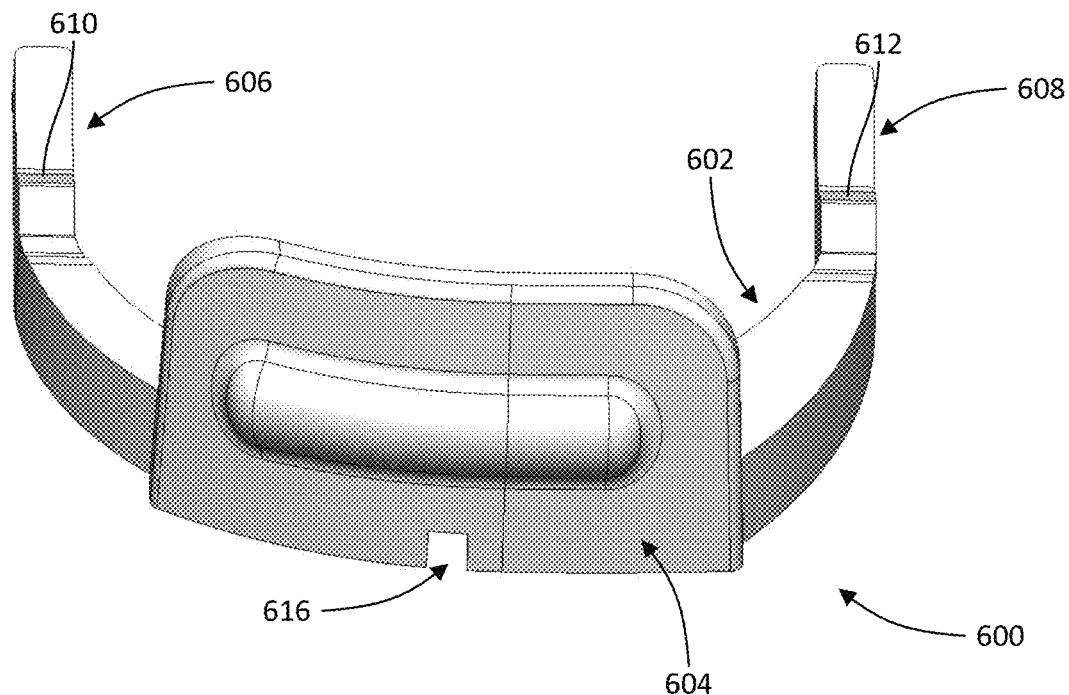
Figure 66A:
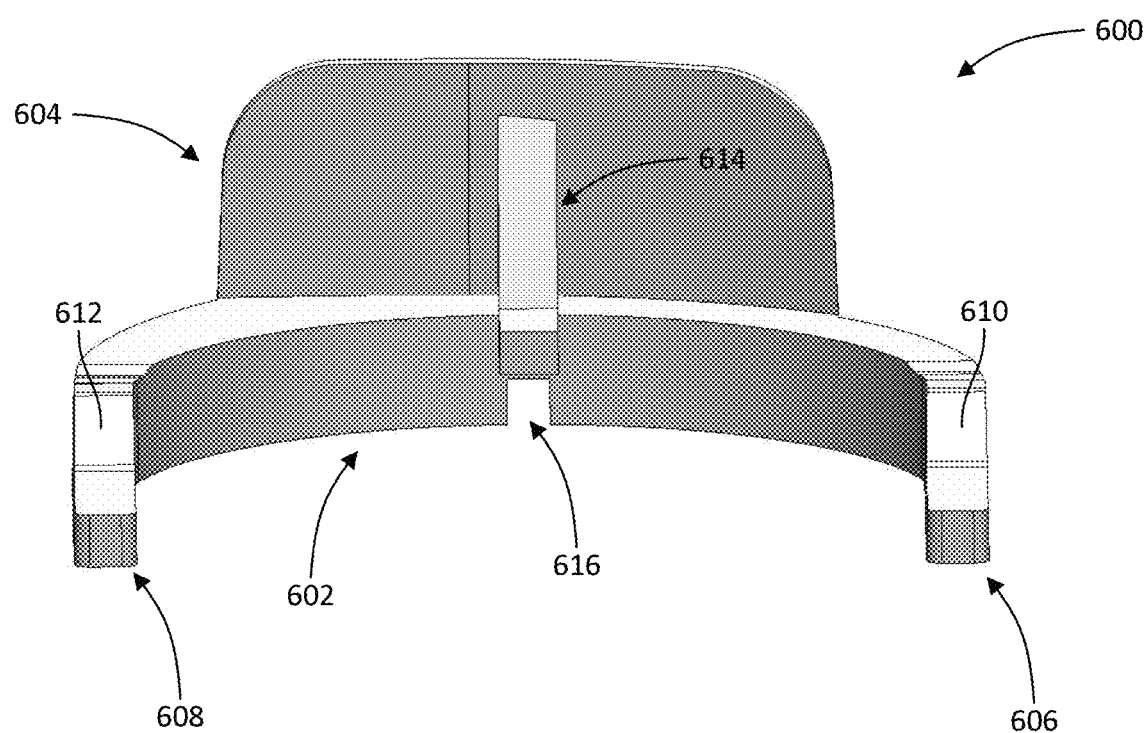
Figure 66B:
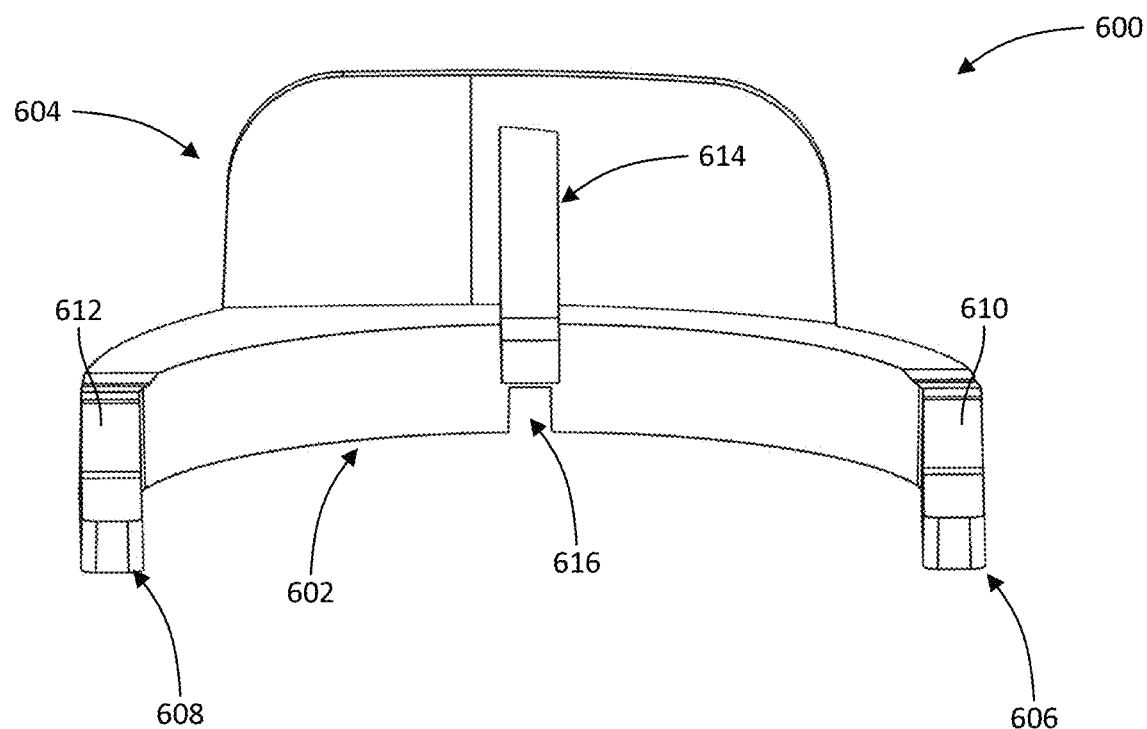
Figure 67A:
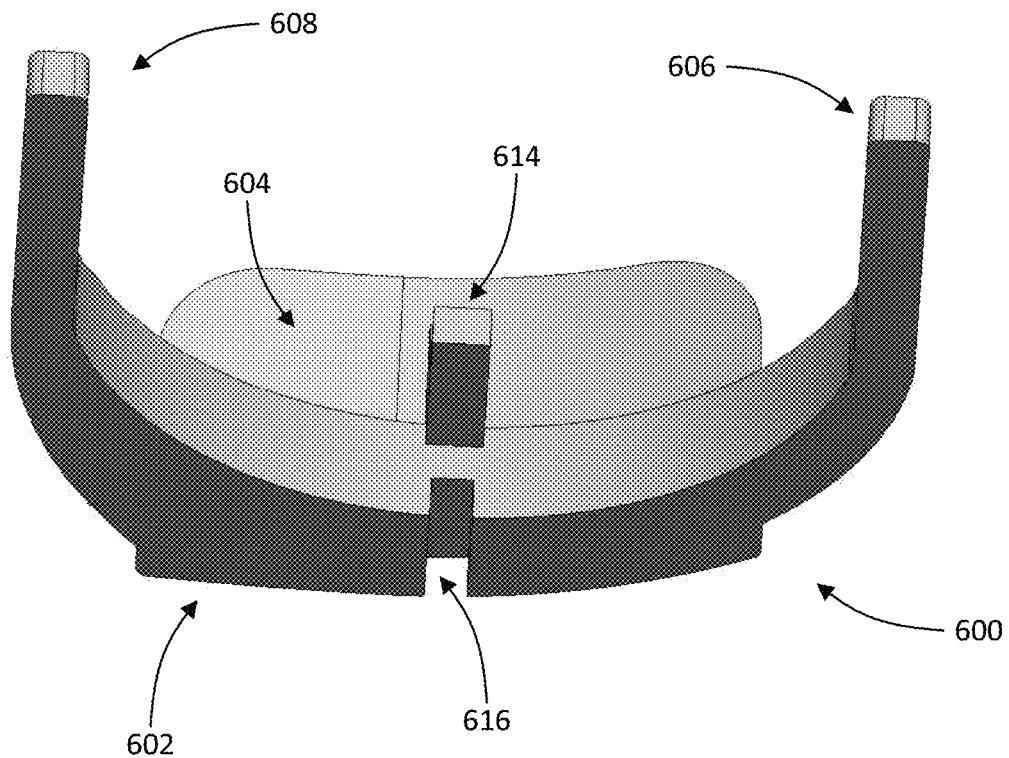
Figure 67B:
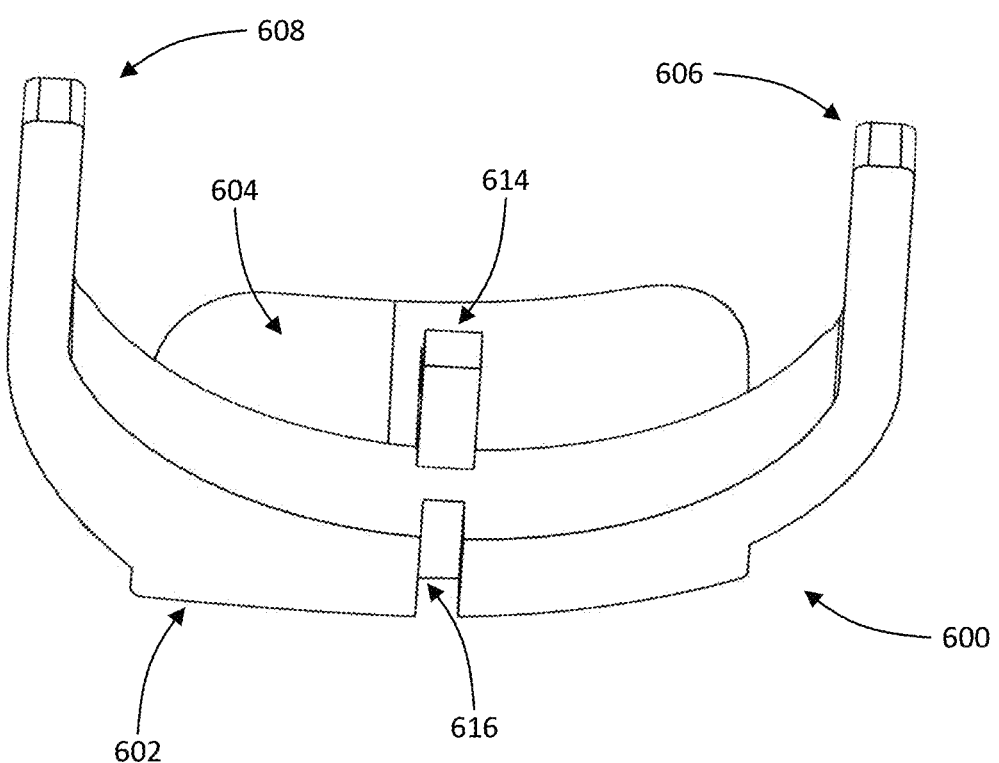
Figure 68A:
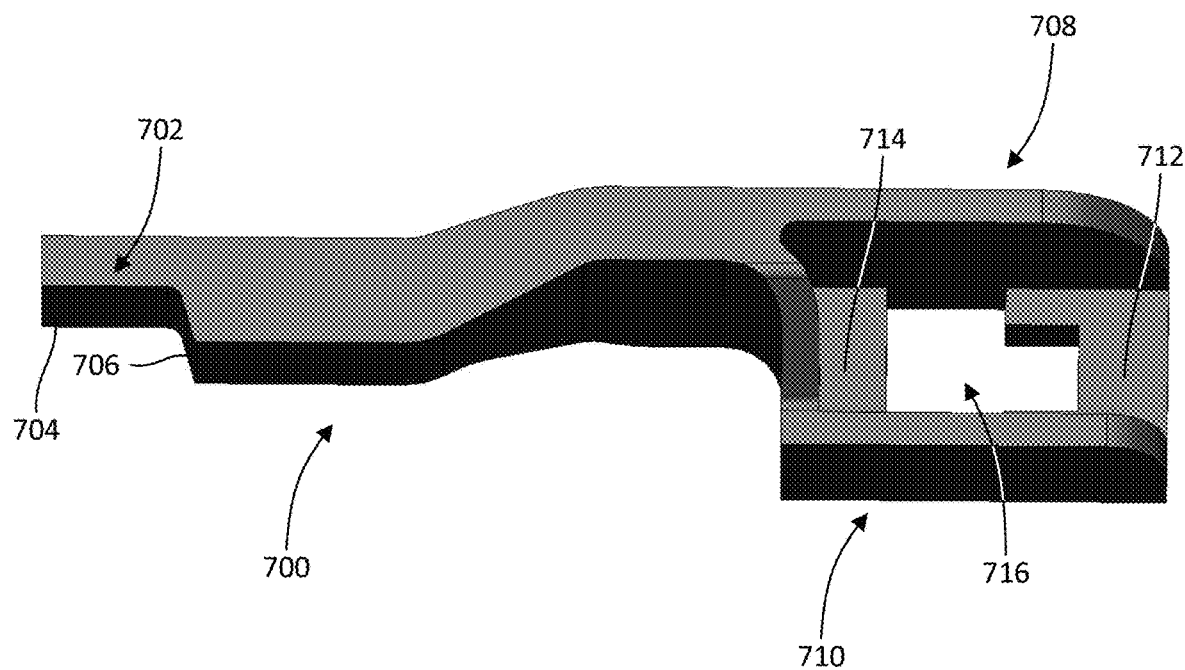
Figure 68B:
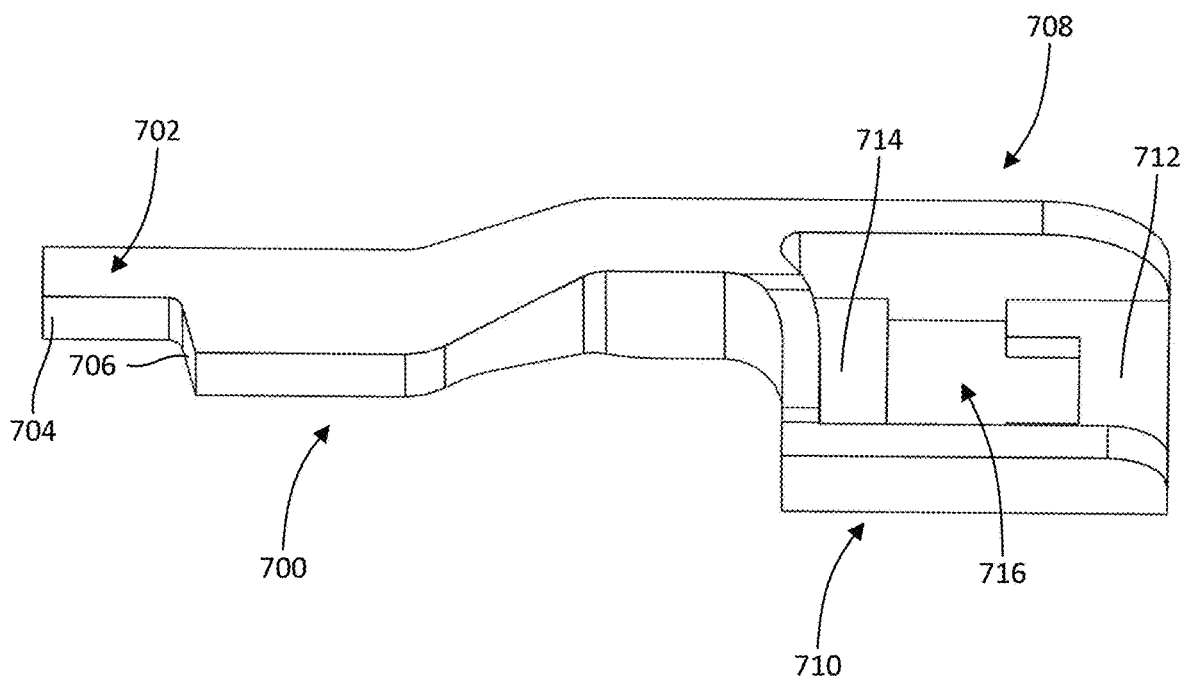
Figure 69A:
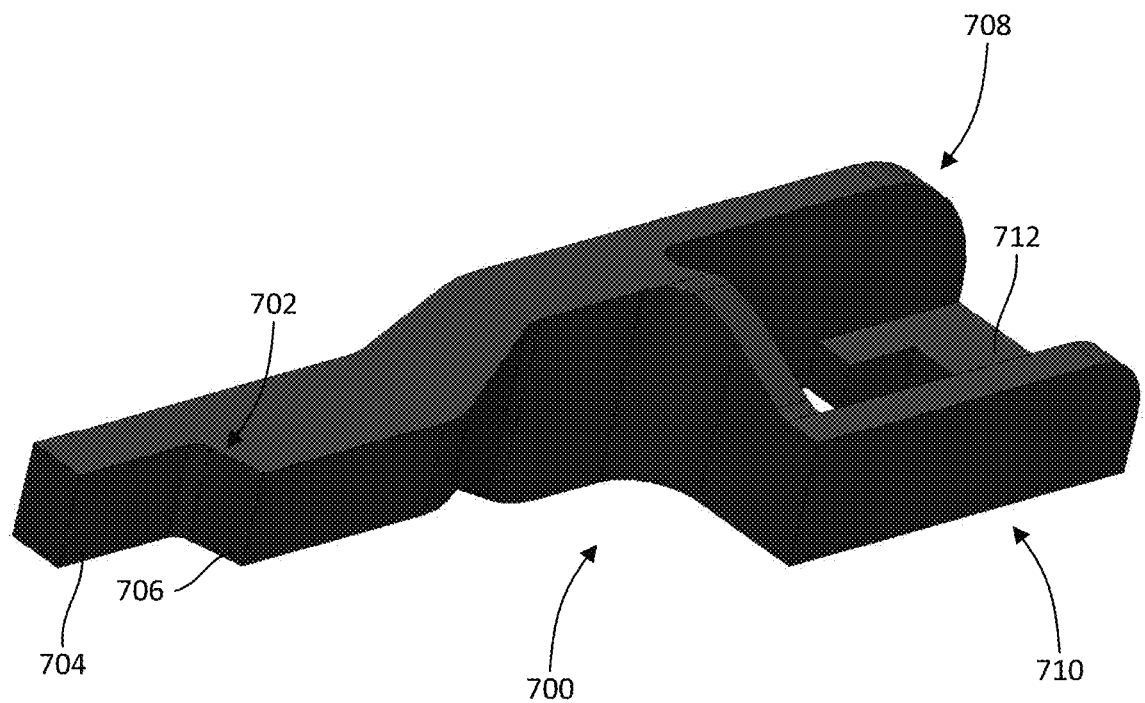
Figure 69B:
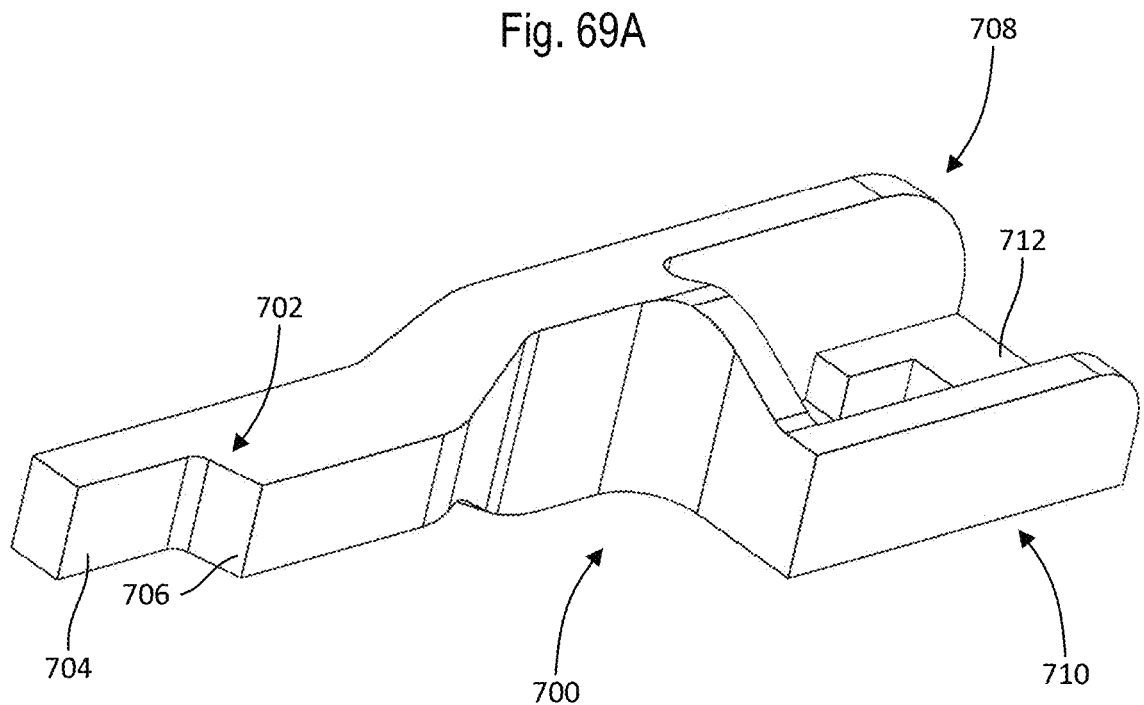
Figure 70A:
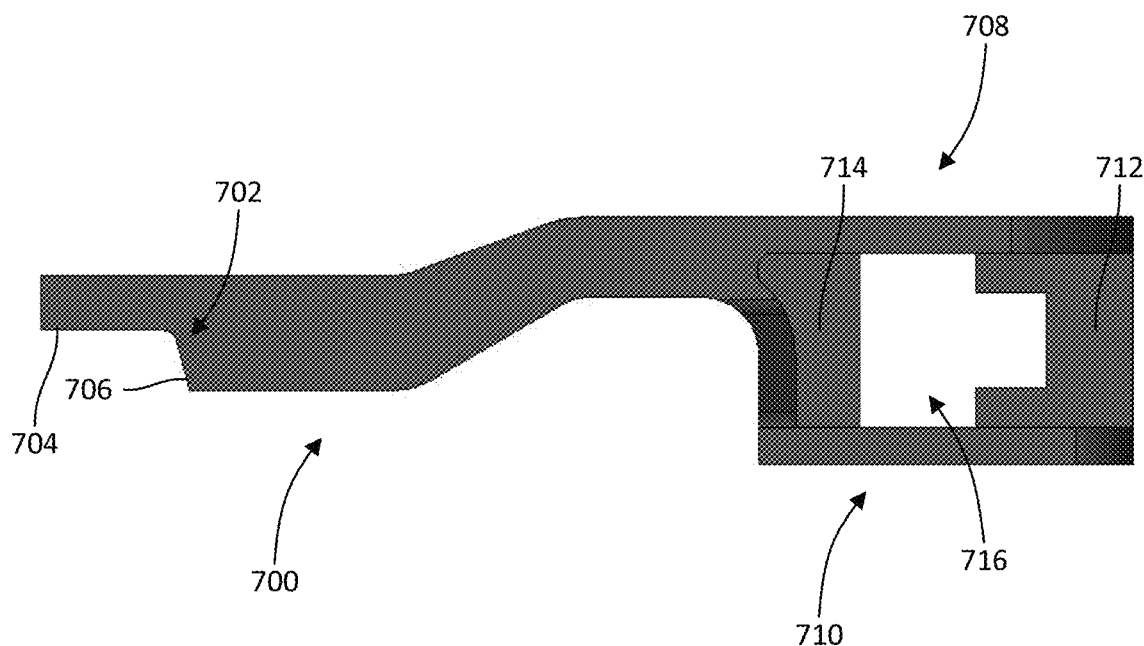
Figure 70B:
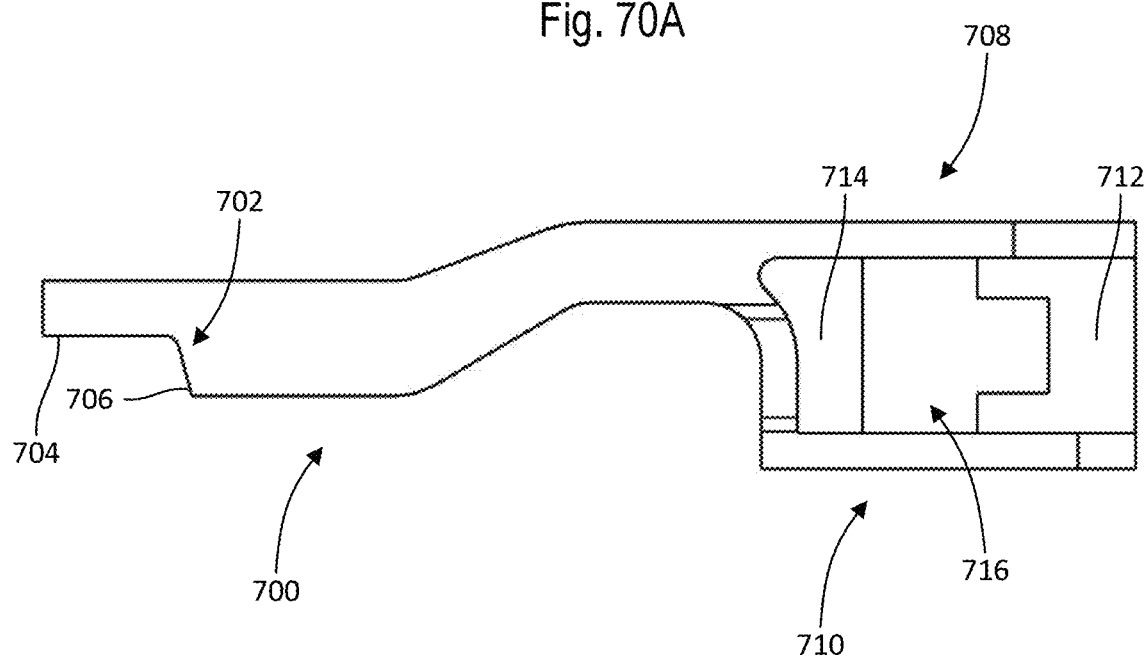

As depicted in FIGS. 62A and 62B, the adhesive film 504 covers the top surface 534*a* of the base 534. In this position, the opening 532 is disposed vertically above a segment of the first portion 538*a* of the fluidic channel 538 which seals all but this portion of the fluidic channel 538. When the microneedle array assembly 500 is assembled, the opening 532 of the adhesive film 504 (and therefore a portion of the first portion 538*a* of the fluidic channel 538) is positioned vertically below the circular aperture 522. As such, the fluidic channel 538 is in open communication with the aperture 522. As further depicted in FIGS. 34A, 34B, 35A, and 35B, when the cartridge 12 is assembled, the first tube 22 is connected to the hollow cylinder 512 and as such, the first tube 22 is in open communication with the fluidic channel 538 via the hollow cylinder 512.

Figure 59A:
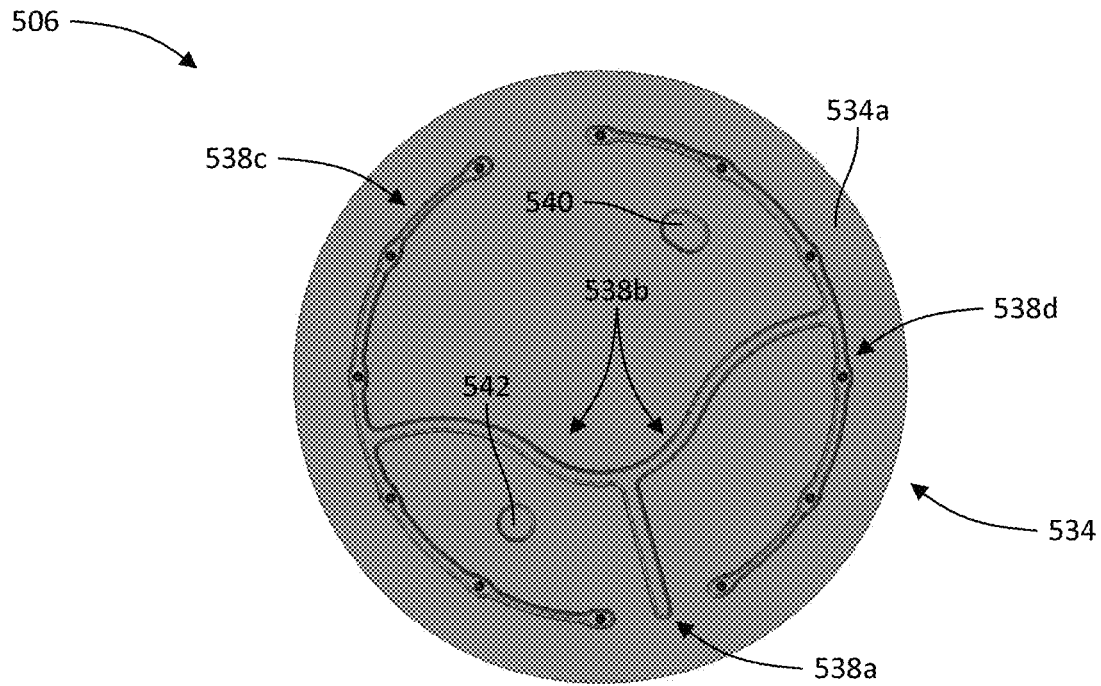
Figure 59B:
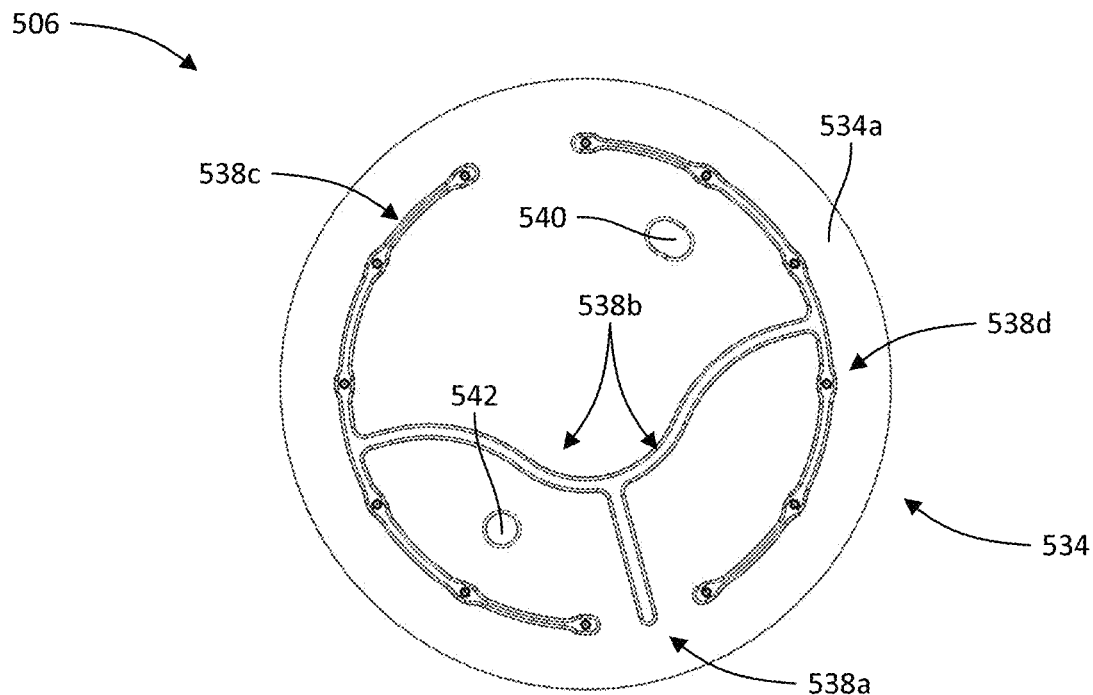
Figure 60A:
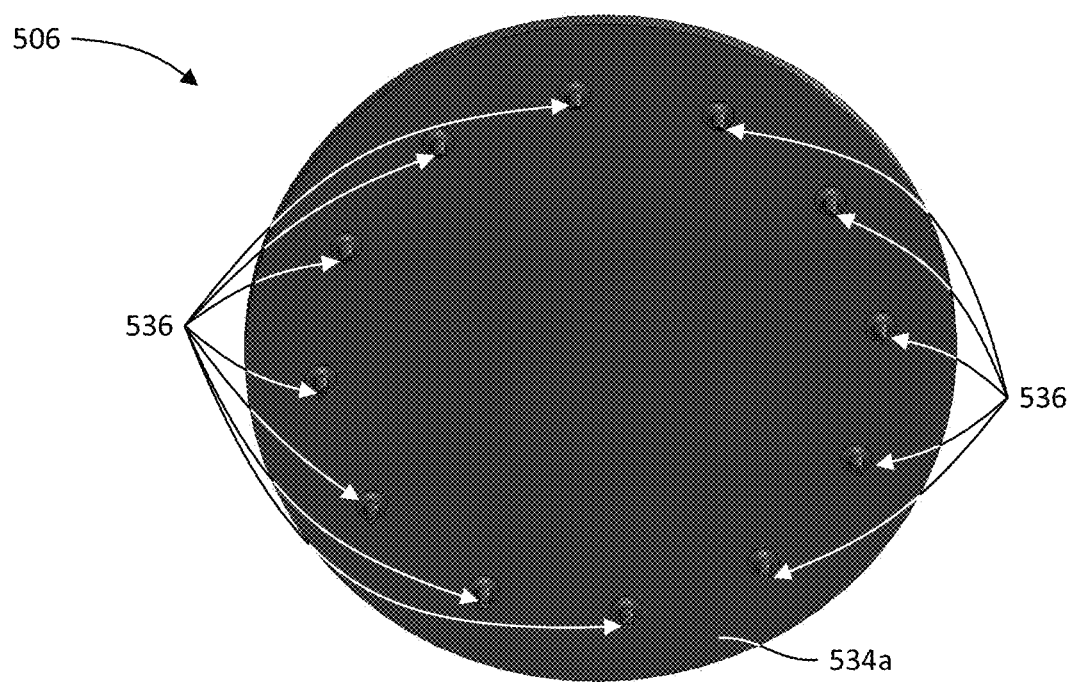
Figure 60B:
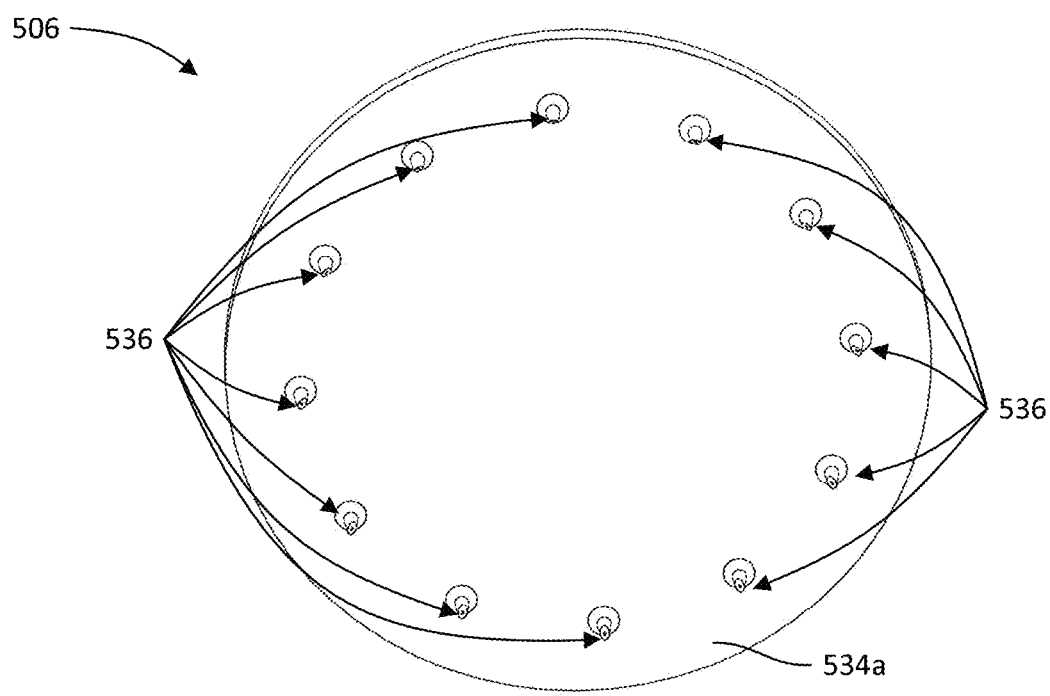
Figure 61A:
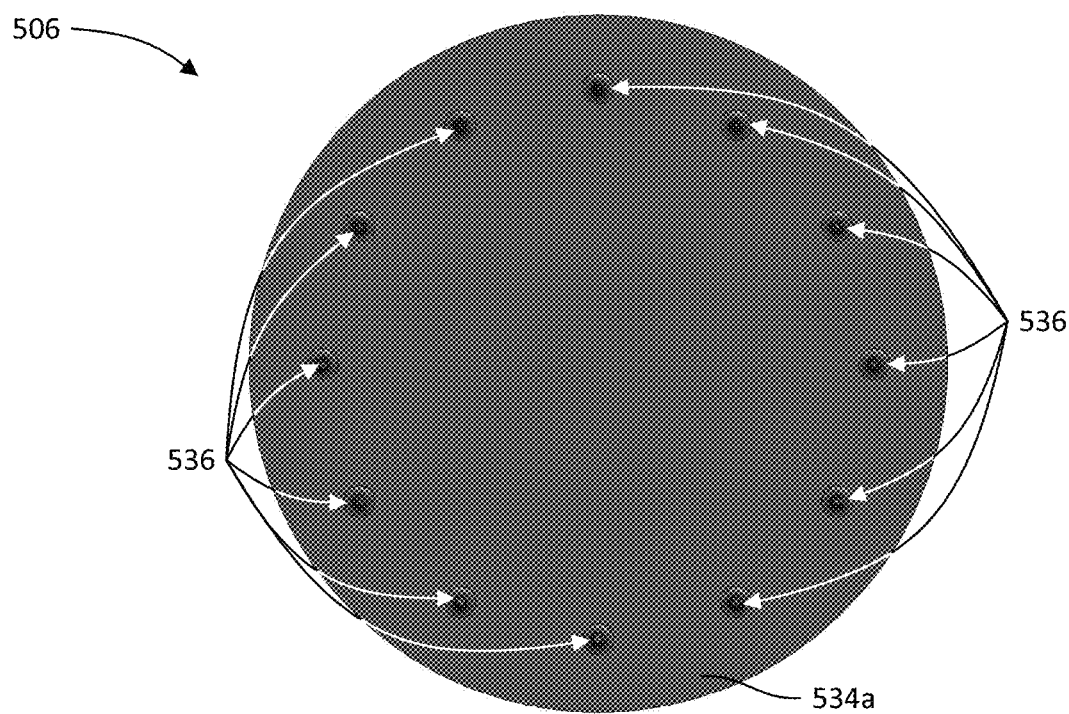
Figure 61B:
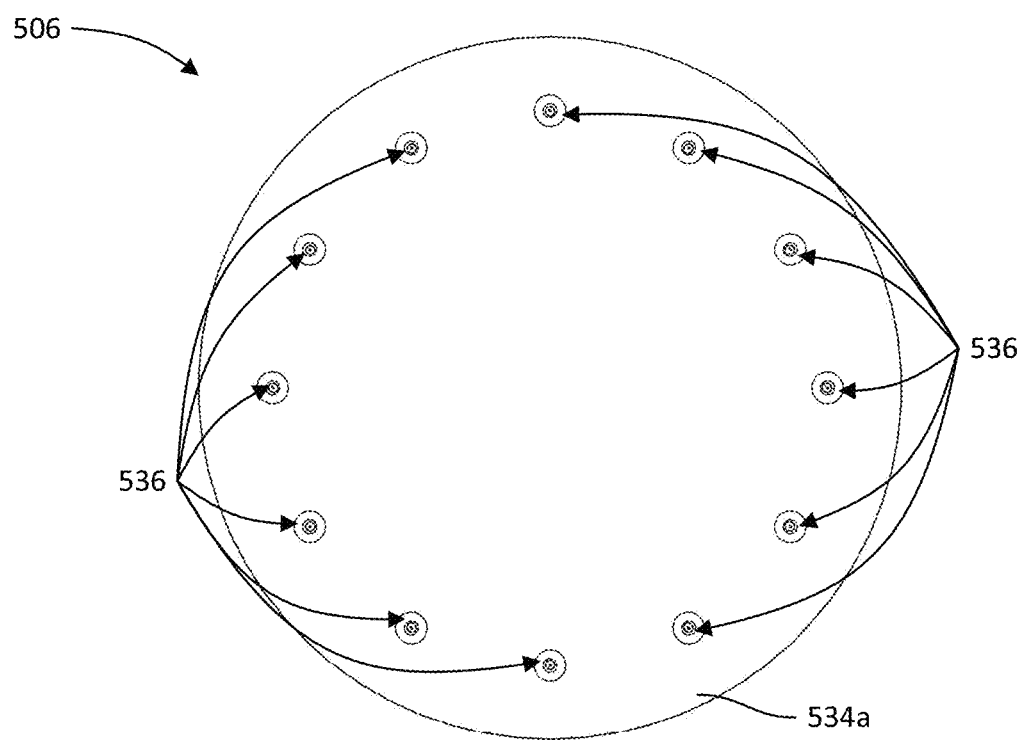

As will be discussed in further detail herein, the dermal patch system 10 delivers the pharmaceutical to a subject via the microneedles 536. As depicted in FIGS. 59A and 59B, an equal number of microneedles 536 are disposed on opposite sides of an end of the second portion 538*b*. That is, as depicted in FIGS. 59A and 59B, three microneedles are disposed on one side of the second portion 538*b* and three microneedles 536 are disposed on the opposite side of the second portion 538*b* of the fluidic channel 538. Providing the same number of microneedles 536 on opposite ends of the second portion 538*b* of the fluidic channel 538 allows substantially the same amount of pharmaceutical to flow through each microneedle 536 at about a same flow rate (e.g., about 1300 µl/min).

While the dermal patch system 10 is depicted as including twelve microneedles 536, in other embodiments, the dermal patch system may include more or less microneedles 536 each in communication with the fluidic channel 538. Furthermore, the microneedles 536 may have the same or varied length. For example, the length of the microneedles may be in a range of about 1 mm-about 3 mm. The length of the microneedles 536 determines a depth into the dermis of the subject that the pharmaceutical is delivered. Furthermore, subjects may have varying depths of dermal layers. For example, the epidermis of one subject may be thicker or thinner compared to the epidermis of another subject. Providing a dermal patch system 10 with microneedles 536 of varying lengths may ensure that a pharmaceutical is delivered to the dermis of a subject as at least one of the microneedles 536 may extend through the epidermis of the subject. In some embodiments, the lengths of the microneedles 536 may be varied by a factor in a range of at least 10% to about 20%. In one embodiment, wherein the pharmaceutical is administered intradermally, the microneedles 536 may have a length between about 1 mm and about 2 mm. In another embodiment, wherein the pharmaceutical is administered subcutaneously, the microneedles 536 may have a length between about 2 mm and about 3 mm.

Referring now to FIGS. 63A and 63B-67A and 67B, the retraction button 600 is shown in accordance with an exemplary embodiment. The retraction button 600 includes a U-shaped base 602 and a vertical button portion 604 that extends vertically from and perpendicular to the U-shaped base 602. The U-shaped base 602 includes a first arm 606 and a second arm 608. The first arm 606 and the second arm 608 include an angled surface 610 and 612 respectively. The U-shaped base 602 has a shape that is similar to the shape of the microneedle array housing 244 such that the first arm 606 and the second arm 608 extend around microneedle array housing 244. The retraction button 600 further includes a blocking feature 614. The blocking feature 614 extends vertically from and perpendicular to the U-shaped base 602 and extends longitudinally from and perpendicular to the vertical button portion 604.

The retraction button 600 further includes a gap 616 that extends through the U-shaped base 602 and the vertical button portion 604. The gap 616 is shaped and dimensioned to extend over the third button guide 274.

As depicted in FIGS. 3A and 3B, the cartridge 12 further includes a trigger 700. With particular reference to FIGS. 68A and 68B-70A and 70B, the trigger 700 includes a notch 702 that is defined by a first surface 704 and a second surface 706. The trigger 700 further includes a first outer wall 708 and a second outer wall 710 that is parallel to the first outer wall 708. The trigger 700 also includes a first bottom wall 712 and a second bottom wall 714 that extend between the first outer wall 708 and the second outer wall 710. The first bottom wall 712 and the second bottom wall 714 define a T-shaped opening 716 that also extends between the first outer wall 708 and the second outer wall 710.

When the trigger 700 is inserted into the cartridge 12, a portion of the bottom surface of the trigger 700 rests upon the outer surface 248*a* of the microneedle array housing 244 and another portion of the bottom surface of the trigger 700 rests upon the top surface 408*a* of the trigger portion 402 of the pump assembly 400. Furthermore, the first outer wall 708 and the second outer wall 710 are disposed between the first and second trigger guides 262.

Figure 78:
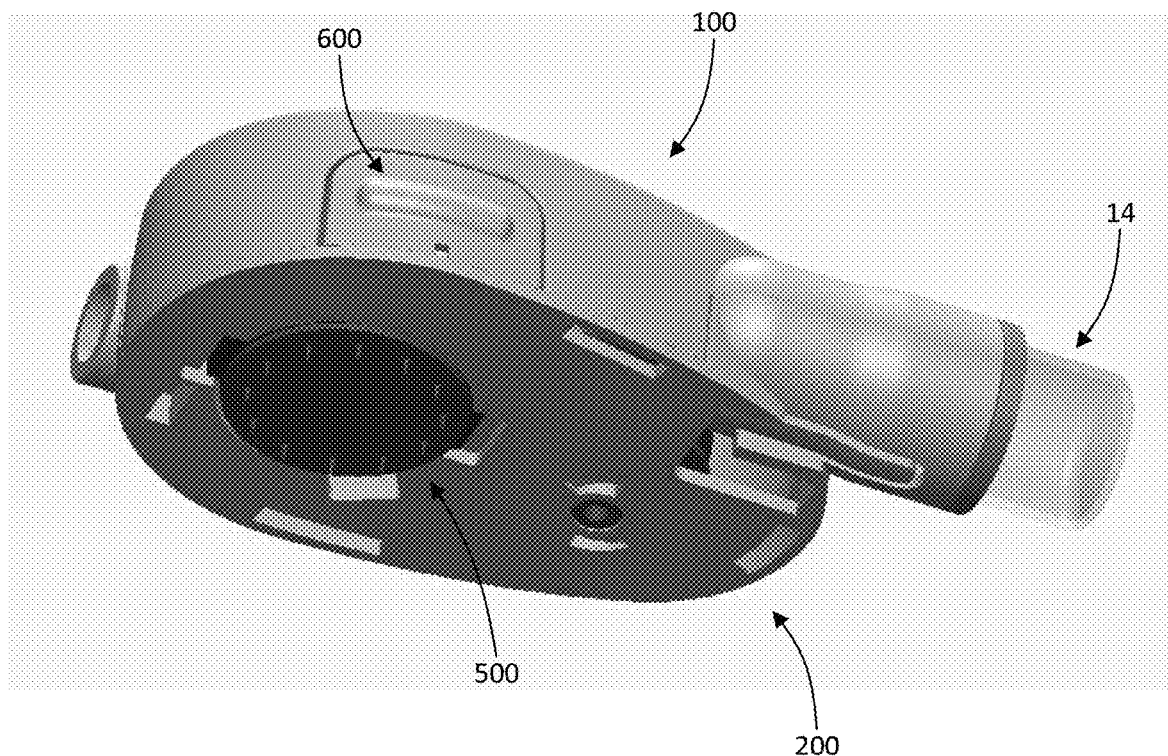
FIG. 78 depicts a microneedle array of the cartridge in a deployed position in accordance with an exemplary embodiment.

The cartridge 12 is moveable between an undeployed position (FIGS. 3A and 3B) to a deployed position (FIGS. 77 and 78).

In the undeployed position, the handle 302 of the pull mechanism 300 is disposed within the handle receptacle of the cartridge 12 and the cord 304 of the pump assembly 400 extends through the aperture 434 and wraps around the middle support portion 422 of the pump assembly 400. As depicted in FIGS. 34A, 34B, 35A, and 35B, the cartridge 12 includes a tensioner 28. The tensioner 28 extends through the first tensioner opening 256 and the second tensioner opening 258 of the microneedle array housing 244 which allows the tensioner 28 to couple to the microneedle array housing 244. Furthermore, the tensioner 28 includes an aperture that allows the cord 304 to extend therethrough. As further depicted in FIGS. 3A and 3B, when the cartridge 12 is in the undeployed position, the tensioner 28 causes the portion of the cord 304 that wraps around middle support portion 422 of the pump assembly 400 to be taut while portion of the cord 304 that is between the handle 302 and the tensioner 28 has some slack.

Figure 74:
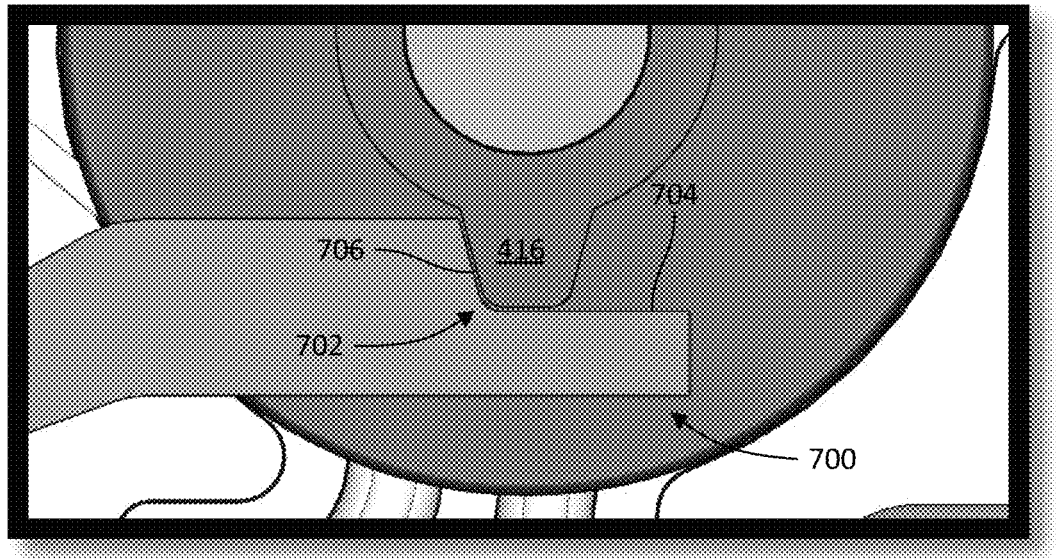
FIG. 74 depicts a trigger and a trigger portion of the pump assembly of the cartridge in a first position in accordance with an exemplary embodiment.
Figure 75:
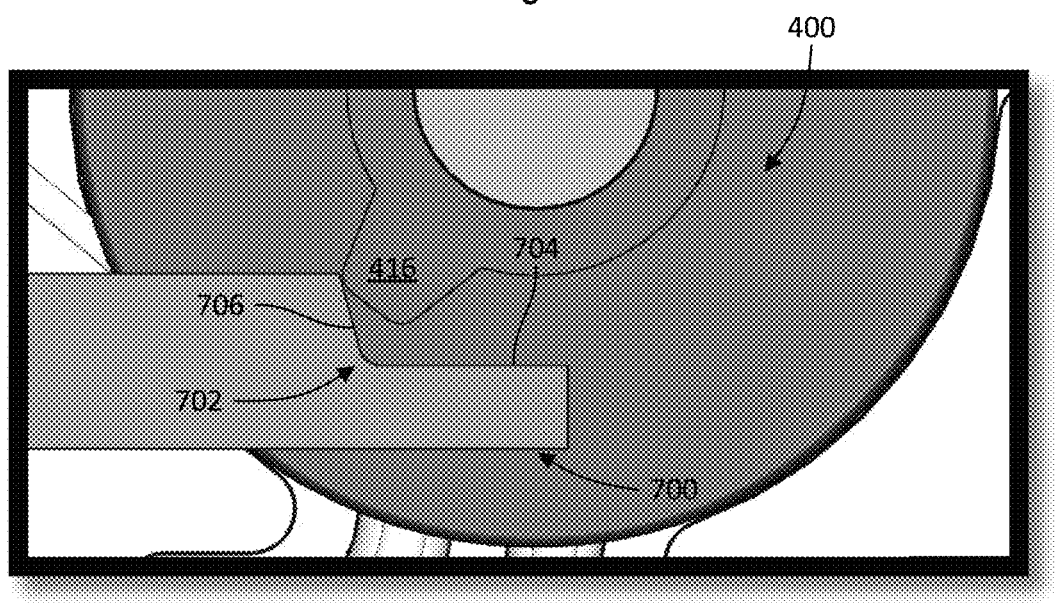
FIG. 75 depicts a trigger and a trigger portion of the pump assembly of the cartridge in a second position in accordance with an exemplary embodiment.

As further depicted in FIG. 74, in the undeployed position, the extension 416 of the pump assembly 400 is disposed within the notch 702 such that the extension 416 contacts the first surface 704 and the second surface 706 of the notch 702.

Furthermore, in the undeployed position, the T-shaped column 516 of the microneedle array holder 502 extends through the aperture 260 of the microneedle array housing 244. In this position, the T-shaped column 516 also extends through the T-shaped opening 716 and rests upon the first bottom wall 712 which prevents microneedle array assembly 500 from moving through the microneedle array aperture 242 of the base 200. As such, the microneedles 536 are retained within the cartridge 12 when the microneedle array assembly 500 is in the undeployed position. Also, as depicted in FIG. 76, the microneedle array assembly 500 compresses the injection spring 26 between the top surface 508a of the microneedle array assembly 500 and the inner surface 248b of the microneedle array housing 244, such that the spring is in a compressed state.

As depicted in FIGS. 34A, 34B, 35A, and 35B, when the retraction button 600 is in the undeployed position, the first arm 606 of the retraction button 600 is disposed between the first button guide 270 and the outer surface 246a of the microneedle array housing 244 and the second arm 608 of the retraction button 600 is disposed between the second button guide 272 and the outer surface 246a of the microneedle array housing 244. Furthermore, in this position, the first and second arms 606 and 608 are positioned below the extensions 510 of the microneedle array holder 502 and the third button guide 274 extends through the gap 616. When the microneedle array assembly 500 is in the undeployed position, the microneedle array holder 502 prevents a user from activating the retraction button 600 by pushing it into the cartridge (also referred to moving the retraction button 600 to a deployed position from an undeployed position) as the blocking feature 614 extends through the opening 254 of the microneedle array housing 244 and contacts base 508 which prevents the retraction button 600 from moving.

In order to move the cartridge to the deployed position, the cartridge 12 must be placed in a substantially vertical position. As depicted in FIGS. 3A and 3B, when the cartridge 12 is not in a substantially vertical position, the ball 21 is disposed within the ball retention groove. When the ball 21 is within the ball retention groove and the handle 302 is pulled, the angled surface 316 of the handle 302 contacts the ball 21 and pushes the ball 21 into the inner surface of the handle receptacle which prevents the handle 302 from being pulled further. When the cartridge 12 is in a substantially vertical position, the ball 21 falls into and is retained by the rounded inner surface 312 of the handle 302 which allows a user to pull the handle 302 to remove the pull mechanism 300 from the cartridge 12.

Pulling the pull mechanism 300 causes the cartridge 12 to move from the undeployed position to the deployed position. More particularly, pull mechanism 300 causes the pump portion 404 to rotate in a clockwise direction. As the pump portion 404 rotates, the latch 240 engages with various teeth 436 of the pump portion 404. This engagement may slow a rotation of the pump portion 404 as the engagement must be overcome to cause the pump portion 404 to rotate. In addition, the engagement provides a tactile feel to the user and stabilizes a rate of pull for the user. When the pump portion 404 rotates, the protrusions 444 of the cog 426 compress the first tube 22 and the second tube 24 at various locations as the cog 426 rotates. When the vial 14 is inserted into the cartridge 12 this compression causes the cog 426 to act as a peristaltic pump by causing an amount of a pharmaceutical to travel through the first tube 22 and pumps air into the vial 14 via the second tube 24 which aids in expelling pharmaceutical from the vial 14.

Furthermore, when the pump portion 404 rotates, the ball 406 travels within the spiral ball retention groove until the ball 406 reaches an inner end of the spiral ball retention groove. While the ball 406 is traveling, the trigger portion 402 remains stationary. When the ball 406 reaches the end of the spiral ball retention groove, the ball engages the end of the spiral groove 418 of the trigger portion 402 and engages with the end of the spiral groove 432 of the pump portion 404 which causes the trigger portion 402 to rotate with the pump portion 404. As will be discussed in further detail herein, the rotation of the trigger portion 402 causes the microneedle array assembly 500 to move to the deployed position for administering the pharmaceutical. As such, the pump portion 404 rotates (and as such pumps an amount of pharmaceutical through first tube 22) while the trigger position 402 remains stationary thereby priming an amount of pharmaceutical at the microneedles 536 before the microneedles 536 are deployed to puncture the subject's skin.

The amount the pump portion 404 rotates while the trigger portion 402 is stationary determines and can be proportional in various embodiments to an amount of pharmaceutical primed for administration. By way of example, in some embodiments, the amount of the pharmaceutical that is released from the vial for priming the microneedles can be proportional to a degree of rotation of the pump portion 404. That is, the more or less the pump portion 404 rotates while the trigger portion 402 is stationary, the more or less pharmaceutical is primed. As such, the amount the pump portion rotates before the ball 406 engages with the ends of the spiral grooves 418 and 432 may be increased or decreased by increasing or decreasing a distance covered by the grooves 418 and 432. In the embodiments disclosed herein, the pump portion 404 rotates three times before the ball 406 causes the trigger portion 402 to rotate with the pump portion 404. It is understood that this number of rotations may be increased or decreased by increasing or decreasing the length of the grooves 418 and 432 as needed.

When the ball 406 engages the ends of the grooves 418 and 432, the pump portion rotates in a clockwise direction such that the extension 416 rotates into the second surface 706 of the notch 702 of the trigger 700. This rotation pushes the trigger 700 from a first position away from the pump assembly 400 in the direction of arrow A to a second position. This movement causes the first bottom wall to move away from and disengage from the first bottom wall 712 of the trigger 700. When disengaged, the injection spring 26 is allowed to decompress and move the microneedle array assembly 500 to the deployed position. In this position, the microneedles 536 extend through the microneedle array assembly aperture 260 and can puncture the subject's skin when the cartridge 12 is affixed to the skin of the subject.

The pump assembly 400 continues to rotate until the end of the cord 304 releases from the pump assembly 400. That is, the pump assembly 400 continues to rotate until the end of the cord 304 passes through the aperture 434. As such, an amount of pharmaceutical pumped out of the vial 14 is proportional to the length of the cord 304 as a longer cord 304 allows for more rotation of the pump assembly 400 and a shorter cord 304 results in less rotation of the pump assembly 400 pump assembly 400.

Figure 79:
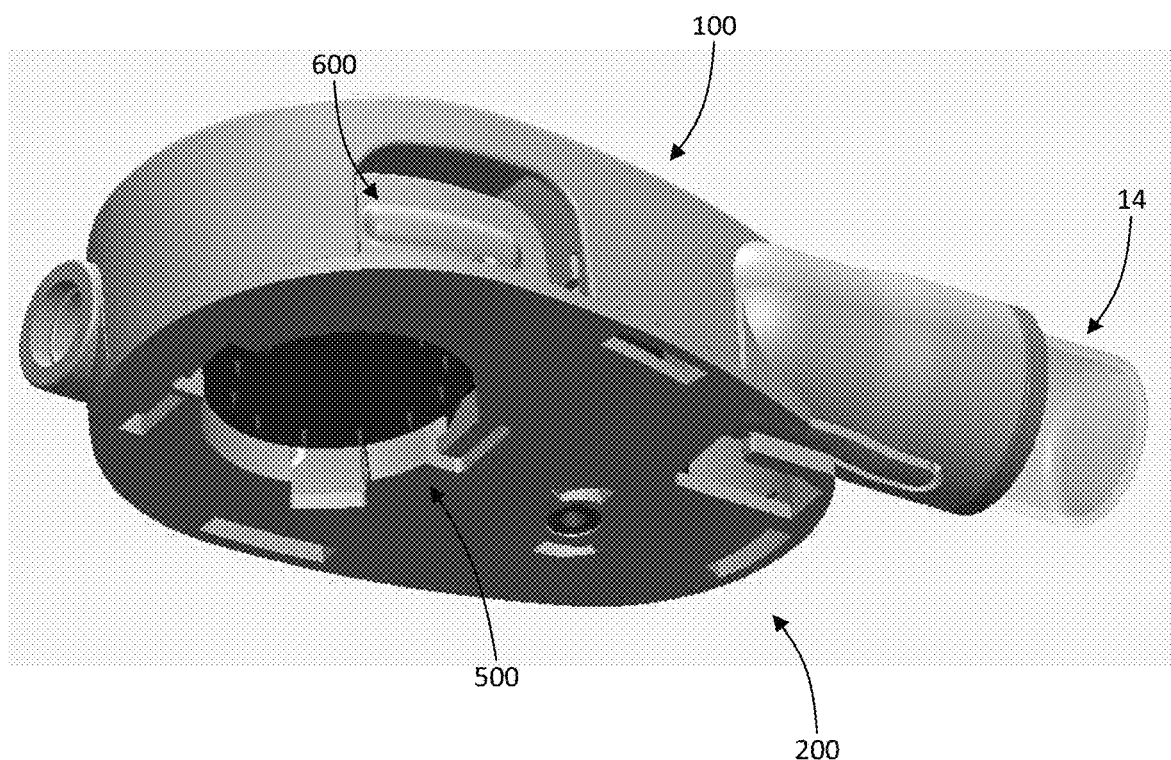
FIG. 79 depicts the microneedle array of the cartridge in a retracted position in accordance with an exemplary embodiment.

The microneedle array assembly 500 is moveable from the deployed position (FIG. 78) to a retracted position (FIG. 79).

When the microneedle assembly 500 is in the deployed position, the blocking feature 614 of the retraction button 600 no longer contacts the base 508 which allows a user to push the retraction button in the direction of arrow C and into the cartridge 12. When pushed, the first button guide 270, the second button guide 272 and the third button guide 274 direct the retraction button 600 towards the microneedle array housing 244. As the first arm 606 and the second arm 608 move, the angled surfaces 610 and 612 contact the extensions 510 which causes the microneedle array assembly 500 to move upward in the direction of arrow D and out of the subject's skin thereby compressing the injection spring 26.

Figure 80:
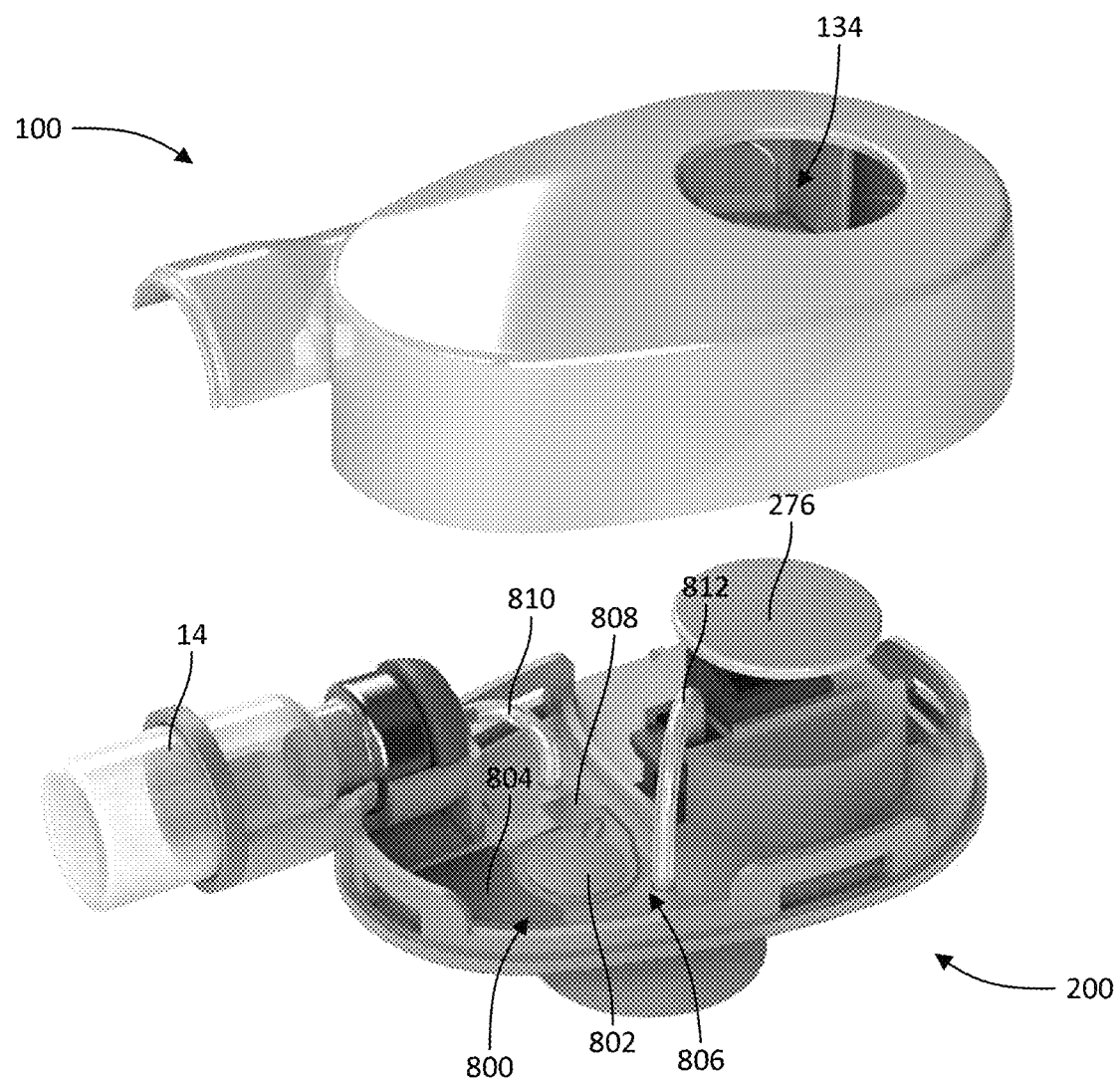
FIG. 80 depicts the cartridge of the dermal patch system with a piezoelectric pump in accordance with an exemplary embodiment.

Referring now to FIG. 80, in another embodiment, the pump assembly 400 may be removed and replaced with a piezoelectric pump system 800. In such an embodiment, the piezoelectric pump system 800 can include a piezoelectric pump 802, a battery (e.g., a printed battery) 804, one or more laminate layers 806 stacked upon one another, a pump controller 808, a first tube 810 and a second tube 812. Furthermore, in such an embodiment, the stop 16 includes one hollow needle (e.g., the hollow needle 18) that is employed to connect the first tube 810 to the vial 14. The first tube 810 and the second tube 812 are connected to the piezoelectric pump 802 via one or more fluidic channels (e.g., microfluidic channels) (not shown). The second tube 812 is connected to the hollow cylinder 512 which allows the second tube 812 to carry a pharmaceutical to the microneedles 536.

In this embodiment, the cover 100 is modified to include a button aperture 134 that extends to the top wall 102. The base 200 includes a button 276. When the cover 100 is connected to the base 200 the button 276 extends through the button aperture 134. The button 276 is connected to the trigger 700 and when pushed, moves the trigger 700 from the first position to the second position to release the microneedle array assembly 500 as previously discussed herein. Furthermore, pushing the button 276 activates the piezoelectric pump 802 via a switch to pump the pharmaceutical from the vial 14 to the microneedles 536. After the pharmaceutical is administered, a user can push the retraction button 600 to retract the microneedles 536 into the Referring now to FIG. 81, in some embodiments, the cover 100 includes a quick response ("QR") code 30 disposed on the outer surface 102a of the top wall 102. As will be discussed in further detail herein, the QR code 30 can be associated with an electronic medical record ("EMR") stored in an electronic medical record database.

In these embodiments, a user of a computer system 32 may scan the QR code 30 to view and/or update an EMR 34 that is associated with the QR code 30. The EMR 34 can be stored within an EMR database 36 that is in communication with the computer system 32. Furthermore, the QR code 30 may be employed to preserve the chain of custody of the dermal patch system 10.

Figure 81:
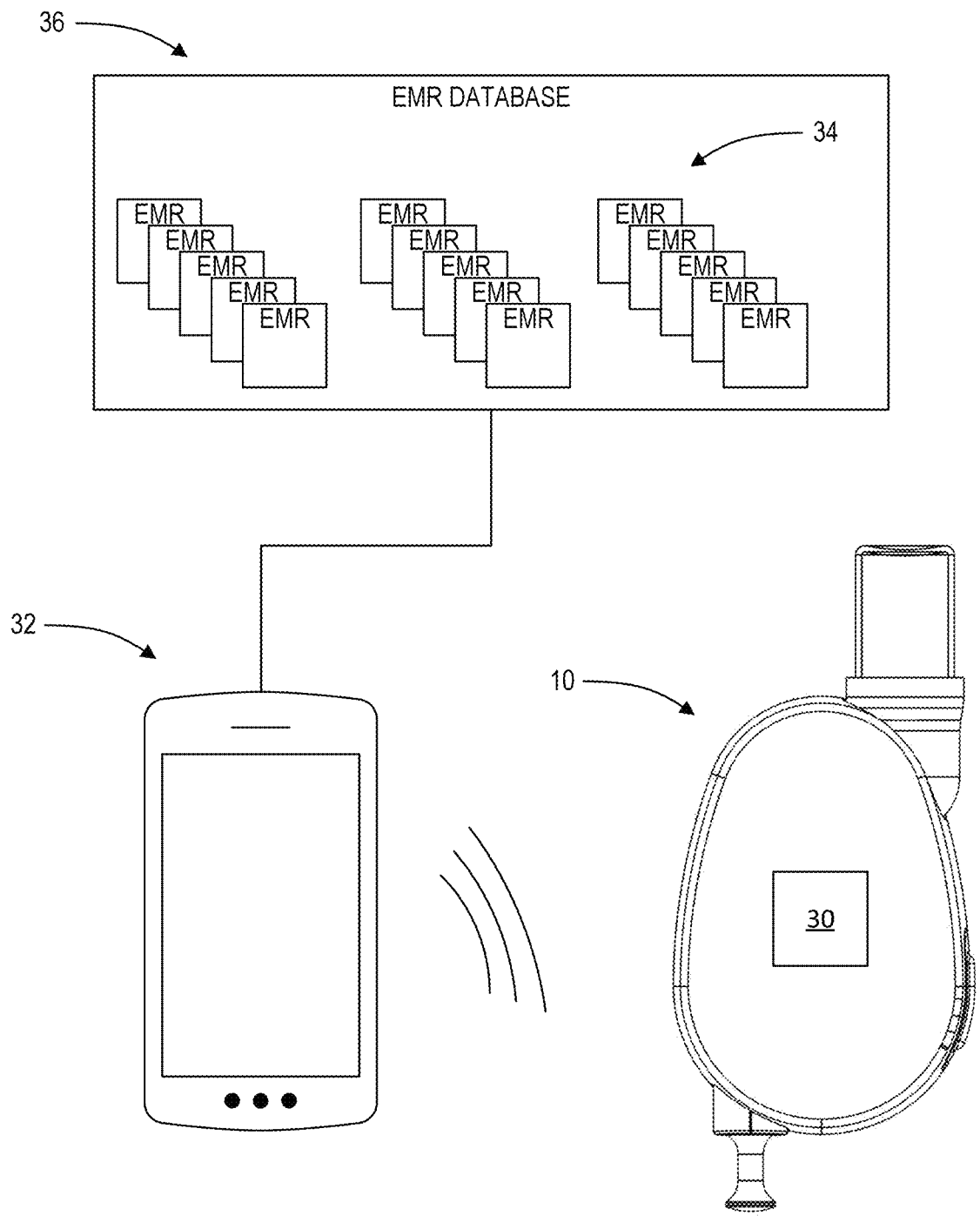
FIG. 81 depicts a dermal patch system with a quick response ("QR") code and a computer system that is in communication with an electronic medical record ("EMR") database in accordance with an exemplary embodiment.

The computer system 32 may include an application that provides access to the EMR database 36 via a network connection and allows a user to photograph or scan the QR code 30. As shown in FIG. 81 the EMR database 36 includes a plurality of EMRs 34 each of which is associated with an individual subject. The application causes the computer system 32 to scan or retrieve an image of the QR code 30, analyze the QR code 30 and associate the QR code 30 with an EMR 34. In some embodiments, the computer system 32 may then update the associated EMR 34 to indicate the subject has been administered the pharmaceutical from the vial 14. The computer system 32 may update the EMR 34 automatically or based on a user input.

Figure 82:
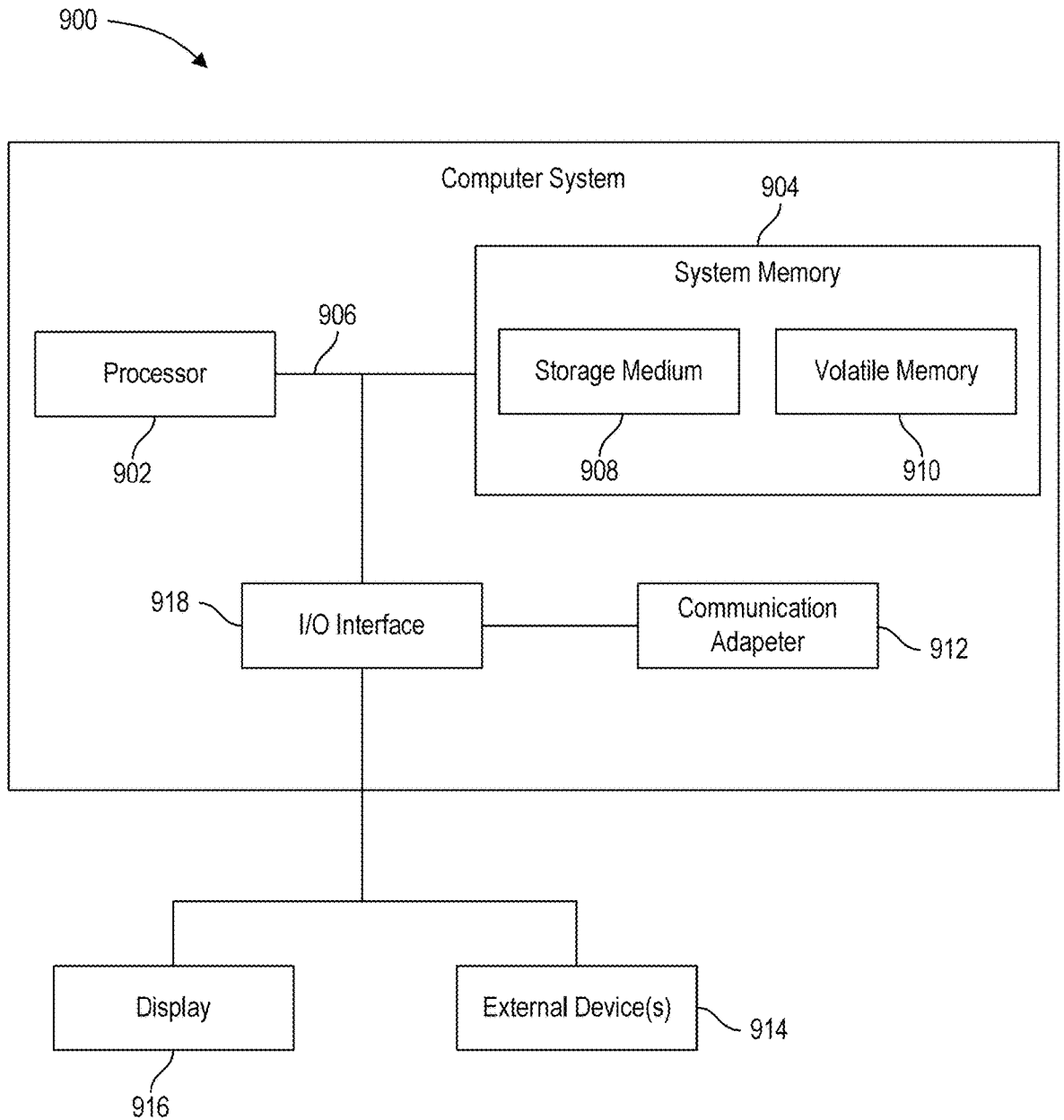
FIG. 82 schematically depicts a computer system in accordance with an exemplary embodiment.

Referring now to FIG. 82, a computer system 900 is shown in accordance with an exemplary embodiment. The computer system 900 may serve as any computer system disclosed herein (e.g., the computer system 32). As used herein a computer system (or device) is any system/device capable of receiving, processing, and/or sending data. Computer systems include, but are not limited to, microprocessor-based systems, personal computers, servers, hand-held computing devices, tablets, smartphones, multiprocessor-based systems, mainframe computer systems, virtual reality ("VR") headsets and the like.

As shown in FIG. 82, the computer system 900 includes one or more processors or processing units 902, a system memory 904, and a bus 906 that couples the various components of the computer system 900 including the system memory 904 to the processor 902. The system memory 904 includes a computer readable storage medium 908 and volatile memory 910 (e.g., Random Access Memory, cache, etc.). As used herein, a computer readable storage medium includes any media that is capable of storing computer readable; program instructions and is accessible by a processor. The computer readable storage medium 908 includes non-volatile and non-transitory storage media (e.g., flash memory, read only memory (ROM), hard disk drives, etc.). Computer program instructions as described herein include program modules (e.g., routines, programs, objects, components, logic, data structures, etc.) that are executable by a processor. Furthermore, computer readable program instructions, when executed by a processor, can direct a computer system to function in a particular manner such that a computer readable storage medium comprises an article of manufacture. Specifically, the computer readable program instructions when executed by a processor can create a means for carrying out at least a portion of the steps of the methods disclosed herein.

The bus 906 may be one or more of any type of bus structure capable of transmitting data between components of the computer system 900 (e.g., a memory bus, a memory controller, a peripheral bus, an accelerated graphics port, etc.).

The computer system 900 may further include a communication adapter 912 which allows the computer system 900 to communicate with one or more other computer systems/devices via one or more communication protocols (e.g., Wi-Fi, BTLE, etc.) and in some embodiments may allow the computer system 900 to communicate with one or more other computer systems/devices over one or more networks (e.g., a local area network (LAN), a wide area network (WAN), a public network (the Internet), etc.).

In some embodiments, the computer system 900 may be connected to one or more external devices 914 and a display 916. As used herein, an external device includes any device that allows a user to interact with a computer system (e.g., mouse, keyboard, touch screen, etc.). An external device 914 and the display 916 may be in communication with the processor 902 and the system memory 904 via an Input/Output (I/O) interface 918.

The display 916 may display a graphical user interface (GUI) that may include a plurality of selectable icons and/or editable fields. A user may use an external device 914 (e.g., a mouse) to select one or more icons and/or edit one or more editable fields. Selecting an icon and/or editing a field may cause the processor 902 to execute computer readable program instructions stored in the computer readable storage medium 908. In one example, a user may use an external device 914 to interact with the computer system 900 and cause the processor 902 to execute computer readable program instructions relating to at least a portion of the steps of the methods disclosed herein.

Figure 83:
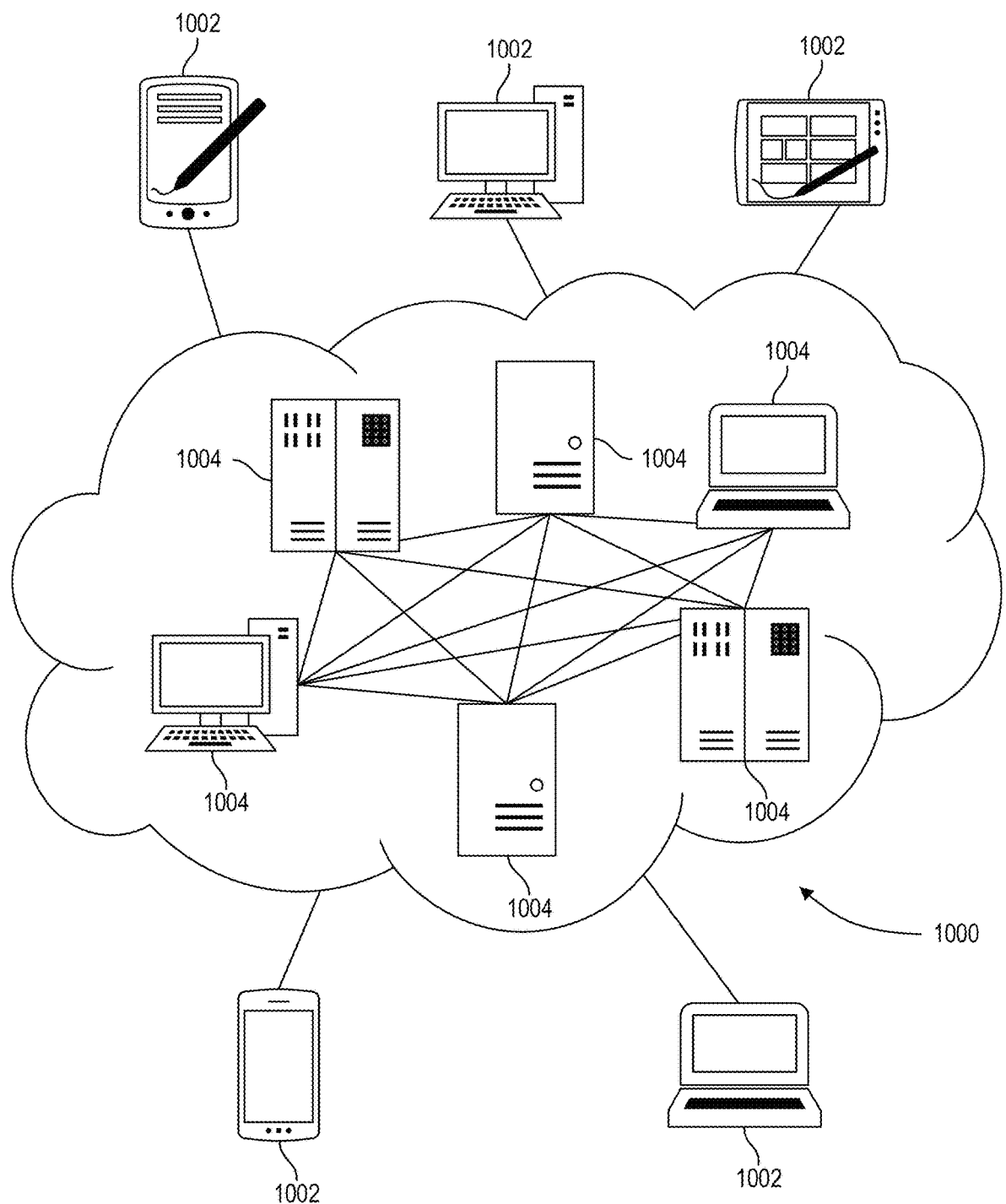
FIG. 83 schematically depicts a cloud computer environment in accordance with an exemplary embodiment.

Referring now to FIG. 83, a cloud computing environment 1000 is depicted in accordance with an exemplary embodiment. The cloud computing environment 1000 is connected to one or more user computer systems 1002 and provides access to shared computer resources (e.g., storage, memory, applications, virtual machines, etc.) to the user computer systems 1002. As depicted in FIG. 83, the cloud computing environment includes one or more interconnected nodes 1004. Each node 1004 may be a computer system or device local processing and storage capabilities. The nodes 1004 may be grouped and in communication with one another via one or more networks. This allows the cloud computing environment 1000 to offer software services to the one or more computer services to the one or more user computer systems 1002 and as such, a user computer system 1002 does not need to maintain resources locally.

In one embodiment, a node 1004 includes computer readable program instructions for carrying out various steps of various methods disclosed herein. In these embodiments, a user of a user computer system 1002 that is connected to the cloud computing environment may cause a node 1004 to execute the computer readable program instructions to carry out various steps of various methods disclosed herein.

Figure 84:
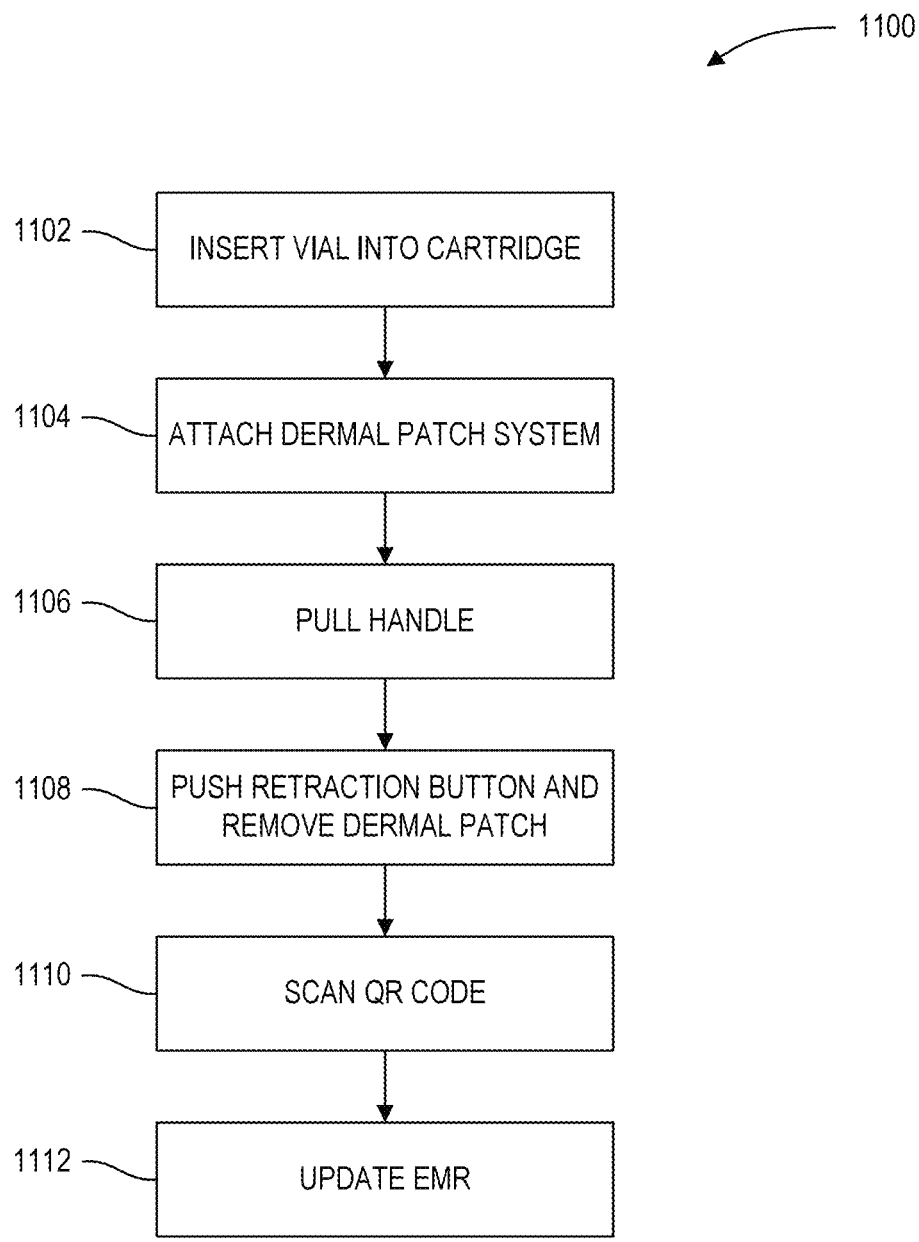
FIG. 84 is a flow chart of a method for administering a pharmaceutical to a subject in accordance with an exemplary embodiment.

Referring now to FIG. 84, a method 1100 for administering a pharmaceutical is shown in accordance with an exemplary embodiment.

At 1102, as user inserts the vial 14 into the cartridge 12 as previously discussed herein.

At 1104, the user attaches the dermal patch system 10 to the skin of the subject via an adhesive film on a bottom surface of the dermal patch system 10 as previously discussed herein.

At 1106, the user of the dermal patch system 10 pulls the handle 302 of the pull mechanism 300 to deliver a pharmaceutical stored in the vial 14 to the subject as previously discussed herein. In some embodiments, the user can pull the handle 302 after placing the dermal patch system 10 in a proper orientation (e.g., by moving an arm of the subject to which the dermal patch system 10 is attached) as previously discussed herein.

At 1108, the user of the dermal patch system 10 pushes the retraction button 600 to remove the microneedles 536 from the skin of the subject and removes the dermal patch from the subject as previously discussed herein.

At 1110, the user of the dermal patch system 10 uses the computer system 32 to scan a QR code 30 of the dermal patch system 10 and associate the QR code 30 with an EMR 34 as previously discussed herein.

At 1112, the computer system 32 updates the EMR 34 to indicate that the subject was administered the pharmaceutical automatically or based on a user input as previously discussed herein.

As previously discussed, the above may be implemented by way of computer readable instructions, encoded or embedded on computer readable storage medium (which excludes transitory medium), which, when executed by a processor(s), cause the processor(s) to carry out the methods of the present disclosure.

While various embodiments have been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A dermal patch system for administering a pharmaceutical comprising:
    a vial that stores a pharmaceutical, and
    a cartridge coupled to the vial, wherein the dermal patch includes:
        a pull mechanism,
        a pump, and
        a plurality of microneedles in communication with the vial, wherein the microneedles are configured to move between an undeployed position to a deployed position,
    wherein, when pulled, the pull mechanism is configured to cause the pump to pump the pharmaceutical from the vial and to the microneedles, and cause the microneedles to move to the deployed position, and
    wherein the pump comprises a pump portion having a cog, wherein the cog includes a plurality of protrusions that are configured to compress a tube as the cog rotates thereby causing the pharmaceutical to be expelled from the vial.

2. The dermal patch system of claim 1, wherein the pump is configured to prime the microneedles with an amount of pharmaceutical before the microneedles are moved to the deployed position.

3. The dermal patch system of claim 1, wherein the cartridge further includes:
    a tube configured to carry the pharmaceutical from the vial to the plurality of microneedles.

4. The dermal patch system of claim 3, wherein pulling the pull mechanism causes the pump to rotate which causes the pump to force the pharmaceutical through the tube via positive displacement.

5. The dermal patch system of claim 4, wherein the tube is a first tube, and the cartridge includes a second tube connected to the vial, and wherein rotation of the pump further causes the pump to force air into the vial through the second tube via positive displacement.

6. The dermal patch system of claim 4, wherein the cartridge further includes: a latch that allows the pump to rotate in a first direction and prevents the pump from rotating in an opposite second direction.

7. The dermal patch system of claim 1, wherein the pull mechanism is configured to move when then the cartridge has a first orientation and is prevented from moving when the cartridge has a different second orientation.

8. The dermal patch system of claim 1, wherein the cartridge further includes:
    a trigger that is configured to move from a first position to a second position when the pull mechanism is pulled, wherein in the first position the trigger retains the microneedles in the undeployed position and configured to release the microneedles in the second position.

9. The dermal patch system of claim 8, wherein the pump is configured to move the trigger from the first position to the second position when the pull mechanism is pulled.

10. The dermal patch system of claim 8, wherein the cartridge further includes an injection spring that is in a compressed state when the trigger is in the first position and in an extended state when the trigger is in the second position, and wherein the injection spring is configured to move the microneedles to the deployed position when in the extend position.

11. The dermal patch system of claim 1, wherein the cartridge further includes: a retraction button configured to move the microneedles from the deployed position to the undeployed position.

12. The dermal patch system of claim 11, wherein the retraction button is prevented from moving the microneedles when the microneedles are in the undeployed position.

13. The dermal patch system of claim 1, wherein the cartridge further includes: a latch that prevents a user from removing the vial from the cartridge.

14. The dermal patch system of claim 1, wherein the pharmaceutical is a vaccine.

15. The dermal patch system of claim 13, wherein the vial includes a fractional dose of the vaccine.

16. The dermal patch system of claim 1, wherein the cartridge includes a quick response code that is
associated with an electronic medical record.

\* \* \* \* \*